United States Patent
Alley et al.

(10) Patent No.: US 11,319,526 B2
(45) Date of Patent: May 3, 2022

(54) METHODS AND COMPOSITIONS FOR MAKING ANTIBODIES AND ANTIBODY DERIVATIVES WITH REDUCED CORE FUCOSYLATION

(71) Applicant: Seagen Inc., Bothell, WA (US)

(72) Inventors: Stephen C. Alley, Bothell, WA (US); Scott C. Jeffrey, Bothell, WA (US); Django Sussman, Bothell, WA (US); Dennis R. Benjamin, Bothell, WA (US); Brian Toki, Bothell, WA (US); Patrick J. Burke, Bothell, WA (US)

(73) Assignee: Seagen Inc., Bothell, WA (US)

( * ) Notice: Subject to any disclaimer, the term of this patent is extended or adjusted under 35 U.S.C. 154(b) by 5 days.

(21) Appl. No.: 16/414,633

(22) Filed: May 16, 2019

(65) Prior Publication Data
US 2019/0276796 A1 Sep. 12, 2019

Related U.S. Application Data

(60) Continuation of application No. 15/729,258, filed on Oct. 10, 2017, now Pat. No. 10,443,035, which is a continuation of application No. 14/632,925, filed on Feb. 26, 2015, now Pat. No. 9,816,069, which is a continuation of application No. 14/043,742, filed on Oct. 1, 2013, now Pat. No. 8,993,326, which is a division of application No. 13/405,143, filed on Feb. 24, 2012, now Pat. No. 8,574,907, which is a division of application No. 12/434,533, filed on May 1, 2009, now Pat. No. 8,163,551.

(60) Provisional application No. 61/107,289, filed on Oct. 21, 2008, provisional application No. 61/092,700, filed on Aug. 28, 2008, provisional application No. 61/050,173, filed on May 2, 2008.

(51) Int. Cl.
| | |
|---|---|
| *C07H 13/04* | (2006.01) |
| *C07H 7/02* | (2006.01) |
| *C07H 15/10* | (2006.01) |
| *C12N 5/00* | (2006.01) |
| *C07K 16/00* | (2006.01) |

(52) U.S. Cl.
CPC .......... *C12N 5/0037* (2013.01); *C07H 13/04* (2013.01); *C07K 16/00* (2013.01); *C07K 2317/72* (2013.01); *C07K 2317/732* (2013.01)

(58) Field of Classification Search
None
See application file for complete search history.

(56) References Cited

U.S. PATENT DOCUMENTS

| | | |
|---|---|---|
| 4,407,817 A | 10/1983 | Chan |
| 4,444,887 A | 4/1984 | Hoffmann |
| 4,474,893 A | 10/1984 | Reading |
| 4,486,414 A | 12/1984 | Pettit |
| 4,676,980 A | 6/1987 | Segal et al. |
| 4,714,681 A | 12/1987 | Reading |
| 4,716,111 A | 12/1987 | Osband |
| 4,816,397 A | 3/1989 | Boss |
| 4,816,444 A | 3/1989 | Pettit |
| 4,816,567 A | 3/1989 | Cabilly |
| 4,879,278 A | 11/1989 | Pettit |
| 4,925,648 A | 5/1990 | Hansen |
| 4,946,778 A | 8/1990 | Ladner |
| 4,978,744 A | 12/1990 | Pettit |
| 4,986,988 A | 1/1991 | Pettit |
| 5,034,517 A | 7/1991 | Umezawa |
| 5,076,973 A | 12/1991 | Pettit |
| 5,122,464 A | 6/1992 | Wilson |
| 5,138,036 A | 8/1992 | Pettit |
| 5,155,027 A | 10/1992 | Sledziewski |
| 5,210,078 A | 5/1993 | Toyokuni |
| 5,223,409 A | 6/1993 | Ladner et al. |
| 5,225,539 A | 7/1993 | Winter |
| 5,258,498 A | 11/1993 | Huston |
| 5,336,603 A | 8/1994 | Capon |
| 5,349,053 A | 9/1994 | Landolfi |
| 5,359,046 A | 10/1994 | Capon |
| 5,374,746 A | 12/1994 | Ok |
| 5,403,484 A | 4/1995 | Ladner |
| 5,410,024 A | 4/1995 | Pettit |
| 5,413,923 A | 5/1995 | Kucherlapati |
| 5,427,908 A | 6/1995 | Dower |
| 5,461,143 A | 10/1995 | Wong |
| 5,504,191 A | 4/1996 | Pettit |
| 5,516,637 A | 5/1996 | Huang |
| 5,521,284 A | 5/1996 | Pettit |
| 5,530,097 A | 6/1996 | Pettit |
| 5,530,101 A | 6/1996 | Queen et al. |
| 5,545,806 A | 8/1996 | Lonberg et al. |

(Continued)

FOREIGN PATENT DOCUMENTS

| | | |
|---|---|---|
| EP | 0012023 A1 | 6/1980 |
| EP | 0105360 A1 | 4/1984 |

(Continued)

OTHER PUBLICATIONS

Adam, et al. "CD70 (TNFSF7) is Expressed at High Prevalence in Renal Cell Carcinomas and is Rapidly Internalised on Antibody Binding," British J. of Cancer. 95:298-306 (2006).

(Continued)

*Primary Examiner* — Michail A Belyavskyi
(74) *Attorney, Agent, or Firm* — Morrison & Foerster LLP

(57) ABSTRACT

The invention provides methods and compositions for preparing antibodies and antibody derivatives with reduced core fucosylation.

63 Claims, 9 Drawing Sheets

Specification includes a Sequence Listing.

(56) References Cited

U.S. PATENT DOCUMENTS

| | | | |
|---|---|---|---|
| 5,554,725 | A | 9/1996 | Pettit |
| 5,565,332 | A | 10/1996 | Hoogenboom et al. |
| 5,569,825 | A | 10/1996 | Lonberg |
| 5,571,698 | A | 11/1996 | Ladner |
| 5,573,920 | A | 11/1996 | Randle |
| 5,573,924 | A | 11/1996 | Beckmann |
| 5,580,717 | A | 12/1996 | Dower |
| 5,585,089 | A | 12/1996 | Queen et al. |
| 5,595,976 | A | 1/1997 | Billington |
| 5,599,902 | A | 2/1997 | Pettit |
| 5,601,819 | A | 2/1997 | Wong |
| 5,605,690 | A | 2/1997 | Jacobs |
| 5,625,126 | A | 4/1997 | Ladner et al. |
| 5,633,425 | A | 5/1997 | Lonberg et al. |
| 5,635,483 | A | 6/1997 | Pettit |
| 5,661,016 | A | 6/1997 | Lonberg et al. |
| 5,658,727 | A | 8/1997 | Barbas |
| 5,663,149 | A | 9/1997 | Pettit |
| 5,665,860 | A | 9/1997 | Pettit |
| 5,698,426 | A | 12/1997 | Huse |
| 5,733,743 | A | 3/1998 | Johnson et al. |
| 5,750,753 | A | 5/1998 | Kimae |
| 5,770,407 | A | 6/1998 | Wong |
| 5,780,225 | A | 7/1998 | Wigler |
| 5,780,588 | A | 7/1998 | Pettit |
| 5,807,715 | A | 9/1998 | Morrison |
| 5,814,318 | A | 9/1998 | Lonberg et al. |
| 5,821,047 | A | 10/1998 | Garrard |
| 5,885,793 | A | 3/1999 | Griffiths |
| 5,888,809 | A | 3/1999 | Allison |
| 5,914,111 | A | 6/1999 | Wallner |
| 5,916,771 | A | 6/1999 | Hori |
| 5,939,598 | A | 8/1999 | Kucherlapati |
| 5,945,404 | A | 8/1999 | Sugai |
| 5,969,108 | A | 10/1999 | Mccafferty |
| 6,034,065 | A | 3/2000 | Pettit |
| 6,075,134 | A | 6/2000 | Bertozzi |
| 6,130,237 | A | 10/2000 | Denny |
| 6,143,724 | A | 11/2000 | Ohira |
| 6,214,345 | B1 | 4/2001 | Firestone |
| 6,239,104 | B1 | 5/2001 | Pettit |
| 6,323,315 | B1 | 11/2001 | Pettit |
| 6,342,219 | B1 | 1/2002 | Thorpe |
| 6,458,937 | B1 | 10/2002 | Bertozzi |
| 6,489,302 | B1 | 12/2002 | Wiessler |
| 6,713,287 | B1 | 3/2004 | Wong |
| 6,884,869 | B2 | 4/2005 | Senter |
| 6,936,701 | B2 | 8/2005 | Bertozzi |
| 6,979,675 | B2 | 12/2005 | Tidmarsh |
| 7,160,865 | B2 | 1/2007 | Lampidis |
| 7,214,660 | B2 | 5/2007 | Defrees |
| 7,261,892 | B2 | 8/2007 | Terrett |
| 7,265,084 | B2 | 9/2007 | Defrees |
| 7,335,500 | B2 | 2/2008 | Wong |
| 7,351,408 | B2 | 4/2008 | Bertozzi |
| 7,491,390 | B2 | 2/2009 | Law |
| 7,498,298 | B2 | 3/2009 | Doronina |
| 7,641,903 | B2 | 1/2010 | Law |
| 7,659,241 | B2 | 2/2010 | Senter |
| 7,662,387 | B2 | 2/2010 | Law |
| 7,829,531 | B2 | 11/2010 | Senter |
| 7,851,437 | B2 | 12/2010 | Senter |
| 7,968,687 | B2 | 6/2011 | Mcdonagh |
| 8,067,546 | B2 * | 11/2011 | McDonagh ........ C07K 16/2875 530/387.3 |
| 8,163,551 | B2 | 4/2012 | Alley |
| 8,242,167 | B2 | 8/2012 | Lampidis |
| 8,278,349 | B2 | 10/2012 | Kloog |
| 8,299,033 | B2 | 10/2012 | Priebe |
| 8,337,838 | B2 | 12/2012 | Law |
| 8,562,987 | B2 | 10/2013 | Mcdonagh |
| 8,574,907 | B2 | 11/2013 | Alley |
| 8,609,104 | B2 | 12/2013 | Law |
| 8,633,021 | B2 | 1/2014 | Xia |
| 8,663,642 | B2 | 3/2014 | Law |
| 8,834,882 | B2 | 9/2014 | Silence |
| 8,993,326 | B2 | 3/2015 | Alley |
| 9,051,372 | B2 | 6/2015 | Law |
| 9,051,972 | B2 | 6/2015 | Garvey |
| 9,272,031 | B2 * | 3/2016 | Loetscher ............... C07K 16/18 |
| 9,322,036 | B2 * | 4/2016 | Collingwood ..... C07K 14/4703 |
| 9,428,585 | B2 | 8/2016 | Mcdonagh |
| 9,504,702 | B2 | 11/2016 | Senter |
| 9,701,752 | B2 | 7/2017 | Mcdonagh |
| 9,765,148 | B2 | 9/2017 | Silence |
| 9,765,149 | B2 | 9/2017 | Silence |
| 9,816,069 | B2 | 11/2017 | Alley |
| 9,919,061 | B2 * | 3/2018 | McDonagh ............ A61K 38/05 |
| 2003/0083263 | A1 | 5/2003 | Doronina |
| 2003/0096743 | A1 | 5/2003 | Senter |
| 2003/0105000 | A1 | 6/2003 | Pero |
| 2003/0130189 | A1 | 7/2003 | Senter |
| 2004/0110282 | A1 | 6/2004 | Kanda et al. |
| 2004/0157782 | A1 | 6/2004 | Doronina |
| 2004/0131612 | A1 | 7/2004 | Watkins |
| 2004/0132140 | A1 | 7/2004 | Satoh et al. |
| 2004/0180002 | A1 | 9/2004 | Young |
| 2005/0009751 | A1 | 1/2005 | Senter |
| 2005/0010664 | A1 | 1/2005 | Hubbard |
| 2005/0043250 | A1 | 2/2005 | Lampidis |
| 2005/0106644 | A1 | 5/2005 | Cairns |
| 2005/0113308 | A1 | 5/2005 | Senter |
| 2005/0118656 | A1 | 6/2005 | Terrett |
| 2005/0123547 | A1 | 6/2005 | Terrett |
| 2005/0191299 | A1 | 9/2005 | Swamy |
| 2005/0238649 | A1 | 10/2005 | Doronina |
| 2006/0009400 | A1 | 1/2006 | Eckhardt |
| 2006/0074008 | A1 | 4/2006 | Senter |
| 2006/0083736 | A1 | 4/2006 | Law |
| 2006/0233794 | A1 | 10/2006 | Law |
| 2006/0246456 | A1 | 11/2006 | Tsuchiya |
| 2007/0190597 | A1 | 8/2007 | Agnew |
| 2007/0249014 | A1 | 10/2007 | Agnew |
| 2007/0292422 | A1 | 12/2007 | Law |
| 2008/0025989 | A1 | 1/2008 | Law |
| 2008/0026943 | A1 | 1/2008 | Fischer |
| 2008/0138341 | A1 | 6/2008 | Law |
| 2008/0138343 | A1 | 6/2008 | Law |
| 2008/0166756 | A1 | 7/2008 | Tsuchiya et al. |
| 2008/0226657 | A1 | 9/2008 | Doronina |
| 2008/0248051 | A1 | 10/2008 | Doronina |
| 2008/0248053 | A1 | 10/2008 | Doronina |
| 2009/0047296 | A1 | 2/2009 | Doronina |
| 2009/0074772 | A1 | 3/2009 | Law |
| 2009/0148942 | A1 | 6/2009 | Mcdonagh |
| 2009/0305972 | A1 | 12/2009 | Chahal |
| 2009/0317869 | A1 | 12/2009 | Alley |
| 2010/0129362 | A1 | 5/2010 | Law |
| 2010/0150925 | A1 | 6/2010 | Law |
| 2010/0158910 | A1 | 6/2010 | Law |
| 2010/0183636 | A1 | 7/2010 | Law |
| 2011/0003338 | A1 | 1/2011 | Bayer |
| 2011/0003758 | A1 | 1/2011 | Priebe |
| 2011/0097308 | A1 | 4/2011 | Xia |
| 2012/0045436 | A1 | 2/2012 | Mcdonagh |
| 2012/0183997 | A1 | 7/2012 | Alley |
| 2012/0202762 | A1 | 8/2012 | Magnani |
| 2012/0276108 | A1 | 11/2012 | Priebe |
| 2012/0294863 | A1 | 11/2012 | Law |
| 2014/0031536 | A1 | 1/2014 | Alley |
| 2014/0141016 | A1 | 5/2014 | Silence et al. |
| 2014/0147450 | A1 | 5/2014 | Silence et al. |
| 2014/0178936 | A1 | 6/2014 | Mcdonagh |
| 2014/0235643 | A1 | 8/2014 | Silence et al. |
| 2015/0238509 | A1 | 8/2015 | Benjamin |
| 2015/0266963 | A1 | 9/2015 | Silence et al. |
| 2015/0337259 | A1 | 11/2015 | Alley |
| 2017/0022282 | A1 | 1/2017 | Mcdonagh |

(56) References Cited

U.S. PATENT DOCUMENTS

| | | |
|---|---|---|
| 2017/0342157 A1 | 11/2017 | McDonagh et al. |
| 2018/0155677 A1 | 6/2018 | Alley |

FOREIGN PATENT DOCUMENTS

| | | | |
|---|---|---|---|
| EP | 0184187 A2 | 6/1986 | |
| EP | 0217577 A2 | 4/1987 | |
| EP | 0239400 A2 | 9/1987 | |
| EP | 0171496 A3 | 11/1987 | |
| EP | 0173494 A3 | 11/1987 | |
| EP | 0367166 A1 | 5/1990 | |
| EP | 0404097 A3 | 10/1991 | |
| EP | 0519596 A1 | 12/1992 | |
| EP | 0592106 A1 | 4/1994 | |
| EP | 0598877 A1 | 6/1994 | |
| EP | 1676910 A1 | 7/2006 | |
| JP | 2504153 A | 11/1990 | |
| JP | 6507169 A | 8/1994 | |
| WO | WO198303679 A1 | 10/1983 | |
| WO | WO198601533 A1 | 3/1986 | |
| WO | WO198605807 A1 | 10/1986 | |
| WO | WO198702671 A1 | 5/1987 | |
| WO | WO198901036 A1 | 2/1989 | |
| WO | WO198910929 A2 | 11/1989 | |
| WO | WO199002809 A1 | 3/1990 | |
| WO | WO199007861 A1 | 7/1990 | |
| WO | WO199100360 A1 | 1/1991 | |
| WO | WO199109967 A1 | 7/1991 | |
| WO | WO199110737 A1 | 7/1991 | |
| WO | WO199110741 A1 | 7/1991 | |
| WO | WO199117271 A1 | 11/1991 | |
| WO | WO199201047 A1 | 1/1992 | |
| WO | WO199205793 A1 | 4/1992 | |
| WO | WO199208802 A1 | 5/1992 | |
| WO | WO199218619 A1 | 10/1992 | |
| WO | WO199219632 A1 | 11/1992 | |
| WO | WO199308829 A1 | 5/1993 | |
| WO | WO199311161 A1 | 6/1993 | |
| WO | WO199311236 A1 | 6/1993 | |
| WO | WO199317715 A1 | 9/1993 | |
| WO | WO199325788 A1 | 12/1993 | |
| WO | WO199404690 A1 | 3/1994 | |
| WO | WO199515982 A2 | 6/1995 | |
| WO | WO199520401 A1 | 8/1995 | |
| WO | WO199515982 A3 | 12/1995 | |
| WO | WO199604388 A1 | 2/1996 | |
| WO | WO199633735 A1 | 10/1996 | |
| WO | WO199634096 A1 | 10/1996 | |
| WO | WO199816654 A1 | 4/1998 | |
| WO | WO199824893 A2 | 6/1998 | |
| WO | WO199825940 A1 | 6/1998 | |
| WO | WO199824893 A3 | 8/1998 | |
| WO | WO199846645 A2 | 10/1998 | |
| WO | WO199850433 A2 | 11/1998 | |
| WO | WO199854365 A1 | 12/1998 | |
| WO | WO199850433 A3 | 2/1999 | |
| WO | WO199846645 A3 | 4/1999 | |
| WO | WO200194629 A2 | 12/2001 | |
| WO | WO2002088172 A2 | 11/2002 | |
| WO | WO2003026577 A2 | 4/2003 | |
| WO | WO2003046581 A2 | 6/2003 | |
| WO | WO2004010957 A2 | 2/2004 | |
| WO | WO2004033651 A2 | 4/2004 | |
| WO | WO2004073656 A2 | 9/2004 | |
| WO | WO2004091499 A2 | 10/2004 | |
| WO | WO2004099231 A2 | 11/2004 | |
| WO | WO2004073656 A3 | 2/2005 | |
| WO | WO2005061523 A1 | 7/2005 | |
| WO | WO2006044643 A2 | 4/2006 | |
| WO | WO2006113909 A2 | 10/2006 | |
| WO | WO2005081711 A2 | 11/2006 | |
| WO | WO2007038637 A2 | 4/2007 | |
| WO | WO2007048122 A2 | 4/2007 | |
| WO | WO2007081031 A1 | 7/2007 | |
| WO | WO2007111952 A2 | 10/2007 | |
| WO | WO2008052030 A2 | 5/2008 | |
| WO | WO2008074004 A2 | 6/2008 | |
| WO | WO2009108926 A1 | 9/2009 | |
| WO | WO2009135181 A2 | 11/2009 | |
| WO | WO2009143078 A2 | 11/2009 | |
| WO | WO2010005735 A2 | 1/2010 | |
| WO | WO2009143078 A9 | 3/2010 | |
| WO | WO2010111713 A2 | 9/2010 | |
| WO | WO2011137527 A1 | 11/2011 | |
| WO | WO2012019165 A2 | 2/2012 | |

OTHER PUBLICATIONS

Agathanggelou et al. "Expression of Immune Regulatory Molecules in Epstein-Barr Virus-Associated Nasopharyngeal Carcinomas With Prominent Lymphoid Stroma. Evidence for a Functional Interaction Between Epithelial Tumor Cells and Infiltrating Lymphoid Cells," Am J. Pathol. 147(4):1152-1160 (1995).

Agematsu et al., "B Cell Subpopulations Separated by CD27 and Crucial Collaboration of CD27+ Cells and Helper T Cells in Immunoglobulin Production," Eur. J. Immunol, 27(8):2073-2079 (1997).

Agematsu et al., "Generation of Plasma Cells From Peripheral Blood Memory B Cells: Synergistic Effect of Interleukin-10 and CD27/CD70 Interaction," Blood, 91(1):173-180 (1998).

Akewanlop, C. et al. (May 15, 2001). "Phagocytosis of Breast Cancer Cells Mediated by Anti-MUC-1 Monoclonal Antibody, DF3, and its Bispecific Antibody," Cancer Res. 61:4061-4065.

Akiba et al., "Critical Contribution of OX40 Ligand to T Helper Cell Type 2 Differentiation in Experimental Leishmaniasis," J. Exp. Med., 191(2):375-380 (2000).

Albermann et al. "Preparative Synthesis of GDP-β-L-Fucose by Recombinant Enzymes From Enterobacterial Sources," Glycobiology, 2000, vol. 10, No. 9, pp. 875-881.

Alton, Gordon et al. "Direct Utilization of Man Nose for Mammalian Glycoprotein Biosynthesis," Glycobiology, 1998, vol. 8, No. 3, pp. 285-295.

Altschul, S.F. et al. (Oct. 5, 1990). "Basic Local Alignment Search Tool," J. Mol. Biol. 215(3):403-410.

Altschul, S.F.et al. (1997). "Gapped BLAST and PSI-BLAST: A New Generation of Protein Database Search Programs," Nucleic Acids Res. 25(17):3389-3402.

Ames, R.S. et al. (Aug. 18, 1995). "Conversion of Murine Fabs Isolated From a Combinatorial Phage Display Library to Full Length Immunoglobulins," J. Immunol. Methods 184(2):177-186.

Ananth, S. et al. (May 1999). "Transforming Growth Factor β1 Is a Target for the von Hippel-Lindau Tumor Suppressor and a Critical Growth Factor for Clear Cell Renal Carcinoma," Cancer Res. 59(9):2210-2216.

Araki, Masatake et al., "E-Selection Binding Promotes Neutrophil Activation in Vivo in Eselectin Transgenic Mice," Biochemical and Biophysical Research Communications (Jun. 18, 1996); 224(3):825-830.

Aybay, Cemalettin et al., "Development of a Rapid, Single-Step Procedure Using Protein G Affinity Chromatography to Deplete Fetal Calf Serum of Its IgG and to Isolate Murine IgG1 Monoclonal Antibodies From Supernatants of Hybridoma Cells," Journal of Immunological Methods (2000; accepted Sep. 27, 1999); 233:77-81.

Baert, et al., "Influence of Immunogenicity on the Long-Term Efficacy of Infliximab in Crogn's Disease," N. Engl. J. Med., 348(7):601-608 (2003).

Bahler et al., "Antigen Selection in Human Lymphomagenesis," Cancer Res., 52(19 Suppl.):5547s-5551s (Oct. 1, 1992).

Bahler et al., "Clonal Evolution of a Follicular Lymphoma: Evidence for Antigen Selection," PNAS, 89 (15):6770-6774 (Aug. 1992).

Baisch, Gabi et al. "Synthetic Potential of Cloned Fucosyl-Transferase III and VI," Bioorganic & Medicinal Chemistry Letters (1997; accepted Aug. 18, 1997); 7(19):2447-2450.

Barbin, Karin et al. "Influence of Variable N-Glycosylation on the Cytolytic Potential of Chimeric CD19 Antibodies," J. Immunother. (Mar./Apr. 2006); 29(2):122-133.

(56) References Cited

OTHER PUBLICATIONS

Baskin, Jeremy et al. "Bioorthogonal Click Chemistry: Covalent Labeling in Living Systems," QSAR Comb. Sci. (Aug. 15, 2007); 26(11-12): 1211-1219.
Baxevanis, A.D. et al. (Apr. 1993). "Interactions of Coiled Coils in Transcription Factors: Where Is the Specificity?," Curr. Op. Gen. Devel. 3(2):278-285.
Beacham, Annabel et al. "Inhibition of Fucosyl Transferase and Fucosidase by a Rigid Bicyclic Mimic of a-L-Fucose," Tetrahedron Letters (1998); 39:151-154.
Becker, D.J. et al. (Jul. 2003, e-pub. Mar. 19, 2003). "Fucose: Biosynthesis and Biological Function in Mammals," Glycobiology 13(7):41R-53R.
Beidler, C.B. et al. (Dec. 1, 1988). "Cloning and High Level Expression of a Chimeric Antibody With Specificity for Human Carcinoembryonic Antigen," J. Immunol. 141(11) :4053-4060.
Bentama, A. et al. (Jun. 2003). "Synthesis of New α-Heterocyclic α-Aminoesters," Amino Acids 24(4):423-426.
Bernheim, A. et al. (Mar. 1993). "Cytogenetic Studies in Three Xenografted Nasopharyngeal Carcinomas," Cancer Genet. Cytogenet. 66(1):11-15.
Better, M. et al. (May 20, 1988). "*Escherichia coli* Secretion of an Active Chimerica Antibody Fragment," Science 240:1041-1043.
Betti, M. et al. (Nov. 5, 1960). International Union of Pure and Applied Chemistry. "Definitive Rules for Nomenclature of Organic Chemistry," J. Am. Chem. Soc. 82:5566-5574.
Bindon et al., "Human Monoclonal IgG Isotypes Differ in Complement Activating Function at the Level of C4 As Well As C1q", J. Exp. Med. 168:127-142, (1988).
Bitter, G.A. et al. (1987). "Expression and Secretion Vectors for Yeast," Methods in Enzymol. 153:516-544.
Bohmann, D. et al. (Dec. 4, 1987). "Human Proto-Oncogene c-jun Encodes a DNA Binding Protein With Structural and Functional Properties of Transcription Factor AP-1," Science 238(4832):1386-1392.
Bowman et al., "The Cloning of CD70 and Its Identification as the Ligand for CD27," J. Immunol. 152(4):1756-1761 (1994).
Braun, Curtis et al. "Mechanism-Based Inhibition of Yeast a-Glucosidase and Human Pancreatic a-Amylase by a New Class of Inhibitors," The Journal of Biological Chemistry (Nov. 10, 1995); 270(45):26778-26781.
Breistøl, K. et al. (Jun. 15, 1999). "Antitumor Activity of P-4055 (elaidic Acid-Cytarabine) Compared to Cytarabine in Metastatic and s.c. Human Tumor Xenograft Models," Cancer Res 59(12):2944-2949.
Brinkmann, U. et al. (May 11, 1995). "Phage Display of Disulfide-Stabilized Fv Fragments," J. Immunol. Methods 182(1):41-50.
Brown, Jillian R. et al. "Glycan Antagonists and Inhibitors: A Fount for Drug Discovery," Critical Reviews in Biochemistry and Molecular Biology (2007; published online Oct. 11, 2008); 42:481-515.
Brugnoni et al., "CD70 Expression on T-Cell Subpopulations: Study of Normal Individuals and Patients With Chronic Immune Activation," Immunol. Lett. 55(2):99-104 (1997).
Buchwald, H. et al. (Oct. 1980). "Long-Term, Continuous Intravenous Heparin Administration by an Implantable Infusion Pump in Ambulatory Patients With Recurrent Venous Thrombosis," Surgery 88:507-516.
Burgess et al., "Possible Dissociation of the Heparin-Binding and Mitogenic Activities of Heparin-Binding (Acidic Fibroblast) Growth Factor-1 From Its Receptor-Binding Activities by Site-Directed Mutagenesis of a Single Lysine Residue," J. Cell Biol. 111:2129-2138, (1990).
Burkart, M.D. et al. (1997). "A New Method for the Synthesis of Fluoro-Carbohydrates and Glycosides Using Selectfluor," J. Am. Chem. Soc. 119: 11743-11746.
Burkart, Michael D. et al. "Chemo-Enzymatic Synthesis of Fluorinated Sugar Nucleotide: Useful Mechanistic Probes for Glycosyltransferases," Bioorganic & Medicinal Chemistry (Apr. 14, 2000); 8:1937-1946.
Burton, D.R. et al. (1994). "Human Antibodies From Combinatorial Libraries," Advances in Immunology 57:191-280.
Busson, P. et al. (Oct. 15, 1988). "Establishment and Characterization of Three Transplantable EBV-Containing Nasopharyngeal Carcinomas," Int. J. Cancer 42(4):599-606.
Butters, T. D. et al. "Molecular Requirements of Imino Sugars for the Selective Control of N-Linked Glycosylation and Glycosphingolipid Biosynthesis," Tetrahedron: Asymmetry (2000; accepted Oct. 25, 1999); 11:113-124.
Cai, Shaopei et al. "Synthesis of Carbocyclic Analogs of Guanosine 5'-(.Beta.-I-Fucopyranosyl Diphosphate) (GDP-Fucose) as Potential Inhibitors of Fucosyltransferases," J. Org. Chem. (Sep. 21, 1992); 57:6693-6696.
Calderón, Felix et al. "Structure/Activity Relationship of Carba- and C-Fucopyranosides as Inhibitors of an α1,6-Fucosyltransferase by Molecular Modeling and Kinetic Studies," Letters in Organic Chemistry (2005; accepted Nov. 11, 2004); 2:247-251.
Carter, P. et al. (Feb. 1992). "High Level *Escherichia coli* Expression and Production of a Bivalent Humanized Antibody Fragment," Bio/Technology 10:163-167.
Carter, P. et al. (Oct. 1995). Toward the Production of Bispecific Antibody Fragments for Clinical Applications. J. Hematotherapy 4:463-470.
Carter, P., "Improving the Efficacy of Antibody-Based Cancer Therapies," Nature Reviews, (1):118-129 (Nov. 2001).
Casset, F. et al. (2003) "A Peptide Mimetic of an Anti-CD4 Monoclonal Antibody by Rational Design," BBRC 307:198-205.
Cattan, A.R. (1996) "A Comparison of a CB17 scid Mouse Model and the Tetrazolium-Dye Assay Using Human Haematological Tumour Cell Lines," Cancer Chemother. Pharmacol. 38(6):548-552.
Cattan, A.R. (Jul. 1994). "The C.B.17 scid Mouse Strain as a Model for Human Disseminated Leukaemia and Myeloma in vivo," Leuk. Res. 18(7):513-522.
Cazes, J. (1983). "Lest We Exaggerate," J. Liq. Chromatogr. 6(9):1557-1558.
Chang, G.J. et al. (Aug. 2002). "Targeted Gene Therapy With CD40Ig to Induce Long-Term Acceptance of Liver Allografts," Surgery 132(2):149-156.
Chang, Jungshan et al., "GMI-1070, A Novel Pan-Selectin Antagonist, Reverses Acute Vascular Occlusions in Sickle Cell Mice," Blood (Sep. 9, 2010) 116(10):1779-1786.
Chari, R.V.J. et al. (Jan. 1, 1992). "Immunoconjugates Containing Noveal maytansinoids: Promising Anticancer Drugs," Cancer Res, 52:127-131.
Chen et al., "Enhancement and Destruction of Antibody Function by Somatic Mutation: Unequal Occurrence Is Controlled by V Gene Combinatorial Associations," EMBO 14 (12):2784-2794, (1995).
Chen et al., "Potentiation of Antitumor Immunity by Antibody-Directed Enzyme Prodrug Therapy," Int. J. Cancer, 94(6):850-858, (2001).
Chen, Y. et al. "Selection and Analysis of an Optimized Anti-VEGF Antibody: Crystal Structure of an Affinity-Matured Fab in Complex with Antigen," J Mol. Biol 293:865-881 (1999).
Chothia, C. et al. (1987). "Canonical Structures for the Hypervariable Regions of Immunoglobulins," J. Mol. Biol. 196:901-917.
Chothia, C. et al. (Dec. 5, 1985). "Domain Association in Immunoglobulin Molecules. The Packing of Variable Domains," J. Mol. Biol. 186(3):651-663.
Clackson, T. et al. (Aug. 15, 1991). "Making antibody fragments using phage display libraries," Nature 352:624-628.
Clark, Julia L. et al. "Expression of Human a-L-Fucosyltransferase Gene Homologs in Monkey Kidney COS Cells and Modification of Potential Fucosyltransferase Acceptor Substrates by an Endogenous Glycosidase," Glycobiology (1999; accepted Jul. 7, 1998); 9(2):191-202.
Cockett, M.I. et al. (Jul. 1990). "High Level Expression of Tissue Inhibitor of Metalloproteinases in Chinese Hamster Ovary Cells Using Glutamine Synthetase Gene Amplification," Bio/Technology 8(7):662-667 (Jul. 1990).
Codelli, Julian A. et al. "Second-Generation Difluorinated Cyclooctynes for Copper-Free Click Chemistry," J. Am. Chem. Soc., (May 1, 2008); 130:11486-11493.

(56) References Cited

OTHER PUBLICATIONS

Cohen, "Optimization of Dose-Time Factors for a Tumor and Multiple Associated Normal Tissues," Int. J. Radiat. Oncology .Biol. Phvs. 1.3:251-258 (1987).
Colbère-Garapin, F. et al. (Jul. 25, 1981). "A New Dominant Hybrid Selective Marker for Higher Eukaryotic Cells," .J. Mol. Biol. 150(1):1-14.
Coleman, PM., "Effects of Aminio Acid Sequence Changes on Antibody-Antigen Interactions," Res. Immunology. 145:33-36 (1994).
Compain, Philippe et al. "Carbohydrate Mimetics-Based Glycosyltransferase Inhibitors," Bioorganic & Medicinal Chemistry (Mar. 26, 2001); 9:3077-3092.
Compain, Philippe et al. "Design, Synthesis and Biological Evaluation of Iminosugar-Based Glycosyltransferase Inhibitors," Current Topics in Medicinal Chemistry (2003); 3:541-560.
Cox, J.P. et al. (Apr. 1994). "A Directory of Human Germ-Line V Kappa Segments Reveals a Strong Bias in Their Usage," Eur. J. Immunol. 24(4):827-636.
Crouse, G.F. et al. (Feb. 1963). "Expression and Amplification of Engineered Mouse Dihydrofolate Reductase Minigenes," Mol. Cell, Biol. 3:257-266.
Cummings, Varki A. et al, "Chapter 40 Natural and Synthetic Inhibitors of Glycosylation," Essentials of Glcyobiology (Cold Spring Harbor Laboratory Press; ©1999); 18 pages.
Datta, K. et al. (Mar. 1, 2001). "The 104-123 Amino Acid Sequence of the Beta-Domain of Von Hippel-Lindau Gene Product Is Sufficient to Inhibit Renal Tumor Growth and Invasion," Cancer Res. 61(5):1768-1775.
Davies, J. et al. (Aug. 2001). "Expression of GnTIII in a Recombinant Anti-CD20 CHO Production Cell Line: Expression of Antibodies With Altered Glycoforms Leads to an Increase in ADCC Through Higher Affinity for FC gamma RIII," Biotechnol. Bioeng. 74(4):288-294.
Davis, R.L. et al. (Mar. 9, 1990). "The MyoD DNA Binding Domain Contains a Recognition Code for Muscle-Specific Gene Activation," Cell 60(5):733-746.
De Bont, E.S. et al. (Oct. 15, 2001). "Mobilized Human CD34+ Hematopoietic Stem Cells Enhance Tumor Growth in a Nonobese Diabetic/Severe Combined Immunodeficient Mouse Model of Human Non-Hodgkin's Lymphoma," Cancer Res. 61(20):7654-7659.
De Jong et al., "Regulation of Expression of CD27, A T Cell-Specific Member of a Novel Family of Membrane Receptors," J. Immunol. 146(8):2488-2494 (Apr. 15, 1991).
De Pascalis, R. et al. (2002) "Grafting of "Abbreviated" Complementarity-Determining Regions Containing Specificity-Determining Residues Essential for Ligand Contact to Engineer a Less Immunogenic Humanized Monoclonal Antibody," J Immunol. 169:3076-3084.
Den Haan et al., "Identification of a Graft Versus Host Disease-Associated Human Minor Histocompatibility Antigen," Science, 268(5216):1476-1480 (1995).
Derossi, Charles et al. "Ablation of Mouse Phosphomannose Isomerase (Mp1) Causes Mannose 6-Phosphate Accumulation, Toxicity, and Embryonic Lethality," The Journal of Biological Chemistry (2006; in Press Dec 8, 2005); 281(9):5916-5927.
Dewan, M.Z. et al. (Aug. 2005). "Hodgkin's Lymphoma Cells Are Efficiently Engrafted and Tumor Marker CD30 Is Expressed With Constitutive Nuclear Factor-KB Activity in Unconditioned NOD/SCID/γc(null) Mice," Cancer Sci. 96 (8):466-473.
Diehl, V. et al. (Jun. 20, 1978). "Long-Term Cultivation of Plasma Cell Leukemia Cells and Autologous Lymphoblasts (LCL) in vitro: a comparative study," Blut 36(6):331-338.
Dillman, R. O. "Monoclonal Antibodies for Treating Cancer", Ann. Int. Med., 111:592-603 (Oct. 1989).
Doronina, S.O. et al. (Aug. 2003). "Erraturm: Development of Potent Monoclonal Antibody Auristatin Conjugates for Cancer Therapy," Nat. Biotechnol. 21(8):941.
Drachman, et al., "SGN-70: Phase 1a Study of a Novel Humanized Antibody Targeting CD70 for the Treatment of Autoimmune Diseases." American College of Rheumatology, Abstract No. 1273, Atlanta, Georgia, Nov. 6-11, 2010 (poster).
Drexler, H.G. (1993). "Recent Results on the Biology of Hodgkin and Reed-Sternberg cells: II. Continuous Cell Lines," Leuk. Lymphoma 9:1-25.
Drexler, H.G. et al. (Aug. 2000). "Malignant Hematopoietic Cell Lines: In Vitro Models for the Study of Multiple Myeloma and Plasma Cell Leukemia," Leukemia Research 24(8):681-703.
During, M.J. et al. (Apr. 1989). "Controlled Release of Dopamine From a Polymeric Brain Implant: In Vivo Characterization," Ann. Neural. 25(4):351-356.
Emery, S.C. et al., "Humanised Monoclonal Antibodies for Therapeutic Applications," Exp. Opin. Invest. Drugs, 3(3):241-251 (1994).
EP 1 871 418, Supplementary European Search Report dated Dec. 7, 2009.
EP 12 166 726, European Search Report dated Sep. 13, 2012.
EP 1594542, European Search Report dated Mar. 12, 2007.
EP 1799262, Supplemental European Search Report dated Sep. 17, 2009.
EP 6 751 010, European Exam Report dated Jul. 22, 2011.
EP 98 99 4484, European Search Report dated Aug. 10, 2009.
European Search Report of Mar. 12, 2007 for European Application EP 04 71 3441.
Ferrara, Claudia et al. "The Carbohydrate at FcγRIIIa Asn-162—An Element Required for High Affinity Binding to Non-Fucosylated IgG Glycoforms," The Journal of Biological Chemistry (2006; in Press Dec. 5, 2005); 281(8):5032-5036.
Fessner, Wolf-Dieter et al. "Enzymes in Organic Synthesis, 15 Short Enzymatic Synthesis of L-Fucose Analogs," Eur. J. Org. Chem. (2000; Rec'd Mar. 5, 1999); 15:125-132.
Final Office Action, dated Apr. 21, 2017, for U.S. Appl. No. 14/632,925, filed Feb. 26, 2015, 4 pages.
Foecking, M.K. et al. (1986). "Powerful and Versatile Enhancer-Promoter Unit for Mammalian Expression Vectors," Gene 45(1):101-105.
Freshney, "Culture of Animal Cells, A Manual of Basic Technique," Alan R. Liss, Inc., 4, (1983).
Fukuda, Minoru, Cell Surface Carbohydrates and Cell Development; (© 1992 by CRC Press, Inc.); Book cover; publication page; pages 1-2.
Galan, M. Carmen et al. "The Design and Synthesis of a Selective Inhibitor of Fucosyltransferase VI," Org. Biomol. Chem. (Apr. 1, 2004); 2:1376-1380.
Gamblin, David P. et al. "Glycoprotein Synthesis: An Update," Chem. Rev. (Apr. 20, 2009); 109:131-163.
Geng, Fei et al., "The Expression of Core Fucosylated E-Cadherin in Cancer Cells and Lung Cancer Patients: Prognostic Implications," Cell Research (Jun. 18, 2004); 14(5):423-433.
Ghetie, M.-A. et al. (1990). "Disseminated or Localized Growth of a Human B-Cell Tumor (DAUDI) in SCID Mice," Int. J. Cancer 15:481-485.
Ghetie, M.A. et al. (Mar. 1, 1994). "Anti-CD19 Inhibits the Growth of Human B-Cell Tumor Lines In Vitro and of Daudi Cells in SCID Mice by Inducing Cell Cycle Arrest," Blood 83(5):1329-1336.
Ghetie, V. et al. (2000). "Multiple Roles for the Major Histocompatibility Complex Class I-Related Receptor FcRn," Annu. Rev. Immunol. 18:739-766.
Ghetie, V. et al. (2002). "Transcytosis and Catabolism of Antibody," Immunol. Res. 25(2):97-113.
Gillies, S.D. et al. (Dec. 20, 1989). "High-Level Expression of Chimeric Antibodies Using Adapted cDNA Variable Region Cassettes," J. Immunol. Methods 125(1-2):191-202.
Giralt et al., "Leukemia Relapse After Allogeneic Bone Marrow Transplantation: A Review," Blood, 84(11):3603-3612 (Dec. 1, 1994).
Gonzalez, Concepci6 C. et al., "Fragmentation of Carbohydrate Anomeric Alkoxy Radicals: A New Synthesis of Chiral 1-halo-1-iodo Alditols," Chemistry—A European Journal, (Jan. 1, 2003); 9(23):5800-5809.
Goodarzi, M. T. et al., "Decreased Branching, Increased Fucosylation and Changed Sialylation of Alpha-1-Proteinase Inhibitor in Breast and Ovarian Cancer," Clinica Chimica Acta (Feb. 13, 1995); 236:161-171.

(56) References Cited

OTHER PUBLICATIONS

Goodwin et al., "Molecular and Biological Characterization of a Ligand for CD27 Defines a New Family of Cytokines with Homology to Tumor Necrosis Factor," Cell, 73(3): 447-456 (May 7, 1993).
Goon, Scarlett et al. "Metabolic Substrate Engineering as a Tool for Glycobiology," Journal of Carbohydrate Chemistry (Dec. 31, 2002); 21(7):943-977.
Gordon et al., "Humanized Anti-CD70 Auristatin Antibody-Drug Conjugates Show Potent in Vitro Cytotoxicity in Renal Cell Carcinoma Primary Cultures Established from Patient Tumor Isolates," Abstract No. 3733, 97th Annual Meeting of the American Association for Cancer Research, Apr. 1-5, 2006, Washington, D.C.
Gosselin, Sylvie et al. "A Continuous Spectrophotometric Assay for Glycosyltransferases," Analytical Biochemistry (1994); 220:92-97.
Gravestein et al., "Cloning and Expression of Murine CD27: Comparison With 4-1 BB, another Lymphocyte-Specific Member of the Nerve Growth Factor Receptor Family," Eur. J. Immunol., 23(4):943-950 (1993).
Gravestein et al., "Novel mAbs Reveal Potent Co-Stimulatory Activity of Murine CD27," Int. Immunol. 7(4):551-557 (1995).
Greenstein, S. et al. (Apr. 2003). "Characterization of the MM.1 Human Multiple Myeloma (MM) Cell Lines: A Model System to Elucidate the Characteristics, Behavior, and Signaling of Steroid-Sensitive and -Resistant MM Cells," Experimental Hematology 31(4):271-282.
Grewal. "CD70 As a Therapeutic Target in Human Malignancies," Expert Opin. Ther. Targets. 12(3):341-351, (2008).
Gross, Volker et al. "Inhibition of Protein N-Glycosylation by 2-Deoxy-2-Fluoro-D-Galactose," Biochem. J. (Feb. 12, 1992); 285:821-826.
Gruss et al., "Pathophysiology of Hodgkin's Disease: Functional and Molecular Aspects," Baillieres Clin. Haematol. 9(3):417-446 (Sep. 1996).
Grün, Bernhard R. et al. "Metabolism and Actions of 2-Deoxy-2-Fluoro-D-Galactose In Vivo," Eur. J. Biochem. (1990); 190:11-19.
Gura, T. (1997). "Systems for identifying new drugs are often faulty," Science 278(5340): 1041-1042.
Hai, T. et al. (May 9, 1991). "Cross-family Dimerization of Transcription Factors Fos/Jun and ATF/CREB Alters DNA Binding Specificity," Proc. Natl. Acad. Sci. USA 88(9):3720-3724.
Hai, T.W. et al. (Dec. 1989). "Transcription Factor ATF cDNA Clones: An Extensive Family of Leucine Zipper Proteins Able to Selectively Form DNA-Binding Heterodimers," Genes Dev. 3(12B):2083-2090.
Haltiwanger, Robert S., "Fucose Is on the TRAIL of Colon Cancer," Gastroenterology (May 1, 2009) 137(1):36-39.
Hanson, Sarah R. et al. "Probing Glycans With the Copper(I)-Catalyzed [3+2] Azide -Alkyne Cycloaddition," QSAR Comb. Sci. (Sep. 27, 2007); 26(11-12):1243-1252.
Hara, S. et al. (Dec. 2001). "Over Expression of Inhibitor of Caspase 3 Activated Deoxyribonuclease in Human Renal Cell Carcinoma Cells Enhances Their Resistance to Cytotoxic Chemotherapy In Vivo," J. Urol. 166(6):2491-2494.
Harlow et al., "Antibodies, A Laboratory Manual," Cold Spring Harbor Laboratory. pp. 140-243, (1988).
Held-Feindt et al., "CD70/CD27 Ligand, A Member of the TNF Family, Is Expressed in Human Brain Tumors," Int. J. Cancer, 98(3):352-356 (2002).
Hieter, P.A. et al. (Feb. 10, 1982). "Evolution of Human Immunoglobulin Kappa J Region Genes," J. Biol. Chem. 257(3):1516-1522.
Higgins, D.G. et al. (1996). "Using CLUSTAL for Multiple Sequence Alignments," Methods Enzyniol. 266:383-402.
Hintzen et al., "A Soluble Form of the Human T Cell Differentiation Antigen CD27 is Released After Triggering of the TCR/CD3 Complex," J. Immunol. 147(1):29-35 (Jul. 1, 1991).
Hintzen et al., "CD27: Marker and Mediator of T-Cell Activation?," Immunol. Today, 15(7):307-311 (1994).
Hintzen et al., "CD70 Represents the Human Ligand for CD 27," Int. Immunol., 6(3):477-480 (1994).
Hintzen et al., "Characterization of the Human CD27 Ligand, a Novel Member of the TNF Gene Family," J. Immunol. 152(4):1762-1773 (1994).
Hintzen et al., "Engagement of CD27 With its Lligand CD70 Provides a Second Signal for T Cell Activation," J. Immunol. 154(6):2612-2623 (1995).
Hintzen et al., "Regulation of CD27 Expression on Subsets of Mature T-Lymphocytes." J. Immunol. 151(5):2426-2435 (Sep. 1, 1993).
Hishima et al., "CD70 Expression in Thymic Carcinoma," Am. J. Surg. Pathol. 24(5):742-746 (2000).
Holliger, P. et al. (Jul. 1993), "'Diabodies': Small Bivalent and Bispecific Antibody Fragments," Proc. Natl. Acad. Sci, USA 90:6444-6448.
Holliger, P. et al. (Sep. 2005). "Engineered Antibody Fragments and the Rise of Single Domains," Nat. Biotechnol. 23(9):1126-1136.
Holm, P. et al. (Feb. 2007). "Functional Mapping and Single Chain Construction of the Anti-Cytokeratin 8 Monoclonal Antibody TS1," Mol. Immunol. 44(6):1075-1084.
Hoogenboom, H.R. et al. (Sep. 20, 1992). "By-Passing Immunisation Human Antibodies From Synthetic Repertoires of Germline VH Gene Segments Rearranged in vitro," J. Mol. Biol. 227(2):381-388.
Howard III, M.A. et al. (Jul. 1989). "Intracerebral Drug Delivery in Rats With Lesion-Induced Memory Deficits," J. Neurosurg. 71(1):105-112.
Hsu, Tsui-Ling et al. "Alkynyl Sugar Analogs for the Labeling and Visualization of Glycoconjugates in Cells," PNAS, (Feb. 20, 2007); 104(8):2614-2619.
Hu, Z. et al. (Oct. 9, 2001, e-pub. Oct. 2, 2001). "Targeting Tissue Factor on Tumor Vascular Endothelial Cells and Tumor Cells for Immunotherapy in Mouse Models of Prostatic Cancer," Proc. Natl. Acad. Sci. USA 98(21):12180-12185.
Huston, J.S. et al. (1991). "Protein Engineering of Single-Chain Fv Analogs and Fusion Proteins," Methods in Enzymology 203:46-88.
Hämmerling, G. et al. (1961). "Monoclonal Antibodies and T-Cell Hybridomas," in Monoclonal Antibodies and T-Cell Hybridomas, pp. 563-681.
Ichikawa, Yoshitaka et al. "Chemical-Enzymatic Synthesis and Conformational Analysis of Sialyl Lewis x and Derivatives," J. Am. Chem. Soc. (Jun. 4, 1992); 114:9263-9298.
Idusogie, E.E. et al. (2001). "Engineered Antibodies With Increased Activity to Recruit Complement," J.Immunol. 166:2571-2575.
Idusogie, E.E. et al. "Mapping of the C1q Binding Site on Rituxan, a Chimeric Antibody With a Human IgG1 Fc," J. Imrmmol.164:4178-4184 (2000).
Ihara, Hideyuki et al. "Crystal Structure of Mammalian a1,6-fucosyltransferase, FUT8," Glycobiology (2007; Advance Access Pub Dec. 15, 2006); 17(5):455-466.
Ihara, Hideyuki et al. "Reaction Mechanism and Substrate Specificity for Nucleotide Sugar of Mammalian a1,6-Fucosyltransferase-A Large-Scale Preparation and Characterization of Recombinant Human FUT8," Glycobiology (2006; Advance Access Pub Dec. 11, 2005); 16(4):333-342.
Iida, Shigeru et al. "Nonfucosylated Therapeutic IgG1 Antibody Can Evade the Inhibitory Effect of Serum Immunoglobulin G on Antibody-Dependent Cellular Cytotoxicity Through Its High Binding to FcyRII la," Clin Cancer Res. (May 1, 2006); 12(9):2879-2887.
Imahori, Y. et al., "2-Deoxy-2-[18F]Fluoro-L-Fucose, A Potential Agent for Regional Fucose Utilization Studies Associated with Glycoprotein Synthesis," CYRIC Annual Repoti (1984); 12 pages.
Imai-Nishiya, Harue et al. "Double Knockdown of a1,6-Fucosyltransferase (FUTB) and GDP-Man Nose 4,6-Dehydratase (GMO) in Antibody-Producing Cells: A New Strategy for Generating Fully Non-Fucosylated Therapeutic Antibodies With Enhanced ADCC," BMC Biotechnology (Nov. 30, 2007); 7:84; 13 pages.
Inouye, S. et al. (May 10, 1985). "Up-Promoter Mutations in the Ipp Gene of *Escherichia coli*," Nucleic Acids Res. 13(9):3101-3109.
International Search Report corresponding to PCT/US2013/056223 dated Jan. 31, 2014, 3 pages.

(56) References Cited

OTHER PUBLICATIONS

International Search Report dated Jun. 2, 2006 in International Application No. PCT/US05/36994.
International Search Report dated Nov. 25, 2009, for International Application No. PCT/US09/42610 filed on May 1, 2009, 4 pages.
Invalidation Trial filed Jun. 5, 2015 against JP Patent No. 5624535 (corresponds to U.S. Pat. No. 8,163,551).
Ishiwata, Kiichi, et al. "6-[18F] Fluoro-L-Fucose: A Possible Tracer for Assessing Glycoconjugate Synthesis in Tumors with Positron Emission Tomography," J. Nucl. Med. (May 10, 1990); 31:1997-2003.
Jacquot et al., "CD154/CD40 and CD70/CD27 Interactions Have Different and Sequential Functions in T Cell-Dependent B Cell Responses: Enhancement of Plasma Cell Differentiation by CD27 Signaling", J. Immunol. 159(6):2652-2657 (1997).
Janeway et al., "Antigen Recognition by B-Cell and T-Cell Receptors," Immunobiology 5:100-101, (2001).
Jefferis, Roy "Glycosylation as a Strategy to Improve Antibody-Based Therapeutics," Nature Reviews Drug Discovery (Mar. 2009); 8:227-234.
Jeffrey et al., "Development arid Properties of Beta-Glucuronide Linkers for Monoclonal Antibody-Drug Conjugates", Bioconjug. Chem., 17(3):831-840 (2006).
Jespers, L.S. et al. (Sep. 1994). "Guiding the Selection of Human Antibodies From Phage Display Repertoires to a Single Epitope of an Antigen," Biotechnology 12(9):899-903.
Johns, T.G. et al. (Mar. 20, 2002). "Novel Monoclonal Antibody Specific for the De2-7 Epidermal Growth Factor Receptor (EGFR) That Also Recognizes the EGFR Expressed in Cells Containing Amplification of the EGFR Gene," Int. J. Cancer 96(3):398-408.
Jones, Mark B. et al. "Characterization of the Cellular Uptake and Metabolic Conversion of Acetylated N-Acetylmannosamine (ManNAc) Analogues to Sialic Acids," Biotechnology and Bioengineering 85(4):394-405 (Feb. 20, 2004).
Jones, P. et al. (May 29, 1986) "Replacing the Complementarity-Determining Regions in a Human Antibody With Those From a Mouse," Nature 321:522-525.
Kabat, E.A. et al. (1991). Sequences of Proteins of Immunological Interest NIH Publ. No. 91-3242, vol. I, pp. 647-669.
Kamel-Reid, S. et al. (Dec. 23, 1988). "Engraftment of Immune-Deficient Mice With Human Hematopoietic Stem Cells," Science 242(4886):1706-1709.
Kaminska, J. et al., "Chemical Modifications of a1,6-Fucosyltransferase Define Amino Acid Residues of Catalytic Importance," Biochimie (Jan. 28, 2003); 85:303-310.
Kanda, Y. et al. (Jun. 19, 2007). "Establishment of a GDF-Mannose 4,6-Dehydratase (GMD) Knockout Host Cell Line: A New Strategy for Generating Completely Non-Fucosylated Recombinant Therapeutics," Journal of Biotechnology 130(3):300-310.
Kanda, Yutaka et al. "Comparison of Biological Activity Among Nonfucosylated Therapeutic IgG1 Antibodies with Three Different N-Linked Fc Oligosaccharides: The High-Mannose, Hybrid, and Complex Types," Glycobiology (Sep. 25, 2006); 17(1):104-118.
Karlin, S. et al. (Jun. 1993). "Applications and Statistics for Multiple High-Scoring Segments in Molecular Sequences," Proc. Natl. Acad. Sci. USA 90:5873-5877.
Karlin, S. et al. (Mar. 1990). "Methods for Assessing the Statistical Significance of Molecular Sequence Features by Using General Scoring Schemes," Proc. Natl. Acad. Sci. USA 87(6):2264-2268.
Kataoka, Y. et al. (Jul. 2001). "The Role of Donor T Cells for Target Organ Injuries in Acute and Chronic Graft-Versus-Host Disease," Immunology 103(3):310-318.
Keler, T. et al. (Jun. 1, 2000). "Differential Effect of Cytokine Treatment on Fcα Receptor I- and Fcγ receptor I-Mediated Tumor Cytotoxicity by Monocyte-Derived Macrophages," J. Immunol. 164(11):5746-5752.
Kettleborough, C.A. et al. (Apr. 1994). "Isolation of Tumor Cell-Specific Single-Chain Fv From Immunized Mice Using Phage-Antibody Libraries and the Re-Construction of Whole Antibodies From These Antibody Fragments," Eur. J. Immunol, 24(4):952-958.

Kettleburough et al, "Humanization of a Mouse Monoclonal Antibody by CDR-Grafting: The Importance of framework Residues on Loop Conformation," Protein Engineering, 4(7):773-783, (1991).
Kim, Eun Jeong et al. "Characterization of the Metabolic Flux and Apoptotic Effects of O-Hydroxyl- and N-Acyl-modified N-Acetylmannosamine Analogs in Jurkat Cells," The Journal of Biological Chemistry, (Feb. 13, 2004); 279(18):18342-18352.
Kim, Y.S. et al. (Jun. 15, 1998). "Targeting the IL-15 Receptor With an Antagonist IL-15 Mutant/Fcγ2a Protein Blocks Delayed-Type Hypersensitivity," J. Immunol, 160(12):5742-5748, 15 pages.
Klussman, et al., "Immune Modulation Mediated by the Humanized Anti-CD70 Monoclonal Antibody SGN-70," Experimental Biology, San Diego, California, Apr. 5-9, 2008 (poster).
Knoll et al., "Targeted Therapy of Experimental Renal Cell Carcinoma with a Novel Conjugate of Monoclonal Antibody 138H11 and Calicheamicin ØH11", Cancer Research, 60:6089-6094 (2000).
Kobata et al., "CD27-CD70 Interactions Regulate B-Cell Activation by T Cells," PNAS, 92(24):11249-11253 (Nov. 1995).
Kontermann, R.E. et al. (Jul. 1997). "Complement Recruitment Using Bispecific Diabodies," Nat. Biotech. 15(7):629-631.
Korytnky, W. et al. (1982). "A Convenient Synthesis of 1,2-Difluoro-1,2-Dideoxyhexoses Using Xenon Fluoride," Tetrahedron 38(16):2547-2550.
Kostelny, S.A. et al. (Mar. 1, 1992). "Formation of a Bispecific Antibody by the Use of Leucine Zippers," J. Immunol. 148(5):1547-1553.
Kreitman, R.J. et al. (Mar. 31, 1999). "Complete Regression of Human B-Cell Lymphoma Xenografts in Mice Treated With Recombinant Anti-CD22 Immunotoxin RFB4(dsFv-)-PE38 at Doses Tolerated by Cynomolgus Monkeys," Int. J. Cancer 81(1):148-155.
Kussie et al., "A Single Engineered Amino Acid Substitution Changes Antibody Fine Specificity", J. Immunol. 152:146-152, (1994).
Köhler, G. (Apr. 1980). "Immunoglobulin Chain Loss in Hybridoma Lines," Proc. Natl. Acad.Sci, USA 77(4):2197-2199.
Köhler, G. et al. (Aug. 7, 1975). "Continuous Culture of Fused Cells Secreting Antibody of Predefined Specificity," Nature, 256:495-497.
Kötzler, Miriam P. et al., "Donor Assists Acceptor Binding and Catalysis of Human a1. 6-Fucosyltransferase," ACS Chemical Biology (Jun. 3, 2013); 8:1830-1840.
Landolfi, N.F. (Feb. 1, 1991). "A Chimeric IL-2/Ig molecule Possesses the Functional Activity of Both Proteins," J. Immunol 146:915-919.
Landschulz, W.H. et al. (Jun. 24, 1988). "The Leucine Zipper: A Hypothetical Structure Common to a New Class of DNA Binding Proteins," Science 240(4860):1759-1764.
Langer, R. (Sep. 28, 1990). "New Methods of Drug Delivery," Science 249(4976):1527-1533.
Langer, R. et al. (1983). "Chemical and Physical Structure of Polymers as Carries for Controlled Release of Bioactive Agents: A Review," Macromol. Sci. Rev. Macromol. Chem. 23:61-126.
Lard, L. R. et al., "Neutrophil Activation in Sickle Cell Disease," Journal of Leukocyte Biology (Sep. 1999; accepted Mar. 30, 1999); 66:411-415.
Larrick, J.W. et al. (Jul. 1980). "Characterization of a Human Macrophage-Like Cell Line Stimulated in vitro: A Model of Macrophage Functions," J. Immunology 125(1):6-12.
Laughlin, Scott T. et al. "Imaging the Glycome," PNAS (Jan. 6, 2009); 106(1):12-17.
Laughlin, Scott T. et al. "Metabolic Labeling of Glycans with Azido Sugars and Subsequent Glycan-Profiling and Visualization via Staudinger Ligation," Nature Protocols (Nov. 15, 2007); 2(11):2930-2944.
Law et al. "Lymphocyte Activation Antigen CD70 Expressed by Renal Cell Carcinoma Is a Potential Therapeutic Target for Anti-CD70 Antibody-Drug Conjugates," Cancer Res., 2006; 66(4):2328-2337.
Law et al., "Anti-CD70 Antibody Drug Conjugates Mediate Renal Carcinoma Cell Killing Through Cytotoxic Drug Delivery Antibody-Dependent Cellular Cytotoxicity (abstract only)", Proc Amer Assoc Cancer Res. 46:6143 (2005).

(56) References Cited

OTHER PUBLICATIONS

Law et al., "Anti-CD70 Auristatin Conjugates with Potent and Selective Activity Against Renal Cell Carcinoma," poster presentation, 4th International Kidney Cancer Symposium, Oct. 21-23, 2005, Chicago, IL.

Law et al., "Novel Antibody-Based Therapeutic Agents Targeting CD70: A Potential Approach for Treating Waldenstrom's Macroglobulinemia," Clinical Lymphoma & Myeloma 9(1):90-93, (2009).

Lazar et al., "Transforming Growth Factor A: Mutation of Aspartic Acid 47 and Leucine 48 Results in Different Biological Activities," Mol. Cell. Biol. 8:1247-1252, (1988).

Lee, Ho H. et al. "Analogs of Cell Surface Carbohydrates. Synthesis of D-Galactose Derivatives Having an Ethynyl, Vinyl or Epoxy Residue at C-5," Carbohydrate Research (1988; accepted for pub revised form May 15, 1987); 176:59-72.

Lee, Lac V. et al. "A Potent and Highly Selective Inhibitor of Human a-1,3-Fucosyltransferase via Click Chemistry," J. Am. Chem. Soc. (May 7, 2003); 125:9588-9589.

Lens et al., "Aberrant Expression and Reverse Signaling of CD70 on Malignant B Cells," Br. J. Haematol., 106(2):491-503 (1999).

Lens et al., "Antigen-Presenting Cell-Derived Signals Determine Expression Levels of CD70 on Primed T Cells", Immunol. 90:38-45 (1997).

Lens et al., "Control of Lymphocyte Function Through CD27-CD70 Interactions," Semin Immunol. 10(6):491-499 (1998).

Lens et al., "Phenotype and Function of Human B Cells Expressing CD70 (CD27 ligand)," Eur. J. Immunol. 26 (12):2964-2971 (1996).

Levy, R.J. et al. (Apr. 12, 1985). "Inhibition of Calcification of Bioprosthetic Heart Valves by Local Controlled-Release Diphosphonate," Science 228(4696):190-192.

Lim, Amareth et al. "Glycosylation Profiling of a Therapeutic Recombinant Monoclonal Antibody with Two N-Linked Glycosylation Sites Using Liquid Chromatography Coupled to a Hybrid Quadrupole Time-of-Fight Mass Spectrometer," Analytical Biochemistry (Jan. 9, 2008); 375:163-172.

Liu et al., "Chimeric Mouse-Human IGG1 Antibody That Can Mediate Lysis of Cancer Cells", Proc Natl Acad Sci 84(1):3439-3443, (1987).

Liu, A.Y. et al. (Nov. 15, 1987). "Production of a Mouse-Human Chimeric Monoclonal Antibody to CD20 Wth Potent Fc-Dependent Biologic Activity," J Immunol. 139(10):3521-3526.

Locksley et al., "The TNF and TNF Receptor Superfamilies: Integrating Mammalian Biology", Cell, 104(4): 487-501 (Feb. 23, 2001).

Logan, J. et al. (Jun. 1984). "Adenovirus Tripartite Leader Sequence Enhances Translation of Mrnas Late After Infection," Proc. Natl. Acad. Sci. USA 81(12):3655-3659.

Lonberg, N. (1995). "Human Antibodies From Transgenic Mice," Int. Rev. Immunol. 13(1):65-93.

Lund, J. et al. (Dec. 1, 1996). "Multiple Interactions of IgG With Its Core Oligosaccharide Can Modulate Recognition by Complement and Human Fcγ Receptor I and Influence the Synthesis of Its Oligosaccharide Chains," J. Immunol. 157(11):4963-4969.

Lühn, Kerstin et al. "The Gene Defective in Leukocyte Adhesion Deficiency II Encodes a Putative GDP-Fucose Transporter," Nature Genetics (May 2001; accepted Mar. 28, 2001); 28:69-72.

MacCallum, et al. "Antibody-Antigen Interactions: Contact Analysis and Binding Site Topography", J. Mol. Biol. 262:732-745 (1996).

Maeda, Takahiro et al. "FRET-Based Direct and Continuous Monitoring of Human Fucosyltransferases Activity: An Efficient synthesis of Versatile GDP-L-Fucose Derivatives from Abundant D-Galactose," Chem. Eur. J. (2008; published online Oct. 11, 2007); 14:478-487.

Manocha et al., "Blocking CD27-CD70 Costimulatory Pathway Suppresses Experimental Colitis", J Immunol 183:270-276 (2009).

Marks, J.D. et al. (1991). "By-Passing Immunization: Human Antibodies From V-Genen Libraries Displayed on Phage," J. Mol. Biol. 222:581-597.

Matsuda, F. et al. (1993). "Structure and Physical Map of 64 Variable Segments in the 3' 0.8-Megabase Region of the Human Immunoglobulin Heavy-Chain Locus," Nature Genetics 3:88-94.

Matsuda, H. et al. (Mar. 1997). "Development of Atopic Dermatitis-Like Skin Lesion With IgE Hyperproduction in NC/Nga Mice," Int. Immunol. 9(3):461-466.

Matsumura, Kengo et al. "Carbohydrate Binding Specificity of a Fucose-specific Lectin From Aspergil/us Oryzae—A Novel Probe for Core Fucose," The Journal of Biological Chemistry (Feb. 8, 2007); 282(21):15700-15708.

Mattila, P.S. et al. (Sep. 1995). "Extensive Allelic Sequence Variation in the J Region of the Human Immunoglobulin Heavy Chain Gene Locus," Eur. J. Immunol. 25(9):2578-2582.

Maurer et al., "CD27 Expression by a Distinct Subpopulation of Human B Lymphocytes," Eur. J. Immunol. 20(12):2679-2684 (1990).

May, Jr. Jesse A., et al. "Synthesis and Biological Activity of Potential Antimetabolites of L-Fucose," Journal of Medicinal Chemistry, 1979, vol. 22, No. 8, pp. 971-976.

McCune, J.M. et al. (Sep. 23, 1988). "The SCID-hu Mouse: Murine Model for the Analysis of Human Hematolymphoid Differentiation and Function," Science 241(4873):1632-1639.

McEarchern et al., "A Humanized Anti-CD70 Monoclonal Antibody Targets CD70-Expressing Multiple Myeloma," Publication No. 1591, 47th Annual Meeting and Exposition of the American Society of Hematology, Dec. 10-13, 2005, Atlanta, Georgia.

McEarchern et al., "Engineered Anti-CD70 Antibody Variants Support Multiple Effector Functions and Exhibit Potent In Vitro and In Vivo Antitumor Activities (abstract only)", Proc Amer Assoc Cancer Res. 46:6142 (2005).

McEarchern et al., "Engineered Anti-CD70 Antibody Wth Multiple Effector Functions Exhibits In Vitro and In Vivo Antitumor Activities," Blood, Feb. 1, 2007; 109(3):1185-1192.

McEarchern et al., "Preclinical Characterization of SGN-70, A Humanized Antibody Directed Against CD70", Clin. Cancer Res., 14(23):7763-7772 (2008).

McEarchern et al., "SGN-70, A Humanized Anti-CD70 Antibody, Target CD70-Expressing Hematologic Tumors", ASH, Orlando, Florida, Dec. 9-12, 2006 (poster).

McEarchern et al., "Targeting CD70 for the Treatment of Autoimmune Disorders", ACR, San Francisco, California, Oct. 24-29, 2008 (poster).

McEarchern, Julie, "Antitumor Activities of Engineered Anti-CD70 Antibody (h1 F6)", Presentation by Seattle Genetics at Annual Meeting of American Association for Cancer Research Apr. 16-20:1-15 (2005).

Merchant, A. M. et al. (Jul. 1998). "An Efficient Route to Human Bispecific IgG," Nature Biotechnology 16:677-681.

Milstein, C. et al. (Oct. 6, 1983). "Hybrid Hybridomas and Their Use in Immunohistochemistry," Nature 305:537-539.

Miyake, H. et al. (May 2002). "Introducing the Clusterin Gene Into Human Renal Cell Carcinoma Cells Enhances Their Metastatic Potential," J. Urol. 167(5):2203-2208.

Miyoshi, E. et al. "Fucosylated Haptoglobin Is a Novel Marker for Pancreatic Cancer: Detailed Analysis of Oligosaccharide Structures," Proteomics (Mar. 28, 2008); 8:3257-3262.

Mori, Katsuhiro et al. "Engineering Chinese Hamster Ovary Cells to Maximize Effector Function of Produced Antibodies Using FUT8 siRNA," Biotechnology and Bioengineering (Aug. 26, 2004); 88(7):901-908.

Mori, Katsuhiro et al. "Non-Fucosylated Therapeutic Antibodies: The Next Generation of Therapeutic Antibodies," Cytotechnology (Oct. 31, 2007); 55:109-114.

Moriwaki, Kenta et al., "Fucosylation and Gastrointestinal Cancer," World J. Hepatol. (Apr. 27, 2010); 2(4):151-161.

Morrison et al. "Chimeric Human Antibody Molecules: Mouse Antigen-Binding Domains With Human Constant Region Domains," Proc. Natl. Acad. Sci. USA 61:6851-6855, (Nov. 1984).

Morrison, "In Vitro Antibodies; Strategies for Production and Application," Annual Rev Immuno; 10(1):239-265, (1992).

Morrison, S.L. (Sep. 1985). "Transfectomas Provide Novel Chimeric Antibodies," Science 229(4719):1202-1207.

(56) References Cited

OTHER PUBLICATIONS

Mosier, D.E. et al. (Sep. 15, 1988). "Transfer of a Functional Human Immune System to Mice With Severe Combined Immunodeficiency," Nature 335(6187):256-259.

Munn, D.H. et al. (Jul. 1, 1990). "Phagocytosis of Tumor Cells by Human Monocytes Cultured in Recombinant Macrophage Colony-Stimulating Factor," J. Exp. Med, 172(1):231-237.

Murray, Brion W. et al. "Mechanism of Human a-1,3-Fucosyltransferase V: Glycosidic Cleavage Occurs Prior to Nucleophilic Attack," Biochemistry (1997; revised manuscript); 36:823-831.

Murre, C. et al. (Mar. 10, 1989). "A New DNA Binding and Dimerization Motif in Immunoglobulin Enhancer Binding, daughterless, MyoD, and myc Proteins," Cell 56(5):777-783.

Nakajima et al., "Involvement of CD70-CD27 Interactions in the Induction of Experimental Autoimmune Encephalomyelitis," J. Neuroimmunol. 109(2):188-196 (2000).

Nakajima et al., "Roles of IL-4 and IL-12 in the Development of Lupus in NZB/W F1 Mice," J. Immunol. 156 (3):1466-1472 (1997).

Nature Rev Drug Discov., "Pfizer Deal for Selectin Inhibitor Highlights Potential of Glycomimetic Drugs," (Dec. 1, 2011); 10(12):890. (no author specified).

Nicolaou, K.C. et al. (1994). "Calicheamicin ϴl1: A Rationally Designed Molecule with Extremely Potent and Selective DNA Cleaving Properties and Apotosis Inducting Activity," Agnew, Chem. Intl. Ed. Engl., 33:183-186.

Niittymäki, Jaana "GDP-L-Fucose: Synthesis and Role in Inflammation," Academic Dissertation Mar. 23, 2007, Department of Bacteriology and Immunology, Haartman Institute and Biomedicum Helsinki and Division of Biochemistry, Department of Biological and Environmental Sciences, Faculty of Biosciences University of Helsinki and Glycoscience Graduate School; pp. 7-54.

Niittymäki, Jaana et al. "Cloning and Expression of Murine Enzymes Involved in the Salvage Pathway of GDP-L-Fucose L-Fucokinase and GDP-L-Fucose Pyrophosphorylases" Eur. J. Biochem. (2004; accepted Oct. 30, 2003); 271:78-86.

Nishimura, Y. et al. (Feb. 15, 1987). "Recombinant Human-Mouse Chimeric Monoclonal Antibody Specific for Common Acute Lymphocytic Leukemia Antigen," Cancer. Res. 47(4):999-1005.

Niwa, R. et al. (Mar. 15, 2004). "Defucosylated Chimeric Anti-CC Chemokine Receptor 4 IgG1 With Enhanced Antibody-Dependent Cellular Cytotoxicity Shows Potent Therapeutic Activity to T-Cell Leukemia and Lymphoma," Cancer Res. 64(6):2127-2133.

Non-Final Office Action, dated Feb. 28, 2013, for U.S. Appl. No. 13/271,143, filed Oct. 11, 2011, 7 pages.

Non-Final Office Action, dated May 15, 2019, for U.S. Appl. No. 15/614,571, filed May 15, 2019, 15 pages.

Non-Final Office Action, dated Nov. 14, 2016, for U.S. Appl. No. 15/217,109, filed Jul. 22, 2016, 6 pages.

Non-Final Office Action, dated Nov. 25, 2016, for U.S. Appl. No. 14/632,925, filed Feb. 26, 2015, 4 pages.

Norris, Andrew et al. "Inhibition Kinetics of Carba- and C-fucosyl Analogues of GDF-Fucose Against Fucosyltransferase v: Implication for the Reaction Mechanism," Bioorganic & Medicinal Chemistry Letters (2004; accepted Dec. 2, 2003); 14:571-573.

O'Shea, E.K. et al. (Jan. 27, 1989). "Evidence That the Leucine Zipper Is a Coiled Coil," Science 243(4890):538-542.

Oberthür, M. et al. (Aug. 3, 2005). "A Systematic Investigation of the Synthetic Utility of Glycopeptide Glycosyltransferases," J Am. Chem. Soc. 127(30): 10747-10752.

Ochakovskaya, R. et al. (Jun. 2001). "Therapy of Disseminated B-Cell Lymphoma Xenografts in Severe Combined Immunodeficient Mice With an Anti-CD74 Antibody Conjugated With (111)indium, (67)gallium, or (90)yttrium," Clin. Cancer Res. 7(6):1505-1510.

Oelke et al. "Overexpression of CD70 and Overstimulation of IgG Synthesis by Lupus T Cells and T Cells Treated With DNA Methylation Inhibitors", Arthritis & Rheumatism, 50(6):1850-1860 (2004).

Oflazoglu et al. "Blocking of CD27-CD70 Pathway by Anti-CD70 Antibody Ameliorates Joint Disease in Murine Collagen-Induced Arthritis," J Immunol. 183:3770-3777, (2009).

Oflazoglu et al."In Vivo Characterization of the Mechanism of Action of c1 F6, an Anti-CD70 Antibody," Abstract No. 3732, 97th Annual Meeting of the American Association for Cancer Research, Apr. 1-5, 2006, Washington, D.C.

Oflazoglu et al., "Inhibition of Collagen-induced Arthritis by an Antibody Targeting CD70," FOCIS 2006, Boston, MA, Jun. 7, 2008 (poster).

Oi, V.T, et al. (1986). "Chimeric Antibodies," Bio Techniques 4:214-219.

Okazaki, A. et al. (Mar. 5, 2004). "Fucose Depletion From Human IgG1 Oligosaccharide Enhances Binding Enthalpy and Association Rate Between IgG1 and FcγRIIIa," J. Mol. Biol. 336(5):1239-1249.

Okeley, N.M. et al. (Apr. 2, 2013). "Development of Orally Active Inhibitors of Protein and Cellular Fucosylation," Proc. Natl. Acad. Sci. U.S.A. 110(14):5404-5409.

Okeley, Nicole et al., "Enhancement of Antibody Effector Function Activities Through Biochemical Inhibition of Fucosylation," Abstract No. 608 (2011); 1 page.

Omasa Takeshi et al. "Decrease in Antithrombin III Fucosylation by Expressing GDP-Fucose Transporter siRNA in Chinese Hamster Ovary Cells," Journal of Bioscience and Bioengineering (May 15, 2008); 10(2):168-173.

Opposition filed Oct. 20, 2014 against EP Patent No. 2282773 (corresponds to U.S. Pat. No. 8,163,551).

Orengo et al. "Reciprocal Expression of CD70 and of Its Receptor, CD27, in Human Long Term-Activated T and Natural Killer (NK) Cells: Inverse Regulation by Cytokines and Role in Induction of Cytotoxicity," Clin. Exp. Immunol. 107(3):608-613 (1997).

Ortmann, Monika et al. "Sialylated Glycoconjugates in Chromophobe Cell Renal Carcinoma Compared With Other Renal Cell Tumors," Virchows Archiv B Cell Pathol (Jun. 6, 1991); 61:123-132.

Oshima et al., "Characterization of Murine CD70 by Molecular Cloning and mAb," Int. Immunol. 10(4):517-526 (1998).

Padlan, E.D. (1991). "A Possible Procedure for Reducing the Immunogenicity of Antibody Variable Domains While Preserving Their Ligand-Binding Properties," Mol. Immunol. 28(4/5)489-498.

Palma, C. et al. (Jan. 2000). "Anti-Tumour Activity of Tachykinin NK1 Receptor Antagonists on Human Glioma U373 Mg Xenograft," Br. J. Cancer 82(2):480-487.

Pan, Y. T. et al. "Castanospermine Inhibits the Processing of the Oligosaccharide Portion of the Influenza Viral Hemagglutinin," Biochemistry (Aug. 2, 1983); 22:3975-3984.

Panneerselvam, K. et al. "Human Fibroblasts Prefer Mannose over Glucose as a Source of Man nose for N-Glycosylation," The Journal of Biological Chemistry (Jun. 10, 1997); 272(37):23123-23129.

Papac, Damon I. et al. "A High-Throughput Microscale Method to Release N-Linked Oligosaccharides From Glycoproteins for Matrix-Assisted Laser Desorption/Ionization Time-of-Flight Mass Spectrometric Analysis," Glycobiology (1998; accepted Dec. 15, 1997); 8(5):445-454.

Park, Dongkyu et al. "Characterization and Role of Fucose Mutarotase in Mammalian Cells," Glycobiology (Jun. 15, 2007); 17(9):955-962.

Park, Sungjin et al. "Chemical Tools for Functional Studies of Glycans," Chem. Soc. Rev. (Mar. 11, 2008); 37:1579-1591.

Paul, W. (1993) "Fundamental Immunology," Raven Press, 3rd Edition, 292-295.

PCT Application No. PCT/GB91/01134, filed Jul. 10, 1991.

PCT Application No. PCT/US02/13435, filed Apr. 30, 2002.

PCT Application No. PCT/US03/24209, filed Jul. 31, 2003.

PCT Search Report and Written Opinion dated Jun. 2, 2006 for application PCT/US05/36994.

PCT Search Report and Written Opinion dated Oct. 16, 2007 for application PCT/US06/15145.

PCT Search Report dated Oct. 4, 2007 for application PCT/US2006/037753 (WO 2007/038637 A3).

PCT Search Report dated Dec. 4, 2008 for application PCT/US2007/087401 (WO 2008/074004 A3).

PCT Search Report dated Dec. 22, 2004 for application PCT/US04/05247 (WO 2004/073656 A3) (Corrected Version).

PCT Search Report dated Dec. 22, 2004 for application PCT/US04/05247.

(56) References Cited

OTHER PUBLICATIONS

PCT/US04/05247 (published as WO 2004/073656 A3), International Search Report dated Dec. 22, 2004 (Corrected Version as published on Sep. 1, 2005).
PCT/US04/05247 (published as WO 2004/073656 A3), International Search Report dated Dec. 22, 2004.
PCT/US05/36994 (published as WO 2006/044643 A3), International Search Report and Written Opinion dated Jun. 2, 2006.
PCT/US06/015145 (published as Wo 2006/113909A3), International Search Report and Written Opinion dated Oct. 16, 2007.
PCT/US06/037753 (published as WO 2007/038637 A3), International Search Report dated Oct. 4, 2007.
PCT/US07/087401 (published as WO 2008/074004 A3), International Search Report dated Oct. 7, 2008.
Pearson, W.R. et al. (Apr. 1988). "Improved Tools for Biological Sequence Comparison," Proc. Natl. Acad. Sci. USA 85(8)2444-2448.
Peipp, Matthias et al. "Antibody Fucosylation Differentially Impacts Cytotoxicity Mediated by NK and PMN Effector Cells," Blood (Pre-published online Jun. 19, 2008; doi:10.1182/blood-2008-03-144600.
Peitsch et al., "Comparative Molecular Modeling of the Fas-Ligand and Other Members of the TNF Family," Mol. Immunol. 32(10):761-772 (1995).
Pelphrey, P.M. et al. (Mar. 8, 2007, e-pub. Feb. 2, 2007). "Highly Efficient Ligands for Dihydrofolate Reductase From Cryptosporidium Hominis and Toxoplasma gondii Inspired by Structural Analysis," J Med. Chem. 50(5):940-950.
Persic, L. et al. (Mar. 10, 1997). "An Integrated Vector System for the Eukaryotic Expression of Antibodies or Their Fragments After Selection From Phage Display Libraries," Gene 187(1):9-18. Abstract Only.
Perussia, B. et al. (2000). "Assays for Antibody-Dependent Cell-Mediated Cytotoxicity (ADCC) and Reverse ADCC (Redirected Cytotoxicity) in Human Natural Killer Cells," Methods in Molecular Biology 121:179-192.
Plückthun, A. (1994) "Antibodies from *Escherichia coli*," Chapter 11 in Handbook of Experimental Pharmacology 113:269-315.
Prescher, Jennifer A. et al., "Chemistry in Living Systems," Nature Chemical Biology (Jun. 1, 2005); 1(1):13-21.
Prewett, M. et al. (Dec. 1998). "Mouse-Human Chimeric Anti-Epidermal Growth Factor Receptor Antibody C225 Inhibits the Growth of Human Renal Cell Carcinoma Xenografts in Nude Mice," Clin. Cancer Res. 4(12):2957-2966.
Proudfoot, N.J. (Aug. 7, 1986). "Transcriptional Interference and Termination Between Duplicated A-Globin Gene Constructs Suggests a Novel Mechanism for Gene Regulation," Nature 322:562-565.
Qiao, Lei et al. "Synergistic Inhibition of Human a-1,3-Fucosyltransferase V," J. Am. Chem. Soc. (Jan. 25, 1996); 118:7653-7662.
Quan, et al. (2002). "The Rise of Monoclonal Antibodies As Therapeutics," in Anti-IgE and Allergic Disease, Jardieu and Fick Jr., eds., Marcel Dekker, New York, NY, Chapter 20, pp. 427-469.
Queen, C. et al. (Dec. 1989), "A Humanized Antibody That Binds to the Interleukin 2 Receptor," Proc. Natl Acad. Sci. USA 86:10029-10033.
Rabuka, David et al. "A Chemical Reporter Strategy to Probe Glycoprotein Fucosylation," J. Am. Chem. Soc. (Jun. 29, 2006); 28:12078-12079.
Ranheim et al., "Expression of CD27 and Its Ligand, CD70, on Chronic Lymphocytic Leukemia B Cells", Blood, 85(12):3556-3565, (1995).
Reff, M. et al., "Future of Monoclonal Antibodies in the Treatment of Hematologic Malignancies," Cancer Control. 9(2):152-166 (2002).
Reichmann, L. et al. (Mar. 1988). "Reshaping Human Antibodies for Therapy," Nature 332:323-327.

Rillahan, Cory D. et al., "Global Metabolic Inhibitors of Sialyl-and Fucosyltransferases Remodel the Glycome," Nature Chemical Biology (Jul. 2012; published on line Jun. 10, 2012 DOI: 10.1038/NCHEMBI0.999); 8:661-668.
Rillahan, Cory D., "High-Throughput Screening for Inhibitors of Sialyi- and Fucosyltransferases," Angew. Chem. Int. Ed. (Nov. 9, 2011); 59:12534-12537.
Rodrigues, M.L. et al. (Dec. 15, 1993). "Engineering Fab' Fragments for Efficient F(ab)2 Formation in *Escherichia coli* and for Improved in Vivo Stability," J. Immunology 151(12):6954-6961.
Roguska, M.A. et al. (Feb. 1, 1994). "Humanization of Murine Monoclonal Antibodies Through Variable Domain Resurfacing," Proc. Natl. Acad. Sci. USA 91(3):969-973.
Roman, C. et al. (Aug. 1990). "Ig/EBP-1: A Ubiquitously Expressed Immunoglobulin Enhancer Binding Protein That Is Similar to C/EBP and Heterodimerizes With C/EBP," Genes Dev. 4(8):1404-1415.
Rosnet, O. et al. (1996). "Expression and Signal Transduction of the FLT3 Tyrosine Kinase Receptor," Acta. Haemato. 95(3-4):218-223.
Rudikoff, S. et al. (Mar. 1982). "Single Amino Acid Substitution Altering Antigen-Binding Specificity," Proc. Natl. Acad. Sci. USA 79:1979-1983.
Rüther, U. et al. (1983). "Easy Identification of cDNA Clones," EMBO 2(10):1791-1794.
Sambrook, J. et al. (1989). Molecular Cloning: A Laboratory Manual ColdSpring Harbor Laboratory Press, Cold Spring Harbor, N.Y.; 2nd ed., 28 pages, Table of Contents.
Sampathkumar, Srinivasa-Gopalan et al. "Metabolic Installation of Thiols into Sialic Acid Modulates Adhesion and Stem Cell Biology," Nature Chemical Biology (Mar. 2006; published online Feb. 12, 2006); 2(3)149-152.
Sasakawa, T. et al. (Nov. 2001). "Atopic Dermatitis-Like Skin Lesions Induced by Topical Application of Mite Antigens in NC/Nga Mice," Int. Arch. Allergy Immunol. 126:239-247.
Saudek, CD. et al. (Aug. 31, 1989). "A Preliminary Trial of the Programmable Implantable Medication System for Insulin Delivery," N. Engl. J. Med. 321(9):574-579.
Sawa, Masaaki et al. "Glycoproteomic Probes for Fluorescent Imaging of Fucosylated Glycans In Vivo," PNAS (Aug. 15, 2006); 103(33):12371-12376.
Saxon, Eliana et al. "Investigating Cellular Metabolism of Synthetic Azidosugars with the Staudinger Ligation," J. Am. Chem. Soc. (Jul. 17, 2002); 124:14893-14902.
Sayegh, M.H. et al. (May 1, 1995). "CD28-B7 Blockade After Alloantigenic Challenge In Vivo Inhibits Th1 Cytokines But Spares Th2," J. Exp. Med 181(5):1869-1874.
Schnell et al. "Current Strategies of Antibody-Based Treatment in Hodgkin's Disease", Annals of Oncology. 13(1):57-66, (2002).
Schuster, Manfred et al. "Improved Effector Functions of a Therapeutic Monoclonal Lewis Y-Specific Antibody by Glycoform Engineering," Cancer Res. (Sep. 1, 2005); 65(17):7934-7941.
Schwartz, Reinhard et al. "Glycoconjugates of Murine Tumor Lines with Different Metastatic Capacities. I. Differences in Fucose Utilization and in Glycoprotein Patterns," Int. J. Cancer (Feb. 2, 1984); 33:503-509.
Sefton, M.V. (1989). "Implantable Pumps," in CRC Crit. Ref. Biomed. Eng. 14(3):201-240.
Shaw, D.R. et al. (Dec. 7, 1988). "Mouse/Human Chimeric Antibodies to a Tumor-Associated Antigen: Biologic Activity of the Four Human IgG Subclasses," J. Natl. Cancer Inst. 80(19):1553-1559.
Sheid, B. et al., "Enzymatic Formation of Potential Anticancer and Antiviral Inosine Analogues," Experientia 52:878-881 (Jun. 11, 1996).
Shi, W. et al. (Jul. 1, 2002), "Inhibition of Renal Cell Carcinoma Angiogenesis and Growth by Antisense Oligonucleotides Targeting Vascular Endothelial Growth Factor," Br. J. Cancer 87:119-126.
Shields, R.L. et al. (Jul. 26, 2002, e-pub. May 1, 2002). "Lack of Fucose on Human IgG1 N-Linked Oligosaccharide Improves Binding to Human FcγRIII and Antibody-dependent Cellular Toxicity," J. Biol. Chem. 277:26733-26740.

(56) References Cited

OTHER PUBLICATIONS

Shields, R.L. et al. (Mar. 2, 2001). "High Resolution Mapping of the Binding Site on Human IgG1 for FcγRI, FcγII. FcγIII. and FcRn and Design of IgG1 Variants With Improved Binding to the FcγR," J. Biol.Chem. 276(9):6591-6604.
Shin, E.K. et al. (Dec. 1991). "Physicai Map of the 3' Region of the Human Immunoglobulin Heavy Chain Locus: Clustering of Autoantibody-Related Variable Segments in One Hapiotype," EMBO J. 10(12):3641-3645.
Shinkawa, Toyohide et al., "The Absence of Fucose But Not the Presence of Galactose or Bisecting N-Acetylglucosamine of Human IgG1 Complex-Type Oligosaccharides Shows the Critical Role of Enhancing Antibody-Dependent Cellular Cytotoxicity," Journal of Biological Chemistry, (Jan. 31, 2003); 278(5):3466-3473.
Shitara, K. et al. (Jun. 1993). "A Mouse/Human Chimeric Anti-(Ganglioside GD3) Antibody With Enhanced Antitumor Activities," Cancer Immunol. Immunother, 36(6):373-380.
Shopes, B. et al. (May 1, 1992). "A Genetically Engineered Human IgG Mutant With Enhanced Cytolytic Activity," J. Imniunol. 148:2918-2922.
Shu, L. et al. (Sep. 1, 1993). "Secretion of a Single-Gene-Encoded Immunoglobulin From Myeloma Cells," Proc. Natl. Acad. Sci. USA 90(17):7995-7999.
Skerra, A. et al. (May 20, 1988). "Assembly of a Functional Immunoglobulin Fv Fragment in *Escherichia coli*," Science 240(4855):1038-1041.
Skolnick and Fetrow. From Genes to Protein Structure and Function: Novel Applications of Computational Approaches in the Genomic Era, Trends in Biotechnology, 2000. vol. 18, pp. 34-39.
Slayback, D.L. et al. (Nov. 2000). "Genetic Factors Influencing the Development of Chronic Graft-Versus-Host Disease in a Murine Model," Bone Marrow Transpl. 26(9):931-938.
Smith et al., "A Receptor for Tumor Necrosis Factor Defines an Unusual Family of Cellular and Viral Proteins," Science, 248(4958):1019-1023 (1990).
Smith, R.I. et al. (Mar. 1, 1995). "Addition of a Mu-Tailpiece to IgG Results in Polymeric Antibodies With Enhanced Effector Functions Including Complement-Mediated Cytolysis by IgG4," J. Immunol. 154(5):2226-2236. Abstract Only.
Sommers, Linda E. et al. "Transport of Sugar Nucleotides into Rat Liver Golgi," The Journal of Biological Chemistry (Sep. 25, 1992; for publication Mar. 25, 1982); 257(18):10811-10817.
Speers, Anna E. et al., "Proteomics of integrai Membrane Proteins—Theory and Application," Chem. Rev. (published on Web Aug. 8, 2007); 107:3687-3714.
Staňková, Jana et al., "Fucose-Activated Killer (FAK) Cells: Anomalous Killers With Augmented Cytotoxic Activity," The Journal of Immunology (Dec. 6, 1985); 135(6):3718-3728,
Stein et al., "A5 Cluster Report: CDw70", pp. 446-449 from Leucocyte Typing IV White Cell Differentiation Antigens, Knapp, eds., Oxford University Press, 1989.
Stella, V.J. et al. (1985). "Prodrugs: A Chemical Approach to Targeted Drug Delivery," in Directed Drug Delivery, pp. 247-267.
Streicher, B. et al. (Oct. 31, 2003). "Synthesis of Amino-Substituted Hexo- and Heptopyranoses From D-Galactose," Carbohydr. Res. 338(22):2375-2385.
Studnicka, G.M. et al. (Jun. 1994). "Human-Engineered Monoclonal Antibodies Retain Full Specific Binding Activity by Preserving Non-CDR Complementarity-Modulating Residues," Protein Engineering 7(6):805-814. Abstract Only.
Sturla Laura et al. "Expression, Purification and Characterization of GDP-D-Mannose 4,6-Dehydratase From *Escherichia coli*," FEBS Letters (Jun. 4, 1997); 412:126-130.
Sufrin, Janice R. et al. "Halogenated L-Fucose and D-Galactose Analogs: Synthesis and Metabolic Effects," J. Med. Chem. (1980); 23(2):143-149.
Sugita et al., "Participation of the CD27 Antigen in the Regulation of IL-2-Activated Human Natural Killer Cells," J. Immunol. 149(4):1199-1203 (1992).

Sun, L.K. et al. (Jan. 1987). "Chimeric Antibody With Human Constant Regions and Mouse Variable Regions Directed Against Carcinoma-Associated Antigen 17-1A," Proc. Natl. Acad. Sci. USA 84(1):214-218.
Supplementary European Search Report dated Dec. 9, 2015, corresponding to EP Application No. 13 83 1167; 11 pages.
Supplementary European Search Report, dated Oct. 11, 2012, corresponding to EP application No. 09 73 9983.6; 7 pages.
Supplementary European Search Report, dated Oct. 2, 2012, corresponding to EP application No. 09 73 9983.6; 2 pages.
Suresh, M.R. et al. (1986). "Bispecific Monoclonal Antibodies From Hybrid Hybridomas," Methods in Enzymology 121:210-228, 19 pages.
Takahashi Tomoaki et al. "A Sequence Motif Involved in the Donor Substrate Binding by a1,6-fucosyltransferase: the Role of the Conserved Residues," Glycobiology (2000; accepted Nov. 15, 1999); 10(5):503-510.
Tanaka Toru et al. "Design and Synthesis of Peptide Mimetics of GDP-Fucose: Targeting Inhibitors of Fucosyltransferases," Synlett (2004); 2:243-246.
Tarling Chris A. et al. "Identification of the Catalytic Nucleophile of the Family 29 a-L-Fucosidase from Thermotoga maritima through Trapping of a Covalent Glycosyl-Enzyme Intermediate and Mutagenesis," The Journal of Biological Chemistry (Sep. 15, 2003); 278(48):47394-47399.
Taylor, L. et al. (Sep. 2002). "In vitro and in vivo Activities of OX40 (CD134)-IgG Fusion Protein Isoforms With Different Levels of Immune-Effector Functions," J. Leu. Biol. 72(3):522-529.
Telvekar; V.N. (2004). "A Simple System for Preparation of Protected Glycosidic Carbohydrate Nitriles from Corresponding Oximes," Synthetic Communications 34(13):2331-2336.
Tesciuba, A.G. et al, (Aug. 15, 2001). "Inducible Costimulator Regulates Th2-Mediated Inflammation, But Not Th2 Differentiation, In a Model of Allergic Airway Disease," J. Immunol. 167(4):1996-2003.
Tesselaar et al., "Characterization of Murine CD70, The Ligand of the TNF c CD27," J. Immunol. 159(10):4959-4965 (1997).
Tesselaar et al., "Lethal T Cell Immunodeficiency Induced by Chronic Costimulation Via CD27-CD70 Interactions," Nature Immunol 4(1):49-54, (2003).
Tomkinson, A. et al. (May 1, 2001). "A Murine IL-4 Receptor Antagonist That Inhibits IL-4- and IL-13-Induced Responses Prevents Antigen-Induced Airway Eosinophilia and Airway Hyperresponsiveness," J. Immunol. 166(9):5792-5800.
Torelli, A. et al. (Feb. 1994). "Advance and Adam: Two Algorithms for the Analysis of Global Similarity Between Homologous Informational Sequences," Comput. Appl. Biosci. 10(1):3-5.
Tournoy, K.G. et al. (Jun. 1, 2001). "The Allergen-Induced Airway Hyperresponsiveness in a Human-Mouse Chimera Model of Asthma Is T Cell and IL-4 and IL-5 Dependent," J. Immunol. 166(11):6982-6991.
Traunecker, A. et al. (1991). "Bispecific Single Chain Molecules (Janusins) Target Cytotoxic Lymphocytes on HIV Infected Cells," EMBO J. 10(12):3655-3659.
Tsuchiya, S. et al. (Aug. 1980). "Establishment and Characterization of a Human Acute Monocytic Leukemia Cell Line (THP-1)," Int. J.Cancer 26(2):171-176.
Tutt, A. et al. (Jul. 1, 1991) "Trispecific F(ab')3 Derivatives that use Cooperative Signaling Via the TCR/CD3 Complex and CD2 to Activate and Redirect Resting Cytotoxic T Cells," J. Immunol. 147(1):60-69.
U.S. Appl. No. 12/253,895, filed Oct. 17, 2008, Knobel et al. (not submitted herewith pursuant to the waiver of 37 C.F.R. § 1.98(a)(2)(iii) issued by the Office on Sep. 21, 2004).
U.S. Appl. No. 11/833,954, filed Aug. 3, 2007, Doronina et al.(not submitted herewith pursuant to the waiver of 37 C.F.R. § 1.98(a)(2)(iii) issued by the Office on Sep. 21, 2004).
U.S. Appl. No. 12/265,451, filed Nov. 5, 2008, Hsu et al.(not submitted herewith pursuant to the waiver of 37 C.F.R. § 1.98(a)(2)(iii) issued by the Office on Sep. 21, 2004).
U.S. Appl. No. 61/080,169, filed Jul. 11, 2008, McDonagh et al.(not submitted herewith pursuant to the waiver of 37 C.F.R. § 1.98(a)(2)(iii) issued by the Office on Sep. 21, 2004).

(56) References Cited

OTHER PUBLICATIONS

U.S. Appl. No. 60/449,055, filed Feb. 20, 2003, Law et al.(not submitted herewith pursuant to the waiver of 37 C.F.R. § 1.98(a)(2)(iii) issued by the Office on Sep. 21, 2004).
U.S. Appl. No. 60/645,355, filed Jan. 19, 2005. , Law et al. (not submitted herewith pursuant to the waiver of 37 C.F.R. § 1.98(a)(2)(iii) issued by the Office on Sep. 21, 2004).
Uchida, J. et al. (Jun. 21, 2004). "The Innate Mononuclear Phagocyte Network Depletes B Lymphocytes Through Fc Receptor-Dependent Mechanisms During Anti-CD20 Antibody Immunotherapy," J. Exp. Med. 199(12):1659-1669.
Ulgar Victor et al. "New N-Alkylsulfonamides and Alkyl Sulfonates Derived From 6-C-Sulfosugars," Tetrahedron (Jul. 15, 2002); 58:7967-7973.
Umaña, P. et al. (Feb. 1999). "Engineered Glycoforms of an Antineuro-Blastoma IgG 1 With Optimized Antibody-Dependent Cellular Cytotoxic Activity," Nat. Biotechnol. 17:176-180.
U.S. Appl. No. 10/546,304 Amendment filed Nov. 21, 2008 in response to Final Office Action dated May 22, 2006.
U.S. Appl. No. 10/546,304 Final Office Action dated May 22, 2008.
U.S. Appl. No. 10/546,304, Non-Final Office Action dated Feb. 13, 2009.
U.S. Appl. No. 10/546,304, Non-Final Office Action dated Jul. 23, 2007.
U.S. Appl. No. 10/546,304, Notice of Allowance dated Sep. 18, 2009.
U.S. Appl. No. 10/546,304, Restriction Requirement dated Apr. 13, 2007.
U.S. Appl. No. 10/983,340 Amendment filed Jul. 9, 2007 in response to Office Action dated Mar. 9, 2007.
U.S. Appl. No. 10/983,340 Office Action dated Oct. 4, 2007.
U.S. Appl. No. 11/251,173, Non-Final Office Action dated Apr. 10, 2008.
U.S. Appl. No. 11/251,173, Non-Final Office Action dated Jul. 10, 2007.
U.S. Appl. No. 11/251,173, Non-Final Office Action dated Jul. 25, 2008.
U.S. Appl. No. 11/251,173, Notice of Allowance dated Oct. 23, 2006.
U.S. Appl. No. 11/251,173, Restriction Requirement dated Mar. 21, 2007.
U.S. Appl. No. 11/735,365, Non-Final Office Action dated Jan. 13, 2009.
U.S. Appl. No. 11/735,365, Non-Final Office Action dated Apr. 30, 2009.
U.S. Appl. No. 11/735,365, Notice of Allowance dated Aug. 18, 2009.
U.S. Appl. No. 11/735,365, Restriction Requirement dated Sep. 30, 2008.
U.S. Appl. No. 11/735,376, Non Final Office Action dated May 26, 2010.
U.S. Appl. No. 11/735,376, Non Final Office Action dated Aug. 3, 2009.
U.S. Appl. No. 11/735,376, Notice of Abandonment dated Dec. 27, 2010.
U.S. Appl. No. 11/735,376, Restriction Requirement dated Nov. 5, 2008
U.S. Appl. No. 11/912,096, Non Final Office Action dated Feb. 7, 2011.
U.S. Appl. No. 11/912,096, Notice of Allowance dated Jul. 11, 2011.
U.S. Appl. No. 11/912,096, Restriction Requirement dated Nov. 12, 2010.
U.S. Appl. No. 12/265,451, Final Office Action dated Apr. 1, 2011.
U.S. Appl. No. 12/265,451, Final Office Action dated Dec. 16, 2013.
U.S. Appl. No. 12/265,451, Non-Final Office Action dated Jul. 9, 2013.
U.S. Appl. No. 12/265,451, Non-Final Office Action dated Jul. 21, 2010.
U.S. Appl. No. 12/265,451, Restriction Requirement dated Apr. 13, 2010.
U.S. Appl. No. 12/370,151, Non-Final Office Action dated Jan. 19, 2011.
U.S. Appl. No. 12/370,151, Notice of Allowance dated Apr. 3, 2012.
U.S. Appl. No. 12/370,151, Notice of Allowance dated Jun. 21, 2011.
U.S. Appl. No. 12/370,151, Notice of Allowance dated Aug. 23, 2012.
U.S. Appl. No. 12/467,182, Non Final Office Action dated Aug. 23, 2011.
U.S. Appl. No. 12/467,182, Restriction Requirement dated Apr. 21, 2001.
U.S. Appl. No. 12/635,571, Final Office Action dated Mar. 7, 2012.
U.S. Appl. No. 12/635,571, Non Final Office Action dated Oct. 13, 2011.
U.S. Appl. No. 12/635,607, Advisory Action dated Aug. 28, 2013.
U.S. Appl. No. 12/635,607, Final Office Action dated Apr. 18, 2013.
U.S. Appl. No. 12/635,607, Non Final Office Action dated May 7, 2012.
U.S. Appl. No. 12/635,607, Non Final Office Action dated Oct. 11, 2011.
U.S. Appl. No. 12/635,607, Non Final Office Action dated Oct. 18, 2012.
U.S. Appl. No. 12/891,716, Non-Final Office Action dated Apr. 26, 2013.
U.S. Appl. No. 12/891,716, Non-Final Office Action dated Dec. 14, 2012.
U.S. Appl. No. 12/891,716, Notice of Allowance dated Oct. 17, 2013.
U.S. Appl. No. 13/271,143, Notice of Allowance dated Apr. 24, 2013.
U.S. Appl. No. 13/271,143, Restriction Requirement dated Dec. 10, 2012.
U.S. Appl. No. 13/491,475, Non Final Office Action dated Aug. 2, 2012.
U.S. Appl. No. 13/491,475, Notice of Allowance dated Jan. 22, 2013.
U.S. Appl. No. 13/566,827, Final Office Action dated Jun. 19, 2013.
U.S. Appl. No. 13/566,827, Non Final Office Action dated Feb. 1, 2013.
U.S. Appl. No. 12/265,451, Non-Final Office Action dated Sep. 24, 2014.
U.S. Appl. No. 12/265,451, Notice of Allowance dated Feb. 15, 2015.
U.S. Appl. No. 12/635,607, Non-Final Office Action dated Jul. 24, 2015.
U.S. Appl. No. 13/271,143, Notice of Allowance dated Jun. 24, 2013.
U.S. Appl. No. 14/053,164, Ex Parte Quayle Action dated Feb. 5, 2016.
U.S. Appl. No. 14/053,164, Notice of Allowance dated Apr. 27, 2016.
U.S. Appl. No. 14/053,164, Restriction Requirement dated Sep. 30, 2015.
Vagin, Olga et al., "Inverse Correlation between the Extent of N-Glycan Branching and Intercellular Adhesion in Epithelia," The Journal of Biological Chemistry (Jan. 25, 2008); 283(4):2192-2202.
Vajdos, F. et al. (2002) "Comprehensive Functional Maps of the Antigen Binding Site of an Anti-ErbB2 Antibody Obtained with Shotgun Scanning Mutagenesis," J. Mol. Biol. 320:415-428.
Valero-Gonzalez, Jessika et al., "A Proactive Role of Water Molecules in Acceptor Recognition by Protein O-Fucosyltransferase 2," Nature Chemical Biology (Apr. 2016; published online Feb. 8, 2016 DOI:101038/NCHEMBIO.2019); 12:240-246.
Van Heeke, G. et al. (1989). "Expression of Human Asparagine Synthetase in *Escherichia coli*," J. Biol. Chem. 24:5503-5509.
Van Lier et al., "Tissue Distribution and Biochemical and Functional Properties of Tp55 (CD27), A Novel T Cell Differentiation Antigen," J. Immunol. 139(5):1589-1596 (Sep. 1, 1987).
Verhoeyen, M. et al. (Mar. 25, 1988). "Reshaping Human Antibodies: Grafting an Antilysozyme Activity," Science 239(4857):1534-1536.
Vestergaard, C. et al. (May 2000). "The NC/Nga Mouse: A Model for Atopic Dermatitis," Mol. Med.Today 6(5):209-210.

(56) References Cited

OTHER PUBLICATIONS

Vinson, C.R. et al. (Nov. 17, 1989). "Scissors-Grip Model for DNA Recognition by a Family of Leucine Zipper Proteins," Science 246(4932):911-916.
Vocadlo David J. et al. "A Chemical Approach for Identifying O-GlcNAc-Modified Proteins in Cells," FNAS (Aug. 5, 2003); 100(16):9116-9121.
Vogel C. et al. "Synthesis of C-Glycosidic Galacturopates Suitable as Glycosyl Acceptors," Polish J. Chem. (2005); 79:251-265.
Vogel Chr. et al. "Galacturonate aus Acetyl- und Isopropyliden-D-Galactopyranosen," Journal f. prakt. Chemie. Band (1990); 332(1):28-36, translation of Abstract only.
Von Ahsen Oliver et al. "A Miniaturized High-Throughput Screening Assay for Fucosyltransferase VII," Analytical Biochemistry (2008; avail on line Aug. 28, 2007); 372:96-105.
Voronova, A. et al. (Jun. 1990). "Mutations That Disrupt DNA Binding and Dimer Formation in the E47 Helix-Loop-Helix Protein Map to Distinct Domains," Proc. Natl. Acad. Sci. USA 87(12):4722-4726.
Walsh, Gary et al., "Post-Translational Modifications in the Context of Therapeutic Proteins," Nature Biotechnology (Oct. 10, 2006); 24(10):1241-1252.
Wang, Qian II et al. "Efficient Glycoengineering of GM3 on Melanoma Cell and Monoclonal Antibody-Mediated Selective Killing of the Glycoengineered Cancer Cell," Bioorganic & Medicinal Chemistry (Sep. 12, 2007); 15:7561-7567.
Wang, Xiangchun et al., "Core Fucosylation Regulates Epidermal Growth Factor Receptor-mediated Intracellular Signaling," Journal of Biological Chemistry (Feb. 3, 2006); 281(5):2572-2577.
Ward, Peter et al, "Monoclonal Antibody Production," Committee on Methods of Producing Monoclonal Antibodies, Institute for Laboratory Animal Research, National Research Council (© 1999 National Academy of Sciences); ISBN: 0-309-51904-7, 75 pages.
Watanabe, M. et al. (Feb. 1999). "Antibody Dependent Cellular Phagocytosis (ADCP) and Antibody Dependent Cellular Cytotoxicity (ADCC) of Breast Cancer Cells Mediated by Bispecific Antibody, MDX-210," Breast Cancer Res. Treat. 53(3):199-207.
Watt, Gregory et al. "Site-Specific Glycosylation of an Aglycosylated Human IgG1-Fc Antibody Protein Generates Neoglycoproteins with Enhanced Function," Chemistry & Biology (Sep. 19, 2003); 10:807-814.
White, "Antibody-Targeted Immunotherapy for Treatment of Malignancy", Annual Review of Medicine; 52:125-145, (2001).
Wilkinson Brendan L., et al. "Click Chemistry in Carbohydrate Based Drug Development and Glycobiology," In: Drug Design Research Perspectives; Chapter IV; Editor: Stanley F. Kaplan, Nova Science Publishers, Inc. © 2007, pp. 57-102.
Williams, S.C. et al. (Sep. 1991). "A Family of C/EBP-Related Proteins Capable of Forming Covalently Linked Leucine Zipper Dimers in Vitro," Genes Dev. 5(9):1553-1567.
Wilman, D.E.V. (1986). "Prodrugs in Cancer Chemotherapy", in Biochemical Society Transactions, 14:375-382.
Wilson, I.A. et al. (Jul. 1984). "The Structure of an Antigenic Determinant in a Protein," Cell 37:767-778.
Winkler et al. "Changing the Antigen Binding Specificity by Single Point Mutations of an Anti-p24 (HIV-1 antibody", J. Immunol. 165(16):4505-4514, (2000).
Winterbourne, D. J. et al. "2-Deoxy-2-Fluoro-L-Fucose and Its Effect on L-[1-14C] Fucose Utilization in Mammalian Cells," Biochemical and Biophysical Research Communications (Feb. 23, 1979); 87:989-992.
Wischhusen et al. "Identification of CD70-mediated Apoptosis of Immune Effector Cells as a Novel Immune Escape Pathway of Human Gliblastoma," Cancer Res., pp. 2592-2599 (2002).
Witzig et al. "Radioimmunotherapy for Patients Wth Relapsed B-Cell Non-Hodgkin Lymphoma," Cancer Chemother. Pharmacol. 48(suppl. 1):S91-S95 (2001).
Wood, C.R. et al. (Apr. 4-10, 1985). "The Synthesis and in vivo Assembly of Functional Antibodies in Yeast," Nature 314(6010):446-449.
Wright, A. et al. (Jan. 1997). "Effect of Glycosylation on Antibody Function: Implications for Genetics Engineering," Trends Biotechnol. 15:26-31.
Wright, Ann et al. "Effect of Altered CH2-Associated Carbohydrate Structure on the Functional Properties and In Vivo Fate of Chimeric Mouse-Human Immunoglobulin G1," J. Exp. Med., (Sep. 1, 1994); 180:1087-1096.
Wright, Ann et al. "In Vivo Trafficking and Catabolism of IgG1 Antibodies with Fc Associated Carbohydrates of Differing Structure," Glycobiology(Aug. 16, 2000); 10(12):1347-1355.
Written Opinion of the International Searching Authority dated Jun. 2, 2006 in International Application No. PCT/US05/36994.
Wrodnigg, Tanja M. et al. "Natural and Synthetic Iminosugars as Carbohydrate Processing Enzyme Inhibitors for Cancer Therapy," Anti-Cancer Agents in Medicinal Chemistry (2008; accepted Nov. 13, 2006); 3:77-85.
Wu et al. "Humanization for a Murine Monoclonal Antibody by Simultaneous Optimization of Framework and CDR Residues," J. Mol. Biol. 19:294(1):151-62 (1999).
Wu et al. "Simultaneous Humanization and Affinity Optimization of Monoclonal Antibodies," Methods in Mol. Biol. 207:197-212, (2003).
Wuts, Peter G. M. "Reactivities, Reagents, and Reactivity Charts," Green's Protective Groups in Organic Symthesis (published online Aug. 11, 2014; DOI:10.1002/9781118905074.ch10); pp. 406-416.
Xia, Lijun et al. "Surface Fucosylation of Human Cord Blood Cells Augments Binding to P-Selectin and E-Selectin and Enhances Engraftment in Bone Marrow," Blood (Nov. 15, 2004); 104(10):3091-3096.
Yamaguchi, Yoshiki et al. "Glycoform-Dependent Conformational Alteration of the Fc Region of Human Immunoglobulin G1 as Revealed by NMR Spectroscopy," Biochimica et Biophysica Acta (2006; avail on line Oct. 26, 2005); 1760:693-700.
Yuan, Kun et al. "Cell Surface Associated Alpha-L-Fucose Moieties Modulate Human Breast Cancer Neoplastic Progression," Pathol. Oneal. Res. (Jun. 13, 2008); 14:145-156.
Yurchenco, Peter D. et al. "Equilibration of Fucosyl Glycoprotein Pools in HeLa Cells," Biochemistry (1977); 16(5):944-953.
Yurchenco, Peter D. et al. "Fucosyl-Glycoprotein and Precursor Pools in Hela Cells," Biochemistry (1975); 14(14):3107-3114.
Zapata, G. et al. (1995) "Engineering Linear F(ab')2 Fragments for Efficient Production in *Escherichia coli* and Enhanced Antiproliferative Activity," Protein Engineering 8(10):1057-1062.
Zeitler, R. et a., Inhibition of L-Fucokinase from Ra Liver by L-Fucose Analogies in Vitro (1997); 11:265-273.
Zellweger, T. et al. (Jul.-Aug. 2001). "Chemosensitization of Human Renal Cell Cancer Using Antisense Oligonucleotides Targeting the Antiapoptotic Gene Clusterin," Neoplasia 3(4):360-367.
Zeng, Ying et al. "High-Efficiency Labeling of Sialylated Glycoproteins on Living Cells," Nature Methods (Mar. 2009; published online Feb. 22, 2009); 6(3):1S-13S.
Zeng, Ying et al. "High-Efficiency Labeling of Sialylated Glycoproteins on Living Cells," Nature Methods (Mar. 2009; published online Feb. 22, 2009); 6(3):207-209.
Zhao, Yangyang et al. "Deletion of Core Fucosylation on a3β1 Integrin Down-Regulates its Functions," The Journal of Biological Chemistry (Oct. 16, 2006); 281 (50):38343-38350.
Zheng, X.X. "Administration of Noncytolytic IL-10/Fc in Murine Models of Lipopolysaccharide-Induced Septic Shock and Allogeneic Islet Transplantation," J. Immunol. 154:5590-5600 (May 15, 1995).
Zhou, Qun et al. "Development of a Simple and Rapid Method for Producing Non-Fucosylated Oligomannose Containing Antibodies With Increased Effector Function," Biotechnology and Bioengineering (2008; published online Aug. 6, 2007); 99(3):652-665.
Zips, Daniel et al., "New Anticancer Agents: In Vitro and In Vivo Evaluation," In Vivo (2005; accepted Nov. 25, 2004); 19:1-8.
Zola, Heddy Monoclonal Antibodies: A Manual of Techniques; (© 1987 by CRC Press, Inc.); Book cover; title and publication pages; pp. 26-27.
Sambrook, J. et al. (2001). Molecular Cloning: A Laboratory Manual Cold Spring Harbor Laboratory Press, Cold Spring Harbor, N.Y., 3rd ed., 20 pages, Table of Contents.
Luchansky, Sarah J. et al. "Expanding the Diversity of Unnatural Cell-Surface Sialic Acids," ChemBioChem (2004); 5:371-374.

(56) References Cited

OTHER PUBLICATIONS

Alley, S.C. Curriculum Vitae, 9 pages.
Assignment of U.S. Appl. 61/050,173, 3 pages.
Assignment of U.S. Appl. 61/092,700, 3 pages.
Becton, Dickinson and Company (2014). "Supporting B-Cell Research: Providing innovative and Flexible Ways to Study B-Cell Phenotypes and Functions," in B-Cell Research: Flow Cytomertry Tools for the Study of B-cell Biology, 16 pages.
Brady, P.A. (Dec. 14, 2015). Brief Communication, 29 pages.
Brady, P.A. (Feb. 18, 2016). Summons to Attend Oral Proceedings Pursuant to Rule 115(1)EPC, 5 pages.
Brady, P.A. (Jan. 2, 2017). Interlocutory Decision in Opposition Proceedings, 9 pages.
Brady, P.A. (Jan. 2, 2017). Notice of Opposition, 12 pages.
Bracy, P.A. (Jun. 1, 2016). Submission in Opposition Proceedings, 12 pages.
Brady, P.A. (Mar. 10, 2017). Letter Accompanying Subsequently Filed Items, 5 pages.
Brady, P.A. (May 12, 2017). Opposition by Dr. Hans Ulrich Dörries to European Patent No. 2282773, 2 pages.
Brady, P.A. (May 17, 2017). Setting Out Grounds for Opposition, 162 pages.
Brady, P.A. (Sep. 16, 2016). Brief Communication, 51 pages.
Brady, P.A. (Sep. 26, 2016). Brief Communication, 5 pages.
Brady, P.A. (Sep. 8, 2016). Submission in Opposition Proceedings, 9 pages.
Communication of Amended Entries Concerning the Representative, dated Jun. 8, 2017, (R. 143(1)(h) EPC), 2 pages.
Communication of Notices of Opposition, dated Nov. 21, 2014, (R. 79(1) EPC), 5 pages.
U.S. Appl. No. 61/050,173, 52 pages.
U.S. Appl. No. 61/092,700, 79 pages.
U.S. Appl. No. 61/107,289, 86 pages.
Declaration of Cory Rillahan (Aug. 5, 2016), 6 pages.
Declaration of Stephen C. Alley, (Aug. 31, 2016), 12 pages.
Dörries, H. U. (Apr. 28, 2017). Grounds for Appeal, 29 pages.
Dörries, H. U. (Feb. 3, 2016). In Respons to the Proprietor's Submission Dated Jun. 1, 2015, 20 pages.
Dörries, H. U. (Feb. 3, 2016). Submission in Opposition Proceedings, 3 pages.
Dörries, H. U. (Mar. 1, 2017). Notice of Appeal, 5 pages.
Dörries, H. U. (Mar. 10, 2017). Commencement of Proceedings Before the Board of Appeal, 8 pages.
Dörries, H. U. (Oct. 13, 2016). Brief Communication, 34 pages.
Dörries, H. U. (Oct. 15, 2014). Notice of Opposition, 31 pages.
Dörries, H. U. (Oct. 7, 2016). Opposition by Hans Ulrich Dorries against European Patent No. 2282733, 16 pages.
Dörries, H. U. (Oct. 7, 2016). Submission in Opposition Proceedings, 2 pages.
Dörries, H. U. (Sep. 27, 2017). Opposition by Dr. Hans Ulrich Dorries to European Patent No. 2282773, 4 pages.
Dörries, H. U. (Sep. 27, 2017, 2017). Grounds for Appeal, 21 pages.
Dörries, H. U. (Sep. 6, 2016). In Preparation of Oral Proceedings Scheduled for Nov. 8, 2016, 4 pages.
Dörries, H. U. (Sep. 8, 2016). Further Submission in Preparation of Oral Proceedings, 24 pages.
Dörries, H. U. (Sep. 8, 2016). In Preparation of Oral Proceedings Scheduled for Nov. 8, 2016, 23 pages.
Dörries, H. U. (Sep. 8, 2016). In Preparation of Oral Proceedings Scheduled for Nov. 8, 2016, 33 pages.
Dörries, H. U. (Sep. 8, 2016). Submission in Opposition Proceedings, 5 pages.
E-mail, dated Nov. 27, 2015, Japanese Office with English Translation, 3 pages.
Even, M.S. et al. (Mar. 2006, e-pub. Jan. 19, 2006). "Serum-Free Hybridoma Culture: Ethical, Scientific and Safety Considerations," Trends Biotechnol. 24(3):105-108. Abstract Only.
Extension of Time, dated Apr. 8, 2015, for European Patent Applicaton No. 09739983.6, 4 pages.
Falkner, E. et al. (Apr. 2006, e-pub. Oct. 25, 2005). "Serum Free Cell Culture: The Free Access Online Database," Toxicol. In Vitro. 20(3):395-400, Abstract Only.
Fucosylation Definition, retrieved from https://en.wikipedia.org/wiki/Fucosylation, last visited Mar. 24, 2017, 1 page.
Gstraunthaler, G. (2003). "Alternatives to the Use of Fetal Bovine Serum: Serum-Free Cell Culture," ALTEX 20 (4)275-81, Abstract Only.
Interlocutory Decision in Opposition Proceedings Art. 101(3)(a) and 106(2) EPC (Dec. 15, 2016, 59 pages.
Lemke, T.I. (2008). "Chapter 10: Drug Metabolism," : in Foye's Principles of Medicinal Chemistry, 6th Ed.. 3 pages.
Lonza "Primary Cells vs. Cell Lines," retrieved from http:/www.lonza.com/products-services/bio-research/primary-cells/primary-cells-vs-cell-line.a . . . , last visited Sep. 18, 2017, 4 pages.
Medical Dictionary "Cell Line," retrieved from http://medical-dictionary.thefreedictionary.com/cell+line, last visited Sep. 18, 2017, 10 pages.
Minutes of the Oral Proceedings Before the Opposition Division (Nov. 8, 2016), 8 pages.
Patent Assignment for U.S. Pat. No. 8,163,551-B1, Sep. 10, 2014, 1 page.
Pearson, S. (May 12, 2017). Statement of Grounds for Appeal, 26 pages.
Proprietor's Response to Opponent's Statement of Grounds of Appeal Against the Decision of the Oppositon Division dated Jan. 2, 2017, 42 pages.
Proprietor's Response to Opposition to EP 2282733 ("The Patent") by Hans Ulrich Dorries ("The Opponent"), (Jun. 1, 2015), 25 pages.
Recordation of U.S. Provisional Patent, dated May 21, 2008, U.S. Appl. No. 61/050,173, 4 pages.
Recordation of U.S. Provisional Patent, dated Oct. 29, 2008, U.S. Appl. No. 61/092,700, 5 pages.
Rillahan, C.D., Curriculum Vitae, 4 pages.
Summary of Facts and Submissions (Feb. 18, 2016), 23 pages.
Summary of Facts and Submissions (Jan. 2, 2017), 25 pages.
Zola, H. (1987). Monoclonal Antibodies: A Manual of Techniques, Book cover; title and publication pages; pages 63-64.

\* cited by examiner

A.

B.

A.

D.

A.

B.

B.

SEQUENCE LISTING

<160> NUMBER OF SEQ ID NOS: 10

<210> SEQ ID NO 1
<211> LENGTH: 137
<212> TYPE: PRT
<213> ORGANISM: Mus musculus

<400> SEQUENCE: 1

Met Ala Trp Val Trp Thr Leu Leu Phe Leu Met Ala Ala Gln Ser
1               5                   10                  15

Ala Gly Ala Gln Ile Gln Leu Val Gln Ser Gly Pro Glu Val Lys Lys
            20                  25                  30

Pro Gly Glu Thr Val Lys Ile Ser Cys Lys Ala Ser Gly Tyr Thr Phe
        35                  40                  45

Thr Asn Tyr Gly Met Asn Trp Val Lys Gln Ala Pro Gly Lys Gly Leu
    50                  55                  60

Lys Trp Met Gly Trp Ile Asn Thr Tyr Thr Gly Glu Pro Thr Tyr Ala
65                  70                  75                  80

Asp Ala Phe Lys Gly Arg Phe Ala Phe Ser Leu Glu Thr Ser Ala Ser
                85                  90                  95

Thr Ala Tyr Leu Gln Ile Asn Asn Leu Lys Asn Glu Asp Thr Ala Thr
            100                 105                 110

Tyr Phe Cys Ala Arg Asp Tyr Gly Asp Tyr Gly Met Asp Tyr Trp Gly
        115                 120                 125

Gln Gly Thr Ser Val Thr Val Ser Ser
    130                 135

<210> SEQ ID NO 2
<211> LENGTH: 132
<212> TYPE: PRT
<213> ORGANISM: Mus musculus

<400> SEQUENCE: 2

Met Glu Thr Asp Thr Leu Leu Leu Trp Val Leu Leu Leu Trp Val Pro
1               5                   10                  15

Gly Ser Thr Gly Asp Ile Val Leu Thr Gln Ser Pro Ala Ser Leu Ala
            20                  25                  30

Val Ser Leu Gly Gln Arg Ala Thr Ile Ser Cys Arg Ala Ser Lys Ser
        35                  40                  45

Val Ser Thr Ser Gly Tyr Ser Phe Met His Trp Tyr Gln Gln Lys Pro
    50                  55                  60

Gly Gln Pro Pro Lys Leu Leu Ile Tyr Leu Ala Ser Asn Leu Glu Ser
65                  70                  75                  80

Gly Val Pro Ala Arg Phe Ser Gly Ser Gly Ser Gly Thr Asp Phe Thr
                85                  90                  95

Leu Asn Ile His Pro Val Glu Glu Glu Asp Ala Ala Thr Tyr Tyr Cys
            100                 105                 110

Gln His Ser Arg Glu Val Pro Trp Thr Phe Gly Gly Gly Thr Lys Leu
        115                 120                 125

Glu Ile Lys Arg
    130

<210> SEQ ID NO 3
<211> LENGTH: 467
<212> TYPE: PRT
<213> ORGANISM: Artificial Sequence
<220> FEATURE:
<223> OTHER INFORMATION: murine CDR, murine residues in human FR

<400> SEQUENCE: 3

```
Met Ala Trp Val Trp Thr Leu Leu Phe Leu Met Ala Ala Ala Gln Ser
1               5                   10                  15

Ala Gln Ala Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Thr Asn Tyr Gly Met Asn Trp Val Arg Gln Ala Pro Gly Gln Gly Leu
    50                  55                  60

Lys Trp Met Gly Trp Ile Asn Thr Tyr Thr Gly Glu Pro Thr Tyr Ala
65                  70                  75                  80

Asp Ala Phe Lys Gly Arg Val Thr Met Thr Arg Asp Thr Ser Ile Ser
                85                  90                  95

Thr Ala Tyr Met Glu Leu Ser Arg Leu Arg Ser Asp Asp Thr Ala Val
            100                 105                 110

Tyr Tyr Cys Ala Arg Asp Tyr Gly Asp Tyr Gly Met Asp Tyr Trp Gly
        115                 120                 125

Gln Gly Thr Thr Val Thr Val Ser Ser Ala Ser Thr Lys Gly Pro Ser
    130                 135                 140

Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205

Pro Ser Ser Ser Leu Gly Thr Gln Thr Tyr Ile Cys Asn Val Asn His
    210                 215                 220

Lys Pro Ser Asn Thr Lys Val Asp Lys Lys Val Glu Pro Lys Ser Cys
225                 230                 235                 240

Asp Lys Thr His Thr Cys Pro Pro Cys Pro Ala Pro Glu Leu Leu Gly
                245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser His
        275                 280                 285

Glu Asp Pro Glu Val Lys Phe Asn Trp Tyr Val Asp Gly Val Glu Val
    290                 295                 300

His Asn Ala Lys Thr Lys Pro Arg Glu Glu Gln Tyr Asn Ser Thr Tyr
305                 310                 315                 320

Arg Val Val Ser Val Leu Thr Val Leu His Gln Asp Trp Leu Asn Gly
                325                 330                 335

Lys Glu Tyr Lys Cys Lys Val Ser Asn Lys Ala Leu Pro Ala Pro Ile
            340                 345                 350

Glu Lys Thr Ile Ser Lys Ala Lys Gly Gln Pro Arg Glu Pro Gln Val
        355                 360                 365

Tyr Thr Leu Pro Pro Ser Arg Asp Glu Leu Thr Lys Asn Gln Val Ser
    370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
```

```
                405                 410                 415
Val Leu Asp Ser Asp Gly Ser Phe Phe Leu Tyr Ser Lys Leu Thr Val
            420                 425                 430

Asp Lys Ser Arg Trp Gln Gln Gly Asn Val Phe Ser Cys Ser Val Met
            435                 440                 445

His Glu Ala Leu His Asn His Tyr Thr Gln Lys Ser Leu Ser Leu Ser
            450                 455                 460

Pro Gly Lys
465

<210> SEQ ID NO 4
<211> LENGTH: 467
<212> TYPE: PRT
<213> ORGANISM: Artificial Sequence
<220> FEATURE:
<223> OTHER INFORMATION: murine CDR, murine residues in human FR

<400> SEQUENCE: 4

Met Ala Trp Val Trp Thr Leu Leu Phe Leu Met Ala Ala Ala Gln Ser
1               5                   10                  15

Ala Gln Ala Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Thr Asn Tyr Gly Met Asn Trp Val Arg Gln Ala Pro Gly Gln Gly Leu
    50                  55                  60

Lys Trp Met Gly Trp Ile Asn Thr Tyr Thr Gly Glu Pro Thr Tyr Ala
65                  70                  75                  80

Asp Ala Phe Lys Gly Arg Phe Ala Phe Ser Leu Asp Thr Ser Thr Ser
                85                  90                  95

Thr Ala Tyr Met Glu Leu Arg Ser Leu Arg Ser Asp Asp Thr Ala Val
            100                 105                 110

Tyr Tyr Cys Ala Arg Asp Tyr Gly Asp Tyr Gly Met Asp Tyr Trp Gly
        115                 120                 125

Gln Gly Thr Thr Val Thr Val Ser Ser Ala Ser Thr Lys Gly Pro Ser
    130                 135                 140

Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205

Pro Ser Ser Ser Leu Gly Thr Gln Thr Tyr Ile Cys Asn Val Asn His
    210                 215                 220

Lys Pro Ser Asn Thr Lys Val Asp Lys Lys Val Glu Pro Lys Ser Cys
225                 230                 235                 240

Asp Lys Thr His Thr Cys Pro Pro Cys Pro Ala Pro Glu Leu Leu Gly
                245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser His
        275                 280                 285

Glu Asp Pro Glu Val Lys Phe Asn Trp Tyr Val Asp Gly Val Glu Val
```

```
                    290                 295                 300
His Asn Ala Lys Thr Lys Pro Arg Glu Glu Gln Tyr Asn Ser Thr Tyr
305                 310                 315                 320

Arg Val Val Ser Val Leu Thr Val Leu His Gln Asp Trp Leu Asn Gly
                    325                 330                 335

Lys Glu Tyr Lys Cys Lys Val Ser Asn Lys Ala Leu Pro Ala Pro Ile
                    340                 345                 350

Glu Lys Thr Ile Ser Lys Ala Lys Gly Gln Pro Arg Glu Pro Gln Val
                    355                 360                 365

Tyr Thr Leu Pro Pro Ser Arg Asp Glu Leu Thr Lys Asn Gln Val Ser
                    370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                    405                 410                 415

Val Leu Asp Ser Asp Gly Ser Phe Phe Leu Tyr Ser Lys Leu Thr Val
                    420                 425                 430

Asp Lys Ser Arg Trp Gln Gln Gly Asn Val Phe Ser Cys Ser Val Met
                    435                 440                 445

His Glu Ala Leu His Asn His Tyr Thr Gln Lys Ser Leu Ser Leu Ser
                    450                 455                 460

Pro Gly Lys
465

<210> SEQ ID NO 5
<211> LENGTH: 118
<212> TYPE: PRT
<213> ORGANISM: Artificial Sequence
<220> FEATURE:
<223> OTHER INFORMATION: murine CDR, human FR

<400> SEQUENCE: 5

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
                20                  25                  30

Gly Met Asn Trp Val Arg Gln Ala Pro Gly Gln Gly Leu Glu Trp Met
            35                  40                  45

Gly Trp Ile Asn Thr Tyr Thr Gly Glu Pro Thr Tyr Ala Asp Ala Phe
        50                  55                  60

Lys Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Asp Tyr Gly Asp Tyr Gly Met Asp Tyr Trp Gly Gln Gly Thr
                100                 105                 110

Thr Val Thr Val Ser Ser
            115

<210> SEQ ID NO 6
<211> LENGTH: 118
<212> TYPE: PRT
<213> ORGANISM: Artificial Sequence
<220> FEATURE:
<223> OTHER INFORMATION: murine CDR, murine residues in human FR

<400> SEQUENCE: 6
```

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Gly Met Asn Trp Val Arg Gln Ala Pro Gly Gln Gly Leu Glu Trp Met
        35                  40                  45

Gly Trp Ile Asn Thr Tyr Thr Gly Glu Pro Thr Tyr Ala Asp Ala Phe
    50                  55                  60

Lys Gly Arg Phe Ala Phe Ser Leu Asp Thr Ser Thr Ser Thr Ala Tyr
65                  70                  75                  80

Leu Gln Ile Asn Ser Leu Arg Ser Asp Asp Thr Ala Val Tyr Tyr Cys
                85                  90                  95

Ala Arg Asp Tyr Gly Asp Tyr Gly Met Asp Tyr Trp Gly Gln Gly Thr
                100                 105                 110

Thr Val Thr Val Ser Ser
            115
```

<210> SEQ ID NO 7
<211> LENGTH: 118
<212> TYPE: PRT
<213> ORGANISM: Artificial Sequence
<220> FEATURE:
<223> OTHER INFORMATION: murine CDR, murine residues in human FR

<400> SEQUENCE: 7

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Gly Met Asn Trp Val Arg Gln Ala Pro Gly Gln Gly Leu Lys Trp Met
        35                  40                  45

Gly Trp Ile Asn Thr Tyr Thr Gly Glu Pro Thr Tyr Ala Asp Ala Phe
    50                  55                  60

Lys Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Asp Tyr Gly Asp Tyr Gly Met Asp Tyr Trp Gly Gln Gly Thr
                100                 105                 110

Thr Val Thr Val Ser Ser
            115
```

<210> SEQ ID NO 8
<211> LENGTH: 118
<212> TYPE: PRT
<213> ORGANISM: Artificial Sequence
<220> FEATURE:
<223> OTHER INFORMATION: murine CDR, murine residues in human FR

<400> SEQUENCE: 8

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Gly Met Asn Trp Val Arg Gln Ala Pro Gly Gln Gly Leu Lys Trp Met
        35                  40                  45

Gly Trp Ile Asn Thr Tyr Thr Gly Glu Pro Thr Tyr Ala Asp Ala Phe
    50                  55                  60
```

```
Lys Gly Arg Phe Ala Phe Ser Leu Asp Thr Ser Thr Ser Thr Ala Tyr
 65                  70                  75                  80

Met Glu Leu Arg Ser Leu Arg Ser Asp Asp Thr Ala Val Tyr Tyr Cys
                 85                  90                  95

Ala Arg Asp Tyr Gly Asp Tyr Gly Met Asp Tyr Trp Gly Gln Gly Thr
            100                 105                 110

Thr Val Thr Val Ser Ser
        115

<210> SEQ ID NO 9
<211> LENGTH: 467
<212> TYPE: PRT
<213> ORGANISM: Artificial Sequence
<220> FEATURE:
<223> OTHER INFORMATION: murine CDR, human FR in HV Domain

<400> SEQUENCE: 9

Met Ala Trp Val Trp Thr Leu Leu Phe Leu Met Ala Ala Ala Gln Ser
 1               5                  10                  15

Ala Gln Ala Gln Val Gln Leu Val Gln Ser Gly Ala Glu Val Lys Lys
             20                  25                  30

Pro Gly Ala Ser Val Lys Val Ser Cys Lys Ala Ser Gly Tyr Thr Phe
         35                  40                  45

Thr Asn Tyr Gly Met Asn Trp Val Arg Gln Ala Pro Gly Gln Gly Leu
     50                  55                  60

Glu Trp Met Gly Trp Ile Asn Thr Tyr Thr Gly Glu Pro Thr Tyr Ala
 65                  70                  75                  80

Asp Ala Phe Lys Gly Arg Val Thr Met Thr Thr Asp Thr Ser Thr Ser
                 85                  90                  95

Thr Ala Tyr Met Glu Leu Arg Ser Leu Arg Ser Asp Asp Thr Ala Val
            100                 105                 110

Tyr Tyr Cys Ala Arg Asp Tyr Gly Asp Tyr Gly Met Asp Tyr Trp Gly
        115                 120                 125

Gln Gly Thr Thr Val Thr Val Ser Ser Ala Ser Thr Lys Gly Pro Ser
130                 135                 140

Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205

Pro Ser Ser Leu Gly Thr Gln Thr Tyr Ile Cys Asn Val Asn His
    210                 215                 220

Lys Pro Ser Asn Thr Lys Val Asp Lys Val Glu Pro Lys Ser Cys
225                 230                 235                 240

Asp Lys Thr His Thr Cys Pro Pro Cys Pro Ala Pro Glu Leu Leu Gly
                245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser His
        275                 280                 285

Glu Asp Pro Glu Val Lys Phe Asn Trp Tyr Val Asp Gly Val Glu Val
    290                 295                 300
```

```
His Asn Ala Lys Thr Lys Pro Arg Glu Glu Gln Tyr Asn Ser Thr Tyr
305                 310                 315                 320

Arg Val Val Ser Val Leu Thr Val Leu His Gln Asp Trp Leu Asn Gly
                325                 330                 335

Lys Glu Tyr Lys Cys Lys Val Ser Asn Lys Ala Leu Pro Ala Pro Ile
            340                 345                 350

Glu Lys Thr Ile Ser Lys Ala Lys Gly Gln Pro Arg Glu Pro Gln Val
            355                 360                 365

Tyr Thr Leu Pro Pro Ser Arg Asp Glu Leu Thr Lys Asn Gln Val Ser
    370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415

Val Leu Asp Ser Asp Gly Ser Phe Phe Leu Tyr Ser Lys Leu Thr Val
            420                 425                 430

Asp Lys Ser Arg Trp Gln Gln Gly Asn Val Phe Ser Cys Ser Val Met
        435                 440                 445

His Glu Ala Leu His Asn His Tyr Thr Gln Lys Ser Leu Ser Leu Ser
    450                 455                 460

Pro Gly Lys
465

<210> SEQ ID NO 10
<211> LENGTH: 112
<212> TYPE: PRT
<213> ORGANISM: Artificial Sequence
<220> FEATURE:
<223> OTHER INFORMATION: murine CDR, human FR

<400> SEQUENCE: 10

Asp Ile Val Met Thr Gln Ser Pro Asp Ser Leu Ala Val Ser Leu Gly
1               5                   10                  15

Glu Arg Ala Thr Ile Asn Cys Arg Ala Ser Lys Ser Val Ser Thr Ser
            20                  25                  30

Gly Tyr Ser Phe Met His Trp Tyr Gln Gln Lys Pro Gly Gln Pro Pro
        35                  40                  45

Lys Leu Leu Ile Tyr Leu Ala Ser Asn Leu Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln His Ser Arg
                85                  90                  95

Glu Val Pro Trp Thr Phe Gly Gln Gly Thr Lys Val Glu Ile Lys Arg
                100                 105                 110
```

METHODS AND COMPOSITIONS FOR MAKING ANTIBODIES AND ANTIBODY DERIVATIVES WITH REDUCED CORE FUCOSYLATION

CROSS-REFERENCES TO RELATED APPLICATIONS

This application is a continuation of U.S. patent application Ser. No. 15/729,258, filed on Oct. 10, 2017, which is a continuation of U.S. patent application Ser. No. 14/632,925 filed Feb. 26, 2015 (now U.S. Pat. No. 9,816,069), which is a continuation of U.S. patent application Ser. No. 14/043,742 filed Oct. 1, 2013 (now U.S. Pat. No. 8,993,326), which is a divisional of Ser. No. 13/405,143 filed Feb. 24, 2012 (now U.S. Pat. No. 8,574,907), which is a divisional of Ser. No. 12/434,533 filed May 1, 2009 (now U.S. Pat. No. 8,163,551), which claims the benefit of U.S. Provisional Application No. 61/050,173 filed May 2, 2008 and U.S. Provisional Application No. 61/092,700 filed Aug. 28, 2008 and U.S. Provisional Application No. 61/107,289 filed Oct. 21, 2008, the contents of each are incorporated herein by reference.

STATEMENT AS TO RIGHTS TO INVENTIONS MADE UNDER FEDERALLY SPONSORED RESEARCH AND DEVELOPMENT

Not Applicable

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 761682001801SEQLIST.txt, date recorded: May 17, 2019, size: 20 KB).

BACKGROUND OF THE INVENTION

Recombinant therapeutic proteins are produced by many different methods. One preferred method is production of recombinant proteins from mammalian host cell lines. Cell lines, such as Chinese Hamster Ovary (CHO) cells, are engineered to express the therapeutic protein of interest. Different cell lines have advantages and disadvantages for recombinant protein production, including protein characteristics and productivity. Selection of a cell line for commercial production often balances the need for high productivity with the ability to deliver consistent product quality with the attributes required of a given product. One important class of therapeutic recombinant proteins that require consistent, high quality characteristics and high titer processes are monoclonal antibodies.

Monoclonal antibodies produced in mammalian host cells can have a variety of post-translational modifications, including glycosylation. Monoclonal antibodies, such as IgG1s, have an N-linked glycosylation site at asparagine 297 (Asn297) of each heavy chain (two per intact antibody). The glycans attached to Asn297 on antibodies are typically complex biantennary structures with very low or no bisecting N-acetylglucosamine (bisecting GlcNAc) with low amounts of terminal sialic acid and variable amounts of galactose. The glycans also usually have high levels of core fucosylation. Reduction of core fucosylation in antibodies has been shown to alter Fc effector functions, in particular Fcgamma receptor binding and ADCC activity. This observation has lead to interest in the engineering cell lines so they produce antibodies with reduced core fucosylation.

Methods for engineering cell lines to reduce core fucosylation included gene knock-outs, gene knock-ins and RNA interference (RNAi). In gene knock-outs, the gene encoding FUT8 (alpha 1,6-fucosyltransferase enzyme) is inactivated. FUT8 catalyzes the transfer of a fucosyl residue from GDP-fucose to position 6 of Asn-linked (N-linked) GlcNac of an N-glycan. FUT8 is reported to be the only enzyme responsible for adding fucose to the N-linked biantennary carbohydrate at Asn297. Gene knock-ins add genes encoding enzymes such as GNTIII or a golgi alpha mannosidase II. An increase in the levels of such enzymes in cells diverts monoclonal antibodies from the fucosylation pathway (leading to decreased core fucosylation), and having increased amount of bisecting N-acetylglucosamines. RNAi typically also targets FUT8 gene expression, leading to decreased mRNA transcript levels or knock out gene expression entirely.

Alternatives to engineering cell lines include the use of small molecule inhibitors that act on enzymes in the glycosylation pathway. Inhibitors such as catanospermine act early in the glycosylation pathway, producing antibodies with immature glycans (e.g., high levels of mannose) and low fucosylation levels. Antibodies produced by such methods generally lack the complex N-linked glycan structure associated with mature antibodies.

In contrast, the present invention provides small molecule fucose analogs for use in producing recombinant antibodies that have complex N-linked glycans, but have reduced core fucosylation.

SUMMARY OF THE INVENTION

The invention provides methods and compositions for preparing antibodies and antibody derivatives with reduced core fucosylation. The methods and compositions are premised in part on the unexpected results presented in the Examples showing that culturing host cells, expressing an antibody or antibody derivative, in the presence of a fucose analog (having formula I, II, III, IV, V or VI) produces an antibody having reduced core fucosylation (i.e., reduced fucosylation of N-acetylglucosamine of the complex N-glycoside-linked sugar chains bound to the Fc region through the N-acetylglucosamine of the reducing terminal of the sugar chains). Such antibodies and antibody derivatives may exhibit increased effector function (ADCC), as compared with antibodies or antibody derivatives produced from such host cells cultured in the absence of the fucose analog.

In another aspect, compositions of antibodies and antibody derivatives are provided. The antibodies and antibody derivatives can be produced by the methods described herein.

In another aspect, fucose analogs are provided. The fucose analogs can be added to mammalian cell culture media to inhibit or reduce core fucosylation. Also provided is cell culture media comprising an effective amount of such a fucose analog(s).

These and other aspects of the present invention may be more fully understood by reference to the following detailed description, non-limiting examples of specific embodiments, and the appended figures.

BRIEF DESCRIPTION OF THE DRAWINGS

FIG. 3A shows binding competition for human Fcγ receptor (CD16)-expressing cells. FIG. 3B shows binding competition for murine Fcγ receptor (CD16)-expressing cells.

FIG. 4A: anti-CD70 antibody. FIG. 4B: anti-CD19 antibody. FIG. 4C: anti-CD30 antibody. FIG. 4D: anti-CD33 antibody.

DETAILED DESCRIPTION OF THE INVENTION

Definitions

Figure 1:
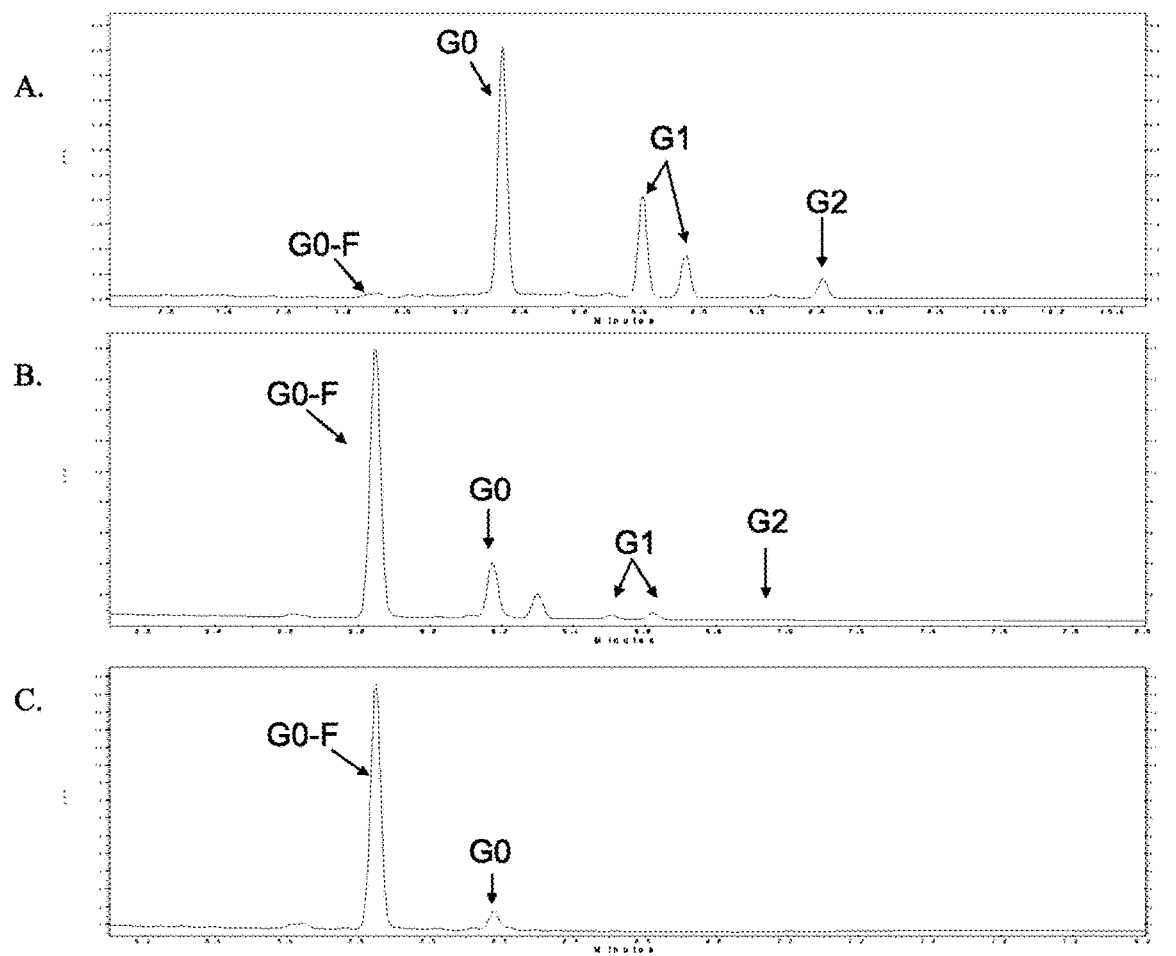
FIG. 1 shows an analysis (electropherograms) of glycans isolated from an anti-CD70 antibody (h1F6) produced from control (A) and alkynyl fucose peracetate (AlkF)-treated host cells (B and C). The panels show the identity and relative distribution of glycans. "G0" refers to the carbohydrate structure where there is no galactose at the two non-reducing termini. "G1" refers to a carbohydrate structure where one of the non-reducing termini has a galactose (a mixture of two isomers). "G2" refers to a carbohydrate structure where both of the non-reducing termini have a galactose. "G0-F" refers to a carbohydrate structure where there is no galactose at either of the two non-reducing termini and there is no core fucosylation. Panel 1A: glycans isolated from control (untreated) h1F6 antibody. Panel 1B: glycans isolated from h1F6 antibodies expressed in the presence of 50 μm alkynyl fucose peracetate. Panel 1C: glycans isolated from h1F6 antibodies expressed in the presence of 50 alkynyl fucose peracetate and treated with β-galactosidase to remove galactose from the G1 and G2 glycans.

The term "antibody" refers to (a) immunoglobulin polypeptides and immunologically active portions of immunoglobulin polypeptides, i.e., polypeptides of the immunoglobulin family, or fragments thereof, that contain an antigen binding site that immunospecifically binds to a specific antigen (e.g., CD70) and an Fc domain comprising a complex N-glycoside-linked sugar chain(s), or (b) conservatively substituted derivatives of such immunoglobulin polypeptides or fragments that immunospecifically bind to the antigen (e.g., CD70). Antibodies are generally described in, for example, Harlow & Lane, Antibodies: A Laboratory Manual (Cold Spring Harbor Laboratory Press, 1988). Unless otherwise apparent from the context, reference to an antibody also includes antibody derivatives as described in more detail below.

An "antibody derivative" means an antibody, as defined above (including an antibody fragment), or Fc domain or region of an antibody comprising a complex N-glycoside linked sugar chain, that is modified by covalent attachment of a heterologous molecule such as, e.g., by attachment of a heterologous polypeptide (e.g., a ligand binding domain of heterologous protein), or by glycosylation (other than core fucosylation), deglycosylation (other than non-core fucosylation), acetylation, phosphorylation or other modification not normally associated with the antibody or Fc domain or region.

The term "monoclonal antibody" refers to an antibody that is derived from a single cell clone, including any eukaryotic or prokaryotic cell clone, or a phage clone, and not the method by which it is produced. Thus, the term "monoclonal antibody" is not limited to antibodies produced through hybridoma technology.

The term "Fc region" refers to the constant region of an antibody, e.g., a $C_H1$-hinge-$C_H2$-$C_H3$ domain, optionally having a $C_H4$ domain, or a conservatively substituted derivative of such an Fc region.

The term "Fc domain" refers to the constant region domain of an antibody, e.g., a $C_H1$, hinge, $C_H2$, $C_H3$ or $C_H4$ domain, or a conservatively substituted derivative of such an Fc domain.

An "antigen" is a molecule to which an antibody specifically binds.

The terms "specific binding" and "specifically binds" mean that the antibody or antibody derivative will bind, in a highly selective manner, with its corresponding target antigen and not with the multitude of other antigens. Typically, the antibody or antibody derivative binds with an affinity of at least about $1 \times 10^{-7}$ M, and preferably $10^{-8}$ M to $10^{-9}$M, $10^{-10}$ M, $10^{-11}$M, or $10^{-12}$ M and binds to the predetermined antigen with an affinity that is at least two-fold greater than its affinity for binding to a non-specific antigen (e.g., BSA, casein) other than the predetermined antigen or a closely-related antigen.

The terms "inhibit" or "inhibition of" means to reduce by a measurable amount, or to prevent entirely.

As used herein, "alkynyl fucose peracetate" refers to any or all forms of alkynyl fucose (5-ethynylarabinose) with acetate groups on positions $R^{1-4}$ (see formula I and II, infra), including 6-ethynyl-tetrahydro-2H-pyran-2,3,4,5-tetrayl tetraacetate, including the (2S,3S,4R,5R,6S) and (2R,3S,4R,5R,6S) isomers, and 5-((S)-1-hydroxyprop-2-ynyl)-tetrahydrofuran-2,3,4-triyl tetraacetate, including the (2S,3S,4R,5R) and (2R,3S,4R,5R) isomers, and the aldose form, unless otherwise indicated by context. The terms "alkynyl fucose triacetate", "alkynyl fucose diacetate" and "alkynyl fucose monoacetate" refer to the indicated tri-, di- and monoacetate forms of alkynyl fucose, respectively.

Unless otherwise indicated by context, the term "alkyl" refers to a substituted or unsubstituted saturated straight or branched hydrocarbon having from 1 to 20 carbon atoms (and all combinations and subcombinations of ranges and specific numbers of carbon atoms therein), with from 1 to 3, 1 to 8 or 1 to 10 carbon atoms being preferred. Examples of alkyl groups are methyl, ethyl, n-propyl, iso-propyl, n-butyl, iso-butyl, sec-butyl, tert-butyl, n-pentyl, 2-pentyl, 3-pentyl, 2-methyl-2-butyl, n-hexyl, n-heptyl, n-octyl, n-nonyl, n-decyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl, and 3,3-dimethyl-2-butyl.

Alkyl groups, whether alone or as part of another group, can be optionally substituted with one or more groups, preferably 1 to 3 groups (and any additional substituents selected from halogen), including, but not limited to: halogen, —O—($C_1$-$C_8$ alkyl), —O—($C_2$-$C_8$ alkenyl), —O—($C_2$-$C_8$ alkynyl), aryl, —C(O)R', —OC(O)R', —C(O)OR', —C(O)$NH_2$, —C(O)NHR', —C(O)N(R')$_2$, —NHC(O)R', —SR', —$SO_3$R', —S(O)$_2$R', —S(O)R', —OH, =O, —$NH_2$, —NH(R'), —N(R')$_2$ and —CN; where each R' is independently selected from —H, —$C_1$-$C_8$ alkyl, —$C_2$-$C_8$ alkenyl, —$C_2$-$C_8$ alkynyl, or aryl. In some embodiments, the —O—($C_1$-$C_8$ alkyl), —O—($C_2$-$C_8$ alkenyl), —O—($C_2$-$C_8$ alkynyl), aryl, and R' groups can be further substituted. Such further substituents include, for example, —$C_1$-$C_8$ alkyl, —$C_2$-$C_8$ alkenyl, —$C_2$-$C_8$ alkynyl, halogen, —O—($C_1$-$C_8$ alkyl), —O—($C_2$-$C_8$ alkenyl), —O—($C_2$-$C_8$ alkynyl), -aryl, —C(O)R", —OC(O)R", —C(O)OR", —C(O)$NH_2$, —C(O)NHR", —C(O)N(R")$_2$, —NHC(O)R", —SR", —$SO_3$R", —S(O)$_2$R", —S(O)R", —OH, —$NH_2$, —NH(R"), —N(R")$_2$ and —CN, where each R" is independently selected from H, —$C_1$-$C_8$ alkyl, —$C_2$-$C_8$ alkenyl, —$C_2$-$C_8$ alkynyl, or aryl wherein said further substituents are preferably unsubstituted. In some embodiments, the —O—($C_1$-$C_8$ alkyl), —O—($C_2$-$C_8$ alkenyl), —O—($C_2$-$C_8$ alkynyl), aryl, and R' groups are not further substituted.

Unless otherwise indicated by context, the terms "alkenyl" and "alkynyl" refer to substituted or unsubstituted straight and branched carbon chains having from 2 to 20 carbon atoms (and all combinations and subcombinations of ranges and specific numbers of carbon atoms therein), with from 2 to 3, 2 to 4, 2 to 8 or 2 to 10 carbon atoms being preferred. An alkenyl chain has at least one double bond in the chain and an alkynyl chain has at least one triple bond in the chain. Examples of alkenyl groups include, but are not limited to, ethylene or vinyl, allyl, -1 butenyl, -2 butenyl, -isobutylenyl, -1 pentenyl, -2 pentenyl, 3-methyl-1-butenyl, -2 methyl 2 butenyl, and -2,3 dimethyl 2 butenyl. Examples of alkynyl groups include, but are not limited to, acetylenic, propargyl, acetylenyl, propynyl, -1 butynyl, -2 butynyl, -1 pentynyl, -2 pentynyl, and -3 methyl 1 butynyl.

Alkenyl and alkynyl groups, whether alone or as part of another group, can be optionally substituted with one or more groups, preferably 1 to 3 groups (and any additional substituents selected from halogen), including but not limited to: halogen, —O—($C_1$-$C_8$ alkyl), —O—($C_2$-$C_8$ alkenyl), —O—($C_2$-$C_8$ alkynyl), -aryl, —C(O)R', —OC(O)R', —C(O)OR', —C(O)$NH_2$, —C(O)NHR', —C(O)N(R')$_2$, —NHC(O)R', —SR', —$SO_3$R', —S(O)$_2$R', —S(O)R', —OH, =O, —$NH_2$, —NH(R'), —N(R')$_2$ and —CN; where each R' is independently selected from H, —$C_1$-$C_8$ alkyl, —$C_2$—C alkenyl, —$C_2$-$C_8$ alkynyl, or aryl. In some embodiments, the —O—($C_1$-$C_8$ alkyl), —O—($C_2$-$C_8$ alkenyl), —O—($C_2$-$C_8$ alkynyl), aryl, and R' groups can be further substituted. Such further substituents include, for example, —$C_1$-$C_8$ alkyl, —$C_2$-$C_8$ alkenyl, —$C_2$-$C_8$ alkynyl, halogen, —O—($C_1$-$C_8$ alkyl), —O—($C_2$-$C_8$ alkenyl), —O—($C_2$-$C_8$ alkynyl), -aryl, —C(O)R", —OC(O)R", —C(O)OR", —C(O)$NH_2$, —C(O)NHR", —C(O)N(R")$_2$, —NHC(O)R", —SR", —$SO_3$R", —S(O)$_2$R", —S(O)R", —OH, —$NH_2$, —NH(R"), —N(R")$_2$ and —CN, where each R" is independently selected from H, —$C_1$-$C_8$ alkyl, —$C_2$-$C_8$ alkenyl, —$C_2$-$C_8$ alkynyl, or aryl, wherein said further substituents are preferably unsubstituted. In some embodiments, the —O—($C_1$-$C_8$ alkyl), —O—($C_2$-$C_8$ alkenyl), —O—($C_2$-$C_8$ alkynyl), -aryl, and R' groups are not further substituted.

Unless otherwise indicated by context, the term "alkylene" refers to a substituted or unsubstituted saturated branched or straight chain hydrocarbon radical having from 1 to 20 carbon atoms (and all combinations and subcombinations of ranges and specific numbers of carbon atoms therein), with from 1 to 8 or 1 to 10 carbon atoms being preferred and having two monovalent radical centers derived by the removal of two hydrogen atoms from the same or two different carbon atoms of a parent alkane. Typical alkylenes include, but are not limited to, methylene, ethylene, propylene, butylene, pentylene, hexylene, heptylene, ocytylene, nonylene, decalene, 1,4-cyclohexylene, and the like.

Alkylene groups, whether alone or as part of another group, can be optionally substituted with one or more groups, preferably 1 to 3 groups (and any additional substituents selected from halogen), including, but not limited to: halogen, —O—($C_1$-$C_8$ alkyl), —O—($C_2$-$C_8$ alkenyl), —O—($C_2$-$C_8$ alkynyl), -aryl, —C(O)R', —OC(O)R', —C(O)OR', —C(O)$NH_2$, —C(O)NHR', —C(O)N(R')$_2$, —NHC(O)R', —SR', —$SO_3$R', —S(O)$_2$R', —S(O)R', —OH, =O, —$NH_2$, —NH(R'), —N(R')$_2$ and —CN; where each R' is independently selected from H, —$C_1$-$C_8$ alkyl, —$C_2$-$C_8$ alkenyl, —$C_2$-$C_8$ alkynyl, or -aryl. In some embodiments, the —O—($C_1$-$C_8$ alkyl), —O—($C_2$-$C_8$ alkenyl), —O—($C_2$-$C_8$ alkynyl), aryl, and R' groups can be further substituted. Such further substituents include, for example, $C_1$-$C_8$ alkyl, —$C_2$-$C_8$ alkenyl, —$C_2$-$C_8$ alkynyl, halogen, —O—($C_1$-$C_8$ alkyl), —O—($C_2$-$C_8$ alkenyl), —O—($C_2$-$C_8$ alkynyl), -aryl, —C(O)R", —OC(O)R", —C(O)OR", —C(O)$NH_2$, —C(O)NHR", —C(O)N(R")$_2$, —NHC(O)R", —SR", —$SO_3$R", —S(O)$_2$R", —S(O)R", —OH, —$NH_2$, —NH(R"), —N(R")$_2$ and —CN, where each R" is independently selected from H, —$C_1$-$C_8$ alkyl, —$C_2$-$C_8$ alkenyl, —$C_2$-$C_8$ alkynyl, or aryl wherein said further substituents are preferably unsubstituted. In some embodiments, the —O—($C_1$-$C_8$ alkyl), —O—($C_2$-$C_8$ alkenyl), —O—($C_2$-$C_8$ alkynyl), -aryl, and R' groups are not further substituted.

Unless otherwise indicated by context, the term "aryl" refers to a substituted or unsubstituted monovalent aromatic hydrocarbon radical of 6-20 carbon atoms (and all combinations and subcombinations of ranges and specific numbers of carbon atoms therein) derived by the removal of one hydrogen atom from a single carbon atom of a parent aromatic ring system. Some aryl groups are represented in the exemplary structures as "Ar". Typical aryl groups include, but are not limited to, radicals derived from benzene, substituted benzene, phenyl, naphthalene, anthracene, biphenyl, and the like.

An aryl group, whether alone or as part of another group, can be optionally substituted with one or more, preferably 1 to 5, or even 1 to 2 groups including, but not limited to: halogen, —$C_1$-$C_8$ alkyl, —$C_2$-$C_8$ alkenyl, —$C_2$-$C_8$ alkynyl, —O—($C_1$-$C_8$ alkyl), —O—($C_2$-$C_8$ alkenyl), —O—($C_2$-$C_8$ alkynyl), -aryl, —C(O)R', —OC(O)R', —C(O)OR', —C(O)$NH_2$, —C(O)NHR', —C(O)N(R')$_2$, —NHC(O)R', —SR', —SO$_3$R', —S(O)$_2$R', —S(O)R', —OH, —NO$_2$, —NH$_2$, —NH(R'), —N(R')$_2$ and —CN; where each R' is independently selected from H, —C$_1$-C$_8$ alkyl, —C$_2$-C$_8$ alkenyl, —C$_2$-C$_8$ alkynyl, or aryl. In some embodiments, the C$_1$-C$_8$ alkyl, —C$_2$-C$_8$ alkenyl, —C$_2$-C$_8$ alkynyl, —O—(C$_1$-C$_8$ alkyl), —O—(C$_2$-C$_8$ alkenyl), —O—(C$_2$-C$_8$ alkynyl), aryl and R' groups can be further substituted. Such further substituents include, for example, —C$_1$-C$_8$ alkyl, —C$_2$-C$_8$ alkenyl, —C$_2$-C$_8$ alkynyl, halogen, —O—(C$_1$-C$_8$ alkyl), —O—(C$_2$-C$_8$ alkenyl), —O—(C$_2$-C$_8$ alkynyl), -aryl, —C(O)R", —OC(O)R", —C(O)OR", —C(O)NH$_2$, —C(O)NHR", —C(O)N(R")$_2$, —NHC(O)R", —SR", —SO$_3$R", —S(O)$_2$R", —S(O)R", —OH, —NH$_2$, —NH(R"), —N(R")$_2$ and —CN, where each R" is independently selected from —H, —C$_1$-C$_8$ alkyl, —C$_2$-C$_8$ alkenyl, —C$_2$-C$_8$ alkynyl, or aryl wherein said further substituents are preferably unsubstituted. In some embodiments, the —C$_1$-C$_8$ alkyl, —C$_2$-C$_8$ alkenyl, —C$_2$-C$_8$ alkynyl, —O—(C$_1$-C$_8$ alkyl), —O—(C$_2$-C$_8$ alkenyl), —O—(C$_2$-C$_8$ alkynyl), aryl and R' groups are not further substituted.

Unless otherwise indicated by context, the term "heterocycle" refers to a substituted or unsubstituted monocyclic ring system having from 3 to 7, or 3 to 10, ring atoms (also referred to as ring members) wherein at least one ring atom is a heteroatom selected from N, O, P, or S (and all combinations and subcombinations of ranges and specific numbers of carbon atoms and heteroatoms therein). The heterocycle can have from 1 to 4 ring heteroatoms independently selected from N, O, P, or S. One or more N, C, or S atoms in a heterocycle can be oxidized. A monocylic heterocycle preferably has 3 to 7 ring members (e.g., 2 to 6 carbon atoms and 1 to 3 heteroatoms independently selected from N, O, P, or S). The ring that includes the heteroatom can be aromatic or non-aromatic. Unless otherwise noted, the heterocycle is attached to its pendant group at any heteroatom or carbon atom that results in a stable structure.

Heterocycles are described in Paquette, "Principles of Modern Heterocyclic Chemistry" (W.A. Benjamin, New York, 1968), particularly Chapters 1, 3, 4, 6, 7, and 9; "The Chemistry of Heterocyclic Compounds, A series of Monographs" (John Wiley & Sons, New York, 1950 to present), in particular Volumes 13, 14, 16, 19, and 28; and J. Am. Chem. Soc. 82:5566 (1960).

Examples of "heterocycle" groups include by way of example and not limitation pyridyl, dihydropyridyl, tetrahydropyridyl (piperidyl), thiazolyl, pyrimidinyl, furanyl, thienyl, pyrrolyl, pyrazolyl, imidazolyl, tetrazolyl, fucosyl, azirdinyl, azetidinyl, oxiranyl, oxetanyl, and tetrahydrofuranyl.

A heterocycle group, whether alone or as part of another group, can be optionally substituted with one or more groups, preferably 1 to 2 groups, including but not limited to: —C$_1$-C$_8$ alkyl, —C$_2$-C$_8$ alkenyl, —C$_2$-C$_8$ alkynyl, halogen, —O—(C$_1$-C$_8$ alkyl), —O—(C$_2$-C$_8$ alkenyl), —O—(C$_2$-C$_8$ alkynyl), -aryl, —C(O)R', —OC(O)R', —C(O)OR', —C(O)NH$_2$, —C(O)NHR', —C(O)N(R')$_2$, —NHC(O)R', —SR', —SO$_3$R', —S(O)$_2$R', —S(O)R', —OH, —NH$_2$, —NH(R'), —N(R')$_2$ and —CN; where each R' is independently selected from H, —C$_1$-C$_8$ alkyl, —C$_2$-C$_8$ alkenyl, —C$_2$-C$_8$ alkynyl, or -aryl. In some embodiments, the O—(C$_1$-C$_8$ alkyl), —O—(C$_2$-C$_8$ alkenyl), —O—(C$_2$-C$_8$ alkynyl), —C$_1$-C$_8$ alkyl, —C$_2$-C$_8$ alkenyl, —C$_2$-C$_8$ alkynyl, aryl, and R' groups can be further substituted. Such further substituents include, for example, —C$_1$-C$_8$ alkyl, —C$_2$-C$_8$ alkenyl, —C$_2$-C$_8$ alkynyl, halogen, —O—(C$_1$-C$_8$ alkyl), —O—(C$_2$-C$_8$ alkenyl), —O—(C$_2$-C$_8$ alkynyl), -aryl, —C(O)R", —OC(O)R", —C(O)OR", —C(O)NH$_2$, —C(O)NHR", —C(O)N(R")$_2$, —NHC(O)R", —SR", —SO$_3$R", —S(O)$_2$R", —S(O)R", —OH, —NH$_2$, —NH(R"), —N(R")$_2$ and —CN, where each R" is independently selected from H, —C$_1$-C$_8$ alkyl, —C$_2$-C$_8$ alkenyl, —C$_2$-C$_8$ alkynyl, or aryl wherein said further substituents are preferably unsubstituted. In some embodiments, the —O—(C$_1$-C$_8$ alkyl), —O—(C$_2$-C$_8$ alkenyl), —O—(C$_2$-C$_8$ alkynyl), —C$_1$-C$_8$ alkyl, —C$_2$-C$_8$ alkenyl, —C$_2$-C$_8$ alkynyl, aryl, and R' groups are not substituted.

By way of example and not limitation, carbon-bonded heterocycles can be bonded at the following positions: position 2, 3, 4, 5, or 6 of a pyridine; position 3, 4, 5, or 6 of a pyridazine; position 2, 4, 5, or 6 of a pyrimidine; position 2, 3, 5, or 6 of a pyrazine; position 2, 3, 4, or 5 of a furan, tetrahydrofuran, thiofuran, thiophene, pyrrole or tetrahydropyrrole; position 2, 4, or 5 of an oxazole, imidazole or thiazole; position 3, 4, or 5 of an isoxazole, pyrazole, or isothiazole; position 2 or 3 of an aziridine; position 2, 3, or 4 of an azetidine. Exemplary carbon bonded heterocycles can include 2-pyridyl, 3-pyridyl, 4-pyridyl, 5-pyridyl, 6-pyridyl, 3-pyridazinyl, 4-pyridazinyl, 5-pyridazinyl, 6-pyridazinyl, 2-pyrimidinyl, 4-pyrimidinyl, 5-pyrimidinyl, 6-pyrimidinyl, 2-pyrazinyl, 3-pyrazinyl, 5-pyrazinyl, 6-pyrazinyl, 2-thiazolyl, 4-thiazolyl, or 5-thiazolyl.

By way of example and not limitation, nitrogen bonded heterocycles can be bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, or 1H-indazole; position 2 of a isoindole, or isoindoline; and position 4 of a morpholine. Still more typically, nitrogen bonded heterocycles include 1-aziridyl, 1-azetidyl, 1-pyrrolyl, 1-imidazolyl, 1-pyrazolyl, and 1-piperidinyl.

Unless otherwise noted, the term "carbocycle," refers to a substituted or unsubstituted, saturated or unsaturated non-aromatic monocyclic ring system having from 3 to 6 ring atoms (and all combinations and subcombinations of ranges and specific numbers of carbon atoms therein) wherein all of the ring atoms are carbon atoms.

Carbocycle groups, whether alone or as part of another group, can be optionally substituted with, for example, one or more groups, preferably 1 or 2 groups (and any additional substituents selected from halogen), including, but not limited to: halogen, C$_1$-C$_8$ alkyl, —C$_2$-C$_8$ alkenyl, —C$_2$-C$_8$ alkynyl, —O—(C$_1$-C$_8$ alkyl), —O—(C$_2$-C$_8$ alkenyl), —O—(C$_2$-C$_8$ alkynyl), aryl, —C(O)R', —OC(O)R', —C(O)OR', —C(O)NH$_2$, —C(O)NHR', —C(O)N(R')$_2$, —NHC(O)R', —SR', —SO$_3$R', —S(O)$_2$R', —S(O)R', —OH, =O, —NH$_2$, —NH(R'), —N(R')$_2$ and —CN; where each R' is independently selected from H, —C$_1$-C$_8$ alkyl, —C$_2$-C$_8$ alkenyl, —C$_2$-C$_8$ alkynyl, or aryl. In some embodiments, the —C$_1$-C$_8$ alkyl, —C$_2$-C$_8$ alkenyl, —C$_2$-C$_8$ alkynyl, —O—(C$_1$-C$_8$ alkyl), —O—(C$_2$-C$_8$ alkenyl), —O—(C$_2$-C$_8$ alkynyl), -aryl and R' groups can be further substituted. Such further substituents include, for example, —C$_1$-C$_8$ alkyl, —C$_2$-C$_8$ alkenyl, —C$_2$-C$_8$ alkynyl, halogen, —O—(C$_1$-C$_8$ alkyl), —O—(C$_2$-C$_8$ alkenyl), —O—(C$_2$-C$_8$ alkynyl), -aryl, —C(O)R", —OC(O)R", —C(O)OR", —C(O)NH$_2$, —C(O)NHR", —C(O)N(R")$_2$, —NHC(O)R", —SR", —SO$_3$R", —S(O)$_2$R", —S(O)R", —OH, —NH$_2$, —NH(R"), —N(R")$_2$ and —CN, where each R" is independently selected from H, —C$_1$-C$_8$ alkyl, —C$_2$-C$_8$ alkenyl, —C$_2$-C$_8$ alkynyl, or aryl wherein said further substituents are preferably unsubstituted. In some embodiments, the —C$_1$-C$_8$ alkyl, —C$_2$-C$_8$ alkenyl, —$C_2$-$C_8$ alkynyl, —O—($C_1$-$C_8$ alkyl), —O—($C_2$-$C_8$ alkenyl), —O—($C_2$-$C_8$ alkynyl), aryl and R' groups are not substituted.

Examples of monocyclic carbocyclic substituents include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, cycloheptyl, cyclooctyl, -1,3-cyclohexadienyl, -1,4-cyclohexadienyl, -1,3-cycloheptadienyl, -1,3,5-cycloheptatrienyl, and -cyclooctadienyl.

When any variable occurs more than one time in any constituent or in any formula, its definition in each occurrence is independent of its definition at every other. Combinations of substituents and/or variables are permissible only if such combinations result in stable compounds.

Unless otherwise indicated by context, a hyphen (-) designates the point of attachment to the pendant molecule. Accordingly, the term "—($C_1$-$C_{10}$ alkylene)aryl" or "—$C_1$-$C_{10}$ alkylene(aryl)" refers to a $C_1$-$C_{10}$ alkylene radical as defined herein wherein the alkylene radical is attached to the pendant molecule at any of the carbon atoms of the alkylene radical and one of the hydrogen atom bonded to a carbon atom of the alkylene radical is replaced with an aryl radical as defined herein.

When a particular group is "substituted", that group may have one or more substituents, preferably from one to five substituents, more preferably from one to three substituents, most preferably from one to two substituents, independently selected from the list of substituents. The group can, however, generally have any number of substituents selected from halogen.

It is intended that the definition of any substituent or variable at a particular location in a molecule be independent of its definitions elsewhere in that molecule. It is understood that substituents and substitution patterns on the compounds of this invention can be selected by one of ordinary skill in the art to provide compounds that are chemically stable and that can be readily synthesized by techniques known in the art as well as those methods set forth herein.

The term "pharmaceutically acceptable" means approved by a regulatory agency of the Federal or a state government or listed in the U.S. Pharmacopeia or other generally recognized pharmacopeia for use in animals, and more particularly in humans. The term "pharmaceutically compatible ingredient" refers to a pharmaceutically acceptable diluent, adjuvant, excipient, or vehicle with which the antibody or antibody derivative is administered.

The term "biologically acceptable" means suitable for use in the culture of cell lines for the manufacture of antibodies. Exemplary biologically acceptable salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate, ethanesulfonate, benzenesulfonate, p-toluenesulfonate, and pamoate (i.e., 1,1'-methylene bis-(2 hydroxy 3-naphthoate)) salts. A biologically acceptable salt may involve the inclusion of another molecule such as an acetate ion, a succinate ion or other counterion. The counterion may be any organic or inorganic moiety that stabilizes the charge on the parent compound. Furthermore, a biologically acceptable salt may have more than one charged atom in its structure. Instances where multiple charged atoms are part of the biologically acceptable salt can have multiple counter ions. Hence, a biologically salt can have one or more charged atoms and/or one or more counterion.

A "biologically acceptable solvate" or "solvate" refer to an association of one or more solvent molecules and a fucose analog. Examples of solvents that form biologically acceptable solvates include, but are not limited to, water, isopropanol, ethanol, methanol, DMSO, ethyl acetate, acetic acid, and ethanolamine.

"Small electron-withdrawing groups" refers to any substituent that has greater electronegativity at the site of substituent attachment than, e.g., a hydrogen atom or hydroxy group or relative to the substituent present in fucose at that site. Generally, the small electron-withdrawing group has 10 or fewer atoms (other than hydrogen) and includes groups such as nitro; cyano and cyanoalkyl (e.g., —$CH_2CH_2CN$); halogen; acetylene or other alkynes or halo alkynes (e.g., —C≡$CCF_3$); alkenes or halo alkenes; allenes; carboxylic acids, ester, amides and halo substituted forms thereof; sulfonic and phosphonic acids, esters and amides, and halo substituted forms thereof; haloalkyl groups (e.g., —$CF_3$, —$CHF_2$, —$CH_2CF_3$), acyl and haloacyl groups (e.g., —C(O)$CH_3$ and —C(O)$CF_3$); alkylsulfonyl and haloalkylsulfonyl (e.g., —S(O)$_2$alkyl and —S(O)$_2$haloalkyl); aryloxy (e.g, phenoxy and substituted phenoxy); aralkyloxy (e.g, benzyloxy and substituted benzyloxy); and oxiranes. Preferred small electron-withdrawing groups are those having 8, 7 or 6 or fewer atoms (other than hydrogen).

Therapeutic agents of the invention are typically substantially pure from undesired contaminant. This means that an agent is typically at least about 50% w/w (weight/weight) purity, as well as being substantially free from interfering proteins and contaminants. Sometimes the agents are at least about 80% w/w and, more preferably at least 90% or about 95% w/w purity. Using conventional protein purification techniques, homogeneous peptides of at least 99% w/w can be obtained.

General

The invention provides compositions and methods for preparing antibodies and antibody derivatives with reduced core fucosylation. The methods are premised in part on the unexpected results presented in the Examples showing that culturing host cells, expressing an antibody or antibody derivative of interest, in culture media comprising a fucose analog produces an antibody or antibody derivative having reduced core fucosylation. As used herein, "core fucosylation" refers to addition of fucose ("fucosylation") to N-acetylglucosamine ("GlcNAc") at the reducing terminal of an N-linked glycan. Also provided are antibodies and antibody derivatives produced by such methods. In other aspects, fucose analogs and culture media comprising an effective amount of a fucose analog(s) are provided.

In some embodiments, fucosylation of complex N-glycoside-linked sugar chains bound to the Fc region (or domain) is reduced. As used herein, a "complex N-glycoside-linked sugar chain" is typically bound to asparagine 297 (according to the number of Kabat), although a complex N-glycoside linked sugar chain can also be linked to other asparagine residues. As used herein, the complex N-glycoside-linked sugar chain has a bianntennary composite sugar chain, mainly having the following structure:

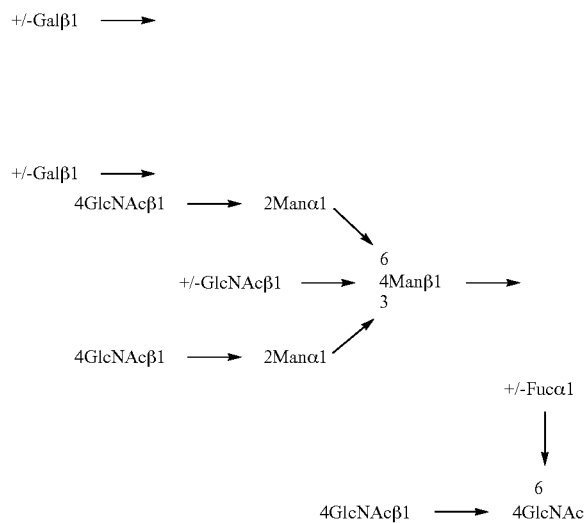

where ± indicates the sugar molecule can be present or absent, and the numbers indicate the position of linkages between the sugar molecules. In the above structure, the sugar chain terminal which binds to asparagine is called a reducing terminal (at right), and the opposite side is called a non-reducing terminal. Fucose is usually bound to N-acetylglucosamine ("GlcNAc") of the reducing terminal, typically by an α1,6 bond (the 6-position of GlcNAc is linked to the 1-position of fucose). "Gal" refers to galactose, and "Man" refers to mannose.

A "complex N-glycoside-linked sugar chain" excludes a high mannose type of sugar chain, in which only mannose is incorporated at the non-reducing terminal of the core structure, but includes 1) a complex type, in which the non-reducing terminal side of the core structure has one or more branches of galactose-N-acetylglucosamine (also referred to as "gal-GlcNAc") and the non-reducing terminal side of Gal-GlcNAc optionally has a sialic acid, bisecting N-acetylglucosamine or the like; or 2) a hybrid type, in which the non-reducing terminal side of the core structure has both branches of the high mannose N-glycoside-linked sugar chain and complex N-glycoside-linked sugar chain.

In some embodiments, the "complex N-glycoside-linked sugar chain" includes a complex type in which the non-reducing terminal side of the core structure has zero, one or more branches of galactose-N-acetylglucosamine (also referred to as "gal-GlcNAc") and the non-reducing terminal side of Gal-GlcNAc optionally further has a structure such as a sialic acid, bisecting N-acetylglucosamine or the like.

According to the present methods, typically only a minor amount of fucose is incorporated into the complex N-glycoside-linked sugar chain(s). For example, in various embodiments, less than about 60%, less than about 50%, less than about 40%, less than about 30%, less than about 20%, less than about 15%, less than about 10%, less than about 5%, or less than about 1% of the antibody or antibody derivative has core fucosylation by fucose. In some embodiments, substantially none (i.e., less than 0.5%) of the antibody or antibody derivative has core fucosylation by fucose.

In certain embodiments, only a minor amount of a fucose analog (or a metabolite or product of the fucose analog) is incorporated into the complex N-glycoside-linked sugar chain(s). For example, in various embodiments, less than about 40%, less than about 30%, less than about 20%, less than about 15%, less than about 10%, less than about 5%, or less than about 1% of the antibody or antibody derivative has core fucosylation by a fucose analog or a metabolite or product of the fucose analog. In some embodiments, substantially none (i.e., less than 0.5%) of the antibody or antibody derivative has core fucosylation by a fucose analog or a metabolite or product of the fucose analog.

Fucose Analogs

In one aspect, fucose analogs are described that reduce the incorporation of fucose into complex N-glycoside-linked sugar chains of antibodies or antibody derivatives produced by host cells. Suitable fucose analogs (identified below as Formula I, II, III, IV, V and VI) are those that can be added to the host cell culture media and that inhibit core fucosylation of complex N-glycoside-linked sugar chains of antibodies or antibody derivatives. The fucose analog is typically taken up by host cells (e.g., by active transport or passive diffusion).

In some embodiments, a fucose analog (or an intracellular metabolite or product of the fucose analog) inhibits an enzyme(s) in the fucose salvage pathway. (As used herein, an intracellular metabolite can be, for example, a GDP-modified analog or a fully or partially de-esterified analog. A product can be, for example, a fully or partially de-esterified analog.) For example, a fucose analog (or an intracellular metabolite or product of the fucose analog) can inhibit the activity of fucokinase, or GDP-fucose-pyrophosphorylase. In some embodiments, a fucose analog (or an intracellular metabolite or product of the fucose analog) inhibits fucosyltransferase (preferably a 1,6-fucosyltransferase, e.g., the FUT8 protein). In some embodiments, a fucose analog (or an intracellular metabolite or product of the fucose analog) can inhibit the activity of an enzyme in the de novo synthetic pathway for fucose. For example, a fucose analog (or an intracellular metabolite or product of the fucose analog) can inhibit the activity of GDP-mannose 4,6-dehydratase or/or GDP-fucose synthetase. In some embodiments, the fucose analog (or an intracellular metabolite or product of the fucose analog) can inhibit a fucose transporter (e.g., GDP-fucose transporter).

In some embodiments, the fucose analog has the following formula (I) or (II):

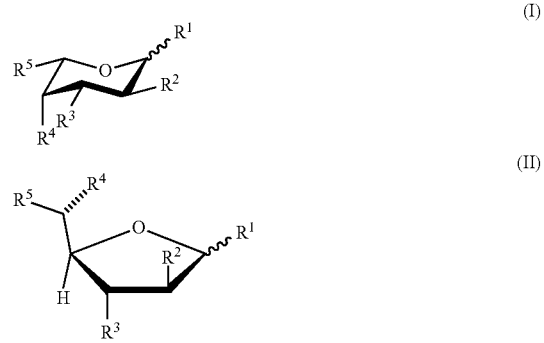

or a biologically acceptable salt or solvate of the analog, wherein each of formula (I) or (II) can be the alpha or beta anomer or the corresponding aldose form. In the above formulae, each of $R^1$-$R^4$ is independently selected from the group consisting of —OH, —OC(O)H, —OC(O)$C_1$-$C_{10}$ alkyl, —OC(O)$C_2$-$C_{10}$ alkenyl, —OC(O)$C_2$-$C_{10}$ alkynyl, —OC(O)aryl, —OC(O)heterocycle, —OC(O)$C_1$-$C_{10}$ alkylene aryl, —OC(O)$C_2$-$C_{10}$ alkenylene aryl, —OC(O)

$C_2$-$C_{10}$ alkynylene aryl, —OC(O)$C_2$-$C_{10}$ alkylene heterocycle, —OC(O)$C_2$-$C_{10}$ alkenylene heterocycle, —OC(O)$C_2$-$C_{10}$ alkynylene heterocycle, —OC(O)$CH_2$O$(CH_2CH_2O)_n$ $CH_3$, —OC(O)$CH_2CH_2$O$(CH_2CH_2O)_n$$CH_3$, —O-tri-$C_1$-$C_3$ alkyl silyl, —O$C_1$-$C_{10}$ alkyl, —O$CH_2$OC(O) alkyl, —O$CH_2$OC(O) alkenyl, —O$CH_2$OC(O) alkynyl, —O$CH_2$OC(O) aryl, —O$CH_2$OC(O) heterocycle, —O$CH_2$OC(O)O alkyl, —O$CH_2$OC(O)O alkenyl, —O$CH_2$OC(O)O alkynyl, —O$CH_2$OC(O)O aryl and —O$CH_2$OC(O)O heterocycle, wherein each n is an integer independently selected from 0-5; and $R^5$ is selected from the group consisting of —C≡CH, —C≡$CCH_3$, —$CH_2$C≡CH, —C(O)O$CH_3$, —CH(OAc)$CH_3$, —CN, —$CH_2$CN, —$CH_2$X (wherein X is Br, Cl or I), and methoxiran.

In some embodiments, the fucose analog has formula (I) or (II), wherein:
each of $R^1$-$R^4$ is independently selected from the group consisting of —OH, —OC(O)H, —OC(O)$C_1$-$C_{10}$ alkyl, —OC(O)aryl, —OC(O)heterocycle, —OC(O)$C_1$-$C_{10}$ alkylene aryl, —OC(O)$C_1$-$C_{10}$ alkylene heterocycle, —OC(O)$CH_2$O$(CH_2CH_2O)_n$$CH_3$, —OC(O)$CH_2CH_2$O$(CH_2CH_2O)_n$$CH_3$, —O-tri-$C_1$-$C_3$ silyl, —O$C_1$-$C_{10}$ alkyl, —O$CH_2$OC(O) alkyl, —O$CH_2$OC(O)O alkyl, —O$CH_2$OC(O) aryl, and —O$CH_2$OC(O)O aryl, wherein each n is an integer independently selected from 0-5; and $R^5$ is selected from the group consisting of —C≡CH, —C≡$CCH_3$, —$CH_2$C≡CH, —C(O)O$CH_3$, —CH(OAc)$CH_3$, —CN, —$CH_2$CN, —$CH_2$X (wherein X is Br, Cl or I), and methoxiran.

In some embodiments, the fucose analog has formula (I) or (II), wherein each of $R^1$-$R^4$ is independently selected from the group consisting of —OH, —OC(O)H, —OC(O)$C_1$-$C_{10}$ alkyl, —OC(O)$C_2$-$C_{10}$ alkenyl, —OC(O)$C_2$-$C_{10}$ alkynyl, —OC(O)aryl, —OC(O)heterocycle, —OC(O)$C_1$-$C_{10}$ alkylene aryl, —OC(O)$C_2$-$C_{10}$ alkenylene aryl, —OC(O)$C_2$-$C_{10}$ alkynylene aryl, —OC(O)$C_2$-$C_{10}$ alkylene heterocycle, —OC(O)$C_2$-$C_{10}$ alkenylene heterocycle, and —OC(O)$C_2$-$C_{10}$ alkynylene heterocycle; and $R^5$ is selected from the group consisting of —C≡CH, —C≡$CCH_3$, —$CH_2$C≡CH, —C(O)O$CH_3$, —CH(OAc)$CH_3$, —CN, —$CH_2$CN, —$CH_2$X (wherein X is Br, Cl or I), and methoxiran.

In some embodiments, the fucose analog has formula (I) or (II), wherein each of $R^1$-$R^4$ is independently selected from the group consisting of —O-tri-$C_1$-$C_3$ silyl and —OC1-$C_{10}$ alkyl; and $R^5$ is selected from the group consisting of —C≡CH, —C≡$CCH_3$, —$CH_2$C≡CH, —C(O)O$CH_3$, —CH(OAc)$CH_3$, —CN, —$CH_2$CN, —$CH_2$X (wherein X is Br, Cl or I), and methoxiran.

In some embodiments, the fucose analog has formula (I) or (II), wherein each of $R^1$-$R^4$ is independently selected from the group consisting of —O$CH_2$OC(O) alkyl, —O$CH_2$OC(O) alkenyl, —O$CH_2$OC(O) alkynyl, —O$CH_2$OC(O) aryl, —O$CH_2$OC(O) heterocycle, —O$CH_2$OC(O)O alkyl, —O$CH_2$OC(O)O alkenyl, —O$CH_2$OC(O)O alkynyl, —O$CH_2$OC(O)O aryl, and —O$CH_2$OC(O)O heterocycle; and $R^5$ is selected from the group consisting of —C≡CH, —C≡$CCH_3$, —$CH_2$C≡CH, —C(O)O$CH_3$, —CH(OAc)$CH_3$, —CN, —$CH_2$CN, —$CH_2$X (wherein X is Br, Cl or I), and methoxiran.

In some embodiments, the fucose analog has formula (I) or (II), wherein each of $R^1$-$R^4$ is independently selected from the group consisting of —OH, —OC(O)H, —OC(O)$C_1$-$C_{10}$ alkyl, —OC(O)$C_2$-$C_{10}$ alkenyl, —OC(O)$C_2$-$C_{10}$ alkynyl, —OC(O)aryl, —OC(O)heterocycle, —OC(O)$C_1$-$C_{10}$ alkylene aryl, —OC(O)$C_2$-$C_{10}$ alkenylene aryl, —OC(O)$C_2$-$C_{10}$ alkynylene aryl, —OC(O)$C_2$-$C_{10}$ alkylene heterocycle, —OC(O)$C_2$-$C_{10}$ alkenylene heterocycle, and —OC(O)$C_2$-$C_{10}$ alkynylene heterocycle; and $R^5$ is selected from the group consisting of —C≡CH, —C≡$CCH_3$, —$CH_2$C≡CH, —C(O)O$CH_3$, —CH(OAc)$CH_3$, —CN, —$CH_2$CN, and methoxiran.

In some embodiments, the fucose analog has formula (I) or (II), wherein each of $R^1$-$R^4$ is independently selected from the group consisting of —OH, —OC(O)H, —OC(O)$C_1$-$C_{10}$ alkyl, —OC(O)$C_2$-$C_{10}$ alkenyl, —OC(O)$C_2$-$C_{10}$ alkynyl, —OC(O)aryl, —OC(O)heterocycle, —OC(O)$C_1$-$C_{10}$ alkylene aryl, —OC(O)$C_2$-$C_{10}$ alkenylene aryl, —OC(O)$C_2$-$C_{10}$ alkynylene aryl, —OC(O)$C_2$-$C_{10}$ alkylene heterocycle, —OC(O)$C_2$-$C_{10}$ alkenylene heterocycle, and —OC(O)$C_2$-$C_{10}$ alkynylene heterocycle; and $R^5$ is selected from the group consisting of —$CH_2$I, —$CH_2$Br, and —$CH_2$Cl.

In some embodiments, the fucose analog has formula (I) or (II), wherein each of $R^1$-$R^4$ is independently selected from the group consisting of —OH, —OC(O)H, —OC(O)$C_1$-$C_{10}$ alkyl, —OC(O)$C_2$-$C_{10}$ alkenyl, —OC(O)$C_2$-$C_{10}$ alkynyl, —OC(O)aryl, —OC(O)heterocycle, —OC(O)$C_1$-$C_{10}$ alkylene aryl, —OC(O)$C_2$-$C_{10}$ alkenylene aryl, —OC(O)$C_2$-$C_{10}$ alkynylene aryl, —OC(O)$C_2$-$C_{10}$ alkylene heterocycle, —OC(O)$C_2$-$C_{10}$ alkenylene heterocycle, and —OC(O)$C_2$-$C_{10}$ alkynylene heterocycle; and $R^5$ is selected from the group consisting of —C≡CH, —C≡$CCH_3$ and —$CH_2$C≡CH.

In some embodiments, the fucose analog has formula (I) or (II), wherein each of $R^1$-$R^4$ is independently selected from the group consisting of —OH, —OC(O)H, —OC(O)$C_1$-$C_{10}$ alkyl, —OC(O)$C_2$-$C_{10}$ alkenyl, —OC(O)$C_2$-$C_{10}$ alkynyl, —OC(O)aryl, —OC(O)heterocycle, —OC(O)$C_1$-$C_{10}$ alkylene aryl, —OC(O)$C_2$-$C_{10}$ alkenylene aryl, —OC(O)$C_2$-$C_{10}$ alkynylene aryl, —OC(O)$C_2$-$C_{10}$ alkylene heterocycle, —OC(O)$C_2$-$C_{10}$ alkenylene heterocycle, and —OC(O)$C_2$-$C_{10}$ alkynylene heterocycle; and $R^5$ is selected from the group consisting of —C≡CH, —C≡$CCH_3$, —$(CH_2)_n$(CN) (where n=0 or 1) and —CO(O)$CH_3$.

In some embodiments, the fucose analog has formula (I) or (II), wherein each of $R^1$-$R^4$ is independently selected from the group consisting of —OH, —OC(O)H, —OC(O)$C_1$-$C_{10}$ alkyl, —OC(O)$C_2$-$C_{10}$ alkenyl, —OC(O)$C_2$-$C_{10}$ alkynyl, —OC(O)aryl, —OC(O)heterocycle, —OC(O)$C_1$-$C_{10}$ alkylene aryl, —OC(O)$C_2$-$C_{10}$ alkenylene aryl, —OC(O)$C_2$-$C_{10}$ alkynylene aryl, —OC(O)$C_2$-$C_{10}$ alkylene heterocycle, —OC(O)$C_2$-$C_{10}$ alkenylene heterocycle, and —OC(O)$C_2$-$C_{10}$ alkynylene heterocycle; and $R^5$ is selected from the group consisting of —C≡CH, —C≡$CCH_3$, —$CH_2$CN and —CO(O)$CH_3$.

In some embodiments, the fucose analog has formula (I) or (II), wherein each of $R^1$-$R^4$ is independently selected from the group consisting of —OH, —OC(O)H, —OC(O)$C_1$-$C_{10}$ alkyl, —OC(O)$C_2$-$C_{10}$ alkenyl, —OC(O)$C_2$-$C_{10}$ alkynyl, —OC(O)aryl, —OC(O)heterocycle, —OC(O)$C_1$-$C_{10}$ alkylene aryl, —OC(O)$C_2$-$C_{10}$ alkenylene aryl, —OC(O)$C_2$-$C_{10}$ alkynylene aryl, —OC(O)$C_2$-$C_{10}$ alkylene heterocycle, —OC(O)$C_2$-$C_{10}$ alkenylene heterocycle, and —OC(O)$C_2$-$C_{10}$ alkynylene heterocycle; and $R^5$ is selected from the group consisting of —C≡CH, —C≡$CCH_3$, —CH(OAc)$CH_3$, —$CH_2$CN, and —CO(O)$CH_3$.

In some embodiments, the fucose analog has formula (I) or (II), wherein $R^5$ is as defined herein, and each of $R^1$-$R^4$ is other than hydroxyl.

In some embodiments, the fucose analog has formula (I) or (II), wherein each of $R^1$-$R^4$ is independently selected from the group consisting of —OH, and —OAc; and $R^5$ is selected from the group consisting of —C≡CH, —C≡$CCH_3$, —CH(OAc)$CH_3$, —$CH_2$CN, and —CO(O)$CH_3$.

In some embodiments, the fucose analog has formula (I) or (II), wherein each of $R^1$-$R^4$ is —OH or an ester selected from the group consisting of —OC(O)H, —OC(O)$C_1$-$C_{10}$ alkyl, —OC(O)$C_2$-$C_{10}$ alkenyl, —OC(O)$C_2$-$C_{10}$ alkynyl, —OC(O)aryl, —OC(O)heterocycle, —OC(O)$C_1$-$C_{10}$ alkylene aryl, —OC(O)$C_2$-$C_{10}$ alkenylene aryl, —OC(O)$C_2$-$C_{10}$ alkynylene aryl, —OC(O)$C_1$-$C_{10}$ alkylene heterocycle, —OC(O)$C_2$-$C_{10}$ alkenylene heterocycle, —OC(O)$C_2$-$C_{10}$ alkynylene heterocycle, —OC(O)$CH_2$O($CH_2CH_2O)_n$ $CH_3$ (where n is 0-5), and —OC(O)$CH_2CH_2$O($CH_2CH_2O)_n$$CH_3$ (where n is 0-5); and $R^5$ is selected from the group consisting of —C≡CH, —C≡$CCH_3$, —$CH_2$C≡CH, —C(O)$OCH_3$, —CH(OAc)$CH_3$, —CN, —$CH_2$CN, —$CH_2$X (wherein X is Br, Cl or I), and methoxiran.

In some embodiments, the fucose analog has a molecular weight of less than 2000 daltons. In some embodiments, the fucose analog has a molecular weight of less than 1000 daltons.

In some embodiments, $R^5$ is not substituted.

In some embodiments, each of $R^1$-$R^4$ is not substituted.

In some embodiments, $R^5$ is not a ketone (—C(O)alkyl).

In some embodiments, $R^5$ is not —CH$CH_3$OAc.

In some embodiments, $R^5$ is not —CH$CH_3$OAc, when each of $R^1$-$R^4$ is —OAc.

In some embodiments, $R^5$ is not —C≡$CH_3$.

In some embodiments, $R^5$ is not —C≡$CH_3$, when any of $R^1$-$R^4$ is —OAc.

In some embodiments, $R^5$ is not —C≡$CH_3$, when any of $R^1$-$R^4$ is —OC(O)alkyl.

In some embodiments, $R^5$ is not —C≡$CH_3$, when each of $R^1$-$R^4$ is —OC(O)alkyl.

In some embodiments, $R^5$ is not —C≡$CH_3$, when each of $R^1$-$R^4$ is OH.

In some embodiments, the fucose analog is alkynyl fucose peracetate. In some embodiments, the fucose analog is alkynyl fucose triacetate. In some embodiments, the fucose analog is alkynyl fucose diacetate. In some embodiments, the fucose analog is mixture of alkynyl fucose peracetate, alkynyl fucose triacetate and alkynyl fucose diacetate.

In some embodiments, the fucose analog is mixture of alkynyl fucose peracetate, alkynyl fucose triacetate, alkynyl fucose diacetate and alkynyl fucose monoacetate.

In any of the various embodiments, the fucose analog is not fucose. In some embodiments, the fucose analog is not alkynyl fucose peracetate. In some embodiments, the fucose analog is not galactose or L-galactose.

In another group of embodiments, the fucose analog has the following formula (III) or (IV):

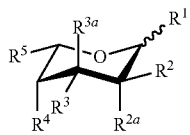

(III)

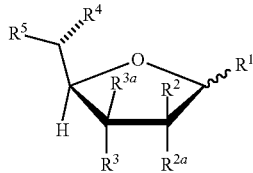

(IV)

or a biologically acceptable salt or solvate thereof, wherein each of formula (III) or (IV) can be the alpha or beta anomer or the corresponding aldose form; and wherein, each of $R^1$-$R^4$ is independently selected from the group consisting of fluoro, chloro, —OH, —OC(O)H, —OC(O)$C_1$-$C_{10}$ alkyl, —OC(O)$C_2$-$C_{10}$ alkenyl, —OC(O)$C_2$-$C_{10}$ alkynyl, —OC(O)aryl, —OC(O)heterocycle, —OC(O)$C_1$-$C_{10}$ alkylene(aryl), —OC(O)$C_2$-$C_{10}$ alkylene(aryl), —OC(O)$C_2$-$C_{10}$ alkynyl(aryl), —OC(O)$C_1$-$C_{10}$ alkylene heterocycle, —OC(O)$C_2$-$C_{10}$ alkenylene(heterocycle), —OC(O)$C_2$-$C_{10}$ alkynyl heterocycle, —O$CH_2$OC(O) alkyl, —O$CH_2$OC(O)O alkyl; —O$CH_2$OC(O) aryl, —O$CH_2$OC(O)O aryl, —OC(O)$CH_2$O($CH_2CH_2O)_n$$CH_3$, —OC(O)$CH_2CH_2$O($CH_2CH_2O)_n$$CH_3$, —O-tri-$C_1$-$C_3$ alkylsilyl and —O$C_1$-$C_{10}$ alkyl, wherein each n is an integer independently selected from 0-5; and each of $R^{2a}$ and $R^{3a}$ is independently selected from the group consisting of H, F and Cl;

$R^5$ is selected from the group consisting of —$CH_3$, —$CHF_2$, —CH=C=$CH_2$, —C≡CH, —C≡$CCH_3$, —$CH_2$C≡CH, —C(O)$OCH_3$, —CH(OAc)$CH_3$, —CN, —$CH_2$CN, —$CH_2$X (wherein X is Br, Cl or I), and methoxiran;

wherein when $R^5$ is other than —CH=C=$CH_2$ or —$CHF_2$, at least one of $R^1$, $R^2$, $R^3$, $R^{2a}$ and $R^{3a}$ is fluoro or chloro.

In some embodiments of formulae (III) or (IV), $R^1$ is F.

In some embodiments of formulae (III) or (IV), $R^2$ is F.

In some embodiments of formulae (III) or (IV), $R^3$ is F.

In some embodiments of formulae (III) or (IV), $R^1$ and $R^2$ are each F.

In some embodiments of formulae (III) or (IV), $R^2$ and $R^{2a}$ are each F.

In some embodiments of formulae (III) or (IV), $R^1$, $R^3$ and $R^4$ are each independently selected from —OH and —OAc; $R^2$ is F; and $R^5$ is —$CH_3$.

In some embodiments of formulae (III) or (IV), $R^1$, $R^3$ and $R^4$ are each independently selected from —OH and —OAc; $R^2$ is F; $R^{2a}$ and $R^{3a}$ are each H; and $R^5$ is —$CH_3$.

In another group of embodiments, the fucose analog has the following formula (V) or (VI):

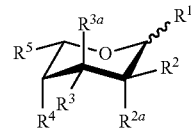

(V)

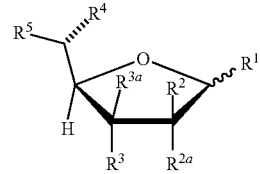

(VI)

or a biologically acceptable salt or solvate thereof, wherein each of formula (V) or (VI) can be the alpha or beta anomer or the corresponding aldose form; and wherein, each of $R^1$, $R^2$, $R^{2a}$, $R^3$, $R^{3a}$ and $R^4$ is independently selected from the group consisting of —OH, —OC(O)H, —OC(O)$C_1$-$C_{10}$ alkyl, —OC(O)$C_2$-$C_{10}$ alkenyl, —OC(O)$C_2$-$C_{10}$ alkynyl, —OC(O)aryl, —OC(O)heterocycle, —OC(O)$C_1$-$C_{10}$ alkylene(aryl), —OC(O)$C_2$-$C_{10}$ alkylene(aryl), —OC(O)$C_2$-$C_{10}$ alkynyl(aryl), —OC(O)$C_1$-$C_{10}$ alkylene heterocycle, —OC(O)$C_2$-$C_{10}$ alkenylene(heterocycle), —OC(O)$C_2$-$C_{10}$ alkynyl heterocycle, —O$CH_2$OC(O) alkyl, —OCH$_2$OC(O)O alkyl, —OCH$_2$OC(O) aryl, —OCH$_2$OC(O)O aryl, —OC(O)CH$_2$O(CH$_2$CH$_2$O)$_n$CH$_3$, —OC(O)CH$_2$CH$_2$O(CH$_2$CH$_2$O)$_n$CH$_3$, —O-tri-C$_1$-C$_3$ alkylsilyl, —OC$_1$-C$_{10}$ alkyl, and a small electron withdrawing group, wherein each n is an integer independently selected from 0-5;

R$^5$ is a member selected from the group consisting of —CH$_3$, —CH$_2$X, —CH(X')—C$_1$-C$_4$ alkyl unsubstituted or substituted with halogen, —CH(X')—C$_2$-C$_4$ alkene unsubstituted or substituted with halogen, —CH(X')—C$_2$-C$_4$ alkyne unsubstituted or substituted with halogen, —CH═C(R$^{10}$)(R$^{11}$), —C(CH$_3$)═C(R$^{12}$)(R$^{13}$), —C(R$^{14}$)═C═C(R$^{15}$)(R$^{16}$), —C$_3$ carbocycle unsubstituted or substituted with methyl or halogen, —CH(X')—C$_3$ carbocycle unsubstituted or substituted with methyl or halogen, C$_3$ heterocyle unsubstituted or substituted with methyl or halogen, —CH(X')—C$_3$ heterocycle unsubstituted or substituted with methyl or halogen, —CH$_2$N$_3$, —CH$_2$CH$_2$N$_3$, and benzyloxymethyl, or R$^5$ is a small electron withdrawing group; wherein R$^{10}$ is hydrogen or C$_1$-C$_3$ alkyl unsubstituted or substituted with halogen; R$^{11}$ is C$_1$-C$_3$ alkyl unsubstituted or substituted with halogen; R$^{12}$ is hydrogen, halogen or C$_1$-C$_3$ alkyl unsubstituted or substituted with halogen; R$^{13}$ is hydrogen, or C$_1$-C$_3$ alkyl unsubstituted or substituted with halogen; R$^{14}$ is hydrogen or methyl; R$^{15}$ and R$^{16}$ are independently selected from hydrogen, methyl and halogen; X is halogen; X' is halogen or hydrogen; and additionally, each of R$^1$, R$^2$, R$^{2a}$, R$^3$ and R$^{3a}$ are optionally hydrogen; optionally two R$^1$, R$^2$, R$^{2a}$, R$^3$ and R$^{3a}$ on adjacent carbon atoms are combined to form a double bond between said adjacent carbon atoms; and provided that at least one of R$^1$, R$^2$, R$^{2a}$, R$^3$, R$^{3a}$, R$^4$ and R$^5$ is a small electron withdrawing group, or R$^5$ comprises a halogen, site of unsaturation, carbocycle, heterocycle or azide, except when (i) R$^2$ and R$^{2a}$ are both hydrogen, (ii) R$^3$ and R$^{3a}$ are both hydrogen, (iii) R$^1$ is hydrogen, (iv) a double bond is present between said adjacent carbon atoms, or (v) R$^5$ is benzyloxymethyl; and wherein the antibody or antibody derivative has reduced core fucosylation compared to the antibody or antibody derivative from the host cell cultured in the absence of the fucose analog.

In some embodiments of formulae (V) and (VI), R$^{2a}$ and R$^{3a}$ are each hydrogen.

In some embodiments of formulae (V) and (VI), R$^5$ is selected from the group consisting of —CH$_3$, —CH$_2$CH$_3$, —CH$_2$C≡CH, —CH═CHCH$_3$, -cyclopropyl, -oxirane, -oxirane substituted with methyl, —CH$_2$F, —CH$_2$Cl, —CH$_2$Br, —CH═C═CH$_2$, —CH$_2$N$_3$ and —CH$_2$CH$_2$N$_3$.

In some embodiments of formulae (V) and (VI), the small electron withdrawing group is selected from fluoro, chloro, bromo, —CHF$_2$, —CH═C═CH$_2$, —C≡VH, —C≡CCH$_3$, —CH$_2$C≡CH, —CO$_2$H, —C(O)OC$_1$-C$_4$ alkyl, —CH(OAc)CH$_3$, —CN, —CH$_2$CN, —CH$_2$X (wherein X is Br, Cl or I), and methoxiran.

In some embodiments of formulae (V) and (VI), at least two of R$^1$, R$^2$, R$^{2a}$, R$^3$, R$^{3a}$ and R$^4$ are independently selected small electron withdrawing groups.

In some embodiments of formulae (V) and (VI), the fucose analog is selected from compounds of Tables 1, 2 or 3.

While the present inventive methods and cell cultures can include the fucose analogs provided in formulae I, II, III, IV, V and VI above, the present invention further provides compounds of each of the above formulae that can be prepared using methodology provided herein. In some embodiments, the compounds of the invention are other than compounds identified in the Examples as 6, 7, 9, 10, 22, 24, 26, 54, 56-58, 61-62, 65 and 66, as well as 2-fluoro-2-deoxyfucose.

Antibodies and Antibody Derivatives

Antibodies that can be produced by the instant methods can be monoclonal, chimeric, humanized (including veneered), or human antibodies. Suitable antibodies also include antibody fragments, such as single chain antibodies, or the like that have a Fc region or domain having a complex N-glycoside-linked sugar chain (e.g., a human IgG1 Fc region or domain). The Fc region or domain can include an Fcgamma receptor binding site. Typically, the antibodies are human or humanized. In some embodiments, the antibodies can be rodent (e.g., mouse and rat), donkey, sheep, rabbit, goat, guinea pig, camelid, horse, or chicken.

The antibodies can be mono-specific, bi-specific, tri-specific, or of greater multi-specificity. Multi-specific antibodies maybe specific for different epitopes of different target antigens or may be specific for different epitopes on the same target antigen. (See, e.g., WO 93/17715; WO 92/08802; WO 91/00360; WO 92/05793; Tutt et al., 1991, *J. Immunol.* 147:60-69; U.S. Pat. Nos. 4,474,893; 4,714,681; 4,925,648; 5,573,920; and U.S. Pat. No. 5,601,819; Kostelny et al., 1992, *J. Immunol.* 148:1547-1553.)

The antibodies can also be described in terms of their binding affinity to a target antigen of $10^{-7}$ M, $5\times10^{-8}$ M, $10^{-8}$ M, $5\times10^{-9}$ M, $10^{-9}$ M, $5\times10^{-10}$ M, $10^{-10}$ M, $5\times10^{-11}$ M, $10^{-11}$M, $5\times10^{-12}$ M, $10^{-12}$M, $5\times10^{-13}$M, $10^{-13}$ M, $5\times10^{-14}$ M, $10^{-14}$ M, $5\times10^{-15}$M, or $10^{-15}$ M.

In some embodiments, the antibody is a chimeric antibody. A chimeric antibody is a molecule in which different portions of the antibody are derived from different animal species, such as antibodies having a variable region derived from a murine monoclonal antibody and a human immunoglobulin constant region. Methods for producing chimeric antibodies are known in the art. (See, e.g., Morrison, *Science,* 1985, 229:1202; Oi et al., 1986, *BioTechniques* 4:214; Gillies et al., 1989, *J. Immunol. Methods* 125:191-202; U.S. Pat. Nos. 5,807,715; 4,816,567; and 4,816,397.)

In some embodiments, the antibody can be a humanized antibody, including a veneered antibody. Humanized antibodies are antibody molecules that bind the desired antigen and have one or more complementarity determining regions (CDRs) from a non-human species, and framework and constant regions from a human immunoglobulin molecule. Often, framework residues in the human framework regions will be substituted with the corresponding residue from the CDR donor antibody to alter, or preferably improve, antigen binding. These framework substitutions are identified by methods well known in the art, e.g., by modeling of the interactions of the CDR and framework residues to identify framework residues important for antigen binding and sequence comparison to identify unusual framework residues at particular positions. (See, e.g., Queen et al., U.S. Pat. No. 5,585,089; Riecbmann et al., 1988, *Nature* 332:323.) Antibodies can be humanized using a variety of techniques known in the art such as CDR-grafting (EP 0 239 400; WO 91/09967; U.S. Pat. Nos. 5,225,539; 5,530,101; and 5,585,089), veneering or resurfacing (EP 0 592 106; EP 0 519 596; Padlan, 1991, *Molecular Immunology,* 28(4/5):489-498; Studnicka et al., 1994, *Protein Engineering* 7(6):805-814; Roguska et al., 1994, *Proc. Natl. Acad. Sci. USA* 91:969-973), and chain shuffling (U.S. Pat. No. 5,565,332) (all of these references are incorporated by reference herein).

The antibody can also be a human antibody. Human antibodies can be made by a variety of methods known in the art such as phage display methods using antibody libraries derived from human immunoglobulin sequences. See e.g., U.S. Pat. Nos. 4,444,887 and 4,716,111; WO 98/46645, WO 98/50433, WO 98/24893, WO 98/16654, WO 96/34096, WO 96/33735, and WO 91/10741. In addition, a human antibody recognizing a selected epitope can be generated using a technique referred to as "guided selection," in which a selected non-human monoclonal antibody, e.g., a mouse antibody, is used to guide the selection of a completely human antibody recognizing the same epitope (see, e.g., Jespers et al., 1994, *Biotechnology* 12:899-903). Human antibodies can also be produced using transgenic mice that express human immunoglobulin genes. Monoclonal antibodies directed against the antigen can be obtained from the immunized, transgenic mice using conventional hybridoma technology. For an overview of the technology for producing human antibodies, see Lonberg and Huszar, 1995, *Int. Rev. Immunol.* 13:65-93. For a detailed discussion of this technology for producing human antibodies and human monoclonal antibodies and protocols for producing such antibodies, see, e.g., PCT publications WO 98/24893; WO 92/01047; WO 96/34096; WO 96/33735; European Patent No. 0 598, 877; U.S. Pat. Nos. 5,413,923; 5,625,126; 5,633,425; 5,569,825; 5,661,016; 5,545,806; 5,814,318; 5,885,793; 5,916,771; and 5,939,598.

Examples of antibodies include HERCEPTIN® (trastuzumab; Genentech), RITUXAN® (rituximab; Genentech), lintuzumab (Seattle Genetics, Inc.), Palivizumab (Medimmune), Alemtuzumab (BTG) and Epratuzumab (Immunomedics).

In exemplary embodiments, an antibody or antibody derivative specifically binds to CD19, CD20, CD21, CD22, CD30, CD33, CD38, CD40, CD70, CD133, CD138, or CD276. In other embodiments, the antibody or antibody derivative specifically binds to BMPR1B, LAT1 (SLC7A5), STEAP1, MUC16, megakaryocyte potentiating factor (MPF), Napi3b, Sema 5b, PSCA hlg, ETBR (Endothelin type B receptor), STEAP2, TrpM4, CRIPTO, CD21, CD79a, CD79b, FcRH2, HER2, HER3, HER4, NCA, MDP, IL20Rα, Brevican, Ephb2R, ASLG659, PSCA, PSMA, GEDA, BAFF-R, CXCR5, HLA-DOB, P2X5, CD72, LY64, FCRH1, or IRTA2.

Antibodies can be assayed for specific binding to a target antigen by conventional methods, such as for example, competitive and non-competitive immunoassay systems using techniques such as Western blots, radioimmunoassays, ELISA (enzyme linked immunosorbent assay), "sandwich" immunoassays, immunoprecipitation assays, immunoradiometric assays, fluorescent immunoassays, and protein A immunoassays. (See, e.g., Ausubel et al., eds., *Short Protocols in Molecular Biology* (John Wiley & Sons, Inc., New York, 4th ed. 1999); Harlow & Lane, *Using Antibodies: A Laboratory Manual* (Cold Spring Harbor Laboratory Press, Cold Spring Harbor, N.Y., 1999.)

Further, the binding affinity of an antibody to a target antigen and the off-rate of an antibody-antigen interaction can be determined by surface plasmon resonance, competition FACS using labeled antibodies or other competitive binding assays. One example of a competitive binding assay is a radioimmunoassay comprising the incubation of labeled antigen (e.g., $^3$H or $^{125}$I) with the antibody of interest in the presence of increasing amounts of unlabeled antibody, and the detection of the antibody bound to the labeled antigen. The affinity of the antibody and the binding off-rates can then be determined from the data by Scatchard plot analysis. Competition with a second antibody can also be determined using radioimmunoassays. In this case, the antigen is incubated with the antibody of interest conjugated to a labeled compound (e.g., $^3$H or $^{125}$I) in the presence of increasing amounts of an unlabeled second antibody. Alternatively, the binding affinity of an antibody and the on- and off-rates of an antibody-antigen interaction can be determined by surface plasmon resonance.

Antibodies can be made from antigen-containing fragments of the target antigen by standard procedures according to the type of antibody (see, e.g., Kohler, et al., *Nature*, 256:495, (1975); Harlow & Lane, *Antibodies, A Laboratory Manual* (C.S.H.P., NY, 1988); Queen et al., *Proc. Natl. Acad. Sci. USA* 86:10029-10033 (1989) and WO 90/07861; Dower et al., WO 91/17271 and McCafferty et al., WO 92/01047 (each of which is incorporated by reference for all purposes). As an example, monoclonal antibodies can be prepared using a wide variety of techniques including, e.g., the use of hybridoma, recombinant, and phage display technologies, or a combination thereof. Hybridoma techniques are generally discussed in, e.g., Harlow et al., supra, and Hammerling, et al., *In Monoclonal Antibodies and T-Cell Hybridomas*, pp. 563-681 (Elsevier, N.Y., 1981). Examples of phage display methods that can be used to make antibodies include, e.g., those disclosed in Briinnan et al., 1995, *J. Immunol. Methods* 182:41-50; Ames et al., 1995, *J. Immunol. Methods* 184:177-186; Kettleborough et al., 1994, *Eur. J. Immunol.* 24:952-958; Persic et al., 1997, *Gene* 187:9-18; Burton et al., 1994, *Advances in Immunology* 57:191-280; PCT Application No. PCT/GB91/01 134; PCT Publications WO 90/02809; WO 91/10737; WO 92/01047; WO 92/18619; WO 93/11236; WO 95/15982; WO 95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108 (the disclosures of which are incorporated by reference herein).

Examples of techniques that can be used to produce single-chain Fvs and antibodies include those described in U.S. Pat. Nos. 4,946,778 and 5,258,498; Huston et al., 1991, *Methods in Enzymology* 203:46-88; Shu et al., 1993, *Proc. Natl. Acad. Sci. USA* 90:7995-7999; and Skerra et al., 1988, *Science* 240:1038-1040.

Examples of antibody derivatives include binding domain-Ig fusions, wherein the binding domain may be, for example, a ligand, an extracellular domain of a receptor, a peptide, a non-naturally occurring peptide or the like. Exemplary fusions with immunoglobulin or Fc regions include: etanercept which is a fusion protein of sTNFRII with the Fc region (U.S. Pat. No. 5,605,690), alefacept which is a fusion protein of LFA-3 expressed on antigen presenting cells with the Fc region (U.S. Pat. No. 5,914,111), a fusion protein of Cytotoxic T Lymphocyte-associated antigen-4 (CTLA-4) with the Fc region (*J. Exp. Med.* 181:1869 (1995)), a fusion protein of interleukin 15 with the Fc region (*J. Immunol.* 160:5742 (1998)), a fusion protein of factor VII with the Fc region (*Proc. Natl. Acad. Sci. USA* 98:12180 (2001)), a fusion protein of interleukin 10 with the Fc region (*J. Immunol.* 154:5590 (1995)), a fusion protein of interleukin 2 with the Fc region (*J. Immunol.* 146:915 (1991)), a fusion protein of CD40 with the Fc region (*Surgery* 132:149 (2002)), a fusion protein of Flt-3 (fms-like tyrosine kinase) with the antibody Fc region (*Acta. Haemato.* 95:218 (1996)), a fusion protein of OX40 with the antibody Fc region (I Leu. Biol. 72:522 (2002)), and fusion proteins with other CD molecules (e.g., CD2, CD30 (TNFRSF8), CD95 (Fas), CD106 (VCAM-I), CD137), adhesion molecules (e.g., ALCAM (activated leukocyte cell adhesion molecule), cadherins, ICAM (intercellular adhesion molecule)-1, ICAM-2, ICAM-3) cytokine receptors (e.g., interleukin-4R, interleukin-5R, interleukin-6R, interleukin-9R, interleukin-10R, interleukin-12R, interleukin-13Ralpha1, interleukin-13Ralpha2, interleukin-15R, interleukin-21Ralpha), chemokines, cell death-inducing signal molecules (e.g., B7-H1, DR6 (Death receptor 6), PD-1 (Programmed death-1), TRAIL R1), costimulating molecules (e.g., B7-1, B7-2, B7-H2, ICOS (inducible co-stimulator)), growth factors (e.g., ErbB2, ErbB3, ErbB4, HGFR), differentiation-inducing factors (e.g., B7-H3), activating factors (e.g., NKG2D), signal transfer molecules (e.g., gp130), BCMA, and TACI.

Methods of Making Non-Core Fucosylated Antibodies and Antibody Derivatives

Antibodies and derivatives thereof that are useful in the present methods can be produced by recombinant expression techniques, from hybridomas, from myelomas or from other antibody expressing mammalian cells. Recombinant expression of an antibody or derivative thereof that binds to a target antigen typically involves construction of an expression vector containing a nucleic acid that encodes the antibody or derivative thereof. Once a nucleic acid encoding such a protein has been obtained, the vector for the production of the protein molecule may be produced by recombinant DNA technology using techniques well known in the art. Standard techniques such as those described in Sambrook and Russell, *Molecular Cloning: A Laboratory Manual* (Cold Spring Harbor Laboratory Press, Cold Spring Harbor, N.Y., 3rd ed., 2001); Sambrook et al., *Molecular Cloning: A Laboratory Manual* (Cold Spring Harbor Laboratory Press, Cold Spring Harbor, N.Y., 2nd ed., 1989); Ausubel et al., *Short Protocols in Molecular Biology* (John Wiley & Sons, New York, 4th ed., 1999); and Glick & Pasternak, *Molecular Biotechnology: Principles and Applications of Recombinant DNA* (ASM Press, Washington, D.C., 2nd ed., 1998) can be used for recombinant nucleic acid methods, nucleic acid synthesis, cell culture, transgene incorporation, and recombinant protein expression.

For example, for recombinant expression of antibody, an expression vector may encode a heavy or light chain thereof, or a heavy or light chain variable domain, operably linked to a promoter. An expression vector may include, e.g., the nucleotide sequence encoding the constant region of the antibody molecule (see, e.g., WO 86/05807; WO 89/01036; and U.S. Pat. No. 5,122,464), and the variable domain of the antibody may be cloned into such a vector for expression of the entire heavy or light chain. The expression vector is transferred to a host cell by techniques known in the art, and the transfected cells are then cultured by techniques known in the art in the presence of a fucose analog to produce the antibody. Typically, for the expression of double-chained antibodies, vectors encoding both the heavy and light chains can be co-expressed in the host cell for expression of the entire immunoglobulin molecule.

A variety of mammalian cells and cell lines can be utilized to express an antibody or derivative thereof. For example, mammalian cells such as Chinese hamster ovary cells (CHO) (e.g., DG44, Dxb11, CHO-K, CHO-K1 and CHO-S) can be used. In some embodiments, human cell lines are used. Suitable myeloma cell lines include SP2/0 and IR983F and human myeloma cell lines such as Namalwa. Other suitable cells include human embryonic kidney cells (e.g., HEK293), monkey kidney cells (e.g., COS), human epithelial cells (e.g., HeLa), PERC6, Wil-2, Jurkat, Vero, Molt-4, BHK, and K6H6. Other suitable host cells include YB2/0 cells. In other embodiments, the host cells are not YB2/0 cells.

In some embodiments, the host cells are from a hybridoma. In some embodiments, the host cells are not a hybridoma produced by a fusion generated with NS0 myeloma cells. In other embodiments, the host cells are not from a hybridoma.

In some embodiments, the host cells do not contain a fucose transporter gene knockout. In some embodiments, the host cells do not contain a fucosyltransferase (e.g., FUT8) gene knockout. In some embodiments, the host cells do not contain a knock-in of a GnTIII encoding nucleic acid. In some embodiments, the host cells do not contain a knock-in of a golgi alpha mannosidase II encoding nucleic acid.

A variety of mammalian host-expression vector systems can be utilized to express an antibody or derivative thereof. For example, mammalian cells such as Chinese hamster ovary cells (CHO) (e.g., DG44, Dxb11, CHO-K1 and CHO-S) in conjunction with a vector such as the major intermediate early gene promoter element from human cytomegalovirus or the Chinese hamster ovary EF-1α promoter, is an effective expression system for the production of antibodies and derivatives thereof (see, e.g., Foecking et al., 1986, Gene 45:101; Cockett et al., 1990, *Bio/Technology* 8:2; Allison, U.S. Pat. No. 5,888,809).

The cell lines are cultured in the appropriate culture medium. Suitable culture media include those containing, for example, salts, carbon source (e.g., sugars), nitrogen source, amino acids, trace elements, antibiotics, selection agents, and the like, as required for growth. For example, commercially available media such as Ham's F10 (Sigma), Minimal Essential Medium (MEM, Sigma), RPMI-1640 (Sigma), Dulbecco's Modified Eagle's Medium ((DMEM, Sigma), PowerCHO™ cell culture media (Lonza Group Ltd.) Hybridoma Serum-Free Medium (HSFM) (GIBCO) are suitable for culturing the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as GENTAMYCIN™), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, can be those previously used with the host cell selected for expression, and will be apparent to the ordinarily skilled artisan.

The culture media preferably is not supplemented with fucose. In some embodiments, the culture media is a serum-free media. In some embodiments, the culture media is an animal-derived protein free (i.e., animal protein free) media.

An effective amount of a fucose analog is added to the culture media. In this context, an "effective amount" refers to an amount of the analog that is sufficient to decrease fucose incorporation into a complex N-glycoside-linked sugar chain of an antibody or antibody derivative by at least 10%, at least 20%, at least 30%, at least 40% or at least 50%. In some embodiments, the effective amount of the fucose analog is sufficient to reduce fucose incorporation into a complex N-glycoside-linked sugar chain of an antibody or antibody derivative by at least 60%, at least 70%, at least 80% or at least 90%.

The cells expressing the antibody or antibody derivative can be cultured by growing the host cell in any suitable volume of culture media supplemented with the fucose analog. The cells may be cultured in any suitable culture system and according to any method known in the art, including T-flasks, spinner and shaker flasks, WaveBag® bags, roller bottles, bioreactors and stirred-tank bioreactors. Anchorage-dependent cells can also be cultivated on microcarrier, e.g., polymeric spheres, that are maintained in suspension in stirred-tank bioreactors. Alternatively, cells can be grown in single-cell suspension. Culture medium may be added in a batch process, e.g., where culture medium is added once to the cells in a single batch, or in a fed batch process in which small batches of culture medium are periodically added. Medium can be harvested at the end of culture or several times during culture. Continuously perfused production processes are also known in the art, and involve continuous feeding of fresh medium into the culture, while the same volume is continuously withdrawn from the reactor. Perfused cultures generally achieve higher cell densities than batch cultures and can be maintained for weeks or months with repeated harvests.

For cells grown in batch culture, the volume of culture medium is typically at least 750 mL, 1 liter, 2 liters, 3 liters, 4 liters, 5 liters, 10 liters, 15 liters, 20 liters or more. For industrial applications, the volume of the culture medium can be at least 100 liters, at least 200 liters, at least 250 liters, at least 500 liters, at least 750 liters, at least 1000 liters, at least 2000 liters, at least 5000 liters or at least 10,000 liters. The fucose analog may be added to the seed train, to the initial batch culture medium, after a rapid growth phase, or continuously with culture medium (e.g., during continuous feeding). For example, the fucose analog may be added to an early seed train or feedstock at a 10× or 100× concentration, such that subsequent additions of culture media change the concentration of fucose analog to a level that is still effective in achieving non-core fucosylation of the antibody or antibody derivative. Alternatively, the fucose analog is added directly to the culture media, obviating the need for dilution. In any case, the fucose analog is typically added relatively early in the cell culturing process and an effective concentration is maintained throughout the culturing process in order to optimize production of the desired antibody or antibody derivative.

In some embodiments, antibodies or antibody derivatives produced by the instant methods comprise at least 10%, at least 20%, at least 30%, at least 40% or at least 50% non-core fucosylated protein (e.g., lacking core fucosylation), as compared with antibodies or antibody derivatives produced from the host cells cultured in the absence of a fucose analog. In some embodiments, antibodies or antibody derivatives produced by the instant methods comprise at least 60%, at least 70%, at least 75%, at least 80%, at least 85%, at least 90% or at least 95% non-core fucosylated antibody or antibody derivative, as compared with antibody or derivative produced from the host cells cultured in the absence of a fucose analog. In some embodiments, a composition of antibodies or antibody derivatives produced by the instant methods comprises less than 100% non-core fucosylated antibodies and/or antibody derivatives.

The amount of the fucose analog (of any of Formulae I, II, III, IV, V and VI) that is effective can be determined by standard cell culture methodologies. For example, cell culture assays may be employed to help identify optimal dosing ranges. The precise amount to be employed also depends on the time of administration, the host cell line, the cell density and the like. Effective doses may be extrapolated from dose-response curves derived from in vitro model test systems.

In some embodiments, the fucose analog is present in the culture medium at a concentration of 10 nM to 50 mM. In some embodiments, the fucose analog is present in the culture medium at a concentration of 10 nM to 10 mM. In some embodiments, the fucose analog is present in the culture medium at a concentration of 100 nM to 5 mM. In some embodiments, the fucose analog is present in the culture medium at a concentration of 100 nM to 3 mM. In some embodiments, the fucose analog is present in the culture medium at a concentration of 100 nM to 2 mM. In some embodiments, the fucose analog is present in the culture medium at a concentration of 100 nM to 1 mM. In some embodiments, the fucose analog is present in the culture medium at a concentration of 1 μM to 1 mM. In some embodiments, the fucose analog is present in the culture medium at a concentration of 10 nM to 1 mM. In some embodiments, the fucose analog is present in the culture medium at a concentration of 10 nM to 500 μM. In some embodiments, the fucose analog is present in the culture medium at a concentration of 1 μM to 500 μM. In some embodiments, the fucose analog is present in the culture medium at a concentration of 1 μM to 250 μM. In some embodiments, the fucose analog is present in the culture medium at a concentration of 10 μM to 100 μM. In some embodiments, the fucose analog is soluble in the culture medium (at the appropriate temperature for host cell maintenance/growth) at a concentration of at least 10 nM. In some embodiments, the fucose analog is soluble in the culture medium (at the appropriate temperature for host cell maintenance/growth) at a concentration of at least 100 nM.

The content (e.g., the ratio) of sugar chains in which fucose is not bound to N-acetylglucosamine in the reducing end of the sugar chain versus sugar chains in which fucose is bound to N-acetylglucosamine in the reducing end of the sugar chain can be determined, for example, as described in the Examples. Other methods include hydrazinolysis or enzyme digestion (see, e.g., *Biochemical Experimentation Methods* 23: Method for Studying Glycoprotein Sugar Chain (Japan Scientific Societies Press), edited by Reiko Takahashi (1989)), fluorescence labeling or radioisotope labeling of the released sugar chain and then separating the labeled sugar chain by chromatography. Also, the compositions of the released sugar chains can be determined by analyzing the chains by the HPAEC-PAD method (see, e.g., *J. Liq Chromatogr.* 6:1557 (1983)). (See generally U.S. Patent Application Publication No. 2004-0110282.)

In some embodiments, the antibodies or antibody derivatives produce by the instant methods have higher effector function (e.g., ADCC activity) than the antibodies or antibody derivatives produced in the absence of a fucose analog. The effector function activity may be modulated by altering the concentration of the fucose analog in the culture medium and/or the duration of exposure to the fucose analog. ADCC activity may be measured using assays known in the art and in exemplary embodiments increases by at least 10%, 20%, 30%, 40%, 50%, 60%, 70%, 80%, 90%, 2-fold, 3-fold, 4-fold, 5-fold, 6-fold, 7-fold, 8-fold, 9-fold, 10-fold, 15-fold or 20-fold, as compared to the core fucosylated parent antibody. The cytotoxic activity against an antigen-positive cultured cell line can be evaluated by measuring effector function (e.g., as described in *Cancer Immunol. Immunother.* 36:373 (1993)).

Antibodies and antibody derivative can be purified using, for example, hydroxylapatite chromatography, gel electrophoresis, dialysis, and affinity chromatography, with affinity chromatography being a preferred purification technique. The suitability of protein A as an affinity ligand depends on the species and isotype of any immunoglobulin Fc domain that is present in the antibody or antibody derivative. Protein A can be used to purify antibodies or antibody derivatives that are based on human IgG1, 2, or 4 heavy chains.

Protein G can be used for mouse isotypes and for some human antibodies and antibody derivatives. The matrix to which the affinity ligand is attached is most often agarose, but other matrices are available. Mechanically stable matrices such as controlled pore glass or poly(styrenedivinyl) benzene allow for faster flow rates and shorter processing times than can be achieved with agarose. Where the antibody or antibody derivative comprises a $C_H3$ domain, the Bakerbond ABX™ resin (J. T. Baker, Phillipsburg, N.J.) is useful for purification. Other techniques for protein purification such as fractionation on an ion-exchange column (cationic or anionic exchange), ethanol precipitation, Reverse Phase HPLC, chromatography on silica, chromatography on heparin SEPHAROSE™ chromatography on an anion or cation exchange resin (such as a polyaspartic acid column), chromatofocusing, SDS-PAGE, and ammonium sulfate precipitation are also available depending on the antibody or antibody derivative to be recovered.

Following any purification step(s), the mixture comprising the antibody or antibody derivative of interest and contaminants may be subjected to low pH hydrophobic interaction chromatography (e.g., using an elution buffer at a pH between about 2.5-4.5, preferably performed at low salt concentrations (e.g., from about 0-0.25M salt)).

Uses of the Antibodies and Antibody Derivatives

Antibodies and antibody derivatives prepared according to the present methods can be used for a variety of therapeutic and non-therapeutic applications. For example, the antibodies can be used as therapeutic antibodies. Antibody derivatives (e.g., a receptor-Fc fusion) can be used as a therapeutic molecule. In some embodiments, the antibody or antibody derivative is not conjugated to another molecule. In some embodiments, the antibody is conjugated to a suitable drug (e.g., an antibody drug conjugate) or other active agent. The antibodies and antibody derivatives can also be used for non-therapeutic purposes, such as diagnostic assays, prognostic assays, release assays and the like.

Pharmaceutical Compositions.

Antibodies and antibody derivatives prepared according to the present methods can be formulated for therapeutic and non-therapeutic applications. The antibodies and derivatives can be formulated as pharmaceutical compositions comprising a therapeutically or prophylactically effective amount of the antibody or derivative and one or more pharmaceutically compatible (acceptable) ingredients. For example, a pharmaceutical or non-pharmaceutical composition typically includes one or more carriers (e.g., sterile liquids, such as water and oils, including those of petroleum, animal, vegetable or synthetic origin, such as peanut oil, soybean oil, mineral oil, sesame oil and the like). Water is a more typical carrier when the pharmaceutical composition is administered intravenously. Saline solutions and aqueous dextrose and glycerol solutions can also be employed as liquid carriers, particularly for injectable solutions. Suitable excipients include, for example, amino acids, starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol, and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. Examples of suitable pharmaceutical carriers are described in "Remington's Pharmaceutical Sciences" by E.W. Martin. Such compositions will typically contain a therapeutically effective amount of the protein, typically in purified form, together with a suitable amount of carrier so as to provide the form for proper administration to the patient. The formulations correspond to the mode of administration.

Typically, compositions for intravenous administration are solutions in sterile isotonic aqueous buffer. When necessary, the pharmaceutical can also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. When the pharmaceutical is to be administered by infusion, it can be dispensed with an infusion bottle containing sterile pharmaceutical grade water or saline. When the pharmaceutical is administered by injection, an ampoule of sterile water for injection or saline can be provided so that the ingredients can be mixed prior to administration.

The invention is further described in the following examples, which are not intended to limit the scope of the invention.

EXAMPLES

Example 1: Synthesis of Alkynyl Fucose Peracetate and General Procedure for Synthesis of Fucose Analogs The preparation of alkynyl fucose peracetate (also referred to as peracetyl alkynyl fucose and alkynyl peracetyl fucose) (Compound 7) was described by Sawa et al., 2006, *Proc. Natl. Acad. Sci. USA* 103:12371-12376 and Hsu et al., 2007, *Proc. Natl. Acad. Sci. USA* 104:2614-2619, with the following modification. A Corey-Fuchs homologation sequence was employed to install the alkynyl group, as described by Pelphrey et al., 2007, *J. Med. Chem.* 50:940-950.

General methods for other fucose analogs: Common reagents and solvents were purchased from either Fisher or Sigma-Aldrich except as follows: L-galactono-1,4-lactone was purchased from Carbosynth Limited. $^1$H-NMR spectra were recorded on a Varian Mercury spectrometer at 400 MHz. LC/MS data were obtained on a Waters Micromass instrument using an HP 1100 HPLC with a PDA detector. The column used was a Phenomenex SynergiMax RP-$C_{12}$ column (2 mm×150 mm) eluting with a MeCN-water gradient containing 0.05% formic acid. Flash column chromatography (FCC) was performed using 230-400 mesh ASTM silica gel from EM Science or using a Chromatotron. Analtech silica gel GHLF plates were used for thin layer chromatography and TLC plates were stained with vanillin or iodine. HPLC was performed using a Waters Alliance system with a PDA detector.

Example 2: Antibody Expression in the Presence of Alkynyl Fucose Peracetate

To determine the effect of alkynyl fucose peracetate on glycosylation of antibodies, a CHO DG44 cell line expressing a humanized IgG1 anti-CD70 monoclonal antibody, h1F6 (see International Patent Publication WO 06/113909) was cultured at 3.0×10$^5$ cells per mL in 30 mLs of CHO culture media at 37°, 5% $CO_2$, by shaking at 100 RPM in 125 mL shake flasks. The CHO culture media was supplemented with insulin like growth factor (IGF), penicillin, streptomycin and either 50 or 100 µM alkynyl fucose peracetate (prepared as described in Example 1). Cultures were fed on day 3 with 2% volume of feed media containing 2.5 or 5 mM alkynyl fucose peracetate for the 50 and 100 µM alkynyl fucose peracetate cultures, respectively. On day four, each culture was split 1:4 into fresh culture media. Cultures were fed with a 6% volume of feed media containing 833 µM or 1.66 mM alkynyl fucose peracetate on days 5, 7, 9 and 10. Conditioned media was collected on day 13 by passing the media through a 0.2 µm filter.

Antibody purification was performed by applying the conditioned media to a protein A column pre-equilibrated with 1× phosphate buffered saline (PBS), pH 7.4. After washing the column with 20 column volumes of 1×PBS, antibodies were eluted with 5 column volumes of Immunopure IgG elution buffer (Pierce Biotechnology, Rockford, Ill.). A 10% volume of 1M tris pH 8.0 was added to eluted fraction. The sample was dialyzed overnight into 1×PBS.

Example 3: LC-MS (Q-Tof) Analysis of Antibodies Produced by Expression in the Presence of Alkynyl Fucose Peracetate To identify the glycosylation pattern present on purified h1F6 antibodies from Example 2, antibody interchain disulfide bonds were reduced by adding 10 µL of 100 mM DTT to 90 µL of 1 mg/mL antibody in PBS and incubation at 37° C. for 15 min. This solution (20 µL) was injected onto a PLRP-S HPLC column (Polymer Laboratories; Amherst, Mass.) running the following gradient: solvent A, 0.05% TFA in water; solvent B, 0.035% TFA in acetonitrile; a linear gradient of 70 to 50% A from 0 to 12.5 min. The HPLC effluent was analyzed with an electrospray ionization Q-Tof mass spectrometer (Waters, Milford, Mass.) with a cone voltage of 35 V collecting from m/z 500 to 4000. Data for the heavy chain were deconvoluted using the Max Ent1 function in MassLynx 4.0.

Surprisingly, the heavy chains of antibodies from cells grown in the presence of alkynyl fucose peracetate showed a decrease by about 146 Da, as compared to control antibodies (i.e., heavy chains of antibodies from cells grown in the absence of alkynyl fucose peracetate). This observation suggested that addition of alkynyl fucose peracetate to the culture did not grossly alter the glycosylation pattern of the antibodies. Instead, addition of alkynyl fucose peracetate caused a minor but detectable change in glycosylation. The change in mass is consistent with the absence of fucose in the antibodies.

Example 4: Capillary Electrophoresis of Oligosaccharides

To further characterize the glycans on the h1F6 antibodies from Example 3, capillary electrophoresis was performed. Samples of the antibodies were buffer-exchanged into water. 300 µg of each sample was treated with PNGaseF overnight at 37° C. to release oligosaccharides. The protein component of the sample was removed by addition of cold methanol (−20° C.) and centrifuged for 10 minutes at 14,000 rpm. The supernatant was dried and oligosaccharides were labeled using APTS (8-aminopyrene-1,3,6-trisulfonic acid, trisodium salt) in 1M sodium cyanoborohydride/THF at 22° C. overnight. Labeled oligosaccharides were diluted with water and analyzed by capillary electrophoresis using a Beckman Coulter PA-800 in a N-CHO coated capillary (Beckman Coulter). For FIG. 1A, the samples were run in N-linked gel buffer (Beckman Coulter, Fullerton, Calif., USA). For FIGS. 1B and 1C, the samples were run in 40 mM EACA, 0.2% HPMC at pH 4.5. Samples were injected for 8 seconds at 0.5 psi and separated at 30 kV for 15 minutes. Labeled oligosaccharides were detected using laser induced fluorescence (LFI) with an excitation wavelength of 488λ. Emission fluorescence was detected at 520λ.

Samples of the antibodies were also treated with β-galactosidase to remove galactose. The antibody samples were buffer exchanged into water. 300 µg of each sample was treated with PNGaseF overnight at 37° C. to release oligosaccharides. The protein component of the sample was removed by addition of cold methanol (−20° C.) and centrifugation for 10 minutes at 14,000 rpm. The supernatants were dried, resuspended in water and treated with β-galactosidase. Oligosaccharides were dried and then labeled using APTS in 1M sodium cyanoborohydride/THF at 22° C. overnight. Labeled oligosaccharides were diluted with water and analyzed by capillary electrophoresis using a Beckman Coulter PA-800, in a N-CHO coated capillary (Beckman Coulter) running in 40 mM EACA, 0.2% HPMC at pH 4.5. Samples were injected for 8 seconds at 0.5 psi and separated at 30 kV for 15 minutes. Labeled oligosaccharides were detected using laser induced fluorescence (LFI) with an excitation wavelength of 488λ. Emission fluorescence was detected at 520λ.

An analysis of the data from the capillary electrophoresis is shown in FIG. 1. Referring to FIG. 1A, the electropherogram of glycans from the control h1F6 antibody are shown. FIG. 1B shows an electropherogram of glycans from the h1F6 antibody produced from a host cell grown in the presence of alkynyl fucose peracetate. A comparison of FIGS. 1A and 1B reveals increased amounts of non-core fucosylated G0-F (and a corresponding decrease in core fucosylated G0 and G1 levels). Because the non-core fucosylated G1 peak co-migrated with the core fucosylated G0, it was difficult to determine the relative distribution of the different glycans. To de-convolute the data, separate antibody samples were treated with β-galactosidase. Referring to FIG. 1C, removing the galactose effectively collapsed the electropherogram to two peaks, G0 and G0-F (lacking fucose). In this β-galactosidase treated sample, approximately 85% of the oligosaccharide is non-core fucosylated and 6% is core fucosylated. The remainder consists of minor species.

Example 5: Antibody Dependent Cellular Cytotoxicity (ADCC) Assay

To confirm that some of the h1F6 antibody produced in Example 2 was not core fucosylated (as compared to the parent antibody), the activity of the antibody was determined by an ADCC assay. The ADCC activity assay was a standard $^{51}$Cr release assay, as described previously (see McEarchern et al., *Blood* 109:1185 (2007)). Briefly, 786-O cell line target tumor cells were labeled with 100 µCiNa [$^{51}$Cr]O$_4$ and then washed. Effector (NK) cells were prepared from non-adherent peripheral blood mononuclear cells (PBMCs) obtained from normal FcγRIIIA 158V donors (Lifeblood, Memphis, Tenn.). The cell fraction was enriched for CD16+NK cells following centrifugation over a Ficoll-Paque density gradient by removal of T, B, and monocyte subsets and negative depletion of CD4, CD8, CD20, and CD14+ cells using immunomagnetic beads (EasySep, Stem-Cell Technologies, Vancouver, BC, Canada). Na$_2$[$^{51}$Cr]O$_4$-labeled 786-O target tumor cells were mixed with mAb and the CD16+ effector cells at an effector:target cell ratio of 10:1.

After a 4 h incubation at 37° C., the radioactivity ($^{51}$Cr) released into the culture supernatant was measured and the percent specific cell lysis calculated as (test sample cpm−spontaneous cpm)/(total cpm−spontaneous cpm)×100. Spontaneous and total cpm were determined from the supernatants of target cells incubated in medium alone and from target cells lysed with 1% triton-X100, respectively.

Figure 2:
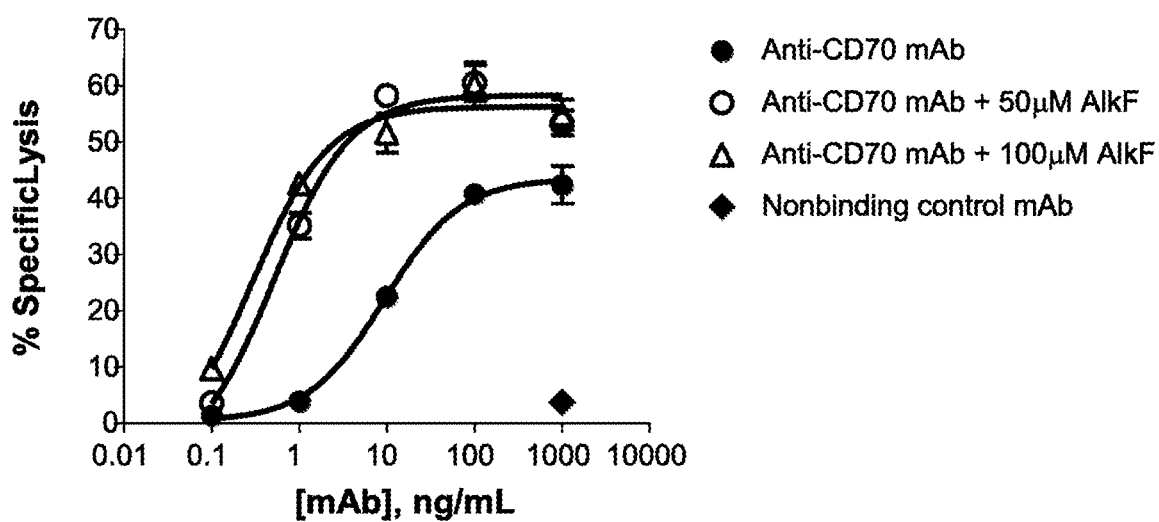
FIG. 2 shows the results of effector function assays (ADCC) with antibodies produced from host cells cultured in the presence of alkynyl fucose peracetate (AlkF). Specific lysis of control anti-CD70 antibody (shaded circles), anti-CD70 antibody from host cells cultured in the presence of 50 μM and 100 μM AlkF (open circles and triangles, respectively) and nonbinding control IgG (shaded diamonds) was determined by $^{51}$Cr release assay. CD70+ 786-O target cells were mixed with NK-enriched PBMCs at an effector to target ratio of 10:1.

Referring to FIG. 2, in the ADCC assay using PBMC as a source of natural killer (NK) cells (having the 158V phenotype), control anti-CD70 mAb (shaded circles) lysed CD70+ target cells in a dose dependent fashion, while no lysis was observed with nonbinding control human IgG (shaded diamonds). In contrast, anti-CD70 antibody isolated from host cells grown in the presence of alkynyl fucose peracetate ("AlkF") has enhanced ADCC activity (open circles and triangles). The half maximal lysis ($EC_{50}$) of control anti-CD70 antibody was about 9 ng/mL while the $EC_{50}$ concentrations of mAb produced in the presence of 50 μM and 100 μM AlkF were 0.5 and 0.3 ng/mL, respectively. The latter antibodies also gave rise to higher maximal specific lysis (53.3±3.8 and 54.8±4.7 percent) compared to that achieved with control anti-CD70 mAb (42.5±5.8 percent).

Example 6: FcγR Binding Assays

Fcγ receptor binding assays were performed to compare the binding of control CD70 antibody with the non-core fucosylated antibodies of Example 2. Briefly, stable CHO DG-44 cell lines expressing human FcγRIIIA V158 or murine FcγRIV were combined with 50 nmol/L or 200 nmol/L Alexa Fluor 488 labeled anti-CD70 IgG1, respectively, in the presence of serial dilutions of each of the following anti-CD70 antibodies in PBS, 0.1% BSA (w/v) buffer: control h1F6 antibody, and h1F6 antibody from host cells cultured with alkynyl fucose peracetate. The mixtures were incubated for 60 minutes on ice in the dark. Labeled cells were detected using an LSRII FACS analyzer and data were analyzed by a nonlinear least squares fit to a 4-parameter logistic equation using Prism v5.01 to estimate $EC_{50}$ values.

Figure 3:
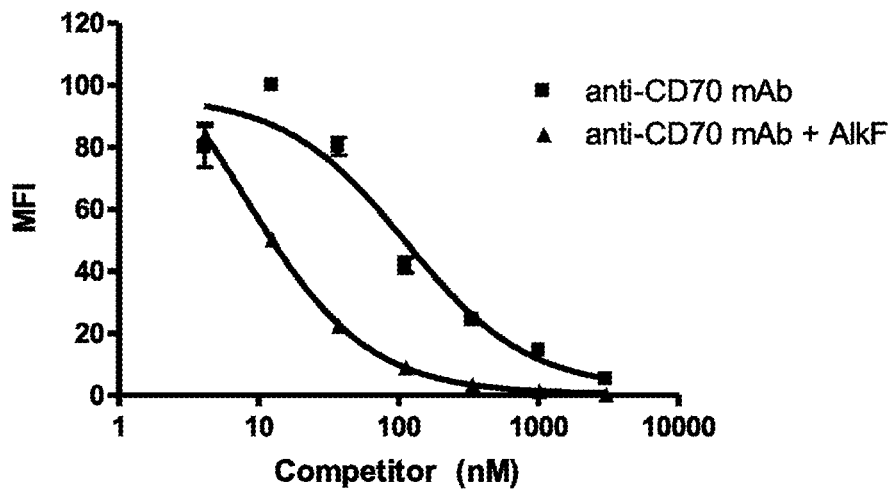
FIGS. 3A and 3B show the results of Fcγ receptor binding assays with control anti-CD70 antibody and antibody from host cells cultured in the presence of 50 μM alkynyl fucose peracetate (AlkF). The relative affinity for each receptor was determined by a competition binding assay between labeled parent antibody and increasing concentrations of unlabeled parent (shaded squares) or non-core fucosylated (shaded triangles) anti-CD70 mAb.
Figure 3:
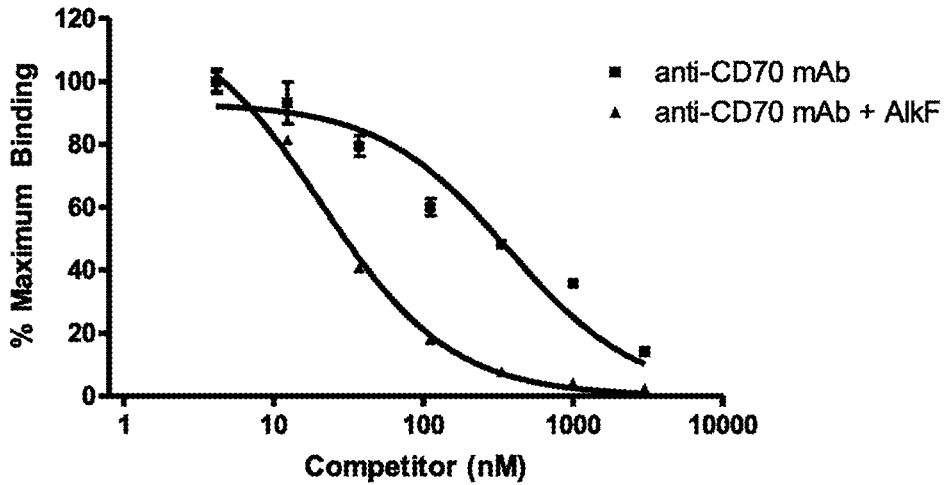
Figure 4A:
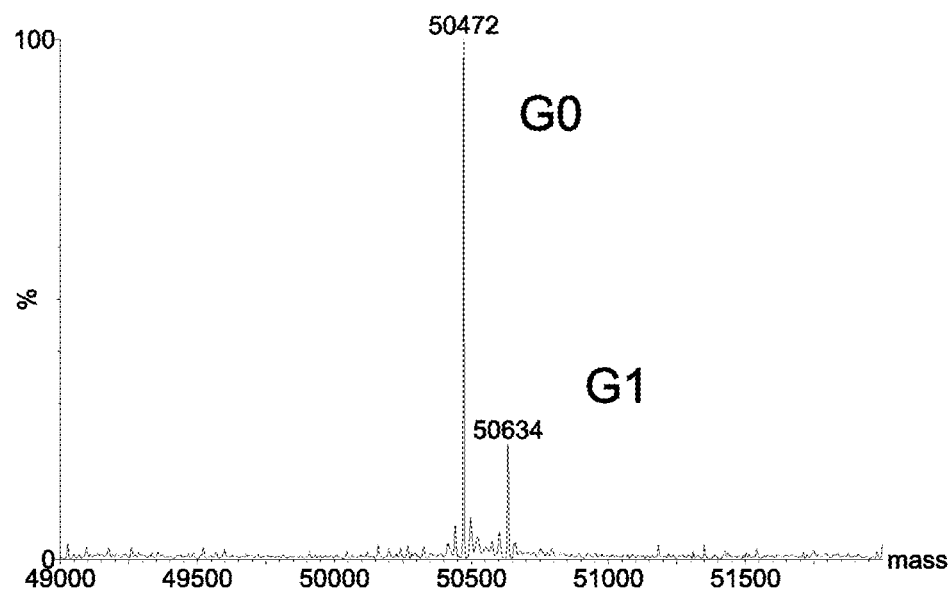
FIGS. 4A, 4B, 4C and 4D show the results of LC-MS (Q-Tof) analysis of four antibodies cultured in the absence or presence of alkynyl fucose peracetate (upper and lower portions, respectively, of each pair of panels). G0, G1 and G0-F are as indicated supra. "G1-F" refers to the carbohydrate structure where one of the non-reducing termini has a galactose and there is no core fucosylation (a mixture of two isomers).
Figure 4A:
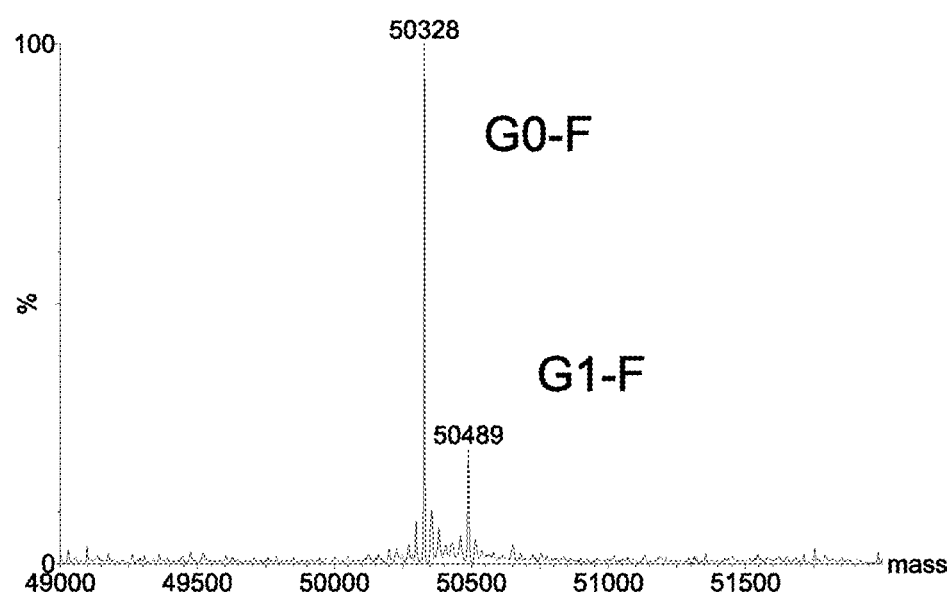
Figure 4B:
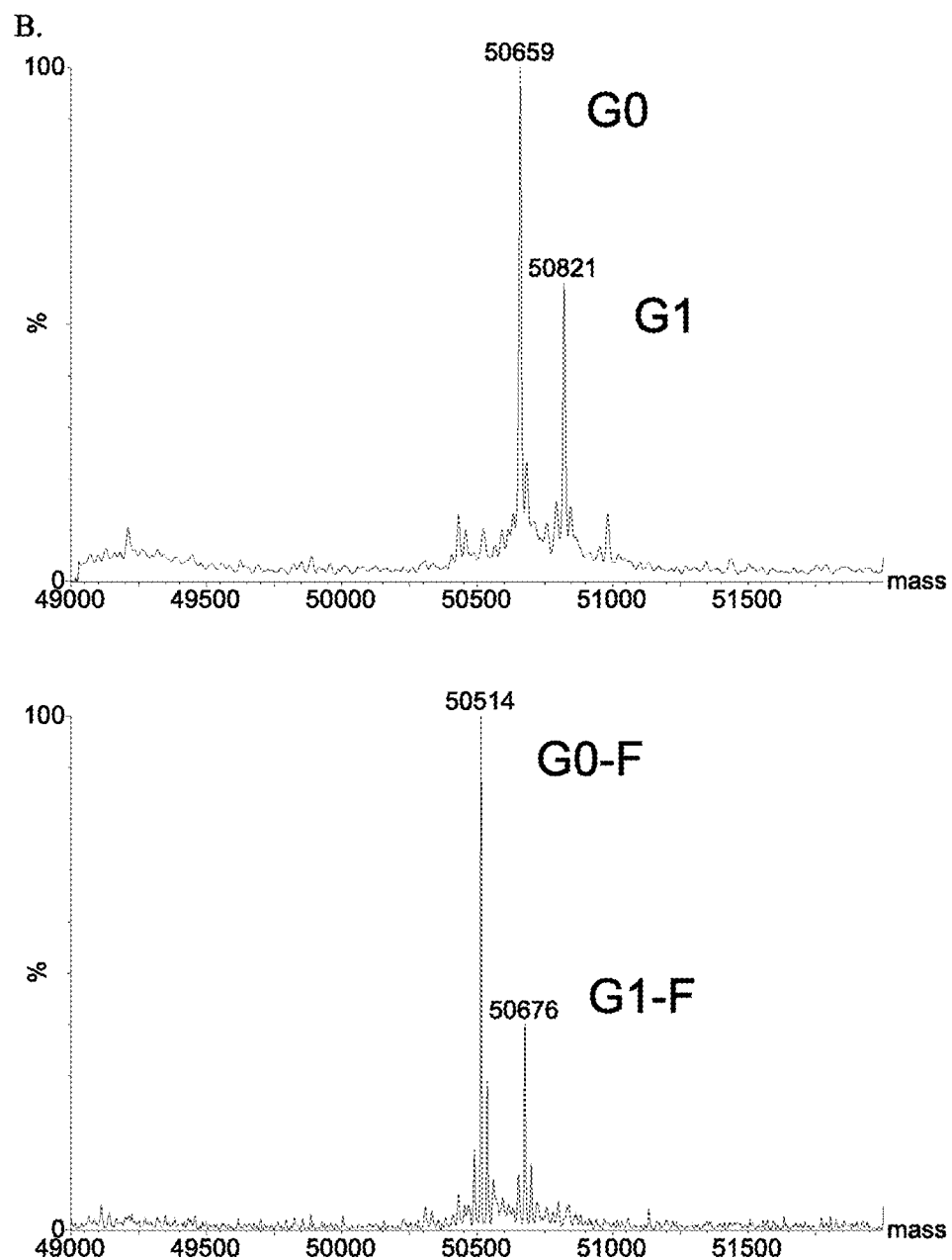
Figure 4C:
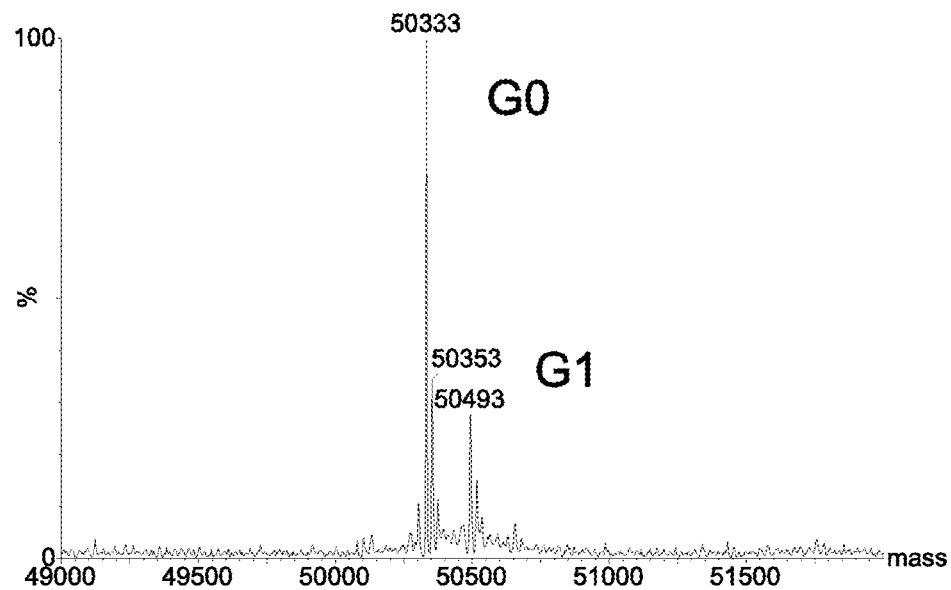
Figure 4C:
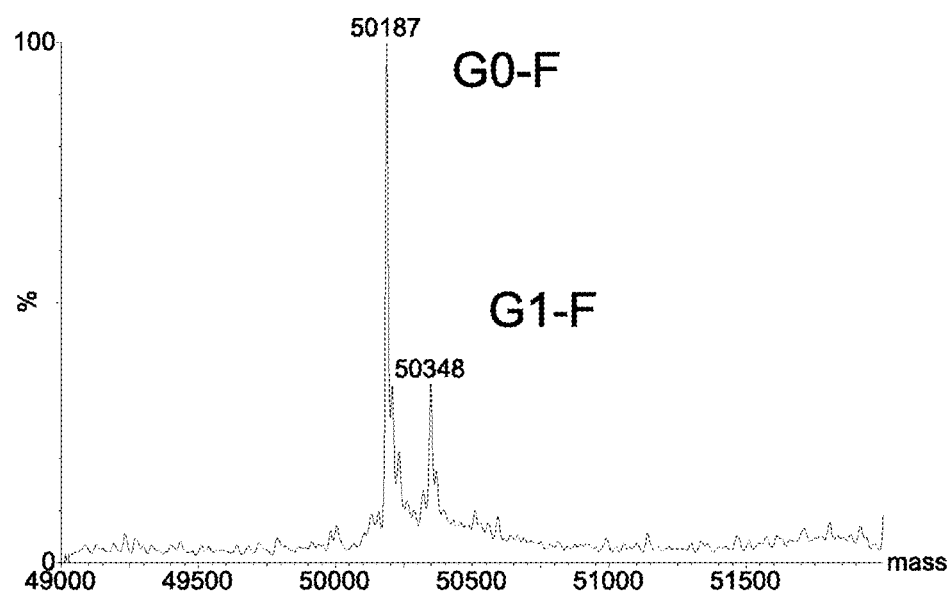
Figure 4D:
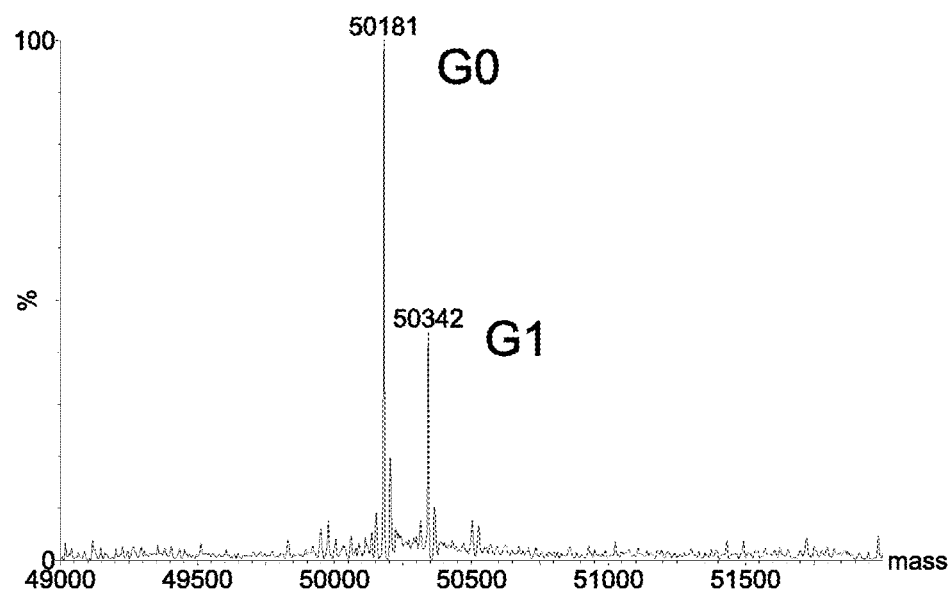
Figure 4D:
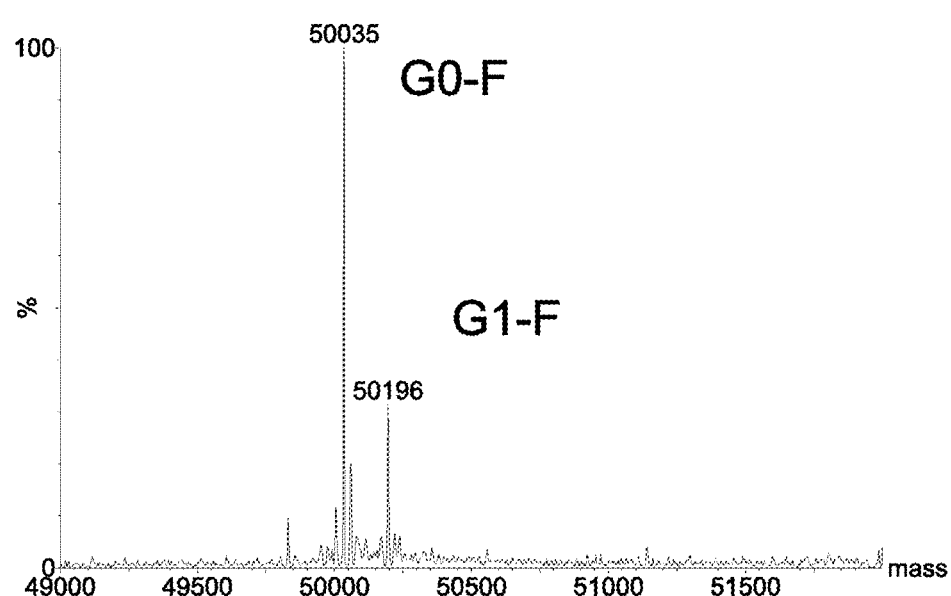

Non-core fucosylated anti-CD70 antibodies (triangles) competed for binding to huFcγ receptors (FIG. 3A) and muFcγ receptors (FIG. 3B) with fluorescently-labeled anti-CD70 parent antibody (squares). The non-core fucosylated anti-CD70 out-competed the parent (control) anti-CD70 antibody for binding to the murine receptor, muFcγRIV, with $EC_{50}$ values of 20.8 nM and 368.9 nM, respectively (an 18 fold difference). Non-core fucosylated anti-CD70 also out-competed the parent antibody in binding to the human receptor, huFcγRIIIA V158, with $EC_{50}$ values of 7.99 nM and 112.9 nM, respectively (a 14-fold difference).

Example 7: Expression of Other Antibodies in the Presence of Alkynyl Fucose Peracetate To confirm the effect of alkynyl fucose peracetate on glycosylation of additional antibodies, antibodies were expressed from the following cell lines: CD70 Ab h1F6 in DG44 cells; CD19 Ab hBU12 in DG44 cells (see U.S. Provisional Application No. 61/080,169, filed Jul. 11, 2008); CD30 Ab cAC10 in DG44 cells; and CD33 Ab HuM195 in SP2/0 and CHO-K1 cell (see also U.S. Ser. No. 12/253,895, filed Oct. 17, 2008). Briefly, the cell lines were initially cultured at $3.0 \times 10^5$ cells per mL in 30 mLs of CHO selection media at 37° C., 5% $CO_2$ and shaking at 100 RPM. The media was supplemented with insulin like growth factor (IGF), penicillin, streptomycin and 50 μM alkynyl fucose peracetate, as described. The cultures were fed on day 3 with 2% volume of feed media containing 2.5 mM alkynyl fucose peracetate. On day four, the cultures were split 1:4 into fresh culture media. Cultures were fed with a 6% volume of feed media containing 833 μM alkynyl fucose peracetate on days 5, 7, 9 and 10. Conditioned media was collected on day 13 by passing the culture through a 0.2 μm filter.

Antibody purification was performed by applying the conditioned media to a protein A column—pre-equilibrated with 1× phosphate buffered saline (PBS), pH 7.4. Antibodies were eluted with 5 column volumes of Immunopure IgG elution buffer (Pierce Biotechnology, Rockford, Ill.). A 10% volume of 1M tris pH 8.0 was added to the eluted fraction. The sample was dialyzed overnight into 1×PBS.

Qtof analysis of the antibodies revealed similar results to those of Example 3. Relative to heavy chains of antibodies produced from host cells grown in the absence of alkynyl fucose peracetate, heavy chains of antibodies from cells grown in the presence of alkynyl fucose peracetate were observed to decrease by about 146 Da, consistent with the absence of fucose. Referring to FIG. 4, for the G0 peak (no galactose) for each antibody, the observed shift in mass between heavy chain from cells grown in the absence and presence of alkynyl fucose peracetate (upper and lower portions of each panel) was a decrease of 144 Da (anti-CD70 antibody, FIG. 4A), 145 Da (anti-CD19 antibody, FIG. 4B), 146 Da (anti-CD30 antibody, FIG. 4C), and 146 Da (anti-CD33 antibody, FIG. 4D). These decreases in molecular weight are inconsistent with loss of any other sugar found in antibody carbohydrate other than fucose: mannose and galactose, 162 Da, N-acetylglucosamine, 203 Da, and sialic acid, 291 Da.

Example 8: Effector Function Assays

The effector functions, ADCC and ACCP, of a non-core fucosylated, humanized CD19 antibody, hBU12, was determined. ADCC activity was generally measured as described in Example 5 using Ramos cells. NK cells were isolated from individuals with 158V and 158F FcγRIIIa phenotypes.

Antibody-dependent cellular phagocytosis (ADCP) was assessed using a previously described method (see McEarchern et al., *Blood* 109:1185 (2007)). Briefly, target Ramos cells were incubated with the fluorescent dye PKH26 (Sigma, St. Louis, Mo.) prior to addition of the antibody and primary human macrophages. Macrophages were generated from normal human PBMCs cultured for 10 to 14 days with 500 U/ml human G-MCSF (PeproTech, Rocky Hill, N.J.). After a 1 h incubation at 37° C., the macrophages were labeled with a FITC-conjugated CD11b antibody (BD Pharmingen). Uptake of the target cells by the macrophages (phagocytosis) was assessed by flow cytometry and visualized by immunofluorescence using a Carl Zeiss Axiovert 200M microscope. Specific phagocytosis was determined by correcting for the hIgG1 background values.

Figure 5A:
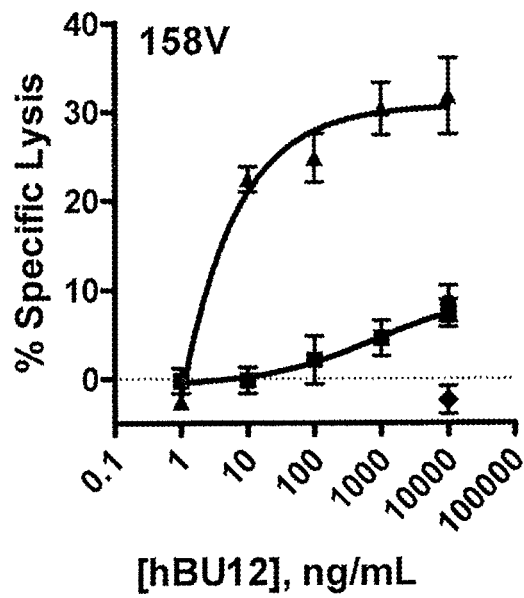
FIGS. 5A and 5B show the results of effector function (ADCC) assays of a humanized CD19 antibody cultured in the absence or presence of alkynyl fucose peracetate (core fucosylated (squares) or non-core fucosylated (triangles), respectively) on NK cells having the 158V and 158F phenotypes (panels A and B, respectively).
Figure 5B:
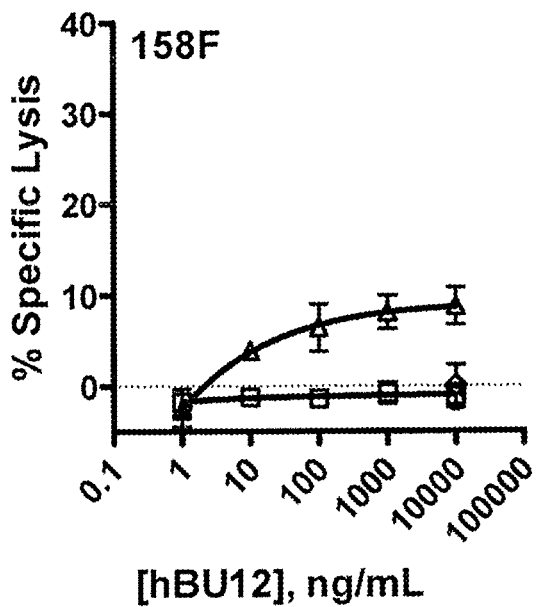

Referring to FIGS. 5A and 5B, the non-core fucosylated CD19 antibody (closed triangles) exhibited an approximately 100-fold increase in $EC_{50}$ in the 158 V background, with a 3.5-fold increase in maximum target cell lysis, as compared with the control (core fucosylated) antibody (closed squares). In the 158F background, the non-core fucosylated CD19 antibody (open triangles) had a 100 fold increase in $EC_{50}$ and a 10-fold increase in maximum target cell lysis, as compared with the control (core fucosylated) antibody. In contrast, no change in ACDP activity was observed between the non-core fucosylated and control antibody (data not shown).

Example 9: Expression of Antibodies from Hybridomas

Three antibody expressing hybridoma lines were tested to determine the effect of alkynyl fucose peracetate on antibody core fucosylation from these cell lines. These hybridomas were: 1) a BALB/C mouse spleen cell and a P2X63-AG 8.653 mouse myeloma cell fusion expressing the chimeric anti-ley antigen antibody BR96; 2) a BALB/C mouse spleen cell and a NS0 mouse myeloma cell fusion expressing a murine anti-Liv1 antibody; and 3) a BALB/C mouse spleen cell and a SP2/0mouse myeloma cell fusion expressing a murine anti-Liv-1 antibody. These hybridomas were cultured at $3.0 \times 10^5$ cells per mL in 30 mLs of Hybridoma Serum Free Media (Invitrogen, Carlsbad Calif.) supplemented with 50 µM alkynyl fucose peracetate at 37° C., 5% $CO_2$ and shaking at 100 RPM in a 125 mL shake flask. Cultures were fed on day 3 with 2% volume of a feed media. On day four, the culture was split 1:4 into fresh culture media. Cultures were fed with a 6% volume of feed media on days 5, 7, 9 and 10. Conditioned media was collected when the viability of the culture dropped below 60% or on day 13 by passing culture through a 0.2 µm filter.

Antibody purification was performed by applying the conditioned media to a protein A column pre-equilibrated with 1× phosphate buffered saline (PBS), pH 7.4. After washing column with 20 column volumes of 1×PBS, antibodies were eluted with 5 column volumes of Immunopure IgG elution buffer (Pierce Biotechnology, Rockford, Ill.). A 10% volume of 1M tris pH 8.0 was added to eluted fraction. The sample was dialyzed overnight into 1×PBS.

At the concentration of alkyl fucose peracetate tested, core fucosylation was inhibited in the hybridoma from the BALB/C-SP2/0 fusion, but not the BALB/C/P2X63-AG 8.653 and NS0 fusions.

Example 10: Synthesis of 5-ethynylarabinose Tetraacetate (7)

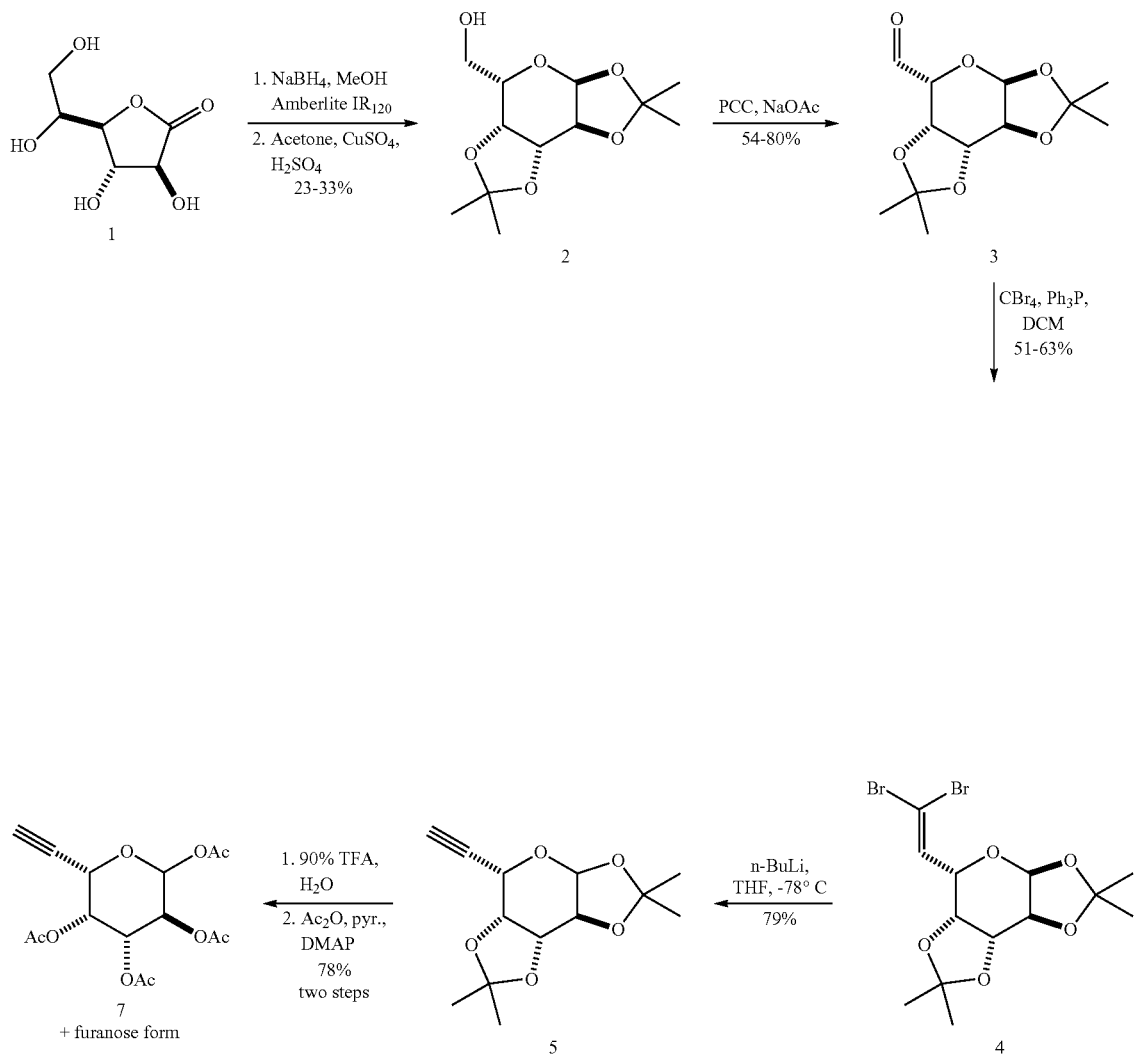

Scheme 1

1,2:3,4-Di-O-isopropylidene-α-L-galactose (2)

The compounds in Scheme 1 were generally prepared as described by Hsu et al., *Proc. Natl. Acad. Sci. USA* 104: 2614-19 (2004). Briefly, L-galactono-1,4-lactone (1) (10 g, 56.1 mmol) in CH$_3$OH (60 ml) was combined with water (250.0 ml) at 0° C. and Amberlite IR 120 (H+) resin (10 g). NaBH$_4$ (1.0 equiv. 2.22 g, 56 mmol) was added portion wise over the course of 1 h (6 additions) with slow stirring. After NaBH$_4$ addition was complete, the reaction mixture was slowly stirred for 1 h at 0° C. and then stirred vigorously at 0° C. for 15 min to promote the decomposition of the remaining NaBH$_4$. The liquid was decanted, the resin washed with methanol (2×25 mL) and the solution concentrated under reduced pressure and then under high vacuum overnight resulting in the formation of a glass. To the resulting solid was added acetone (220.0 ml), CuSO$_4$ (22 g) and H$_2$SO$_4$ (2 ml) and the solution was stirred vigorously at room temperature for at least 24 h. After 24 h, inspection by TLC (50% ethyl acetate in hexanes) showed product formation by staining with vanillin dip stain and heat (R$_f$~0.5). The reaction mixture was neutralized with Ca(OH)$_2$ or Cu(OH)$_2$ (~15 g) and vacuum filtered. The residue was purified by flash radial chromatography with a gradient elution from 10% to 50% ethyl acetate in hexanes. Clean fractions were combined to afford 3.3 g; (23%): $^1$H NMR (CD$_3$OD, 400 MHz) δ: 5.48 (d, J=4.5 Hz, 1H), 4.62 (dd, J=7.8, 2.3 Hz, 1H), 4.24 (dd, J=4.9, 2.3 Hz), 4.27 (dd, J=8.0, 1.8 Hz), 3.85 (m, 1H), 3.64 (m, 2H), 1.51 (s, 3H), 1.39 (s, 3H), 1.32 (s, 6H).

1,2:3,4-di-O-isopropylidene-α-L-galactal Pyranoside (3)

A suspension of pyridinium chlorochromate (PCC) (8.2 g, 38 mmol), sodium acetate (6.2 g, 76 mmol) and 4-A molecular sieves (16 g) in dry methylene chloride (114 ml) was stirred for 1 h. To this mixture was added a solution of the alcohol (Compound 2) (3.3 g, 12.7 mmol) in dry methylene chloride (57 ml) drop-wise, and the mixture was stirred at room temperature for 2 h. The reaction mixture was diluted with hexane/ether (1:1, 300 ml), and the solution was filtered through a bed of silica gel. The filter pad was washed with ethyl acetate (200 mL). The filtrate was concentrated under reduced pressure and high vacuum overnight to give 2.9 g (88%): $^1$H NMR (C$_6$D$_6$; 400 MHz) δ 9.61 (s, 1H), 5.44 (d, J=5.1 Hz, 1H), 4.27 (dd, J=2.3 Hz, 1H), 4.24 (d, J=2.3 Hz, 1H), 4.13 (d, J=2.3 Hz, 1H), 4.04 (dd, J=2.3 Hz, 1H), 1.32 (s, 3H), 1.2 (s, 3H), 0.98 (s, 3H), 0.93 (s, 3H).

Dibromo-olefin (4): To a flame-dried 25 mL round-bottom flask was added CBr$_4$ (2.38 g, 7.14 mmol) and methylene chloride (50 mL). The solution was cooled to 0° C. and Ph$_3$P (3.71 g, 14.3 mmol) was added. The mixture was stirred for 15 min, and the aldehyde (Compound 3) (0.62 g, 2.38 mmol) was added as a solution in methylene chloride (5 mL). The reaction was monitored by TLC. After 5 min., the reaction was complete. The mixture was concentrated under reduced pressure to approximately 5 mL and this was directly purified by flash column chromatography with 10% followed by 25% ethyl acetate in hexanes. The product-containing fractions (stains dark purple with vanillin stain (R$_f$=0.5 in 25% ethyl acetate in hexanes)) were combined and concentrated to give 495 mg. (51%): $^1$H NMR (CDCl$_3$; 400 MHz) δ: 6.86 (d, J=8.2 Hz, 1H), 5.39 (d, J=4.9 Hz, 1H), 4.62 (dd, J=8.0, 1.8 Hz, 1H), 4.37 (dd, J=7.8, 2.3 Hz), 4.03 (dd, J=5.1, 2.5 Hz, 1H), 3.90 (dd, J=5.8, 2.0 Hz, 1H), 1.1 (s, 3H), 1.0 (s, 3H), 0.67 (s, 3H), 0.63 (s, 3H).

6,7-Deoxy-1,2:3,4-di-O-isopropylidene-α-L-galacto-hept-6-ynopyranoside (5)

To the dibromo olefin (Compound 4) (500 mg, 1.2 mmol) in THF (15 mL) at −78° C. was added n-BuLi (3.0 mL of a 1.6M solution in hexanes; 4.87 mmol) and the reaction was stirred for 1 h before being treated with a solution of ammonium chloride. The layers were separated and the aqueous was extracted with hexanes (3×50 mL). The combined extracts were washed with brine and dried over Na$_2$SO$_4$, filtered and concentrated. The resulting residue was purified via radial chromatography to give 483 mg (79%): $^1$H NMR (CDCl$_3$; 400 MHz) δ: 5.39 (d, J=5.0 Hz, 1H), 4.69 (t, J=2.3 Hz, 1H), 4.36 (dd, J=7.6, 2.5 Hz), 4.01 (dd, J=5.0, 2.5 Hz, 1H), 3.94 (dd, J=7.6, 2.0 Hz, 1H), 2.01 (d, J=2.3 Hz, 1H), 1.50 (s, 3H), 1.23 (s, 3H), 1.11 (s, 3H), 0.92 (s, 3H).

5-ethynylarabinose (6)

To a flask containing the alkyne (Compound 5) (0.483 g, 1.9 mmol), TFA solution (10 ml, 90% TFA in H$_2$O) was slowly added at 0° C. The reaction was stirred on ice for 1 h and concentrated in vacuo.

5-ethynylarabinose Tetraacetate (7)

(General Procedure) The resulting residue of 5-ethynylarabinose (Compound 6) was treated with pyridine (10 ml), N,N,dimethylaminopyridine (5.0 mg), and acetic anhydride (10 ml), stirred overnight, concentrated to a residue and diluted with dichloromethane. The mixture was aspirated onto a 4 mm radial chromatotron plate and eluted with 25% followed by 50% ethyl acetate in hexanes. The product was isolate as an inseparable mixture of pyranose and furnanose α and β-anomers. Yield: 495 mg (76%): LRMS (ESI$^+$) m/z 365 (M+Na)$^+$, 283 (M-OAc)$^+$

Example 11. Synthesis of 6-Methyl-L-galactose Pentaacetate

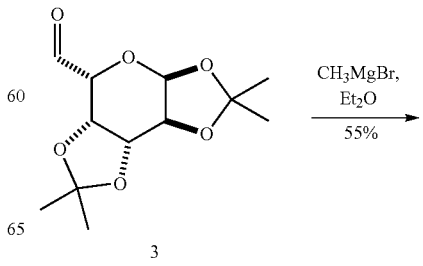

Scheme 2

6-Methyl-L-galactose Pentaacetate (9)

Compound 9 was prepared from Compound 8 by following the general procedure for acetonide hydrolysis and peracetylation in Example 10. LRMS (ESI+) m/z 345 (M-OAc)+.

Example 12: Synthesis of L-Galactose Pentaacetate

Scheme 3

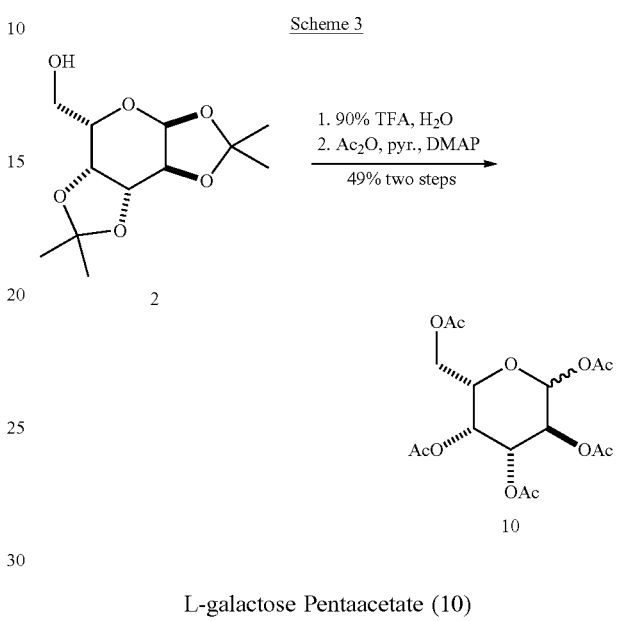

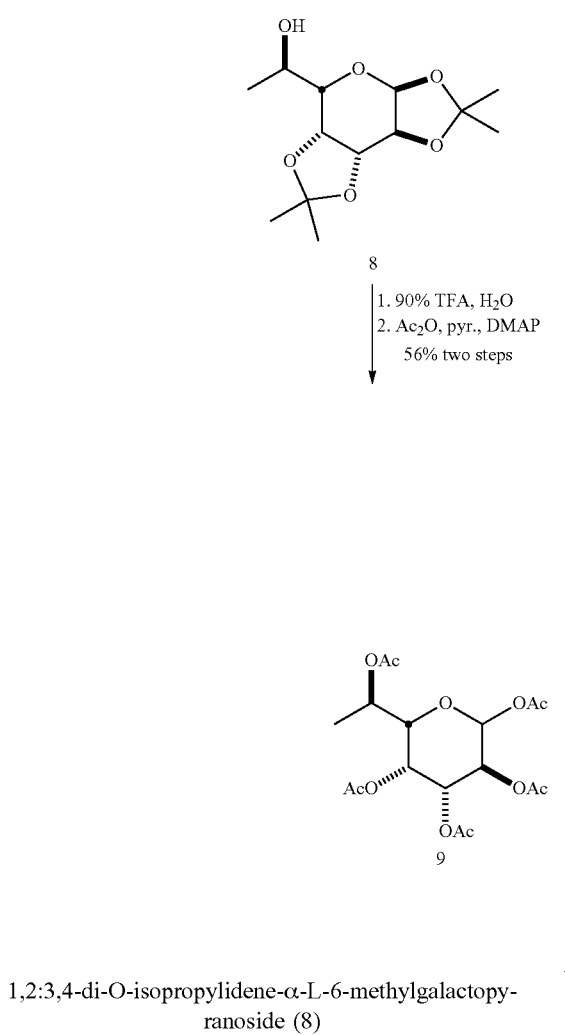

1,2:3,4-di-O-isopropylidene-α-L-6-methylgalactopyranoside (8)

Referring to Scheme 2, to a flame-dried flask was added ether (2 mL) and CH₃MgBr (258 μL of a 3M solution). This was followed by the addition of the aldehyde (Compound 3) (100 mg) in ether (2 mL), added drop-wise. The reaction mixture was stirred at room temperature for several hours and was monitored by TLC. The reaction mixture was quenched with saturated aqueous ammonium chloride and the mixture was extracted with ether (3×50 mL). The combined extracts were washed with water and brine and dried over MgSO₄. Filtration and concentration gave a residue that was analyzed by ¹H NMR revealing a diastereomeric mixture. The residue was purified via radial chromatography on a 1 mm plate eluting with 10% to 25% ethyl acetate in hexanes ($R_f$=0.2; 25% ethyl acetate in hexanes). The yield was 59 mg (55%): ¹H NMR-major isomer (CDCl₃; 400 MHz) δ: 5.61 (d, 1H), 4.62 (dd, 1H), 4.38 (d, 1H), 4.73 (dd, 1H), 4.04 (m, 1H), 1.56 (s, 3H), 1.50 (s, 3H), 1.37 (s, 3H), 1.28 (d, 3H).

L-galactose Pentaacetate (10)

Compound 10 was synthesized from Compound 2 following the general procedure for acetonide hydrolysis and peracetylation in Example 10. (49% overall): LRMS (ESI+) m/z 331 (M-OAc)+.

Example 13: Synthesis of 5-vinylarabinose Tetraacetate

Scheme 4

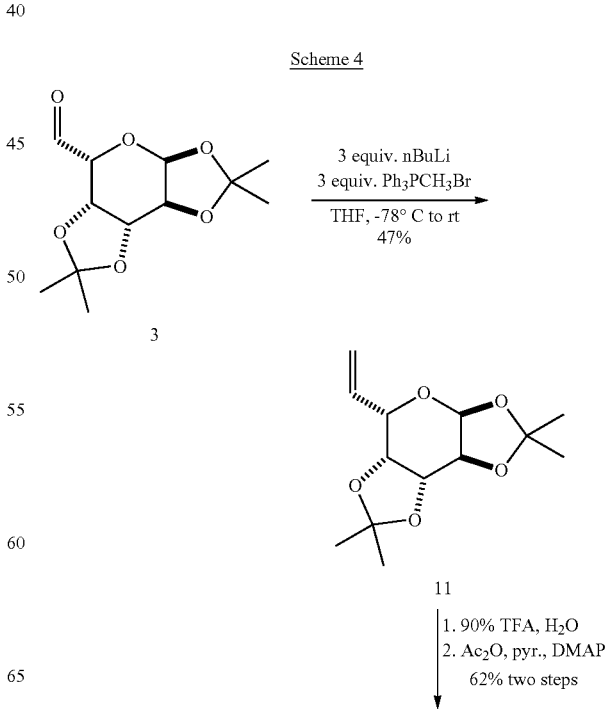

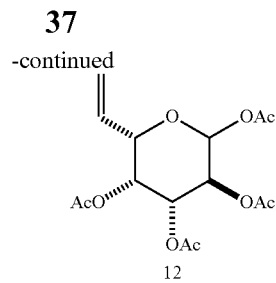

12

6,7-Deoxy-1,2:3,4-di-O-isopropylidene-α-L-galacto-hept-6-enopyranoside (11)

Referring to Scheme 4, to a −78° C. solution of Ph₃PCH₃Br (192 mg, 0.54 mmol) in THF (2 mL) was added n-BuLi (0.34 mL of a 1.6M solution in THF; 0.54 mmol). The mixture was stirred at −78° C. for 15 min, followed by the addition of aldehyde (Compound 3) (46.3 mg, 0.18 mmol). The mixture was allowed to warm to an ambient temperature over 1.5 h before being diluted with diethyl ether (25 mL) and quenched with saturated aqueous ammonium chloride (25 mL). The organic layer was washed with brine, dried over magnesium sulfate, filtered and concentrated under reduced pressure. The resulting residue was purified on silica gel (10% ethyl acetate in hexane; TLC $R_f$=0.56 25% ethyl acetate in hexanes) to give 22.8 mg (49%): ¹H NMR (CDCl₃; 400 mHz) δ: 5.93 (ddd, 1H), 5.59 (d, 1H), 5.37 (dt, 1H), 5.28 (dt, 1H), 4.62 (dd, 1H), 4.31 (m, 2H), 4.23 (dd, 1H), 1.54 (s, 3H), 1.47 (s, 3H), 1.35 (s, 3H).

5-vinylarabinose Tetraacetate (12)

Compound 12 was prepared from Compound 11 following the general procedure for acetonide hydrolysis and peracetylation of Example 10. Yield: 62% overall.

Example 14: Synthesis of 5-(1-propynyl)-arabinose Tetraacetate

Scheme 5

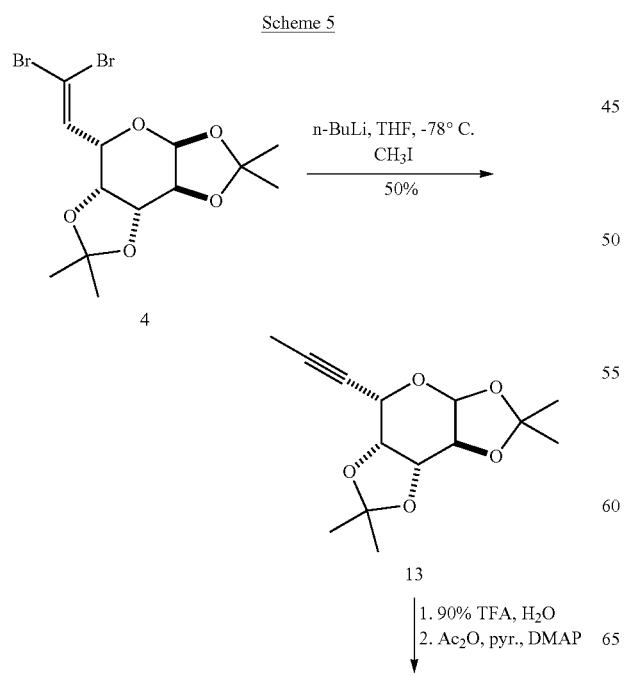

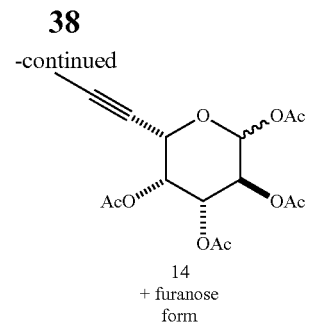

14
+ furanose form

6,7-Deoxy-1,2:3,4-di-O-isopropylidene-α-L-galacto-oct-6-ynopyranoside (13)

Referring to Scheme 5, to a −78° C. solution of the dibromo-olefin (Compound 4) (52 mg, 0.126 mmol) in THF (1.6 mL) was added n-BuLi (0.3 mL of a 1.6M solution in THF; 0.5 mmol) and the mixture was stirred for 1 h at −78° C. A solution of methyl iodide (47 μL, 0.63 mmol) in THF (0.5 mL) was added drop-wise, and the reaction mixture was allowed to warm to an ambient temperature over several hours. The reaction mixture was again cooled to −78° C. and saturated aqueous ammonium chloride (20 mL) was added. The resulting mixture was extracted with ethyl acetate (3×20 mL) and the combined organics were washed with saturated aqueous sodium chloride, dried of magnesium sulfate, filtered and concentrated under reduced pressure. The resulting residue was purified on silica gel eluting with 10% ethyl acetate in hexanes to give 16.9 mg (50%) of product as an oil.

5-(1-propynyl)-arabinose-1,2,3,4-tetraacetate (14)

Compound 14 was prepared from Compound 13 following the general procedure for acetonide hydrolysis and peracetylation in Example 10. Yield: 58% overall.

Example 15: Synthesis of 5-cyano-arabinopyranose-1,2,3,4-tetraacetate and 5-cyano-arabinofuranose-1,2,3,5-tetraacetate Scheme 6

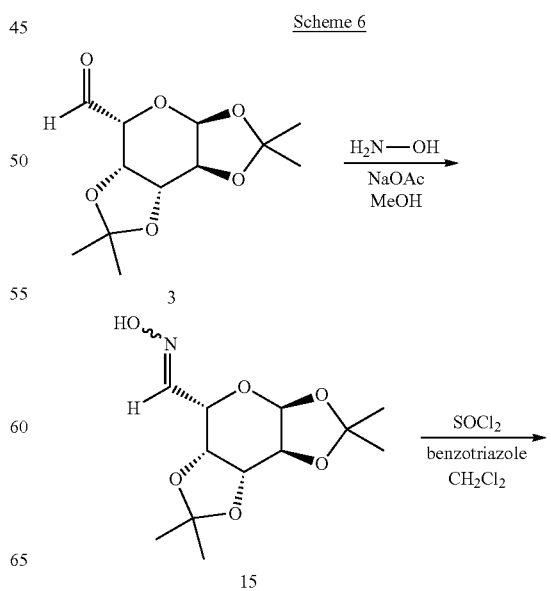

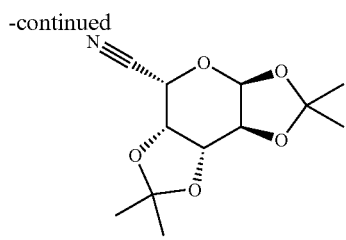

16

1,2:3,4-Di-O-isopropylidene-α-L-galactodialdo-1,5-pyranose-6-oxime (15)

Compound 15 was generally prepared as described by Streicher and Wunsch, *Carbohydr Res.* 338(22):2375-85 (2003). Referring to Scheme 6, the aldehyde (Compound 3) (200 mg, 0.77 mmol), hydroxylamine hydrochloride (161 mg, 2.32 mmol, 3.0 eq.), and NaOAc (127 mg, 1.55 mmol, 2.0 eq.) were diluted in MeOH (10 mL, 0.1 M) followed by the addition of water (1 mL, 10% v/v). The reaction stood for 20 h. The mixture was concentrated down to the aqueous layer to which it was extracted with ether (2×). The combined organics were extracted with NaOH (1×), and the aqueous layer acidified to pH 4-5 with 1 M HCl. The aqueous phase was extracted with ether (3×). The Et$_2$O layer was dried (MgSO$_4$) and concentrated in vacuo to provide the product as a white crystalline solid. Yield: (164 mg, 78%). LRMS (ESI$^+$) m/z 274.1 (M+H)$^+$. $^1$H-NMR (CDCl$_3$) δ: 1:1 mixture of (E):(Z) oxime isomers was detected. 1.33 (s, 12H), 1.46 (s, 6H), 1.54 (s, 3H), 1.55 (s, 3H), 4.29 (dd, J=2.0 Hz, 8.0 Hz, 1H), 4.34-4.36 (m, 2H), 4.43 (dd, J=2.0 Hz, 6.4 Hz, 1H), 4.62-4.63 (m, 3H), 5.00 (d, J=4.0 Hz, 1H), 5.55 (d, J=4.8 Hz, 2H), 6.80 (d, J=4.4 Hz, 1H), 7.46 (d, J=6.0 Hz, 1H).

5-cyano-fucose Diacetonide (16)

Compound 16 was generally prepared as described by Telvekar, *Synthetic Communications* 34(13):2331-2336 (2004). The oxime isomers (Compound 15) (160 mg, 0.5 mmol) were dissolved in CH$_2$Cl$_2$ (2 mL, 0.4 M). To this was added a solution of benzotriazole (70 mg, 0.5 mmol) and thionyl chloride (43 μL, 0.5 mmol) in 0.5 mL of CH$_2$Cl$_2$. The reaction was complete by TLC analysis in 5 min. The contents were filtered and the filtrate washed with sat. NaHCO$_3$ and water. The organic phase was dried (Na$_2$SO$_4$), filtered and evaporated. The crude product was purified by FCC eluting with 4:1 hexanes-EtOAc. Yield: 120 mg (81%). LRMS (ESI$^+$) m/z 256.1 (M+H)$^+$. $^1$H-NMR (CDCl$_3$) δ: 1.35 (s, 3H), 1.39 (s, 3H), 1.54 (s, 3H), 1.55 (s, 3H), 4.34 (dd, J=2.0 Hz, 7.6 Hz, 1H), 4.38 (dd, J=2.8 Hz, 4.8 Hz, 1H), 4.66 (m, 2H), 5.54 (d, J=5.2 Hz, 1H).

5-Cyano-arabinopyranose-1,2,3,4-tetraacetate (19) and 5-cyano-arabinofuranose-1,2,3,5-tetraacetate (20)

Compounds 19 and 20 were prepared from Compound 16 following the general procedure for acetonide hydrolysis and peracetylation of Example 10. The resulting pyranose and furanose forms were separable by FCC (elution gradient—4:1 to 3:2 hexanes-EtOAc). Sequence of elution by TLC: pyranose (Rf 0.34), furanose (Rf.27) in 3:2 hexane-EtOAc. Yield: 59 mg (pyranose), 52 mg (furanose) (98% combined overall yield). LRMS (ESI$^+$) m/z 0.284.1 (M-OAc)$^+$, 366.0 (M+Na)$^+$. $^1$H-NMR assignments were analogous to the alkynyl fucose reported by Hsu et al. (Hsu, Hanson et al., 2007; supra). $^1$H-NMR summary of pyranose forms (CDCl$_3$) δ: 5.89 (d, J=4.0 Hz, 1H, β-pyr), 6.42 (d, J=2.8 Hz, 1H, α-pyr). $^1$H-NMR summary of furanose forms (CDCl$_3$) δ: 6.27 (s, 1H, α-fur), 6.38 (d, J=4.8 Hz, 1H, β-fur).

Example 16: Synthesis of Chloro-, Bromo- and Iodo-Fucose Tetraacetates

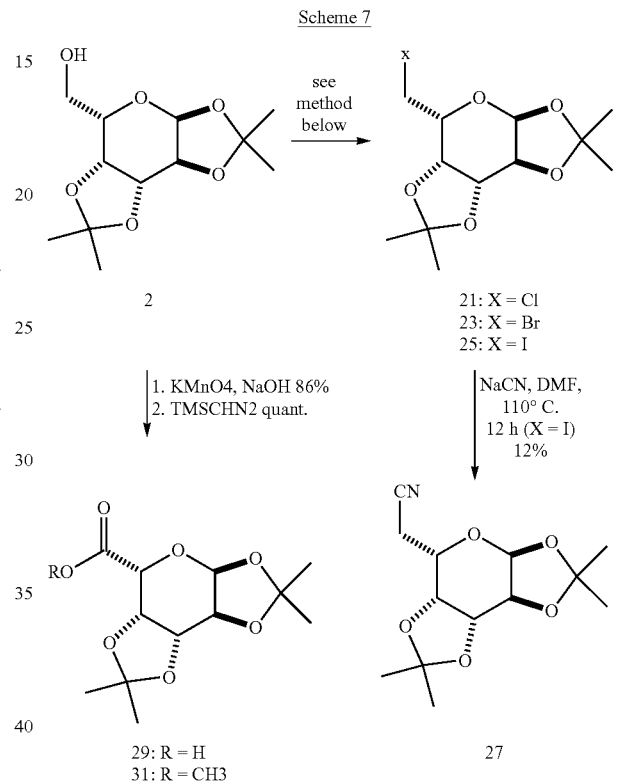

6-Chloro-fucose Diacetonide (21)

Referring to Scheme 7, the alcohol (Compound 2) (100 mg, 0.384 mmol), CCl$_4$ (1 mL, 10 mmol), and PPh3 (300 mg, 1.15 mmol, 3 eq.) were dissolved in CHCl2 (2 mL). The contents were stirred for 24 h following by concentration. The residue was purified by FCC (9:1 hexanes-EtOAc) to afford the product as a pale yellow gel. Yield: 107 mg (55%). LRMS (ESI$^+$) m/z 279 (M+H)$^+$. $^1$H-NMR (CDCl$_3$) δ: 1.34 (s, 3H), 1.36 (s, 3H), 1.45 (s, 3H), 1.54 (s, 3H), 3.58 (dd, J=6.8 Hz, 10.8 Hz, 1H), 3.68 (dd, J=6.8 Hz, 10.8 Hz, 1H), 4.65 (dd, J=2.4 Hz, 7.6 Hz, 1H), 5.54 (d, J=5.2 Hz).

6-Chloro-fucose Tetraacetate (22)

Compound 22 was prepared from Compound 21 following the general procedure for acetonide hydrolysis and peracetylation of Example 10. Yield: 29 mg (38% overall). LRMS (ESI$^+$) m/z 307.1 (M-OAc)$^+$, 389.0 (M+Na)$^+$.

6-Bromo-fucose Diacetonide (23)

Referring to Scheme 7, the alcohol (Compound 2) (150 mg, 0.58 mmol) was dissolved in DMF (2 mL) followed by addition of PPh$_3$ (0.61 g, 2.3 mmol, 4 eq.). N-bromosuccinimide (0.41 g, 2.3 mmol, 4 eq.) in DMF (1 mL) was added over 5 min via syringe. The mixture was heated to 110° C. for 2 h. The reaction was cooled and quenched with MeOH and stirred for 10 min. Ether and sat. NaHCO$_3$ were added and the layers separated. The aqueous layer was further washed with ether and the combined organic extracts were washed with water and dried (Na$_2$SO$_4$). The solvent was evaporated and the residue purified by FCC (9:1 hexanes-EtOAc) to afford the product as a sticky solid. Yield: 123 mg (66%). LRMS (ESI$^+$) m/z 323 (M+H)$^+$. $^1$H-NMR (CDCl$_3$) δ: 1.34 (s, 3H), 1.36 (s, 3H), 1.45 (s, 3H), 1.55 (s, 3H), 3.43 (dd, J=6.8 Hz, 10 Hz, 1H), 3.52 (dd, J=6.8 Hz, 10.4 Hz, 1H), 3.98 (dt, J=2.0 Hz, 6.8 Hz, 1H), 4.33 (dd, J=2.4 Hz, 5.2 Hz, 1H), 4.38 (dd, J=2.0 Hz, 8.0 Hz, 1H), 4.64 (dd, J=2.4 Hz, 8.0 Hz, 1H), 5.55 (d, J=5.2 Hz).

6-Bromo-fucose Qtetraacetate (24)

Compound 24 was prepared from Compound 23 following the general procedure for acetonide hydrolysis and peracetylation of Example 10. Yield: 129 mg (86% overall). LRMS (ESI$^+$) m/z 351.0 (M-OAc)$^+$, 432.9 (M+Na)$^+$.

6-Iodo-fucose Diacetonide (25)

Referring to Scheme 7, the protected sugar (Compound 2) (0.44 g, 1.7 mmol), PPh3 (0.99 g, 3.7 mmol, 2.2 eq.), iodine (0.87 g, 3.4 mmol, 2.0 eq.), and imidazole (0.51 g, 7.4 mmol, 4.4 eq.) were dissolved in toluene/EtOAc (4 mL/2 mL). The mixture was heated to 90° C. for 6 h while stirring. The mixture was cooled in an ice bath, diluted with CHCl$_3$ and extracted with sat. NaHCO$_3$. The organic layer was dried (Na$_2$SO$_4$), filtered and concentrated to an oil. The residue was purified by FCC eluting with hexanes-EtOAc (95:5 to 90:10 gradient). The product was isolated as a clear oil. Yield: 0.27 g (43%). LRMS (ESI$^+$) m/z 371.1 (M+H)$^+$. $^1$H-NMR (CDCl$_3$) δ: 1.32 (s, 3H), 1.34 (s, 3H), 1.44 (s, 3H), 1.53 (s, 3H), 3.20 (dd, J=7.2 Hz, 9.6 Hz, 1H), 3.31 (dd, J=7.2 Hz, 9.6 Hz, 1H), 3.94 (dt, J=1.6 Hz, 7.2 Hz, 1H), 4.29 (dd, J=2.4 Hz, 5.0 Hz, 1H), 4.40 (dd, J=2.0 Hz, 8.0 Hz, 1H), 4.60 (dd, J=2.4 Hz, 7.8 Hz, 1H), 5.53 (d, J=4.8 Hz).

6-Iodo-fucose Tetraacetate (26)

Compound 26 was prepared from Compound 25 following the general procedure for acetonide hydrolysis and peracetylation of Example 10. Yield: 30.5 mg (75% overall). LRMS (ESI$^+$) m/z 399.0 (M-OAc)$^+$.

Example 17: Synthesis of 6-cyano-fucose Tetraacetate

6-Cyano-fucose Diacetonide (27)

Compound 27 was prepared following a procedure by Streicher and Wunsch (*Carbohydr. Res.* 338(22): 2375-85 (2003)). Referring to Scheme 7, iodo-galactose (120 mg, 0.32 mmol) and NaCN (51 mg, 1 M) were heated to 110° C. in DMF for 12 h. The mixture was cooled, partitioned with CH$_2$Cl$_2$-water and the layers separated. The aqueous layer was further washed with CH$_2$Cl$_2$ (2×) and the combined organics washed with brine, dried (Na$_2$SO$_4$), filtered and concentrated to a brown oil. FCC purification (9:1 to 4:1 hexanes-EtOAc gradient) led to the pure product. Yield: 10 mg (12%). $^1$H-NMR (CDCl$_3$) δ: 1.33 (s, 3H), 1.35 (s, 3H), 1.45 (s, 3H), 1.54 (s, 3H), 2.65 (dd, J=6.8 Hz, 16 Hz, 1H), 2.70 (dd, J=6.8 Hz, 16 Hz, 1H), 4.05 (dt, J=2.0 Hz, 7.2 Hz, 1H), 4.24 (dd, J=2.0 Hz, 8.0 Hz, 1H), 4.34 (dd, J=2.8 Hz, 4.8 Hz, 1H), 4.65 (dd, J=2.8 Hz, 8.0 Hz, 1H), 5.50 (d, J=5.2 Hz).

6-Cyano-arabinose Tetraacetate (28)

Compound 28 was prepared from Compound 27 following the general procedure for acetonide hydrolysis and peracetylation of Example 10. Yield: 13 mg (98% overall). LRMS (ESI$^+$) m/z 298.0 (M-OAc)$^+$, 380.1 (M+Na)$^+$.

Example 18: Synthesis of Carboxyfucose Tetraacetate

Carboxyarabinose Diacetonide (29)

Following a procedure for the epimer (Bentama, El Hadrami et al., *Amino Acids* 24(4):423-6 (2003)), the alcohol (Compound 2) (3.44 g, 13.22 mmol) was diluted in 0.5 M NaOH (80 mL, 40 mmol, 3 eq.). After 15 min, KMnO$_4$ (5.22 g, 33.04, 2.5 eq.), dissolved in 106 mL of water, was added. The reaction stirred for 18 h and the solid filtered off. The filtrate was extracted with EtOAc (3×) and organic layers discarded. The aqueous layer was acidified with 1M HCl to pH 2 and extracted with EtOAc (3×). The combined organic layers were dried (MgSO$_4$), filtered, and concentrated to give a white solid that needed no further purification. Yield: 3.1 g (86%). LRMS (ESI$^-$) m/z 273.2 (M–H)$^-$. $^1$H-NMR (CDCl$_3$) δ: 1.36 (s, 6H), 1.46 (s, 3H), 1.54 (s, 3H), 4.40 (dd, J=2.4 Hz, 4.8 Hz, 1H), 4.70 (d, J=2.0 Hz, 1H), 4.64 (dd, J=2.4 Hz, 8.0 Hz, 1H), 5.50 (d, J=4.8 Hz).

Carboxyarabinose Tetraacetate (30)

Compound 30 was prepared from Compound 29 following the general procedure for acetonide hydrolysis and peracetylation of Example 10.

Example 19: Synthesis of Carboxymethylarabinose Tetraacetate

Carboxymethylarabinose diacetonide (31). The acid (Compound 29) (100 mg, 0.365 mmol) was dissolved in MeOH (3.65 mL, 0.1 M) and cooled to 0° C. After 15 min, 1 M TMSCHN$_2$ in ether (1.82 mL, 5 eq.) was added dropwise via syringe over 15 min. No starting material was detected after 30 min. The reaction was quenched with 5% HOAc/MeOH and the contents evaporated to dryness. Yield: Quant. LRMS (ESI$^+$) m/z 289.1 (M+H)$^+$. $^1$H-NMR (CDCl$_3$) δ: 1.34 (s, 6H), 1.46 (s, 3H), 1.53 (s, 3H), 3.83 (s, 3H), 4.39 (dd, J=2.4 Hz, 5.2 Hz, 1H), 4.59 (dd, J=2.4 Hz, 7.6 Hz, 1H), 4.67 (dd, J=2.4 Hz, 7.6 Hz, 1H), 5.67 (d, J=5.2 Hz).

Carboxymethyl-arabinose Tetraacetate (32)

Compound 32 was prepared from Compound 31 following the general procedure for acetonide hydrolysis and peracetylation of Example 10. Yield: 105 mg (77% overall). LRMS (ESI$^+$) m/z 0.317.0 (M-OAc)$^+$, 398.9 (M+Na)$^+$.

Example 20: Synthesis of 5-methyl-oxiran-arabinose Tetraacetate ((3S,4R,5S,6R)-6-((S)-2-methyl-oxiran-2-yl)-tetrahydro-2H-pyran-2,3,4,5-tetrayl tetraacetate) (36)

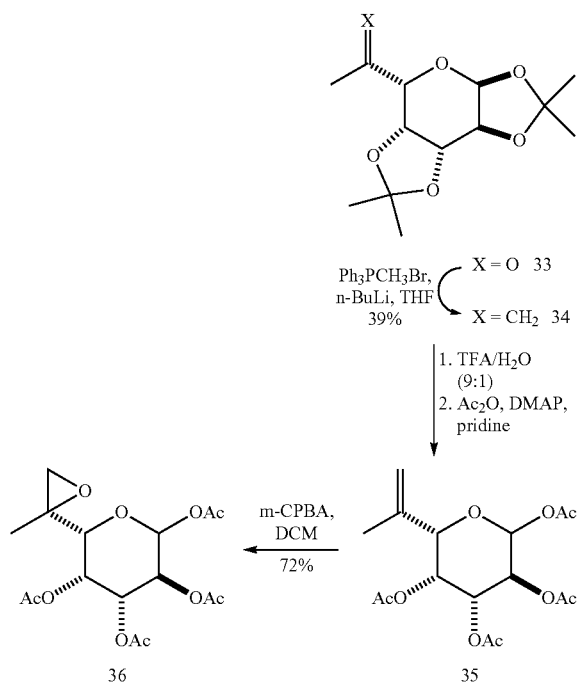

Scheme 8

1-((3aS,5R,5aS,8aR,8bS)-2,2,7,7-tetramethyltetrahydro-3aH-bis[1,3]dioxolo[4,5-b:4',5'-d]pyran-5-yl)ethanone (33)

Referring to Scheme 8, to a mixture of the alcohol (Compound 2) (236 mg, 0.86 mmol) in DCM (10 mL) was added Dess-Martin periodinane (DMP; 438 mg, 1.03 mmol)). After several hours an additional portion DMP (100 mg, 0.23 mmol) was added, and the mixture was stirred for an additional 1 h. The mixture was directly aspirated onto a 1 mm radial chromatotron plate and eluted with 25% ethyl acetate in hexanes. The first major material off the plate was desired product (Rf=0.6; 25% ethyl acetate in hexanes). Yield: 190 mg (81%): LRMS (ESI+) m/z 272; $^1$H-NMR (CDCl$^3$) δ: 5.64 (d, J=5.1 Hz, 1H), 4.63 (dd, J=7.8, 2.6 Hz, 1H), 4.55 (dd, J=7.8, 2.3 Hz), 4.35 (dd, J=5.1, 2.5 Hz), 4.17 (d, J=2.0 Hz, 1H), 2.26 (s, 3H), 1.5 (2, 3H), 1.44 (s, 3H), 1.34 (s, 3H), 1.31 (s, 3H).

(3aS,5S,5aR,8aR,8bS)-2,2,7,7-tetramethyl-5-(prop-1-en-2-yl)tetrahydro-3aH-bis[1,3]dioxolo[4,5-b:4',5'-d]pyran (34)

Referring again to Scheme 8, Compound 34 was prepared from Compound 33 (50 mg, 0.18 mmol) in a fashion similar to that used in preparation of Compound 11, to give 19 mg (39%): $^1$H-NMR (CDCl$_3$) δ: 5.61 (d, J=5.1 Hz, 1H), 5.10 (d, J=2.1 Hz, 1H), 4.99 (dd, J=3.1, 1.6 Hz, 1H), 4.34 (m, 2H), 4.19 (s, 1H), 1.82 (s, 3H), 1.52 (s, 3H), 1.45 (s, 3H), 1.34 (s, 6H).

(3S,4R,5R,6S)-6-(prop-1-en-2-yl)-tetrahydro-2H-pyran-2,3,4,5-tetrayl Tetraacetate (35)

Referring again to Scheme 8, Compound 35 was prepared from Compound 34 (11 mg, 0.04 mmol) following the general procedure for acetonide hydrolysis and peracetylation of Example 10. Yield 81% (11.7 mg, 0.033 mmol)

(3S,4R,5S,6R)-6-((S)-2-methyloxiran-2-yl)-tetrahydro-2H-pyran-2,3,4,5-tetrayl Tetraacetate (36)

Referring to Scheme 8, to a mixture of the peracetate (Compound 35) (6 mg, 0.017 mmol) in DCM (1 mL) was added m-CPBA (12 mg, 0.052 mmol) and the mixture was stirred at an ambient temperature for 16 hours. The reaction mixture was aspirated onto 1 mm radial chromatotron plate and eluted with 25% ethyl acetate in hexanes to give 4.6 mg (72%) of the epoxide. LRMS (ESI+) m/z 397 (M+Na)+.

Example 21: Synthesis of Propargyl Fucose Tetraacetate ((3S,4R,5S,6S)-6-(prop-2-ynyl)-tetrahydro-2H-pyran-2,3,4,5-tetrayl Tetraacetate) (37)

At −40° C., trifluoromethanesulfonic anhydride (166 μL, 0.98 mmol, 1.5 eq.) was added over 2 min via syringe to a solution of the protected galactose (Compound 2) (170 mg, 0.65 mmol) and 2,6-lutidine (96 μL, 0.82 mmol, 1.25 eq.) in methylene chloride (3 mL). The starting material was consumed in 1 h, and the reaction was quenched with sat. NaHCO$_3$. The mixture was extracted with ether (3×) and the combined organic layers dried (MgSO$_4$), filtered, and concentrated. The crude product was purified by flash chromatography (eluting with 9:1 hexanes-EtOAc) to afford the product as a clear oil. The triflate was immediately used in the next step.

nBuLi (0.70 mL, 1.74 mmol, 2.6 M, 3.8 eq.) was added dropwise to a solution of trimethylsilylacetylene (0.23 mL, 1.61 mmol, 3.5 eq.) and HMPA (85 μL) in THF (1.5 mL) at −60° C. After 15 min of stirring, the triflate (180 mg, 0.46 mmol) was added and the contents stirred while warming to room temperature. After stirring overnight, the reaction was quenched with saturated NH$_4$C$_1$ and the mixture extracted with ether (2×). The combined organic layers were dried and concentrated. By LC/MS partial TMS cleavage occurred. Purification was performed using flash chromatography (eluting with 95:5 to 9:1 hexanes-EtOAc) and both products were collected and concentrated to a clear oil. Overall yield: 61 mg (TMS protected), 68 mg (deprotected), 58% yield. TMS protected data: LRMS (ESI+) m/z 341.1 (M+H)+, 363.1 (M+Na)+. 1H-NMR (CDCl$_3$) δ: 0.15 (s, 9H), 1.34 (s, 3H), 1.36 (s, 3H), 1.45 (s, 3H), 1.56 (s, 3H), 2.52 (dd, J=6.4 Hz, 16.8 Hz, 1H), 2.63 (dd, J=8.4 Hz, 16.4 Hz, 1H), 3.91 (dt, J=1.6 Hz, 6.0 Hz, 1H), 4.30 (dd, J=2.4 Hz, 4.8 Hz, 1H), 4.32 (dd, J=2.0 Hz, 8.0 Hz, 1H), 4.62 (dd, J=2.4 Hz, 8.0 Hz, 1H), 5.50 (d, J=5.2 Hz, 1H).

The combined alkynes were deprotected using TFA (1 mL) and water (100 µL) for 2 h. The mixture was concentrated under high vacuum and peracetylated with acetic anhydride (1 mL), pyridine (1 mL), and DMAP (3 mg), for 3 days. The mixture was concentrated and purified by flash chromatography (eluting with 4:1 to 3:2 hexanes-EtOAc). The desired fractions were pooled and concentrated to give the product as a clear sticky solid. Overall yield: 32 mg (51%). LRMS (ESI+) m/z 297.1 (M-OAc)+, 379.0 (M+Na)+.

Example 22: Synthesis of Alkynyl Fucose Tetrapropanoate ((3S,4R,5R)-5-((S)-1-(propionyloxy)prop-2-ynyl)-tetrahydrofuran-2,3,4-triyl Tripropionate Mixture) (38)

To a mixture of Compound 6 (25 mg, 0.143 mmol) in pyridine was added acid chloride (1 mL, propionyl chloride). The reaction mixture solidified and DCM (2 mL), and DMAP (5 mg) was added and the mixture was stirred overnight at an ambient temperature. The reaction mixture was treated with saturated aqueous sodium bicarbonate with stirring for ~10 min. The reaction mixture was poured into water and extracted with ethyl acetate (3×25 mL). The combined extracts were washed with 1N HCl (20 mL), saturated aqueous sodium bicarbonate (20 mL) and brine before being dried over MgSO₄, filtered and concentrated. The resulting residue was purified via radial chromatography on a 1 mm plate eluting with 25% ethyl acetate in hexanes to give a heterogeneous mixture of α and β-pyranose and furanose isomers. Yield: 26.8 mg (47%). LRMS (ESI⁺) m/z 421 (M+Na⁺), 325 (M-propionate)⁺.

Example 23: Synthesis of Alkynyl Fucose Tetra-n-Hexanoates (3S,4R,5R)-5-((S)-1-(hexanoyloxy)prop-2-ynyl)-tetrahydrofuran-2,3,4-triyl Trihexanoate and (2S,3S,4R,5R,6S)-6-ethynyl-tetrahydro-2H-pyran-2,3,4,5-tetrayl Tetrahexanoate Mixture (39 and 40, respectively); and (2R,3S,4R,5R,6S)-6-ethynyl-tetrahydro-2H-pyran-2,3,4,5-tetrayl Tetrahexanoate (41)

Scheme 9

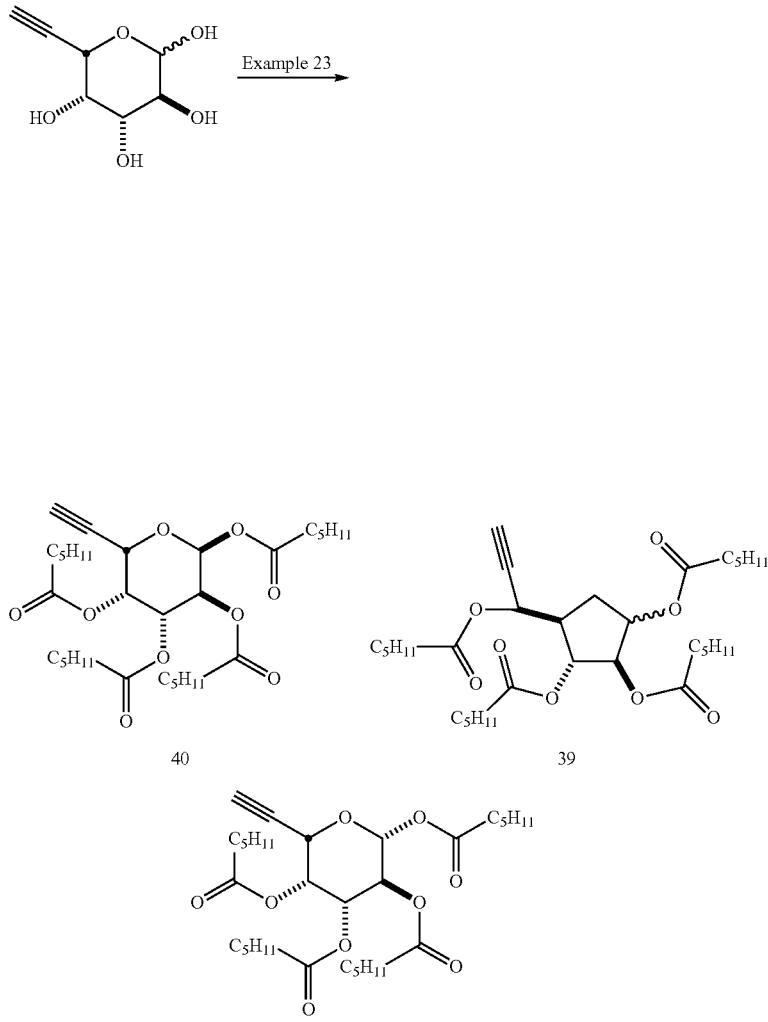

Referring to Scheme 9, to a mixture of Compound 6 (25 mg, 0.143 mmol) in pyridine (1 mL) was added DMAP (~5 mg) and hexanoic anhydride (1 mL). The mixture was stirred overnight at an ambient temperature. The reaction mixture was treated with saturated aqueous sodium bicarbonate with stirring for ~10 min., and the reaction mixture was poured into water and extracted with ethyl acetate (3×25 mL). The combined extracts were washed with 1N HCl (20 mL), saturated aqueous sodium bicarbonate (20 mL) and brine before being dried over MgSO$_4$, filtered and concentrated. The resulting residue was purified via radial chromatography on a 1 mm plate eluting with 25% ethyl acetate hexanes to give to products shown in Scheme 9. (3S,4R,5R)-5-((S)-1-(hexanoyloxy)prop-2-ynyl)-tetrahydrofuran-2,3,4-triyltrihexanoate and (2S,3S,4R,5R,6S)-6-ethynyl-tetrahydro-2H-pyran-2,3,4,5-tetrayl tetrahexanoate mixture: LRMS (ESI$^+$) m/z 589 (M+Na$^+$). (2R,3S,4R,5R,6S)-6-ethynyl-tetrahydro-2H-pyran-2,3,4,5-tetrayl tetrahexanoate:

$^1$H-NMR (CDCl$_3$) δ 5.70 (d, J=8.4 Hz, 1H), 5.52 (dd, J=3.5, 1.2 Hz, 1H), 5.35 (t, J=8.2 Hz, 1H), 5.1 (dd, J=8.2, 3.4 Hz, 1H), 4.60 (dd, J=2.4, 0.6 Hz, 1H), 2.50-1.90 (m, 11H), 1.70-1.50 (m, 9H), 1.19-1.10 (m, 20H), 0.95-0.83 (m, 15H); LRMS (ESI$_+$) m/z 589 (M+Na$_+$).

Example 24: Synthesis of Alkynyl Fucose tetrakis (trimethylacetate) ((2S,3S,4R,5R)-5-((S)-1-(pentanoyloxy)prop-2-ynyl)-tetrahydrofuran-2,3,4-triyl tripentanoate (42) and (2R,3S,4R,5R)-5-((S)-1-(pentanoyloxy)prop-2-ynyl)-tetrahydrofuran-2,3,4-triyl tripentanoate (43)); alkynyl fucose tris(trimethylacetate) (3S,4R,5R,6S)-6-ethynyl-5-hydroxy-tetrahydro-2H-pyran-2,3,4-triyl tripentanoate mixture (44); and alkynyl fucose bis(trimethylacetate (2R,3S,4R,5R,6S)-6-ethynyl-3,5-dihydroxy-tetrahydro-2H-pyran-2,4-diyl dipentanoate (45))

Scheme 10

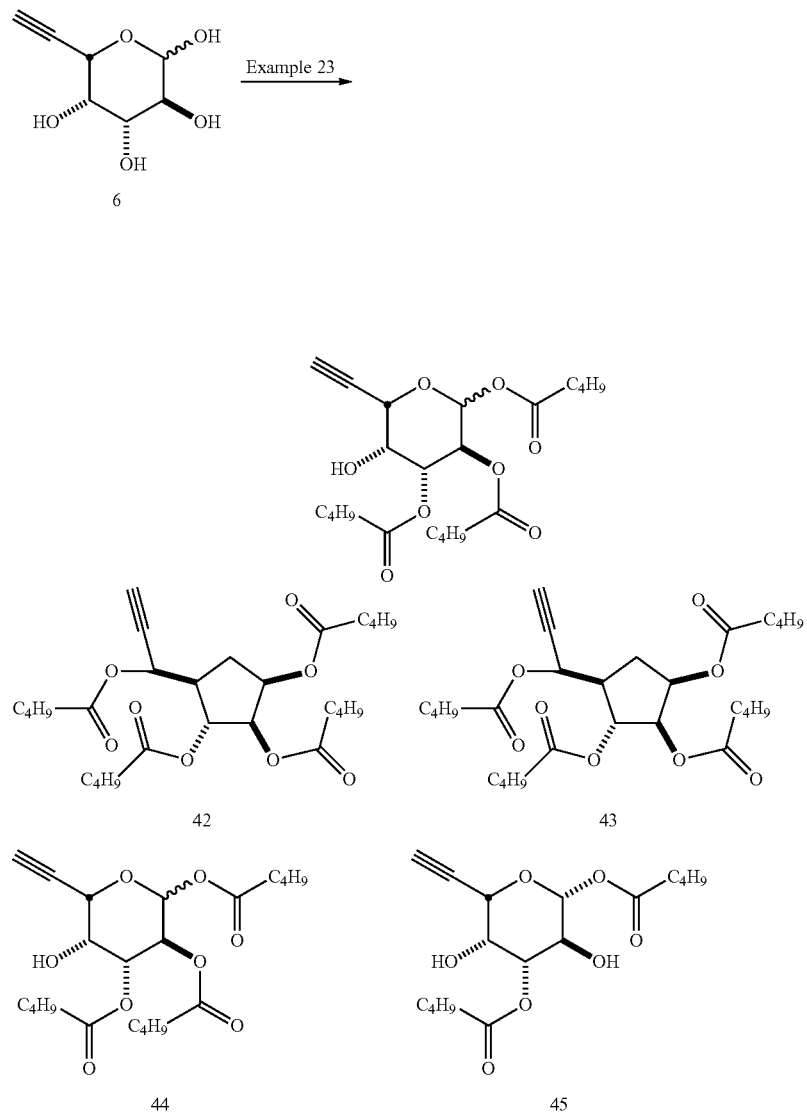

To a mixture of Compound 6 (see Example 10: 25 mg, 0.143 mmol) in pyridine (1 mL) was added DMAP (~5 mg) and trimethyl acetic anhydride (1 mL). The mixture was stirred overnight at an ambient temperature. The reaction mixture was treated with saturated aqueous sodium bicarbonate with stirring for ~10 min., and the reaction mixture was poured into water and extracted with ethyl acetate (3×25 mL). The combined extracts were washed with 1N HCl (20 mL), saturated aqueous sodium bicarbonate (20 mL) and brine before being dried over MgSO$_4$, filtered and concentrated. The resulting residue was purified via radial chromatography on a 1 mm plate eluting with 25% ethyl acetate hexanes to give to products shown in Scheme 10.

(2S,3S,4R,5R)-5-((S)-1-(pentanoyloxy)prop-2-ynyl)-tetrahydrofuran-2,3,4-triyltripentanoate: $^1$H-NMR (CDCl$_3$) δ 6.31 (d, J=6.5 Hz, 1H), 5.68 (dd, J=7.0, 5.8 Hz, 1H), 5.54 (dd, J=9.2, 2.4 Hz, 1H), 5.38 (dd, J=7.0, 4.7 Hz, 1H), 4.29 (dd, J=9.2, 5.6 Hz, 1H), 2.4 (d, J=2.3 Hz, 1H), 1.24 (s, 9H), 1.21 (s, 9H), 1.20 (s, 9H), 1.19 (s, 9H); LRMS (ESI$^+$) m/z 533 (M+Na$^+$), 409.

(2R,3S,4R,5R)-5-((S)-1-(pentanoyloxy)prop-2-ynyl)-tetrahydrofuran-2,3,4-triyl tripentanoate: $^1$H-NMR (CDCl$_3$) δ 6.12 (d, J=0.4 Hz, 1H), 5.59 (dd, J=6.8, 2.2 Hz, 1H), 5.35 (dt, J=4.1, 1.5 Hz, 1H), 5.03 (dd, J=1.0, 0.4 Hz, 1H), 2.46 (d, J=2.3 Hz, 1H), 1.24 (s, 9H), 1.24 (s, 9H), 1.23 (s, 9H), 1.22 (s, 3H); LRMS (ESI$^+$) m/z 533 (M+Na$^+$), 409.

(3S,4R,5R,6S)-6-ethynyl-5-hydroxy-tetrahydro-2H-pyran-2,3,4-triyltripentanoate mixture: LRMS (ESI$^+$) m/z 449 (M+Na$^+$).

(2R,3S,4R,5R,6S)-6-ethynyl-3,5-dihydroxy-tetrahydro-2H-pyran-2,4-diyl dipentanoate: $^1$H-NMR (CDCl$_3$) δ 5.54 (d, J=8.2 Hz, 1H), 4.84 (dd, J=10.0, 3.2 Hz, 1H), 4.52 (dd, J=2.1, 1.1 Hz, 1H), 4.15 (dd, J=3.2, 1.2 Hz, 1H), 4.08 (dd, J=10.0, 8.1 Hz, 1H), 2.58 (d, J=2.2 Hz, 1H), 1.26 (s, 9H), 1.25 (s, 9H); LRMS (ESI$^+$) m/z 365 (M+Na$^+$).

Example 25: Synthesis of (3S,4R,5R,6S)-6-ethynyl-tetrahydro-2H-pyran-2,3,4,5-tetrayl tetrakis(2-methylpropanoate) (46)

Scheme 11

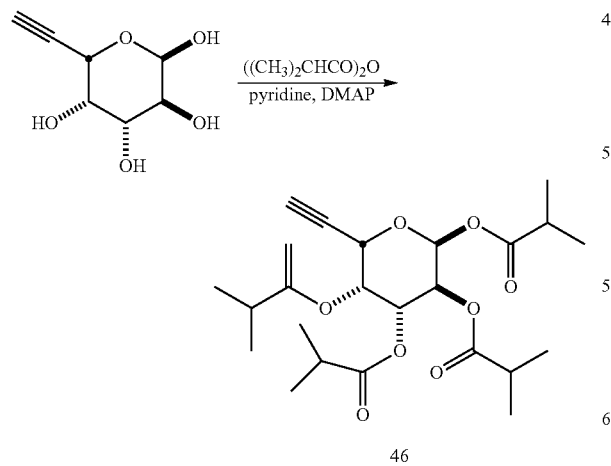

46

(Followed procedure 2) To a mixture of the tetra-ol (5 mg, 0.028 mmol) in pyridine (0.2 mL) was added DMAP (~1 mg) and the anhydride (0.2 mL or 200 mg). The mixture was stirred overnight at an ambient temperature and was treated with saturated aqueous sodium bicarbonated with stirring for 10 min. The mixture was poured into water and extracted with ethyl acetate (3×25 mL). The combined extracts were washed with 1N HCl (20 mL), saturated aqueous sodium bicarbonate (20 mL) and brine before being dried over MgSO$_4$, filtered and concentrated. The resulting residue was purified via radial chromatography on a 1 mm plate eluting with 25% ethyl acetate hexanes to give the product in the α-pyranose form: $^1$H-NMR (CDCl$_3$) δ 6.42 (d, J=3 Hz, 1H), 5.6 (s, 1H), 5.4 (m, 1H), 2.8-2.57 (m, 2H), 2.50-2.38 (m, 3H), 1.30-1.07 (m, 13H), 1.06-1.02 (m, 11H). LRMS (ESI$^+$) m/z 477.1 (M+Na$^+$).

Example 26

Scheme 12

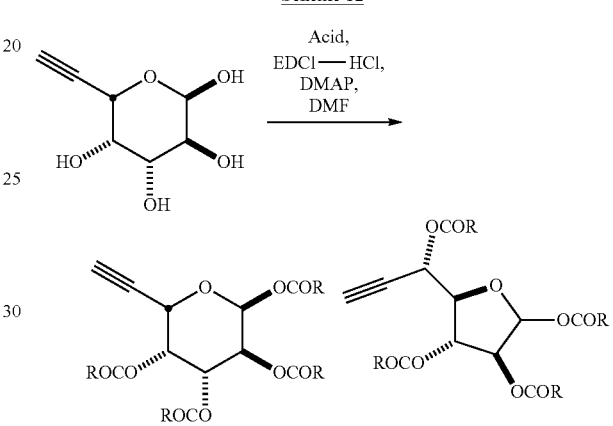

Procedure 3:

To a solution of the tetra-ol (5 mg, 0.028 mmol) in DMF (100 uL) was added nicotinic acid (70 mg, 0.57 mmol), DMAP (0.5 mg) and EDCI-HCl (55 mg, 0.28 mmol). The reaction mixture was stirred at an ambient temperate for 16 h. The mixture was treated with saturated aqueous sodium bicarbonate (5 mL) with stirring for 5 min. The resulting mixture was extracted with ethyl acetate (3×3 mL). The combined extracts were washed with water and brine, dried over MgSO$_4$, filtered and concentrated under reduced pressure. The mixture was purified via radial chromotography on a 1 mm plate eluting with 5% methanol in methylene chloride. A single major band was collected and concentrated to give the perester.

The following were prepared utilizing the procedure above:

(3S,4R,5R,6S)-6-ethynyl-tetrahydro-2H-pyran-2,3,4,5-tetrayl Tetranicotinate (47)

Yield 12.1 mg (72%), LRMS (ESI+) m/z 594.85 (M+H).

(3S,4R,5R,6S)-6-ethynyl-tetrahydro-2H-pyran-2,3,4,5-tetrayl tetrakis(3-(2-methoxyethoxy)propanoate) (48)

Yield 18.5 mg (95%), LRMS (ESI+) m/z 717 (M+Na)+.

(3S,4R,5R,6R)-6-ethynyl-tetrahydro-2H-pyran-2,3,4,5-tetrayl Tetraisonicotinate (49)

Yield 13.0 mg (78%), LRMS (ESI+) m/z 594 (M+H)+.

Example 27: Preparation of (3S,4R,5R,6S)-6-(benzyloxymethyl)tetrahydro-2H-pyran-2,3,4,5-tetrayl Tetraacetate Scheme 13

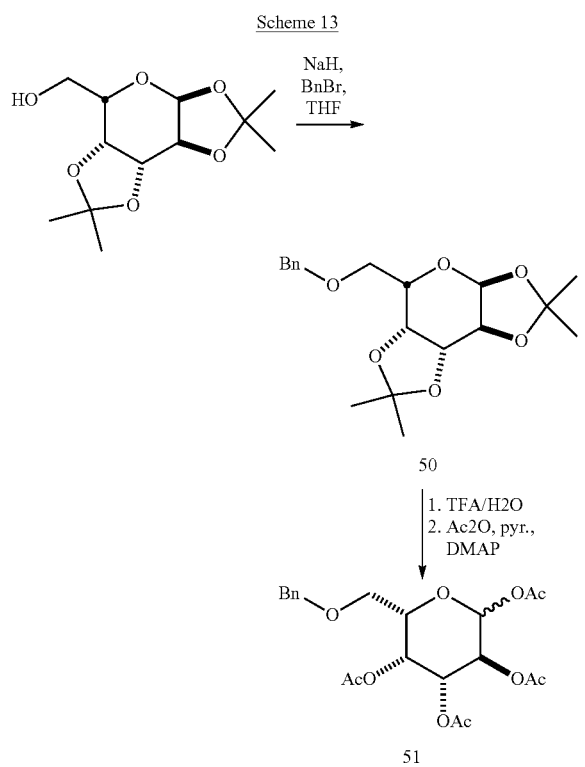

50

51

(3aS,5S,5aR,8aR,8bS)-5-(benzyloxymethyl)-2,2,7,7-tetramethyltetrahydro-3aH-bis[1,3]dioxolo[4,5-b:4',5'-d]pyran (50)

To a mixture of the alcohol (100 mg, 0.38 mmol) and benzyl bromide (83 μL, 0.72 mmol) in THF (2 mL) was added NaH (50 mg of a 60% dispersion in mineral oil) and the reaction mixture was stirred overnight at an ambient temperature. To the mixture was added sat. aq. $NH_4C_1$ (10 mL) and the mixture was extracted with ethyl acetate (3×25 mL). The combined extracts were washed with water and brine and were dried over $MgSO_4$. Filtration and concentration gave a residue that was purified via radial chromatography on a 1 mm plate, eluting with 10% ethyl acetate in hexanes to give 63 mg (47%): $^1$H-NMR ($CDCl_3$) δ 7.37-7.22 (m, 5H), 5.55 (d, J=4.9 Hz, 1H), 4.64-4.53 (m, 3H), 4.32 (dd, J=5.1, 2.3 Hz, 1H), 4.27 (dd, J=7.8, 2.4 Hz, 1H), 4.01 (dt, J=6.4, 1.9 Hz, 1H), 3.72-3.61 (m, 2H), 1.54 (s, 3H), 1.44 (s, 3H), 1.33 (s, 6H).

(3S,4R,5R,6S)-6-(benzyloxymethyl)tetrahydro-2H-pyran-2,3,4,5-tetrayl tetraacetate (51)

To a round-bottom flask charged with the benzyl ether (63 mg, 0.18 mmol) and cooled to 0° C. was added ice-cold TFA/H2O (9:1, 5 mL). The mixture was stirred for 1 h and was concentrated under reduced pressure. The residue was then treated with pyridine (3 mL), DMAP (5 mg) and acetic anhydride (3 mL). The mixture was stirred 16 h at an ambient temperature and was concentrated under reduced pressure. The residue was purified via radial chromatography on a 2 mm plate eluting with 25% ethyl acetate in hexanes to give the a mixture of pyranose and furanose benzy ether peracetates, 97 mg (0.22 mmol, 122%): LRMS (ESI+) m/z 378.9 (M-OAc)+.

Example 28: Preparation of (2R,3R,4S)-2-((S)-1-acetoxyprop-2-ynyl)-5-methoxy-tetrahydrofuran-3,4-diyl diacetate (52)

Scheme 14

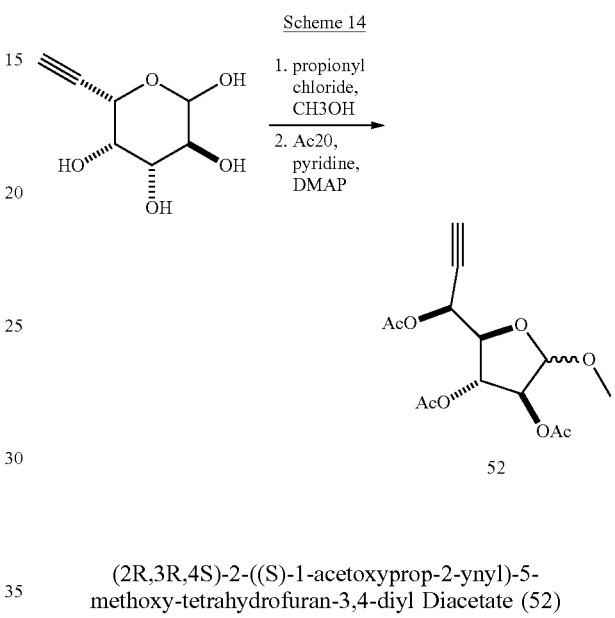

52

(2R,3R,4S)-2-((S)-1-acetoxyprop-2-ynyl)-5-methoxy-tetrahydrofuran-3,4-diyl Diacetate (52)

A round-bottom flask was charged with $CH_3OH$ (2 mL) and propionyl chloride (20 μL) was added. After 5 min, the tetra-ol (~5 mg, 0.028 mmol) was added and the mixture was stirred overnight at an ambient temperature. The mixture was concentrated under reduced pressure, the residue was treated with pyridine (1 mL), DMAP (0.5 mg) and acetic anhydride (1 mL), stirred for ~2 h and concentrated under reduced pressure. The resulting residue was purified by radial chromatography to give a mixture of the two furanose triacetates as an inseparable mixture, 6.1 mg (69%): LRMS (ESI+) m/z 336.95 (M+Na)+.

Example 29: (3S,4R,5S,6R)-6-(difluoromethyl)tetrahydro-2H-pyran-2,3,4,5-tetrayl Tetraacetate Scheme 15

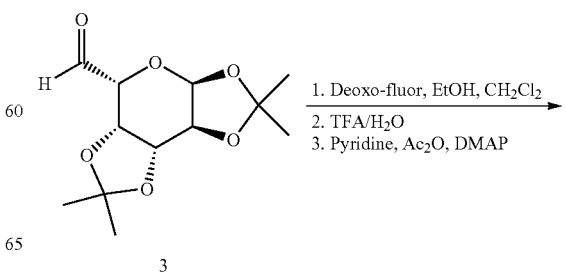

3

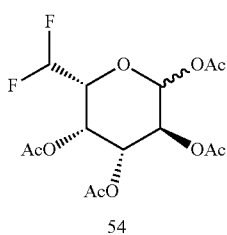

54

(3aS,5R,5aS,8aR,8bS)-5-(difluoromethyl)-2,2,7,7-tetramethyltetrahydro-3aH-bis[1,3]dioxolo[4,5-b:4',5'-d]pyran (53)

A mixture of the aldehyde (70 mg, 0.23 mmol) and absolute ethanol (3.1 μL, 54 μmol, 0.2 eq.) in methylene chloride (115 μL, 2 M) was treated with bis (2-methoxyethyl)aminosulfur trifluoride (Deoxo-fluor, 85 μL, 0.46 mmol, 1.7 eq.) in a sealed Eppendorf tube. The contents stood at 37° C. for 72 h. The reaction was cooled and then purified by flash chromatography (eluting with 9:1 to 4:1 hexanes-EtOAc). The difluoro-diacetonide intermediate was isolated as a clear oil. Yield: 35 mg, 46% yield. $^1$H-NMR (CDCl$_3$) δ: 1.34 (s, 3H), 1.35 (s, 3H), 1.46 (s, 3H), 1.54 (s, 3H), 3.85-3.92 (m, 1H), 4.33-4.38 (m, 2H), 4.62-4.67 (m, 1H), 5.56 (dd, J=2 Hz, 4.8 Hz, 1H), 5.84 (dt, J=6.8 Hz, 54 Hz, 1H).

(3S,4R,5S,6R)-6-(difluoromethyl)tetrahydro-2H-pyran-2,3,4,5-tetrayl Tetraacetate (54)

The aforementioned compound (30 mg, 0.11 mmol) was treated with trifluoroacetic acid (1 mL) and water (100 uL) for 2 h. The mixture was concentrated under high vacuum and peracetylated with acetic anhydride (1 mL), pyridine (1 mL), and DMAP (5 mg), for 1 d. The mixture was concentrated and purified by flash chromatography (eluting with 4:1 to 1:1 hexanes-EtOAc). The desired fractions were pooled and concentrated to give the product as a clear sticky solid. Overall yield: 24 mg (62%). LRMS (ESI$^+$) m/z 309 (M-OAc)$^+$, 391 (M+Na)$^+$.

Example 30: Preparation of 2-Fluoro-2-Deoxyfucose Peracetate (58)

Scheme 16

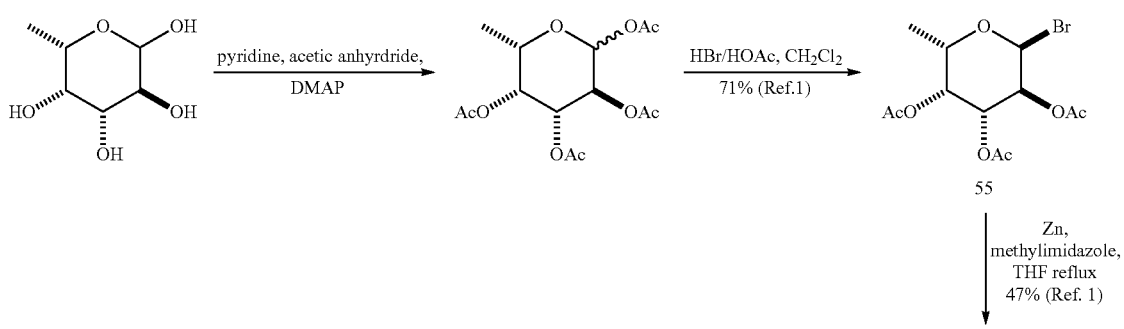

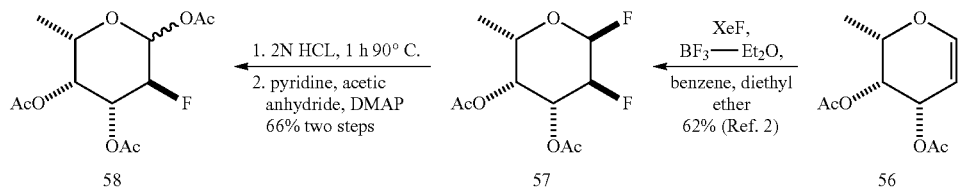

Compounds 56, 57 and 58 were prepared according to the following references:
1. Oberthur, M.; Leimkuhler, C.; Kuguer, R. G.; Lu, W.; Walsh, C. T.; Kahne, D. *J. Am. Chem. Soc.* 2005, 127, 10747-10752
2. a) Murray, B. W.; Wittmann, V.; Burkhart, M. D.; Hung, S-C.; Wong, C-H. *Biochemistry*, 1997, 36, 823-831. b) Korytnky, W.; Valentekovic-Horvath, S.; Petrie, C. R. *Tetrahedron*, 1982, 38(16), 2547-2550.

Example 31: Preparation of (3S,4R,5R,6S)-6-(propa-1,2-dienyl)-tetrahydro-2H-pyran-2,3,4,5-tetrayl Tetraacetate (60)

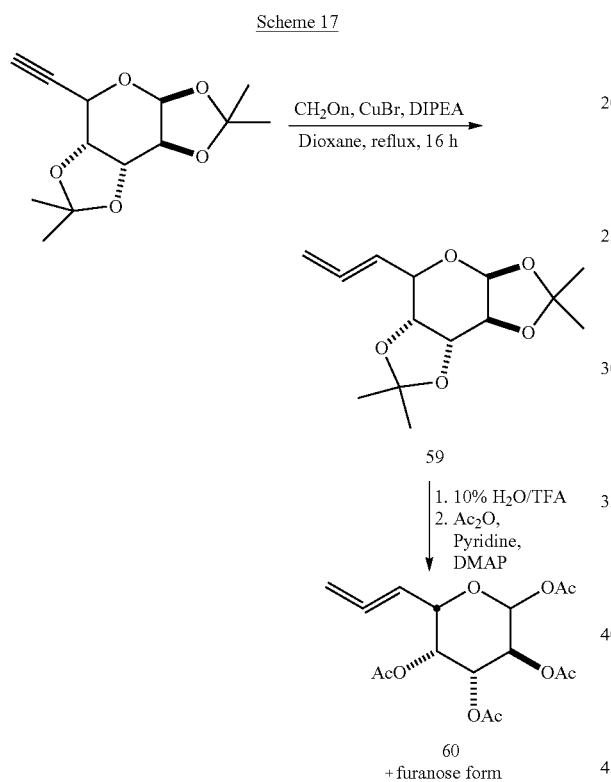

Allenyl Diacetonide (59):

To a suspension of alkyne (compound 5, 25 mg, 0.1 mmol), paraformaldehyde (7 mg, 0.215 mmol), CuBr (5 mg, 0.035 mmol) and dioxane (0.5 mL) in a pressure tube was added DIPEA (28 μL, 0.223 mmol). The pressure tube was sealed and the brown mixture was heated at reflux for 16 h then cooled to rt and filtered. The solid was washed with Et$_2$O, and the combined filtrates were concentrated under reduced pressure. Purification by flash chromatography (25% ethyl acetate in hexanes) afforded the desired allene compound 59, 2.3 mg (9%): $^1$H NMR (CDCl$_3$; 400 mHz) δ: 5.56 (d, J=4.0 Hz, 1H), 5.36 (q, J=8.0 Hz, 1H), 4.84 (m, 2H), 4.62 (dd, J=7.8 Hz, 3.4 Hz, 1H), 4.37 (dd, J=8.2 Hz, 1.7 Hz, 1H), 4.32 (d, 1H, J=2.3 Hz, 1H), 1.54 (s, 3H), 1.49 (s, 3H), 1.36 (s, 3H), 1.34 (s, 3H).

To the acetonide (compound 59, 2.3 mg, 8.5 mmol) in a round-bottom flask and cooled in an ice-bath was added ice-cold 10% H$_2$O/TFA (4 mL) and the mixture was stirred for 1 h. After concentration under reduced pressure, the resulting residue was treated with pyridine (2 mL), DMAP (0.5 mg) and acetic anhydride (2 mL). The reaction mixture was stirred overnight and the mixture was concentrated under reduced pressure and purified by radial chromatography on a 1 mm plate eluting with 25% ethyl acetate in hexanes. A single band was collected and concentrated to give 4.1 mg compound 60 as a mixture of anomeric acetates: LRMS (ESI$^+$) m/z 378.98 (M+Na$^+$)

Example 32 Preparation of 2-Fluoro-2-Deoxyfucose Peracetate

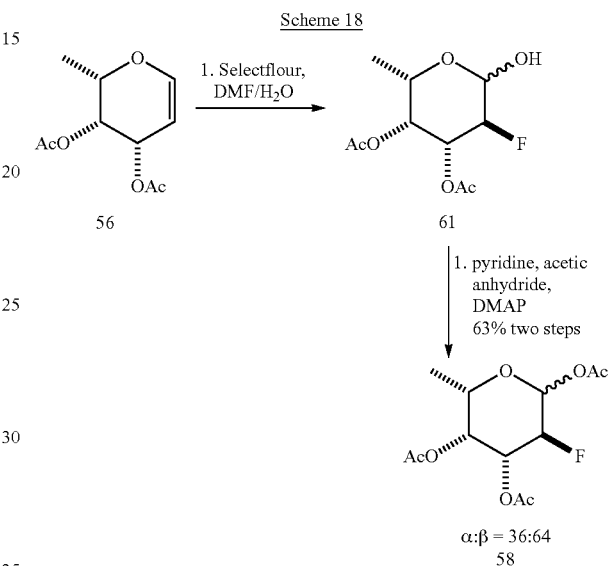

Preparation of 61:

To a solution of compound 56 (500 mg, 2.3 mmol) in DMF/H$_2$O (30 mL of a 1:1 mixture) was added Selectfluor® (1.24 g, 3.5 mmol) and the mixture was stirred at an ambient temperature for 12 h. The mixture was diluted with ethyl acetate (100 mL) and washed with water (3×100 mL). The organic layer was dried over Na$_2$SO$_4$, filtered and concentrated under reduced pressure: LRMS (ESI$^+$) m/z 273.04 (M+Na$^+$). See published procedure: Burkart, M. D.; Zhang, Z.; Hung, S-C.; Wong, C-H. *J. Am. Chem. Soc.* 1997, 119, 11743-11746.

(3S,4R,5R,6S)-3-fluoro-6-methyl-tetrahydro-2H-pyran-2,4,5-triyl Triacetate (58)

To a mixture of compound 61 in pyridine (10 mL) was added acetic anhydride (10 mL) followed by DMAP (10 mg) and the mixture was stirred for 2 h at an ambient temperature. The mixture was concentrated under reduced pressure, dissolved in DCM (5 mL) and aspirated onto a 2 mm radial chromatotron plate; eluting with 25% ethyl acetate in hexanes. A single band was collected and concentrated to give 420 mg of compound 58 (1.44 mmol, 63%) as an inseparable mixture of anomers (α/β=36.64): $^1$H NMR (CDCl$_3$; 400 mHz) δ (α-anomer): 6.43 (d, J=4.11 Hz, 1H), 5.41 (dt, J=10.8, 3.72 Hz, 1H), 5.37 (m, 1H), 4.88 (ddd, J=49.5, 10.2, 3.9 Hz, 1H), 4.25 (q, 1H, J=6.7 Hz, 1H), 2.9 (s, 3H), 2.07 (s, 3H), 1.15 (d, J=6.5 Hz, 3H); β-anomer: 5.77 (dd, J=8.02, 4.2 Hz, 1H), 5.3 (m, 1H), 5.17 (dq, J=9.8, 3.5 Hz, 1H), 4.64 (ddd, J=51.8, 9.8, 8.0 Hz, 1H), 3.98 (dq, J=6.4

Hz, 1.0 Hz, 1H), 2.18 (s, 3H), 2.07 (s, 3H), 1.22 (d, J=6.2 Hz, 3H); LRMS (ESI+) m/z 315.02 (M+Na+).

Example 33: Preparation of L-2-deoxy-2-chlorofucopyranose-1,3,4-triacetate, 62

Scheme 19

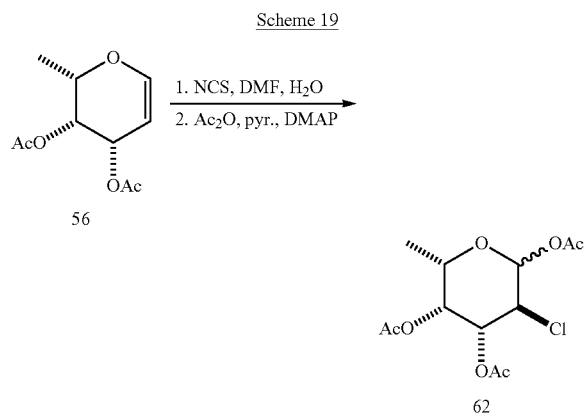

56

L-2-deoxy-2-chlorofucopyranose-1,3,4-triacetate:

To a mixture of the compound 56 (100 mg, 0.47 mmol) in DMF/H$_2$O (2 mL of a 1:1 mixture) was added N-chlorosuccinimide (91 mg, 0.7 mmol) and the mixture was stirred for 16 h at an ambient temperature. The reaction mixture was poured into ethyl acetate (100 mL) and washed with water and brine, dried over MgSO$_4$, filtered and concentrated under reduced pressure. The mixture was taken up in pyridine (2 mL). DMAP (2 mg) was added and acetic anhydride (2 mL) was added. The mixture was stirred for 16 h at an ambient temperature before being concentrated and purified via radial chromatography on a 1 mm plate eluting with 25% ethyl acetate in hexanes to give 98 mg (0.79 mmol, 79%) of the 2-deoxy-2-chlorofucose triacetate 62 as a mixture of anomers (α/β=0.73/1.0) as determined by 1H NMR: LRMS (ESI+) m/z 330.98 (M+Na+).

Example 34: Preparation of (2S,4R,5R,6S)-3,3-difluoro-6-methyl-tetrahydro-2H-pyran-2,4,5-triyl Triacetate (65) and (2R,4R,5R,6S)-3,3-difluoro-6-methyl-tetrahydro-2H-pyran-2,4,5-triyl Triacetate (66)

Scheme 20

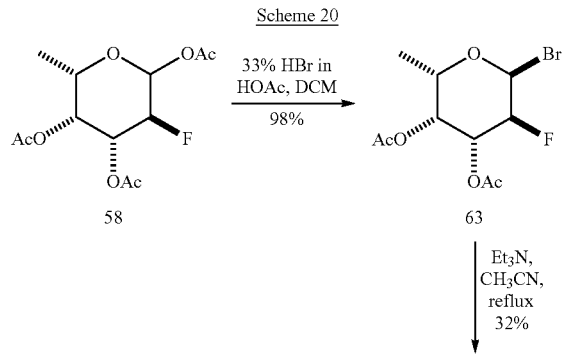

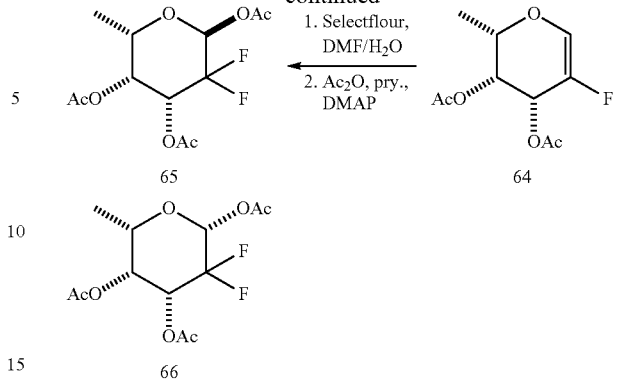

1-α-bromofucopyranose-3,4-diacetate (63): To the 2-fluorofucose triacetate (compound 58, 300 mg, 1.027 mmol) in CH$_2$Cl$_2$ (1 mL) was added 33% HBr in HOAc (0.25 mL). The mixture was stirred for 2 h and was poured into ice-water (100 mL) and extracted (3×50 mL) with DCM. The combined extracts were washed with water and dried with MgSO$_4$. Filtration and concentration gave 0.313 g (1.0 mmol, 98%) of the L-α-1-bromofucopyranoside-3,4-diacetate (63). The material was carried forward without purification: 1H NMR (CDCl$_3$; 400 mHz) δ 6.60 (d, J=4.3 Hz, 1H), 5.48 (dt, J=10.0, 3.5 Hz, 1H), 5.39 (m, 1H), 4.74 (ddd, J=50.5, 10.2, 4.3 Hz, 1H), 4.44 (dq, J=5.9, 1.3 Hz), 2.17 (s, 3H), 2.06 (s, 3H), 1.22 (d, J=6.4 Hz, 3H).

2-fluorofucal-3,4-diacetate, 64

To a mixture of the bromide (63, 312 mg, 1 mmol) in acetonitrile (10 mL) was added Et$_3$N (500 µL, 3 mmol) and the reaction mixture was heated to reflux. The reaction was monitored by TLC. After 2 h, the reaction mixture was poured into ethyl acetate (100 mL) and washed with 1N HCl, water and brine and dried over MgSO$_4$. Filtration and concentration gave a residue that was purified by radial chromatography on a 2 mm plate eluting with 25% ethyl acetate hexanes to give 73 mg (32%): 1H NMR (CDCl$_3$; 400 mHz) δ: 6.74 (dd, J=4.9, 1.2 Hz, 1H), 5.97 (dd, J=3.9, 1.2 Hz, 1H), 5.3 (dt, J=5.3, 1.4 Hz, 1H), 4.15 (q, J=6.7 Hz, 1H), 2.18 (s, 3H), 2.07 (s, 3H), 1.56 (s, 3H), 1.22 (d, J=6.5 Hz, 3H).

2-deoxy-2,2-difluorofucopyranose-1,3,4-triacetate (65 and 66)

To a mixture of the fluorofucal (64, 50 mg, 0.216 mmol) in DMF/H$_2$O (1 mL, 1:1 mixture) was added Selectfluor® and the reaction mixture was stirred overnight at an ambient temperature. The reaction mixture was poured into EtOAc (100 mL) and washed with water (3×50 mL) and brine, dried over NaSO$_4$, decanted and concentrated. The resulting residue was acetylated with a mixture of pyridine (1 mL), DMAP (2 mg) and acetic anhydride (1 mL). The mixture was stirred for several hours and concentrated under reduced pressure and purified on a 1 mm radial chromatotron plate eluting with 10% ethyl acetate in hexanes to give a mixture of anomeric 2-deoxy-2, 2-difluorofucose-1,3,4-diacetates. α-anomer (65): 1H NMR (CDCl$_3$; 400 mHz) δ 6.21 (d, J=7.2, 1H), 5.43 (m, 1H), 5.33 (m, 1H), 4.33 (dq, J=6.5, 0.9 Hz), 2.19 (s, 6H), 2.12 (s, 3H), 1.22 (d, J=6.6 Hz, 3H); LRMS (ESI+) m/z 332.90 (M+Na+): β-anomer (66): 1H NMR (CDCl$_3$; 400 mHz) δ 5.78 (d, J=15.5 Hz, 1H), 5.3 (m, 1H), 5.24 (m, 1H), 4.06 (dq, J=6.5, 1.4 Hz), 2.23 (s, 3H), 2.19 (s, 3H), 2.12 (s, 3H), 1.29 (d, J=6.5 Hz, 1H); LRMS (ESI+) m/z 332.99 (M+Na+).

Example 35: Preparation of (2S,4S,5R,6S)-6-methyl-tetrahydro-2H-pyran-2,4,5-triyl Triacetate

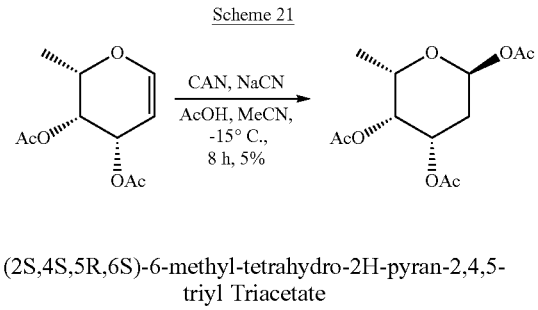

Scheme 21

(2S,4S,5R,6S)-6-methyl-tetrahydro-2H-pyran-2,4,5-triyl Triacetate

To a flame-dried flask maintained under a nitrogen atmosphere was added fucal-3,4-diacetate (110 mg, 0.51 mmol) dissolved in 2.6 mL of anhydrous acetonitrile. Ceric(IV) ammonium nitrate (727 mg, 1.33 mmol) and glacial acetic acid (290 µL, 5.1 mmol) were added and the reaction mixture was then cooled to −15° C. Sodium cyanide (33 mg, 0.66 mmol) was then added and the reaction was stirred at 15° C. under nitrogen for 8 h. The reaction was quenched with 0.1 M sodium thiosulfate (50 mL). The aqueous layer was extracted with dichloromethane (3×50 mL) and the combined organic layer was washed with brine, dried over sodium sulfate, filtered and concentrated. The residue was purified by flash chromatography on silica gel eluted with a hexane:ethyl acetate solvent mixture (90:10 to 75:25) to provide the title compound (8 mg, 5%). TLC (SiO$_2$, 3:1 hexanes/ethyl acetate): R$_f$=0.20. $^1$H NMR (CDCl$_3$; 400 MHz) δ: 6.29 (m, 1H), 5.29 (ddd, J=12.4, 4.8, 2.8 Hz, 1H), 5.22 (m, 1H), 4.17 (q, J=6.8 Hz, 1H), 2.19 (m, 1H), 2.17 (s, 3H), 2.11 (s, 3H), 2.01 (s, 3H), 1.88 (ddt, J=13.6, 4.8, 1.2, 1H), 1.15 (d, J=6.8 Hz).

Example 35: Activity of Fucose Analogs

The effects of fucose analogs on antibody core fucosylation were tested at concentrations of 5004 and 1 mM as follows: A CHO DG44 cell line producing a humanized IgG1 anti-CD70 monoclonal antibody, h1F6 (see International Patent Publication WO 06/113909) was cultured at 7.5×10$^5$ cells per mL in 2 mLs of CHO culture media at 37°, 5% CO$_2$ and shaking at 100 RPM in a 6 well tissue culture plate. Media was supplemented with insulin like growth factor (IGF), penicillin, streptomycin and either 1 mM or 50 µM of the fucose analog (prepared as described supra). On day 5 post inoculation, the culture was centrifuged at 13000 RPM for 5 minutes to pellet cells; antibodies were then purified from supernatant.

Antibody purification was performed by applying the conditioned media to protein A resin pre-equilibrated with 1× phosphate buffered saline (PBS), pH 7.4. After washing resin with 20 resin bed volumes of 1×PBS, antibodies were eluted with 5 resin bed volumes of Immunopure IgG elution buffer (Pierce Biotechnology, Rockford, Ill.). A 10% volume of 1M tris pH 8.0 was added to neutralize the eluted fraction. The amount of non-core fucosylated antibody produced was determined as described in Example 7. The results are shown in the following tables.

TABLE 1

| Name (Chemical name) | R$^5$ | R$^1$—R$^4$ | Inhibition at 50 µM | Inhibition at 1 mM |
|---|---|---|---|---|
| Alkynyl fucose (5-ethynylarabinose) | —C≡CH | —OH | >80% | ND |
| Alkynyl fucose peracetate Alkynyl fucose tetraacetate (5-ethynylarabinose tetraacetate) | —C≡CH | —OAc | >80% | >80% |
| 5-propynyl fucose tetraacetate (5-propynylarabinose tetraacetate) | —C≡CCH$_3$ | —OAc | 50% | >80% |
| propargyl fucose tetraacetate ((3S,4R,5R,6S)-6-(prop-2-ynyl)-tetrahydro-2H-pyran-2,3,4,5-tetrayl tetraacetate) | —CH$_2$C≡CH | —OAc | ~10% | ~10-20% |
| Peracetyl galactose (galactose pentaacetate) | —OAc | —OAc | ~0% | ~0% |
| 5-vinyl fucose tetraacetate (5-ethylenylarabinose tetraacetate) | —CHCH$_2$ | —OAc | ~0% | ~4% |
| 6-cyano fucose tetraacetate (6-cyanofucose tetraacetate) | —CH$_2$CN | —OAc | 30% | >80% |
| 5-cyano fucose tetraacetate (pyranose form) (5-cyanoarabinopyranose tetraacetate) | —CN | —OAc | 20% | ND |
| 5-cyano fucose tetraacetate (furanose form) (5-cyanoarabinofuranose tetraacetate) | —CN | —OAc | 5-10% | ND |
| 5-methylester fucose tetraacetate (5-carboxymethyl arabinose tetraacetate) | —C(O)OCH$_3$ | —OAc | 30% | >80% |

TABLE 1-continued

| Name (Chemical name) | $R^5$ | $R^1$—$R^4$ | Inhibition at 50 µM | Inhibition at 1 mM |
|---|---|---|---|---|
| 5-(CH(OAc)CH₃)peracetyl fucose (6-methylgalactose pentaacetate) | —CH(OAc)CH₃ | —OAc | ~0% | 40% |
| 5-methyloxiran-arabinose tetraacetate ((3S,4R,5S,6R)-6-((S)-2-methyloxiran-2-yl)-tetrahydro-2H-pyran-2,3,4,5-tetrayl tetraacetate) | [methyloxiranyl structure] | —OAc | ~0% | ~35-40% |
| 6-iodo-fucose tetraacetate (6-iodofucose tetraacetate) | —CH₂I | —OAc | 3% | 30% |
| 6-chloro-fucose tetraacetate (6-chlorofucose tetraacetate) | —CH₂Cl | —OAc | 20% | 20-30% |
| 6-bromo-fucose tetraacetate (6-bromofucose tetraacetate) | —CH₂Br | —OAc | 50% | 80% |
| Alkynyl fucose tetrapropanonate (5-ethynylarabinose tetrapropanoate) | —C≡CH | —OC(O)CH₂—CH₃ | >80% | >80% |
| Alkynyl fucose tetra-n-hexanoate (5-ethynylarabinose tetrahexanoate) | —C≡CH | —OC(O)(CH₂)₄—CH₃ | >80% | >80% |
| Alkynyl fucose tetrakis(trimethylacetate) (5-ethynylarabinose tetra(trimethylacetate)) | —C≡CH | —OC(O)C(CH₃)₃ | 20% | 60% |
| Alkynyl fucose tetrakis(trimethylacetate) (5-ethynylarabinose tetra(trimethylacetate)) | —C≡CH | —OC(O)C(CH₃)₃ | 5% | 10% |
| Alkynyl fucose 1,2,3-(trimethylacetate) (5-ethynylarabinose 1,2,3-(trimethylacetate)) | —C≡CH | —OC(O)C(CH₃)₃ and —OH | ~0% | ND |
| Alkynyl fucose di(trimethylacetate) (5-ethynylarabinose 1,3-(trimethylacetate)) | —C≡CH | —OC(O)C(CH₃)₃ and —OH | >80% | ND |
| Alkynyl fucose pemicotinate | —C≡CH | —C(O)-3-pyridyl | >80% | >80% |
| Alkynyl fucose perisonicotinate | —C≡CH | —C(O)-4-pyridyl | >80% | >80% |
| Alkynyl fucose per-PEG ester | —C≡CH | —C(O)—(CH₂CH₂O)₂—OCH₃ | >80% | >80% |
| 1-methyl-2,3,4-triacetyl alkynyl fucose | —C≡CH | $R^1$ = OCH₃ $R^2, R^3, R^4$ = OAc | 68% | >80% |
| Alkynyl fucose perisobutanoate | —C≡CH | —OC(O)CH(CH₃)₂ | >80% | >80% |

"ND" means non-core fucosylated antibody was not detected due to poor antibody production or inhibition of cell growth in the presence of the fucose analog.

TABLE 2

| Name (Chemical name) | $R^5$ | $R^1$ | $R^2/R^{2a}$ | $R^3/R^{3a}$ | Inhibition at 50 µM | Inhibition at 1 mM |
|---|---|---|---|---|---|---|
| 2-deoxy-2-fluorofucose diacetate ($R^4$ = OAc) | —CH₃ | —OH | —F/—H | —OAc/—H | >80% | >80% |
| 2-deoxy-2-chlorofucose triacetate ($R^4$ = OAc) | —CH₃ | —OAc | —Cl/—H | —OAc/—H | 17% | >80% |
| Allene ($R^4$ = OAc) | —CH=C=CH₂ | —OAc | —OAc/—H | —OAc/—H | 23% | 34% |
| 2-deoxy-2-fluorofucose ($R^4$ = OH) | —CH₃ | —OH | —F/—H | —OH/—H | >80% | >80% |
| 2-deoxy-2-fluorofucose peracetate ($R^4$ = OAc) | —CH₃ | —OAc | —F/—H | —OAc/—H | >80% | >80% |
| 1,2-difluoro-1,2-didexoy fucose peracetate ($R^4$ = OAc) | —CH₃ | —F | —F/—H | —OAc/—H | >80% | >80% |

TABLE 2-continued

| Name (Chemical name) | $R^5$ | $R^1$ | $R^2/R^{2a}$ | $R^3/R^{3a}$ | Inhibition at 50 μM | Inhibition at 1 mM |
|---|---|---|---|---|---|---|
| 6,6-difluorofucose tetraacetate ($R^4$ = OAc) | —CHF$_2$ | —OAc | —OAc/—H | —OAc/—H | >80% | >80% |
| 2-deoxy-2,2-difluorofucopyranose triacetate (alpha) ($R^4$ = OAc) | —CH$_3$ | —OAc | —F/—F | —OAc/—H | 0 | 64% |
| 2-deoxy-2,2-difluorofucopyranose triacetate (beta) ($R^4$ = OAc) | —CH$_3$ | —OAc | —F/—F | —OAc/—H | 0 | 75% |
| 6-methyl-tetrahydro-2H-pyran-2,4,5-triyl triacetate ($R^4$ = OAc) | —CH$_3$ | —OAc | —H/—H | —OAc/—H | 0 | 36% |
| 5-Benzyloxy fucose peracetate ($R^4$ = OAc) | —CH$_2$OCH$_2$Ph | —OAc | —OAc/—H | —OAc/—H | 0 | 75% |

"ND" means non-core fucosylated antibody was not detected due to poor antibody production or inhibition of cell growth in the presence of the fucose analog.

Certain other fucose analogs were tested for their ability to be incorporated into antibodies. These fucose analogs were tested at concentrations of 50 μM and 1 mM using the methodology as described above and in Example 7. The results are shown in the following table.

TABLE 3

| Name (Chemical name) | $R^5$ | $R^1$—$R^4$ | % Incorporation |
|---|---|---|---|
| Propargyl fucose or (3S,4R,5R)-6-(prop-2-ynyl)tetrahydro-2H-pyran-2,3,4,5-tetrayl tetraacetate | [propargyl group] | —OAc | 80% (1 mM) |
| 5-(Z)-propenyl fucose peracetate | [(Z)-propenyl group] | —OAc | ~30% |
| Isopropenyl peracetyl fucose or (3S,4R,5R,6S)-6-(prop-1-en-2-yl)-tetrahydro-2H-pyran-2,3,4,5-tetrayl tetraacetate | [isopropenyl group] | —OAc | >80% (1 mM and 50 uM) |
| 5-ethyl fucose or (3S,4R,5S,6S)-6-ethyl-tetrahydro-2H-pyran-2,3,4,5-tetraol | —CH$_3$CH$_2$ | —OH | >80% (1 mM and 50 uM) |
| 5-ethyl fucose peracetate or (3S,4R,5S,6S)-6-ethyl-tetrahydro-2H-pyran-2,3,4,5-tetrayl tetraacetate | —CH$_3$CH$_2$ | —OAc | >90% (1 mM and 50 uM) |
| 5-cyclopropyl fucose or (3S,4R,5S,6S)-6-cyclopropyltetrahydro-2H-pyran-2,3,4,5-tetraol | [cyclopropyl group] | —OH | ~80% |
| 5-cyclopropyl fucose peracetate or (3S,4R,5R,6S)-6-cyclopropyltetrahydro-2H-pyran-2,3,4,5-tetrayl tetraacetate | [cyclopropyl group] | —OAc | ~80% |

TABLE 3-continued

| Name (Chemical name) | $R^5$ | $R^1$—$R^4$ | % Incorporation |
|---|---|---|---|
| 5-propyloxyarabinose tetraacetate or (3S,4R,5S,6R)-6-((S)-2-methyloxiran-2-yl)tetrahydro-2H-pyran-2,3,4,5-tetrayl tetraacetate | (epoxide structure) | —OAc | ~60% |
| Fluoromethylene fucose or (3S,4R,5S)-6-(fluoromethyl)tetrahydro-2H-pyran-2,3,4,5-tetrayl tetraacetate | —CH$_2$F | —OAc | >90% (1 mM and 50 uM) |
| 5-chloromethylene peracetyl fucose or (3S,4R,5S)-6-(chloromethyl)tetrahydro-2H-pyran-2,3,4,5-tetrayl tetraacetate | —CH$_2$Cl | —OAc | ~80% |
| 5-bromomethylene peracetyl fucose or (3S,4R,5S)-6-(bromomethyl)tetrahydro-2H-pyran-2,3,4,5-tetrayl tetraacetate | —CH$_2$Br | —OAc | ~50% (50 uM; 20% at 1 mM) |
| 5-iomethylene-peracetyl fucose or (3S,4R,5S)-6-(iodomethyl)tetrahydro-2H-pyran-2,3,4,5-tetrayl tetraacetate | —CH$_2$I | —OAc | ~30% |
| Azido peracetyl fucose or (3S,4R,5R)-6-(azidomethyl)tetrahydro-2H-pyran-2,3,4,5-tetrayl tetraacetate | —CH$_2$N$_3$ | —OAc | 60% |
| 5-(2-azidoethyl) arabinose tetraacetate or (3S,4R,5R,6S)-6-(2-azidoethyl)tetrahydro-2H-pyran-2,3,4,5-tetrayl tetraacetate | —CH$_2$CH$_2$N$_3$ | —OAc | 20% |
| Isopropyl peracetyl fucose or (3S,4R,5R,6S)-6-isopropyltetrahydro-2H-pyran-2,3,4,5-tetrayl tetraacetate | —CH=C=CH$_2$<br>Isopropyl | —OAc<br>—OAc | ~30%<br>Not detected |

Example 36: Titration Method to Determine Effective Levels of Fucose Analogs A CHO DG44 cell line producing a humanized IgG1 anti-CD70 monoclonal antibody, h1F6 (see International Patent Publication WO 06/113909) was cultured at 3.0×10$^5$ cells per mL in 30 mLs of CHO culture media at 37°, 5% CO$_2$ and shaking at 100 RPM in a 125 mL shake flask. Media was supplemented with insulin like growth factor (IGF), penicillin, streptomycin and either 100 μM, 50 μM, 5 μM, 500 nM, or 50 nM alkynyl fucose peracetate. Cultures were fed on day 3 with 2% volume of a feed media containing 5 mM, 2.5 mM, 250 μM, 25 μM, and 2.5 μM alkynyl fucose peracetate for the respective cultures. On day four, the culture was split 1:4 into fresh culture media. Cultures were fed with a 6% volume of production feed media containing 1.66 mM, 833 μM, 83 μM, 8.3 μM and 833 nM alkynyl fucose peracetate, respectively, on days 5, 7, 9 and 10. Supplementation of the feed media is optional. Conditioned media was collected on day 13 by passing culture through a 0.2 μm filter.

Antibody purification was performed by applying the conditioned media to a protein A column pre-equilibrated with 1× phosphate buffered saline (PBS), pH 7.4. After washing the column with 20 column volumes of 1×PBS, antibodies were eluted with 5 column volumes of Immunopure IgG elution buffer (Pierce Biotechnology, Rockford, Ill.). A 10% volume of 1M tris pH 8.0 was added to eluted fraction. The sample was dialyzed overnight into 1×PBS. The carbohydrate composition was determined using capillary electrophoresis.

Figure 6:
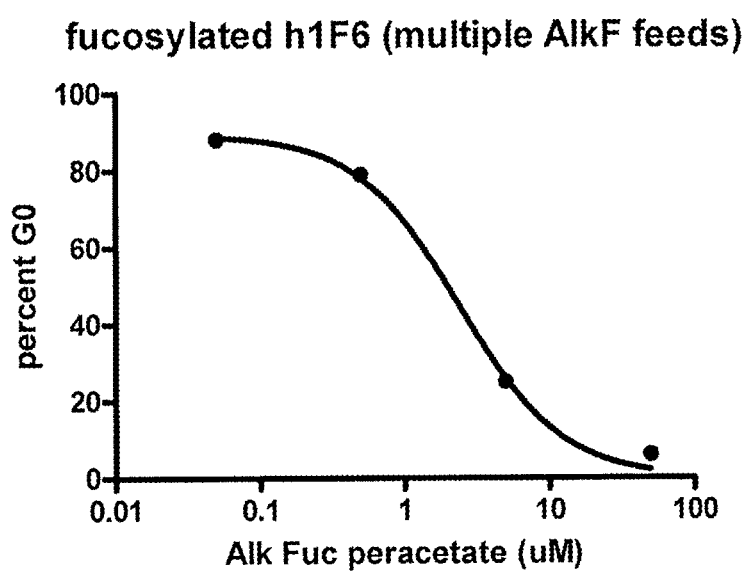
FIG. 6 shows the results of a titration of alkynyl fucose peracetate ("Alk Fuc peracetate") on a culture of host cells expressing h1F6 antibody and the effect on production of Ab with core fucosylation (G0).

Referring to FIG. 6, the results of a titration of alkynyl fucose peracetate ("Alk Fuc peracetate") on a culture of host cells expressing h1F6 antibody and the effect on production of Ab with core fucosylation (G0). As the amount of G0 antibody produced decreased, the amount of non-core-fucosylated antibody increased.

Example 37: Non-Core Fucosylated Antibody Production in Different Culture Media To determine the effect of different culture media on non-core fucosylated antibody production, a CHO DG44 cell line producing a humanized IgG1 anti-CD70 monoclonal antibody, h1F6 (see International Patent Publication WO 06/113909), was cultured in various media. The cells (7.5×

10⁵ cells per mL in 2 mLs) were cultured in PowerCHO (Lonza Group Ltd., Basil, Switzerland) or OptiCHO (Invitrogen, Carlsbad, Calif.) media CHO culture media at 37°, 5% $CO_2$ and shaking at 100 RPM in a 6 well tissue culture plate. Media was supplemented with insulin like growth factor (IGF), penicillin, streptomycin and 50 μM alkynyl fucose peracetate. On day 5 post-inoculation, the culture was centrifuged at 13000 RPM for 5 minutes to pellet cells; antibodies were then purified from supernatant.

Antibody purification was performed by applying the conditioned media to protein A resin pre-equilibrated with 1× phosphate buffered saline (PBS), pH 7.4. After washing resin with 20 resin bed volumes of 1×PBS, antibodies were eluted with 5 resin bed volumes of Immunopure IgG elution buffer (Pierce Biotechnology, Rockford, Ill.). A 10% volume of 1M tris pH 8.0 was added to neutralize the eluted fraction. Production of non-core fucosylated antibody was determined as described in Example 7. The proportion of non-core fucosylated to core fucosylated antibody produced from each media was similar.

The present invention is not limited in scope by the specific embodiments described herein. Various modifications of the invention in addition to those described herein will become apparent to those skilled in the art from the foregoing description and accompanying figures. Such modifications are intended to fall within the scope of the appended claims. Unless otherwise apparent from the context any step, element, embodiment, feature or aspect of the invention can be used in combination with any other. All patent filings, and scientific publications, accession numbers and the like referred to in this application are hereby incorporated by reference in their entirety for all purposes to the same extent as if so individually denoted.

```
                                                    SEQ ID NO: 1
MAWVWTLLFLMAAAQSAGAQIQLVQSGPEVKKPGETVKISCKASGYTFT

NYGMNWVKQAPGKGLKWMGWINTYTGEPTYADAFKGRFAFSLETSASTA

YLQINNLKNEDTATYFCARDYGDYGMDYWGQGTSVTVSS

SEQ ID NO: 2
METDTLLLWVLLLWVPGSTGDIVLTQSPASLAVSLGQRATISCRASKSV

STSGYSFMHWYQQKPGQPPKWYLASNLESGVPARFSGSGSGTDFTLNIH

PVEEEDAATYYCQHSREVPWTFGGGTKLEIKR

SEQ ID NO: 3
MAWVWTLLFLMAAAQSAQAQVQLVQSGAEVKKPGASVKVSCKASGYTFT

NYGMNWVRQAPGQGLKWMGWINTYTGEPTYADAFKGRVTMTRDTSISTA

YMELSRLRSDDTAVYYCARDYGDYGMDYWGQGTTVTVSSASTKGPSVFP

LAPSSKSTSGGTAALGCLVKDYFPEPVTVSWNSGALTSGVHTFPAVLQS

SGLYSLSSVVTVPSSSLGTQTYICNVNHKPSNTKVDKKVEPKSCDKTHT

CPPCPAPELLGGPSVFLFPPKPKDTLMISRTPEVTCVVVDVSHEDPEVK

FNWYVDGVEVHNAKTKPREEQYNSTYRVVSVLTVLHQDWLNGKEYKCKV

SNKALPAPIEKTISKAKGQPREPQVYTLPPSRDELTKNQVSLTCLVKGF

YPSDIAVEWESNGQPENNYKTTPPVLDSDGSFFLYSKLTVDKSRWQQGN

VFSCSVMHEALHNHYTQKSLSLSPGK

SEQ ID NO: 4
MAWVWTLLFLMAAAQSAQAQVQLVQSGAEVKKPGASVKVSCKASGYTFT

NYGMNWVRQAPGQGLKWMGWINTYTGEPTYADAFKGRFAFSLDTSTSTA

YMELRSLRSDDTAVYYCARDYGDYGMDYWGQGTTVTVSSASTKGPSVFP

LAPSSKSTSGGTAALGCLVKDYFPEPVTVSWNSGALTSGVHTFPAVLQS

SGLYSLSSVVTVPSSSLGTQTYICNVNHKPSNTKVDKKVEPKSCDKTHT

CPPCPAPELLGGPSVFLFPPKPKDTLMISRTPEVTCVVVDVSHEDPEVK

FNWYVDGVEVHNAKTKPREEQYNSTYRVVSVLTVLHQDWLNGKEYKCKV

SNKALPAPIEKTISKAKGQPREPQVYTLPPSRDELTKNQVSLTCLVKGF

YPSDIAVEWESNGQPENNYKTTPPVLDSDGSFFLYSKLTVDKSRWQQGN

VFSCSVMHEALHNHYTQKSLSLSPGK

SEQ ID NO: 5
QVQLVQSGAEVKKPGASVKVSCKASGYTFTNYGMNWVRQAPGQGLEWMG

WINTYTGEPTYADAFKGRVTMTRDTSISTAYMELSRLRSDDTAVYYCAR

DYGDYGMDYWGQGTTVTVSS

SEQ ID NO: 6
QVQLVQSGAEVKKPGASVKVSCKASGYTFTNYGMNWVRQAPGQGLEWMG

WINTYTGEPTYADAFKGRFAFSLDTSTSTAYLQINSLRSDDTAVYYCAR

DYGDYGMDYWGQGTTVTVSS

SEQ ID NO: 7
QVQLVQSGAEVKKPGASVKVSCKASGYTFTNYGMNWVRQAPGQGLKWMG

WINTYTGEPTYADAFKGRVTMTRDTSISTAYMELSRLRSDDTAVYYCAR

DYGDYGMDYWGQGTTVTVSS

SEQ ID NO: 8
QVQLVQSGAEVKKPGASVKVSCKASGYTFTNYGMNWVRQAPGQGLKWMG

WINTYTGEPTYADAFKGRFAFSLDTSTAYMELRSLRSDDTAVYYCAR

DYGDYGMDYWGQGTTVTVSS

SEQ ID NO: 9
MAWVWTLLFLMAAAQSAQAQVQLVQSGAEVKKPGASVKVSCKASGYTFT

NYGMNWVRQAPGQGLEWMGWINTYTGEPTYADAFKGRVTMTTDTSTSTA

YMELRSLRSDDTAVYYCARDYGDYGMDYWGQGTTVTVSSASTKGPSVFP

LAPSSKSTSGGTAALGCLVKDYFPEPVTVSWNSGALTSGVHTFPAVLQS

SGLYSLSSVVTVPSSSLGTQTYICNVNHKPSNTKVDKKVEPKSCDKTHT

CPPCPAPELLGGPSVFLFPPKPKDTLMISRTPEVTCVVVDVSHEDPEVK

FNWYVDGVEVHNAKTKPREEQYNSTYRVVSVLTVLHQDWLNGKEYKCKV

SNKALPAPIEKTISKAKGQPREPQVYTLPPSRDELTKNQVSLTCLVKGF

YPSDIAVEWESNGQPENNYKTTPPVLDSDGSFFLYSKLTVDKSRWQQGN

VFSCSVMHEALHNHYTQKSLSLSPGK

SEQ ID NO: 10
DIVMTQSPDSLAVSLGERATINCRASKSVSTSGYSFMHWYQQKPGQPPK

WYLASNLESGVPDRFSGSGSGTDFTLTISSLQAEDVAVYYCQHSREVPW

TFGQGTKVEIKR
```

What is claimed is:

1. A population of humanized anti-CD70 antibodies, wherein the antibodies each comprise:
   (i) a humanized heavy chain comprising the three CDRs from SEQ ID NO:1 and a variable region framework sequence of human germline $V_H$1-2 or $V_H$1-18 and exon $J_H$-6, provided that any of positions H46, H67, H68, H69, H70, H71, H80, H81, H82, H82A and H91 (Kabat numbering) can be occupied by the amino acid occupying the corresponding position from SEQ ID NO:1,
   (ii) a humanized light chain comprising the three CDRs from SEQ ID NO:2 and a variable region framework sequence of human germline $V_\kappa$exon B3 and $J_\kappa$exon $J_{\kappa-}$1, provided that any of positions L25 and L33 can be occupied by the amino acid occupying the corresponding position from SEQ ID NO:2, and
   (iii) an Fc domain, wherein at least 50% of the antibodies in the population of antibodies lack core fucosylation; wherein one or more of the antibodies in the population of humanized anti-CD70 antibodies comprises a fucose analog, or a metabolite or product of the fucose analog, wherein the fucose analog is selected from the group consisting of one of the following formulae (I) or (II):

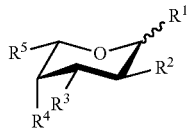
(I)

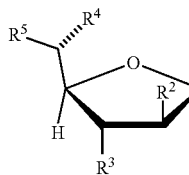
(II)

or a biologically acceptable salt or solvate thereof, wherein:
each of formula (I) or (II) can be the alpha or beta anomer or the corresponding aldose form;
each of $R^1$-$R^4$ is independently selected from the group consisting of —OH, —OC(O)H, —OC(O)$C_1$-$C_{10}$alkyl, —OC(O)$C_2$-$C_{10}$alkenyl, —OC(O)$C_2$-$C_{10}$alkynyl, —OC(O)aryl, —OC(O)heterocycle, —OC(O)$C_1$-$C_{10}$alkylene(aryl), —OC(O)$C_2$-$C_{10}$alkenylene(aryl), OC(O)$C_2$-$C_{10}$alkynyl(aryl), —OC(O)$C_1$-$C_{10}$alkylene heterocycle, —OC(O)$C_2$-$C_{10}$ alkenylene(heterocycle), —OC(O)$C_2$-$C_{10}$alkynyl heterocycle, —OCH$_2$OC(O) alkyl, OCH$_2$OC(O)O alkyl, —OCH$_2$OC(O) aryl, —OCH$_2$OC(O)O aryl, —OC(O)CH$_2$O(CH$_2$CH$_2$O)$_n$CH$_3$, —OC(O)CH$_2$CH$_2$O(CH$_2$CH$_2$O)$_n$CH$_3$, —O—tri—$C_1$-$C_3$ alkyl silyl, and —O$C_1$-$C_{10}$ alkyl, wherein each n is an integer independently selected from 0-5; and
$R^5$ is selected from the group consisting of —C≡CH, —C≡CCH$_3$, —C(O)OCH$_3$, —CH(OAc)CH$_3$, —CH$_2$CN, and —CH$_2$X (wherein X is Br).

2. The population of antibodies of claim 1, wherein at least 70% of the antibodies in the population of antibodies lack core fucosylation.

3. The population of antibodies of claim 1, wherein position H46 of the antibodies is occupied by the amino acid occupying the corresponding position from SEQ ID NO:1.

4. The population of antibodies of claim 1, wherein at least one of positions H46, H67, H68, H69, H70, H71, H80, H81, H82, H82A and H91 (Kabat numbering) in the humanized heavy chain variable region of the antibodies is occupied by the residue occupying the corresponding position in SEQ ID NO:1.

5. The population of antibodies of claim 1, wherein at least one of positions L25 and L33 in the humanized light chain variable region of the antibodies is occupied by the residue occupying the corresponding position in SEQ ID NO:2.

6. The population of antibodies of claim 1, wherein the antibodies comprise a human IgG1 constant domain, wherein the humanized heavy chain comprises the amino acid sequence corresponding to positions 20-467 of SEQ ID NO:3 or positions 20-467 of SEQ ID NO:4.

7. The population of antibodies of claim 1, wherein the antibodies each comprise an antibody effector domain.

8. The population of antibodies of claim 7, wherein the antibody effector domain mediates ADCP.

9. The population of antibodies of claim 1, wherein the antibodies are conjugated to therapeutic agents.

10. The population of antibodies of claim 9, wherein the therapeutic agents are chemotherapeutic agents or immunomodulatory agents.

11. A population of humanized anti-CD70 antibodies, wherein the antibodies each comprise:
(i) a humanized heavy chain variable region comprising the amino acid sequence set forth in SEQ ID NO:5, SEQ ID NO:6, SEQ ID NO:7, SEQ ID NO:8, or amino acids 20-137 of SEQ ID NO:9,
(ii) a humanized light chain variable region comprising the amino acid sequence of SEQ ID NO:10, and
(iii) an Fc domain, wherein at least 50% of the antibodies in the population of antibodies lack core fucosylation:
wherein one or more of the antibodies in the population of humanized anti-CD70 antibodies comprises a fucose analog, or a metabolite or product of the fucose analog,
wherein the fucose analog is selected from the group consisting of one of the following formulae (I) or (II):

(I)

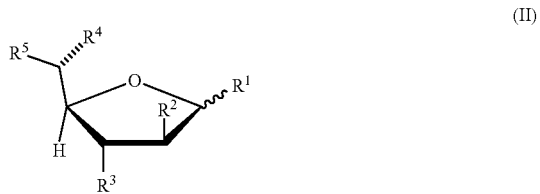
(II)

or a biologically acceptable salt or solvate thereof, wherein:
each of formula (I) or (II) can he the alpha or beta anomer or the corresponding aldose form;
each of $R^1$-$R^4$ is independently selected from the group consisting of —OH, —OC(O)H, —OC(O)$C_1$-$C_{10}$alkyl, —OC(O)$C_2$-$C_{10}$alkynyl, —OC(O)aryl, —OC(O)heterocycle, —OC(O)$C_1$-$C_{10}$alkylene(aryl), —OC(O)$C_2$-$C_{10}$alkenylene(aryl), —OC(O)$C_2$-$C_{10}$alkynyl(aryl), —OC(O)$C_1$-$C_{10}$alkylene heterocycle, —OC(O)$C_2$-$C_{10}$alkenylene(heterocycle), —OC(O)$C_2$-$C_{10}$alkynyl heterocycle, —OCH$_2$OC(O)alkyl, —OCH$_2$OC(O)O alkyl, —OCH$_2$OC(O) aryl, —OCH$_2$OC(O)O aryl, —OC(O)CH$_2$O(CH$_2$CH$_2$O)$_n$CH$_3$, —OC(O)CH$_2$CH$_2$O(CH$_2$CH$_2$O)$_n$CH$_3$, —O—tri—$C_1$-$C_3$alkyl silyl, and —O$C_1$-$C_{10}$alkyl, wherein each n is an integer independently selected from 0-5; and
$R^5$ is selected from the group consisting, of —C≡CH, —C≡CCH$_3$, —C(O)OCH$_3$, —CH(OAc)CH$_3$, —CH$_2$CN, and —CH$_2$X (wherein X is Br).

12. The population of antibodies of claim 11, wherein at least 70% of the antibodies in the population of antibodies lack core fucosylation.

13. The population of antibodies of claim 11, wherein the humanized heavy chain variable region of the antibodies comprise the sequence set forth in SEQ ID NO:7 or SEQ ID NO:8, and the humanized light chain variable region of the antibodies comprise the sequence set forth in SEQ ID NO:10.

14. The population of antibodies of claim 11, wherein the humanized heavy chain variable region of the antibodies comprise the sequence set forth in SEQ ID NO:7 and the humanized light chain variable region of the antibodies comprise the sequence set forth in SEQ ID NO:10.

15. The population of antibodies of claim 14, wherein at least 70% of the antibodies in the population of antibodies lack core fucosylation.

16. The population of antibodies of claim 11, wherein the antibodies are conjugated to therapeutic agents.

17. The population of antibodies of claim 16, wherein the therapeutic agents are chemotherapeutic agents or immunomodulatory agents.

18. A population of anti-CD70 antibodies wherein at least 50% of the antibodies in the population of antibodies lack core fucosylation:
wherein one or more of the antibodies in the population of humanized anti-CD70 antibodies comprises a fucose analog, or a metabolite or product of the fucose analog, wherein the fucose analog is selected from the group consisting of one of the following formulae (I) or (II):

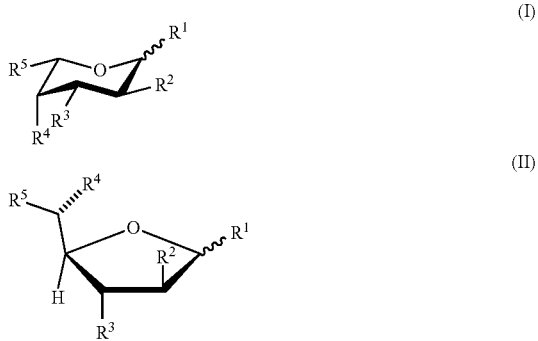

or a biologically acceptable salt or solvate thereof, wherein:
each of formula (I) or (II) can be the alpha or beta anomer or the corresponding aldose form;
each of $R^1$-$R^4$ is independently selected from the group consisting of —OH, —OC(O)H, —OC(O)$C_1$-$C_{10}$alkyl, —OC(O)$C_2$-$C_{10}$alkenyl, —OC(O)$C_2$-$C_{10}$alkynyl, —OC(O)aryl, —OC(O)heterocycle, —OC(O)$C_1$-$C_{10}$alkylene(aryl), —OC(O)$C_2$-$C_{10}$alkenylene(aryl), —OC(O)$C_2$-$C_{10}$alkynyl (aryl), —OC(O)$C_1$-$C_{10}$alkylene heterocycle, —OC(O)$C_2$-$C_{10}$alkenylene (heterocycle), —OC(O)$C_2$-$C_{10}$alkynyl heterocycle, —OCH$_2$OC(O)alkyl, —OCH$_2$OC(O)O alkyl, —OCH$_2$OC(O) aryl, —OCH$_2$OC(O)O aryl, —OC(O)CH$_2$O(CH$_2$CH$_2$O)$_n$CH$_3$, —OC(O)CH$_2$CH$_2$O(CH$_2$CH$_2$O)$_n$CH$_3$, —O—tri—$C_1$-$C_3$alkyl silyl, and —O$C_1$-$C_{10}$alkyl, wherein each n is an integer independently selected from 0-5; and
$R^5$ is selected from the group consisting of —C≡CH, —C≡CCH$_3$, —C(O)OCH$_3$, —CH(OAc)CH$_3$, —CH$_2$CN, and —CH$_2$X (wherein X is Br).

19. The population of antibodies of claim 18, wherein the antibodies are h1F6.

20. The population of antibodies of claim 19, wherein at least 70% of the antibodies in the population of antibodies lack core fucosylation.

21. The population of antibodies of claim 19, wherein the antibodies are conjugated to therapeutic agents.

22. A pharmaceutical composition for the treatment of a CD70-expressing cancer or an immunological disorder, the composition comprising the population of antibodies of claim 1.

23. A kit comprising the population of antibodies of claim 1 and instructions for using the population of antibodies to detect CD70 protein in a subject or a biological sample.

24. A pharmaceutical composition for the treatment of a CD70-expressing cancer or an immunological disorder, the composition comprising the population of antibodies of claim 11.

25. A kit comprising the population of antibodies of claim 11 and instructions for using the humanized antibody to detect CD70 protein in a subject or a biological sample.

26. A pharmaceutical composition for the treatment of a CD70-expressing cancer or an immunological disorder, the composition comprising the population of antibodies of claim 19.

27. A kit comprising the population of antibodies of claim 19 and instructions for using the antibody to detect CD70 protein in a subject or a biological sample.

28. A population of humanized anti-CD70 antibodies, wherein the antibodies each comprise:
(i) a humanized heavy chain comprising the three CDRs from SEQ ID NO:1 and a variable region framework sequence of human germline $V_H$1-2 or $V_H$1-18 and exon $J_H$-6, provided that any of positions H46, H67, H68, H69, H70, H71, H80, H81, H82, H82A and H91 (Kabat numbering) can be occupied by the amino acid occupying the corresponding position from SEQ ID NO:1,
(ii) a humanized light chain comprising the three CDRs from SEQ ID NO:2 and a variable region framework sequence of human germline $V_K$ exon B3 and $J_K$ exon $J_K$-1, provided that any of positions L25 and L33 can be occupied by the amino acid occupying the corresponding position from SEQ ID NO:2, and
(iii) an Fc domain, wherein at least 50% of the antibodies in the population of antibodies lack core fucosylation;
wherein one or more of the antibodies in the population of humanized anti-CD70 antibodies comprises a fucose analog, or a metabolite or product of the fucose analog, wherein the fucose analog is selected from the group consisting of one of the following formulae (III) or (IV):

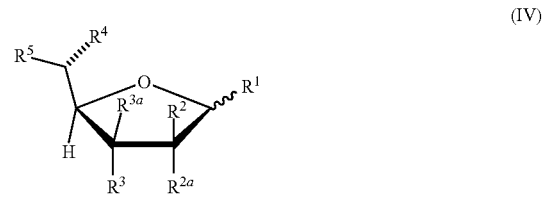

or a biologically acceptable salt or solvate thereof, wherein:
each of formula (III) or (IV) can be the alpha or beta anomer or the corresponding aldose form;
each of $R^1$-$R^4$ is independently selected from the group consisting of fluoro, chloro, —OH, —OC(O)H, —OC(O)$C_1$-$C_{10}$alkyl, —OC(O)$C_2$-$C_{10}$alkenyl, —OC(O)$C_2$-$C_{10}$alkynyl, —OC(O)aryl, —OC(O)heterocycle, —OC(O)$C_1$-$C_{10}$alkylene(aryl), —OC(O)$C_2$-$C_{10}$alkenylene (aryl), —OC(O)$C_2$-$C_{10}$alkynyl(aryl), —OC(O)$C_1$-

$C_{10}$alkylene heterocycle, —OC(O)$C_2$-$C_{10}$alkenylene (heterocycle), —OC(O)$C_2$-$C_{10}$alkynyl heterocycle, —OCH$_2$OC(O) alkyl, —OCH$_2$OC(O)O alkyl, —OCH$_2$OC(O) aryl, —OCH$_2$OC(O)O aryl, —OC(O)CH$_2$O(CH$_2$CH$_2$O)$_n$CH$_3$, —OC(O)CH$_2$CH$_2$O(CH$_2$CH$_2$O)$_n$CH$_3$, —O-tri-$C_1$-$C_3$ alkylsilyl and —OC$_1$-$C_{10}$alkyl, wherein each n is an integer independently selected from 0-5;

each of $R^{2a}$ and $R^{3a}$ is independently selected from the group consisting of H, F and Cl;

$R^5$ is selected from the group consisting of —CH$_3$, —CHF$_2$, —CH=C=CH$_2$, —C≡CCH$_3$, —CH$_2$C≡CH, —C(O)OCH$_3$, —CH(OAc)CH$_3$, —CN, —CH$_2$CN, —CH$_2$X (wherein X is Br, Cl or I), and methoxiran; and wherein when $R^5$ is other than —CH=C=CH$_2$ or —CHF$_2$, at least one of $R^1$, $R^2$, $R^3$, $R^{2a}$ and $R^{3a}$ is fluoro or chloro.

29. The population of antibodies of claim 28, wherein the fucose analog is formula (III) or a biologically acceptable salt or solvate thereof, wherein:
$R^1$ is —OH;
$R^2$ is —F;
$R^{2a}$ is —H;
$R^3$ is —OH;
$R^{3a}$ is —H;
$R^4$ is —OH; and
$R^5$ is —CH$_3$.

30. The population of antibodies of claim 28, wherein the fucose analog is 2-deoxy-2-fluorofucose.

31. The population of antibodies of claim 28, wherein at least 70% of the antibodies in the population of antibodies lack core fucosylation.

32. The population of antibodies of claim 28, wherein position H46 of the antibodies is occupied by the amino acid occupying the corresponding position from SEQ ID NO:1.

33. The population of antibodies of claim 28, wherein at least one of positions H46, H67, H68, H69, H70, H71, H80, H81, H82, H82A and H91 (Kabat numbering) in the humanized heavy chain variable region of the antibodies is occupied by the residue occupying the corresponding position in SEQ ID NO:1.

34. The population of antibodies of claim 28, wherein at least one of positions L25 and L33 in the humanized light chain variable region of the antibodies is occupied by the residue occupying the corresponding position in SEQ ID NO:2.

35. The population of antibodies of claim 28, wherein the antibodies comprise a human IgG1 constant domain, wherein the humanized heavy chain comprises the amino acid sequence corresponding to positions 20-467 of SEQ ID NO:3 or positions 20-467 of SEQ ID NO:4.

36. The population of antibodies of claim 28, wherein the antibodies each comprise an antibody effector domain.

37. The population of antibodies of claim 36, wherein the antibody effector domain mediates ADCP.

38. The population of antibodies of claim 28, wherein the antibodies are conjugated to therapeutic agents.

39. The population of antibodies of claim 38, wherein the therapeutic agents are chemotherapeutic agents or immunomodulatory agents.

40. A population of humanized anti-CD70 antibodies, wherein the antibodies each comprise:
(i) a humanized heavy chain variable region comprising the amino acid sequence set forth in SEQ ID NO:5, SEQ ID NO:6, SEQ ID NO:7, SEQ ID NO:8, or amino acids 20-137 of SEQ ID NO:9, (ii) a humanized light chain variable region comprising the amino acid sequence of SEQ ID NO:10, and (iii) an Fc domain, wherein at least 50% of the antibodies in the population of antibodies lack core fucosylation:

wherein one or more of the antibodies in the population of humanized anti-CD70 antibodies comprises a fucose analog, or a metabolite or product of the fucose analog, wherein the fucose analog is selected from the group consisting of one of the following formulae (III) or (IV):

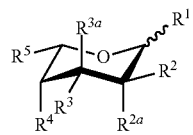
(III)

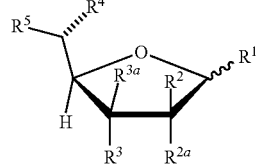
(IV)

or a biologically acceptable salt or solvate thereof, wherein:
each of formula (III) or (IV) can be the alpha or beta anomer or the corresponding aldose form;

each of $R^1$-$R^4$ is independently selected from the group consisting of fluoro, chloro, —OH, —OC(O)H, —OC(O)$C_1$-$C_{10}$alkyl, —OC(O)$C_2$-$C_{10}$alkenyl, —OC(O)$C_2$-$C_{10}$alkynyl, —OC(O)aryl, —OC(O)heterocycle, —OC(O)$C_1$-$C_{10}$alkylene(aryl), —OC(O)$C_2$-$C_{10}$alkenylene (aryl), —OC(O)$C_2$-$C_{10}$alkynyl(aryl), —OC(O)$C_1$-$C_{10}$alkylene heterocycle, —OC(O)$C_2$-$C_{10}$alkenylene (heterocycle), —OC(O)$C_2$-$C_{10}$alkynyl heterocycle, —OCH$_2$OC(O) alkyl, —OCH$_2$OC(O)O alkyl, —OCH$_2$OC(O) aryl, —OCH$_2$OC(O)O aryl, —OC(O)CH$_2$O(CH$_2$CH$_2$O)$_n$CH$_3$, —OC(O)CH$_2$CH$_2$O(CH$_2$CH$_2$O)$_n$CH$_3$, —O-tri-$C_1$-$C_3$ alkylsilyl and —OC$_1$-$C_{10}$alkyl, wherein each n is an integer independently selected from 0-5;

each of $R^{2a}$ and $R^{3a}$ is independently selected from the group consisting of H, F and Cl;

$R^5$ is selected from the group consisting of —CH$_3$, —CHF$_2$, —CH=C=CH$_2$, —C≡CCH$_3$, —CH$_2$C≡CH, —C(O)OCH$_3$, —CH(OAc)CH$_3$, —CN, —CH$_2$CN, —CH$_2$X (wherein X is Br, Cl or I), and methoxiran; and wherein when $R^5$ is other than —CH=C=CH$_2$ or —CHF$_2$, at least one of $R^1$, $R^2$, $R^3$, $R^{2a}$ and $R^{3a}$ is fluoro or chloro.

41. The population of antibodies of claim 40, wherein the fucose analog is formula (III) or a biologically acceptable salt or solvate thereof, wherein:
$R^1$ is —OH;
$R^2$ is —F;
$R^{2a}$ is —H;
$R^3$ is —OH;
$R^{3a}$ is —H;
$R^4$ is —OH; and
$R^5$ is —CH$_3$.

42. The population of antibodies of claim 40, wherein the fucose analog is 2-deoxy-2-fluorofucose.

43. The population of antibodies of claim 40, wherein at least 70% of the antibodies in the population of antibodies lack core fucosylation.

44. The population of antibodies of claim 40, wherein the humanized heavy chain variable region of the antibodies comprise the sequence set forth in SEQ ID NO:7 or SEQ ID NO:8, and the humanized light chain variable region of the antibodies comprise the sequence set forth in SEQ ID NO:10.

45. The population of antibodies of claim 40, wherein the humanized heavy chain variable region of the antibodies comprise the sequence set forth in SEQ ID NO:7 and the humanized light chain variable region of the antibodies comprise the sequence set forth in SEQ ID NO:10.

46. The population of antibodies of claim 45, wherein at least 70% of the antibodies in the population of antibodies lack core fucosylation.

47. The population of antibodies of claim 40, wherein the antibodies are conjugated to therapeutic agents.

48. The population of antibodies of claim 47, wherein the therapeutic agents are chemotherapeutic agents or immunomodulatory agents.

49. A population of anti-CD70 antibodies wherein at least 50% of the antibodies in the population of antibodies lack core fucosylation:
wherein one or more of the antibodies in the population of humanized anti-CD70 antibodies comprises a fucose analog, or a metabolite or product of the fucose analog, wherein the fucose analog is selected from the group consisting of one of the following formulae (III) or (IV):

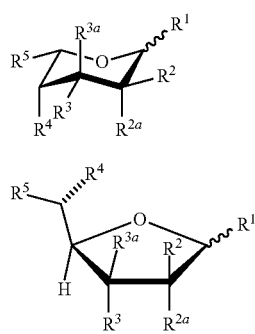

or a biologically acceptable salt or solvate thereof, wherein:
each of formula (III) or (IV) can be the alpha or beta anomer or the corresponding aldose form;
each of $R^1$-$R^4$ is independently selected from the group consisting of fluoro, chloro, —OH, —OC(O)H, —OC(O)$C_1$-$C_{10}$alkyl, —OC(O)$C_2$-$C_{10}$alkenyl, —OC(O)$C_2$-$C_{10}$alkynyl, —OC(O)aryl, —OC(O)heterocycle, —OC(O)$C_1$-$C_{10}$alkylene(aryl), —OC(O)$C_2$-$C_{10}$alkenylene (aryl), —OC(O)$C_2$-$C_{10}$alkynyl(aryl), —OC(O)$C_1$-$C_{10}$alkylene heterocycle, —OC(O)$C_2$-$C_{10}$alkenylene (heterocycle), —OC(O)$C_2$-$C_{10}$alkynyl heterocycle, —OCH$_2$OC(O) alkyl, —OCH$_2$OC(O)O alkyl, —OCH$_2$OC(O) aryl, —OCH$_2$OC(O)O aryl, —OC(O)CH$_2$O(CH$_2$CH$_2$O)$_n$CH$_3$, —OC(O)CH$_2$CH$_2$O(CH$_2$CH$_2$O)$_n$CH$_3$, —O-tri-$C_1$-$C_3$alkylsilyl and —O$C_1$-$C_{10}$ alkyl, wherein each n is an integer independently selected from 0-5;

each of $R^{2a}$ and $R^{3a}$ is independently selected from the group consisting of H, F and Cl;
$R^5$ is selected from the group consisting of —CH$_3$, —CHF$_2$, —CH═C═CH$_2$, —C≡CCH$_3$, —CH$_2$C≡CH, —C(O)OCH$_3$, —CH(OAc)CH$_3$, —CN, —CH$_2$CN, —CH$_2$X (wherein X is Br, Cl or I), and methoxiran; and
wherein when $R^5$ is other than —CH═C═CH$_2$ or —CHF$_2$, at least one of $R^1$, $R^2$, $R^3$, $R^{2a}$ and $R^{3a}$ is fluoro or chloro.

50. The population of antibodies of claim 49, wherein the antibodies are h1F6.

51. The population of antibodies of claim 49, wherein the fucose analog is formula (III) or a biologically acceptable salt or solvate thereof, wherein:
$R^1$ is —OH;
$R^2$ is —F;
$R^{2a}$ is —H;
$R^3$ is —OH;
$R^{3a}$ is —H;
$R^4$ is —OH; and
$R^5$ is —CH$_3$.

52. The population of antibodies of claim 49, wherein the fucose analog is 2-deoxy-2-fluorofucose.

53. The population of antibodies of claim 50, wherein the fucose analog is formula (III) or a biologically acceptable salt or solvate thereof, wherein:
$R^1$ is —OH;
$R^2$ is —F;
$R^{2a}$ is —H;
$R^3$ is —OH;
$R^{3a}$ is —H;
$R^4$ is —OH; and
$R^5$ is —CH$_3$.

54. The population of antibodies of claim 47, wherein the fucose analog is 2-deoxy-2-fluorofucose.

55. The population of antibodies of claim 47, wherein at least 70% of the antibodies in the population of antibodies lack core fucosylation.

56. The population of antibodies of claim 47, wherein the antibodies are conjugated to therapeutic agents.

57. The population of antibodies of claim 56, wherein the therapeutic agents are chemotherapeutic agents or immunomodulatory agents.

58. A pharmaceutical composition for the treatment of a CD70-expressing cancer or an immunological disorder, the composition comprising the population of antibodies of claim 28.

59. A kit comprising the population of antibodies of claim 28 and instructions for using the population of antibodies to detect CD70 protein in a subject or a biological sample.

60. A pharmaceutical composition for the treatment of a CD70-expressing cancer or an immunological disorder, the composition comprising the population of antibodies of claim 40.

61. A kit comprising the population of antibodies of claim 40 and instructions for using the humanized antibody to detect CD70 protein in a subject or a biological sample.

62. A pharmaceutical composition for the treatment of a CD70-expressing cancer or an immunological disorder, the composition comprising the population of antibodies of claim 50.

63. A kit comprising the population of antibodies of claim 50 and instructions for using the antibody to detect CD70 protein in a subject or a biological sample.

* * * * *